United States Patent
Rodgers et al.

(10) Patent No.: US 9,334,274 B2
(45) Date of Patent: May 10, 2016

(54) N-(HETERO)ARYL-PYRROLIDINE DERIVATIVES OF PYRAZOL-4-YL-PYRROLO[2,3-D]PYRIMIDINES AND PYRROL-3-YL-PYRROLO[2,3-D]PYRIMIDINES AS JANUS KINASE INHIBITORS

(71) Applicants: Incyte Corporation, Wilmington, DE (US); Incyte Holdings Corporation, Wilmington, DE (US)

(72) Inventors: James D Rodgers, Landenberg, PA (US); Stacey Shepard, Wilmington, DE (US); Argyrios G Arvanitis, Kennett Square, PA (US); Haisheng Wang, Hockessin, DE (US); Louis Storace, Middletown, DE (US); Beverly Folmer, Hockessin, DE (US); Wenyu Zhu, Media, PA (US); Joseph Glenn, Mount Royal, NJ (US); Lixin Shao, Newark, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 14/250,843

(22) Filed: Apr. 11, 2014

(65) Prior Publication Data

US 2014/0221379 A1    Aug. 7, 2014

Related U.S. Application Data

(63) Continuation of application No. 12/784,916, filed on May 21, 2010, now Pat. No. 8,716,303.

(60) Provisional application No. 61/225,092, filed on Jul. 13, 2009, provisional application No. 61/180,622, filed on May 22, 2009.

(51) Int. Cl.

| | | |
|---|---|---|
| *A01N 43/90* | (2006.01) | |
| *A61K 31/519* | (2006.01) | |
| *C07D 487/00* | (2006.01) | |
| *C07D 487/04* | (2006.01) | |
| *C07D 519/00* | (2006.01) | |
| *C07D 471/04* | (2006.01) | |
| *C07D 491/048* | (2006.01) | |
| *C07D 495/04* | (2006.01) | |
| *C07D 498/04* | (2006.01) | |
| *C07D 513/04* | (2006.01) | |

(52) U.S. Cl.
CPC .......... *C07D 487/04* (2013.01); *C07D 471/04* (2013.01); *C07D 491/048* (2013.01); *C07D 495/04* (2013.01); *C07D 498/04* (2013.01); *C07D 513/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 2,985,589 A | 5/1961 | Broughton et al. | |
| 4,402,832 A | 9/1983 | Gerhold | |
| 4,498,991 A | 2/1985 | Oroskar | |
| 4,512,984 A | 4/1985 | Seufert et al. | |
| 4,548,990 A | 10/1985 | Mueller et al. | |
| 5,510,101 A | 4/1996 | Stroppolo | |
| 5,521,184 A | 5/1996 | Zimmermann | |
| 5,630,943 A | 5/1997 | Grill | |
| 5,856,326 A | 1/1999 | Anthony | |
| 5,919,779 A | 7/1999 | Proudfoot et al. | |
| 6,060,038 A | 5/2000 | Burns | |
| 6,075,056 A | 6/2000 | Quigley, Jr. et al. | |
| 6,136,198 A | 10/2000 | Adam et al. | |
| 6,217,895 B1 | 4/2001 | Guo | |
| 6,335,342 B1 | 1/2002 | Longo et al. | |
| 6,375,839 B1 | 4/2002 | Adam et al. | |
| 6,413,419 B1 | 7/2002 | Adam et al. | |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

Wolff et. al., "Burger's Medicinal Chemistry and Drug Discovery," 5th Ed. Part 1, pp. 975-977 (1995).*

(Continued)

*Primary Examiner* — Jeffrey H Murray
(74) *Attorney, Agent, or Firm* — Fish & Richardson P.C.

(57) ABSTRACT

The present invention relates to N-(hetero)aryl-pyrrolidine derivatives of Formula I:

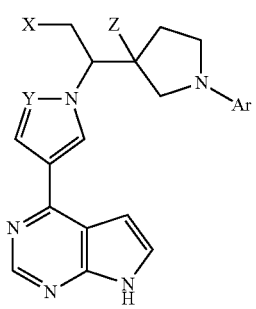

which are JAK inhibitors, such as selective JAK1 inhibitors, useful in the treatment of JAK-associated diseases including, for example, inflammatory and autoimmune disorders, as well as cancer.

34 Claims, No Drawings

(56) References Cited

U.S. PATENT DOCUMENTS

| | | |
|---|---|---|
| 6,486,322 B1 | 11/2002 | Longo et al. |
| 6,548,078 B2 | 4/2003 | Guo |
| 6,569,443 B1 | 5/2003 | Dawson |
| 6,579,882 B2 | 6/2003 | Stewart et al. |
| 6,635,762 B1 | 10/2003 | Blumenkopf et al. |
| 6,712,973 B2 | 3/2004 | Adam et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodgers et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0274257 A1 | 10/2013 | Arvanitis et al. |
| 2013/0296299 A1 | 11/2013 | Rodgers et al. |
| 2014/0005166 A1 | 1/2014 | Rodgers et al. |
| 2014/0031344 A1 | 1/2014 | Arvanitis et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0065447 A1 | 3/2015 | Sandor |
| 2015/0065484 A1 | 3/2015 | Yeleswaram et al. |

(56) References Cited

U.S. PATENT DOCUMENTS

| | | | |
|---|---|---|---|
| 2015/0087632 | A1 | 3/2015 | Rodgers et al. |
| 2015/0087662 | A1 | 3/2015 | Li et al. |
| 2015/0164900 | A1 | 6/2015 | Rodgers et al. |

FOREIGN PATENT DOCUMENTS

| | | |
|---|---|---|
| EP | 0587473 | 3/1994 |
| EP | 0727217 | 8/1996 |
| EP | 1104764 | 6/2001 |
| JP | 07-010876 | 1/1995 |
| JP | 2003/155285 | 5/2003 |
| JP | 2006/518341 | 8/2006 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/51614 | 9/2000 |
| WO | WO 00/53595 | 9/2000 |
| WO | WO 00/63168 | 10/2000 |
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/46184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/129195 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/007839 | 1/2009 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |

(56) References Cited

FOREIGN PATENT DOCUMENTS

| WO | WO 2010/022076 | 2/2010 |
|---|---|---|
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2011/003418 | 1/2011 |
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |
| WO | WO 2012/068440 | 5/2012 |
| WO | WO 2012/068450 | 5/2012 |
| WO | WO 2012/177606 | 12/2012 |
| WO | WO 2013/007765 | 1/2013 |
| WO | WO 2013/007768 | 1/2013 |
| WO | WO 2013/023119 | 2/2013 |
| WO | WO 2013/026025 | 2/2013 |
| WO | WO 2013/036611 | 3/2013 |
| WO | WO 2013/173720 | 11/2013 |
| WO | WO 2014/071031 | 5/2014 |
| WO | WO 2014/138168 | 9/2014 |

OTHER PUBLICATIONS

Banker, et. al., (1996), Modern Pharmaceuticals, p. 596.*
U.S. Appl. No. 14/799,777, filed Jul. 15, 2015, Rodgers et al.
U.S. Appl. No. 14/711,576, filed May 13, 2015, Rodgers et al.
U.S. Appl. No. 14/714,820, filed May 18, 2015, Rodgers et al.
U.S. Appl. No. 14/593,688, filed Jan. 9, 2015, Zhou et al.
U.S. Appl. No. 14/263,476, filed Apr. 28, 2014, Rodgers et al.
U.S. Appl. No. 14/697,236, filed Apr. 27, 2015, Yao et al.
U.S. Appl. No. 14/633,605, filed Feb. 27, 2015, Vaddi.
U.S. Appl. No. 14/699,500, filed Apr. 29, 2015, Zhou et al.
26th Annual JPMorgan Healthcare Conference presentation dated Jan. 8, 2008 (28 pages).
Abe, et al., Heterocycles, "Effective Methods for Introducing Some Aryl and Heteroaryl Substituent onto 1-Azaazulene Nuclei", 66, 229-240 (2005).
Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.
Abelson et al., "Dry eye syndrome: diagnosis, clinical trials, and pharmaceutical treatment-'improving clinical trials'. Lacrimal Gland, Tear Film, and Dry Eye Syndromes 3 Part B", Adv Exp Med Biol, 2002; 506:1079-86.
Abstract of Chilean patent application No. 3496-06 published in Official Gazette of the Republic of Chile (Jun. 1, 2007) and publication (2 pages).
Aho, T. et al., Expression of human pim family genes is selectively up-regulated by cytokines promoting T helper type 1, but not T helper type 2, cell differentiation, Immunology 116: 82-88, 2005.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anderson et al., "Biochemical characterization of GSK1070916, a potent and selective inhibitor of Aurora B and Aurora C kinases with an extremely long residence time", Biochem. J., 420(2), 259-265 (2009).

Bachmann, et al., "The serine/threonine kineaase Pim-1," The International Journal of Biochechemistry and Cell Biology 37: 726-730 (2005).
Barabino et al., "Tear film and ocular surface tests in animal models of dry eye; uses and limitations", Experimental Eye Research, 2004, 79, 613-621.
Barr et al., "Corneal scarring in the Collaborative Longitudinal Evaluation of Keratoconus (CLEK) Study: baseline prevalence and repeatability of detection", Cornea, 1999; 18(1):34-46.
Baudouin et al., "Flow cytometry in impression cytology specimens. A new method for evaluation of conjunctival Inflammation", Invest Ophthalmol Vis Sci, 1997; 38:1458-1464.
Baytel et al., "The human Pim-2 proto-oncogene and its testicular expression" Biochimica et Biophysica Acta 1442: 274-285, (1998).
Beck et al., "Brief Report: Alleviation of Systemic Manifestations of Castleman's Disease by Monoclonal Anti-Interleukin-6 Antibody," N. Engl. J. Med., 1994, 330(9):602-605.
Begley, et al., "Use of the dry eye questionnaire to measure symptoms of ocular irritation in patients with aqueous tear deficient dry eye", Cornea, 2002:21:664-70.
Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.
Berge, et al., "Pharmaceutical salts", J. Pharma. Science (1977) vol. 66(1) pp. 1-19.
Beyer, "Uber die Synthese von 2-Methylmercapto-1.3.4-thiodiazinen and deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.
Bioreversible Carriers in Drug Design, ed. Edward B. Roche, American Pharmaceutical Association and Pergamon Press, 1987.
Blume-Jensen, et al, "Oncogenic kinase signaling", Nature 2001, 411(6835):355-365.
Bock, C., et al. "Managing drug resistance in cancer: lessons from HIV therapy." Nature. (Jul. 2012), vol. 12, pp. 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).
Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.
Bosworth, "JAK1/JAK2 Inhibitor Ruxolitinib Is a Rising Start," Clinical Oncology, Apr. 2011, vol. 06:04, 3 pages.
Boudny, et al., "JAK/STAT signaling pathways and cancer", Neoplasm, 49:349-355, 2002.
Bourcier et al., "Expression of CD40 and CD40 ligand in the human conjunctival epithelium", Invest Ophthalmol Vis Sci, 2000;41:120-126.
Bowman, et al. "STATs in oncogenesis", Oncogene, 19:2474-2488, 2000.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998;67:687-697.
Brignole et al., "Flow cytometric analysis of inflammatory markers in conjunctival epithelial cells of patients with dry eyes", Invest Ophthalmol Vis Sci, 2000; 41:1356-1363.
Brignole et al., "Flow cytometric analysis of inflammatory markers in KCS: 6-month treatment with topical cyclosporin A", Invest Ophthalmol Vis Sci, 2001; 42:90-95.

(56) References Cited

OTHER PUBLICATIONS

Brignole et al., "Flow cytometry in conjunctival impression cytology: a new tool for exploring ocular surface pathologies", Exp Eye Res, 2004;78:473-481.
Bromberg et al., "Inflammation and Cancer: IL-6 and STAT3 Complete the Link," Cancer Cell, 15:79-80 (2009).
Bron, et al., "Grading of corneal and conjunctival staining in the context of other dry eye tests", Cornea, 2003;22(7):640-50.
Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger, et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immunodeficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, Oxidations, 4th ed., Kluwer Academic/Plenum Publishers:New York, pp. 747-757 (2001).
Cermak, et al, "Is complete androgen insensitivity syndrome associated with alterations in the meibomium gland and ocular surface", Cornea, 2003;22:516-521.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia*, 2013, 13(3):333-337.
Chauhan, et al, "Autoimmunity in Dry Eye due to resistance of Th17 to Treg Suppression", J. Immunology, 182(3):1247-52 (2009).
Chemical encyclopedia, vol. 1, pp. 242-243, publication "Soviet Encyclopedia," Moscow, 1988.
Chen et al., "Blockade of interleukin-6 signaling augments regulatory T-cell reconstitution and attenuates the severity of graft-versus-host disease," Blood, 2009, 114(4): 891-900.
Chen, et al., "Stat3 Activation in Human Endometrial and Cervical Cancer", British Journal of Cancer, 96, 591-599, 2007.
Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Cho, et al, "Review of the tear break-up time and a closer look at the tear break-up time of Hong Kong Chinese", Optom Vis Sci, 1993;70(1):30-8.
Choi Ha-Soon, et al, "Design and synthesis of 7H-pyrrolo[2,3-d]pyrimidines as focal adhesion kinase inhibitors. Part 1", Bioorg. & Med. Chem. Lett., 16(8):2173-2176 (2006).

Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Claridge et al., "Discovery of a novel and potent series of thieno[3,2-b]pyridine-based inhibitors of c-Met and VEGFR2 tyrosine kinases," Bioorganic and Medicinal Chemistry Letters, 2008, 18,2793-2798.
Coligan, J.E. et al, Wiley Press; Methods in Molecular Biology: vol. 225, Inflammation Protocols., Winyard, P.G. and Willoughby, D.A., Humana Press (2003).
Communication dated Jan. 22, 2009 for European Appln. No. 06839328.9 (5 pgs.).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988).
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deng Jun, et al, "Rh-catalyzed asymmetric hydrogenation of gamma-phthalimido-substituted esters: an efficient enantioselective synthesis of beta-aryl-gamma-amino acids", Org. Left. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-l-olates", Tetrahedron, 30:3997-4012, 1974.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Dudley, A.C., et al. "A VEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Expert Scientific Group on Phase One Clinical Trials Final Report, Nov. 30, 2006, pp. C1, C35-C38.
Fabrizio Saettone, "Ocular inserts for topical delivery", Advanced Drug Delivery Reviews 16:95-106 (1998).

(56) References Cited

OTHER PUBLICATIONS

Farrell et al., "A classification for dry eyes following comparison of tear thinning time with Schirmer tear test", Acta Ophthalmol (Copenh), 1992; 70(3):357-60.

Farrell et al., "A clinical procedure to predict the value of temporary occlusion therapy in keratoconjunctivitis sicca" Ophthal Physiol Opt, 2003;23:1-8.

Farris, "Tear osmolarity—a new gold standard?" Adv Exp Med Biol, 350:495-503, 1994.

Fayad et al., "Interleukin-6 and interleukin-10 levels in chronic lymphocytic leukemia: correlation with phenotypic characteristics and outcome," Blood, Jan. 2001, 97(1): 256-263.

Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).

Flex E., et al., "Somatically acquired JAK1 mutations in adult acute lymphoblastic leukemia", J. Exp Med. 205:751-8, (2008).

Fonseca, J.E. et al., "Interleukin-6 as a key player in systemic inflammation and joint destruction", Autoimmunity Reviews, 8:538-42, (2009).

Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.

Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).

Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).

Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).

Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).

Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).

Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.

Fujihara et al., "Evaluation of human conjunctival epithelium by a combination of brush cytology and flow cytometry: an approach to the quantitative technique", Diagn Cytopathol, 1997;17:456-60.

Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).

Fukagawa et al., "Histological evaluation of brush cytology of rabbit conjunctiva", Nippon Ganka Gakkai Zasshi, 1993;97:1173-8 (contains English abstract within the article).

Gaertner, "Cyclization of 1-Alkylamino-3-halo-2-alkanolst o 1-Alkyl-3-azetidinols," J. Org. Chem., 1967, 32, 2972-76.

Gaestel et al., "Targeting innate immunity protein kinase signalling in inflammation," Nat Rev Drug Discov., Jun. 2009, 8(6):480-99.

Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).

Glasson et al., "Differences in clinical parameters and tear film of tolerant and intolerant contact lens wearers", Invest Ophthalmol Vis Sci, 2003;44:5116-5124.

Glattfeld, "Improvements in the Preparation of DL-Threonic and DL-Erythronic Acids", J. Am. Chem. Soc. 62:974-977 (1940).

Gilchrist et al., "5H-2-Pyrindines from 2-Bromocyclopentene-1-carboxaldehyde," Tetrahedron, Jan. 1, 1995, pp. 9119-9126.

Gobbels et al., Tear secretion in dry eyes as assessed by objective fluorophotometry. Ger J Ophthalmol, 1992; 1:350-353.

Golding et al., "X-ray and scanning electron microscopic analysis of the structural composition of tear ferns", Cornea Jan. 1994;13(1):58-66.

Gomtsyan, et al, "Design, synthesis, and structure-activity relationship of 6-alkynylpyrimidines as potent adenosine kinase inhibitors", J. Med. Chem. 45(17):3639-3648 (2002).

Goodman, et al., "IL-6 Signaling in Psoriasis Prevents Immune Suppression by Regulatory T Cells," J. Immunol , Sep. 2009, 183: 3170-3176.

Gooseman, et al., "The intramolecular b-fluorine . . . ammonium interaction in 4- and 8-membered rings", Chem. Commun, vol. 30, pp. 3190-3192 (2006).

Gone, M.E. et al., "Clinical Resistance to STI-571 Cancer Therapy Caused by BCR-ABL Gene Mutation or Amplification." Science, 293:876, 2001.

Gotlieb, Alice, Presentation at the 2008 American Academy of Dermatology, 66th Annual Meeting, San Antonio, TX. Feb. 1, 2008, symposium-303 (12 pp.).

Goto et al., Color mapping of tear lipid layer thickness distribution from the image analysis in DR-1 tear lipid layer interference images (ARVO abstract). ARVO 2004.

Goto et al., "Computer-synthesis of an interference color chart of human tear lipid layer by a colorimetric approach",Invest Ophthalmol Vis Sci, 2003;44:4693-7.

Goto et al., "Differentiation of lipid tear deficiency dry eye by kinetic analysis of tear interference images", Arch Ophthalmol, 2003;121:173-80.

Goto et al., "Evaluation of the tear film stability after laser in situ keratomileusis using the tear film stability analysis system", Am J Ophthalmol, 2004b Jan;137(1):116-20.

Goto et al., "Tear Film Stability Analysis System: Introducing a new application for videokeratography", Cornea, 2004a; Nov;23(8):S65-S70.

Goto, et al., Kinetic analysis of tear interference images in aqueous tear deficiency dry eye before and after punctal occlusion. Invest Ophthalmol Vis Sci, 2003;44:1897-905.

Gottlieb, A.B., et al, "Psoriasis: Emerging Therapeutic Strategies", Nat Rev Drug Disc., 4:19-34 (2005).

Grabbe, et al., "Immunoregulatory mechanisms involved in elicitation of allergic—contact hypersensitivity", Immunol Today, Jan; 19(1):37-44 (1998) (only 1 page provide and marked "best available copy").

Green, T.W. and Wuts, P.G.M.. Protective Groups in Organic Synthesis, 3rd. Ed., Wiley & Sons, Inc., New York (1999).

Gregory, et al., "Clinical and laboratory features of myelofibrosis and limitations of current therapies", Clinical Advances in Hematology and Oncology, (Sep. 2011) vol. 9, No. 9, pp. 1-3.

Grivennikov, et al., "IL-6 and STAT3 are required for survival of intestinal epithelial cells and the development of colitis-associated cancer", Cancer Cell, 15:103-111 (2009).

Groneberg et al., "Animal models of allergic and inflammatory conjunctivitis," Allergy, 2003, 58, 1101-1113.

Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.

Guillon, Jean-Pierre, "Tear film photography and contact lens wear", J Br Contact Lens Assoc, 1982;5:84-7.

Gura, Science, vol. 278, No. 5340, pp. 1041-1042 (1997).

(56) References Cited

OTHER PUBLICATIONS

Guschin, et al, "A major role for the protein tyrosine kinase JAK1 in the JAKISTAT signal transduction pathway in response to interleukin-6", Embo J 14:1421-1429 (1995).
Hamze' et al., "Synthesis of Various 3-Substituted 1,2,4-Oxadiazole-Containing Chiral β3—and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi, et al., "Pro-drugs as Novel Delivery Systems," vol. 14 of the A.C.S. Symposium Series (1975).
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," Transplantation, 2010, Abstract, 1 page.
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 mailed Dec. 17, 2009 (7 pages).
International Preliminary Report on Patentability for PCT/US2009/036635 mailed Sep. 14, 2010 (6 pages).
International Preliminary Report on Patentability for PCT/US2009/059203 mailed Apr. 5, 2011 (6 pages).
International Preliminary Report on Patentability for PCT/US2010/021003 mailed Jul. 19, 2011(11 pages).
International Preliminary Report on Patentability for PCT/US2011/037291 mailed Nov. 27, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2013/041601, issued Nov. 18, 2014, 7 pages.
International Search Report and the Written Opinion, PCT/US2012/051439, mailed Nov. 30, 2012 (15 pages).
International Search Report and the Written Opinion, PCT/US2012/053921, mailed Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (Apr. 24, 2007).
International Search Report and Written Opinion for PCT/US2008/083319, 29 pages mailed Mar. 13, 2009.
International Search Report and Written Opinion for PCT/US2011/025433, 12 pages (mailed Jul. 20, 2011).
International Search Report and Written Opinion for PCT/US2011/027665 mailed Jun. 27, 2011 (14 pages).
International Search Report and Written Opinion for PCT/US2011/037291, 11 pages (Apr. 19, 2012).
International Search Report and Written Opinion for PCT/US2011/061351 mailed Feb. 17, 2012 (12 pages).
International Search Report and Written Opinion for PCT/US2011/061374 mailed Mar. 27, 2012 (10 pages).
International Search Report and Written Opinion for PCT/US2012/025581, 16 pages (mailed Apr. 26, 2011).
International Search Report and Written Opinion for PCT/US2012/043099, 11 pages (Sep. 13, 2012).
International Search Report and Written Opinion for PCT/US2012/050252 mailed Jan. 2, 2013, 17 pages.
International Search Report for PCT/US2008/66658 mailed Dec. 23, 2008 (4 pages).
International Search Report for PCT/US2010/021003 mailed Aug. 16, 2010 (8 pages).
International Search Report for PCT/US2010/035728 mailed Jul. 8, 2010 (3 pages).
International Search Report for PCT/US2010/035783 mailed Aug. 23, 2010 (4 pages).
International Search Report for PCT/US2010/047252 mailed Nov. 17, 2010 (4 pages).
International Search Report for PCT/US2010/052011 mailed Nov. 30, 2010 (3 pages).
International Search Report and Written Opinion in International Application No. PCT/US2014/020554, dated Jul. 16, 2014, 17 pages.
International Search Report in International Application No. PCT/US2013/041601, mailed Sep. 3, 2013, 3 pages.
International Search Report and Written Opinion in International Application No. PCT/US2013/067794, mailed Dec. 17, 2013, 14 pages.
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (-)-CP55,940", Organic Letters, 2005; 7(19); 4181-4183.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron, Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).

(56) References Cited

OTHER PUBLICATIONS

Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Dec. 2006, 86(12): 1243-1260.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, 2004; May;45(5):1369-74).
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Left. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, 2nd Ed. (1999) pp. 1949-1950, 1958-1959, 1976, and 1983-1985.

Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 a Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Lima and Barreiro, "Bioisosterism: a useful strategy for molecular modification and drug design," Curr Med Chem. 2005;12(1):23-49.
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdC12 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Manjula, et al., "Rapid Method of Converting Primary Amides to Nitriles and Nitriles to Primary Amides by ZnC12 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.
Mar., Jerry, Advanced Organic Chemistry: Reactions, Mechanisms, and Structure, 3rd ed., John Wiley & Sons:New York, pp. 845-855 (1985).

(56) References Cited

OTHER PUBLICATIONS

Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.

Maruyama et al., "Effect of environmental conditions on tear dynamics in soft contact lens wearers", Invest Ophthalmol Vis Sci, 2004;45(8):2563-8.

Mathers et al., "Assessment of the tear film with tandem scanning confocal microscopy", Cornea, 1997;16:162-8.

Mathers et al., "Tear film changes associated with normal aging", Cornea, 1996; 15:229-334.

Mathers et al., "Tear flow and evaporation in patients with and without dry eye", Ophthalmology, 1996; 103:664-669.

Mathers et al., "Video imaging of the meibomian gland", Arch Ophthalmol, 1994;112:448-9.

Mathers, "Evaporation from the ocular surface", Exp Eye Res, 2004; 78:389-394.

Maxson et al., "Oncogenic *CSF3R* Mutations in Chronic Neutrophilic Leukemia and Atypical CML," *N. Engl. J. Med.*, 2013, 368(19):1781-1790.

Mayo Clinic. Available at: < http://www.mayoclinic.com/health/pancreatic-cancer/DS00357 >. 2 pages, retrieved from the Internet Apr. 3, 2013.

Mayo Clinic. Available at: < http://www.mayoclinic.com/health/prostate-cancer-prevention/MC00027 >. 3 pages, retrieved from the Internet Apr. 3, 2013.

Mayo Clinic. Available at: <http://www.mayoclinic.com/health/crohns-disease/DS00104/DSECTION=treatments-and-drugs> 6 pages, retrieved from the Internet May 27, 2013.

Mayo Clinic. Available at: <http://www.mayoclinic.com/health/multiple-sclerosis/DS00188/DSECTION=treatments-and-drugs>. 3 pages, retrieved from the Internet May 27, 2013.

Mayo Clinic. Available at: <http://www.mayoclinic.com/health/myasthenia-gravis/DS00375> 2 pages, retrieved from the Internet May 27, 2013.

Mayo Clinic. Available at: <http://www.mayoclinic.com/health/rheumatoid-arthritis/DS00020/DSECTION=treatments-and-drugs> 3 pages, retrieved from the Internet Jun. 26, 2013.

McNamara et al., "Fluorometry in contact lens research: The next step", Optom Vis Sci, 1998; 75:316-322.

Mengher et al., "Non-invasive tear film break-up time: sensitivity and specificity", Acta Ophthalmol (Copenh), 1986; 64(4):441-4.

Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).

Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.

Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.

Methods in Molecular Biology: vol. 225, Inflammation Protocols., Winyard, P.G. and Willoughby, D.A., Humana Press, 2003.

Meydan et al., "Inhibition of acute lymphoblastic leukaemia by a Jak-2 inhibitor", Nature. Feb. 15, 1996;379(6566):645-8.

Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).

Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi, et al., "Human Tyrosine Kinase 2 Deficiency Reveals Its Requisite Roles in Multiple Cytokine Signals Involved in Innate and Acquired Immunity", Immunity 25:745-55 (2006).

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.

Mishima, et al., "Determination of tear volume And tear flow", Invest Ophthalmol, 1966; 5:264-276.

Mishima, S., "Some physiological aspects of the precorneal tear film", Arch Ophthalmol, 1965;73:233-241.

Mitsunobu, O., "The Use of Diethyl Axodicarboxylate and Triphenylphosphine in Synthesis and Transformation of Natural Products." Synthesis (1): 1-28 (1981).

Miyata, et al., "Stereospecific nucleophilic addition reactions to olefins.", J. Org. Chem. 56:6556-6564 (1991).

Miyaura et al., "Palladium-Catalyzed Cross-Coupling Reactions of Organoboron Compounds," Chem. Rev., 1995, 95, 2457-2483.

Miyoshi et al., "Interleukin-8 concentrations in conjunctival epithelium brush cytology samples correlate with neutrophil, eosinophil infiltration, and corneal damage", Cornea, 2001;20:743-7.

Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).

Mosby's Dictionary of Medicine, Nursing, & Health Professions, sicca complex, 2009, Elsevier, printed from http://www.credoreference.com/entry/ehsmosbymed/sicca_complex, 2 pages.

Mullighan, et al, "JAK mutations in high-risk childhood acute lymphoblastic leukemia", Proc Natl Acad Sci USA. 106:9414-8 (2009).

Naka T., "The paradigm of IL-6: from basic science to medicine", Arthritis Res., 2002;4 Suppl 3:S233-42.

Nakagawara, Akira, "Trk receptor tyrosine kinases: A bridge between cancer and neural development." Cancer Letters, 169:107-114, 2001.

Nally et al., "Ocular discomfort and tear film break-up time in dry eye patients: A correlation", Invest Ophthalmol Vis Sci, 2000;41:4:1436 (Poster Presentation).

Naqvi, et al., "A potential role of ruxolitinib in leukemia", Expert Opinion on Investigational Drugs, (Aug. 2011) vol. 20, No. 8, pp. 1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).

Naus, et al., "6-(Het)aryl-7-Deazapurine Ribonucleosides as Novel Potent Cytostatic Agents", J. Med. Chem., 53(1):460-470 (2010).

Neidle, Stephen, Cancer Drug Design and Discovery, (Elsevier/Academic Press, 2008) pp. 427-431.

Nelson et al., "Tear film osmolality determination: an evaluation of potential errors in measurement" Curr Eye Res, Sep;5(9):677-81, 1986.

Neubauer, H., et al., "Jak2 Deficiency Defines an Essential Developmental Checkpoint in Definitive Hematopoiesis", Cell, 93(3): 397-409 (1998).

Neuner et al., "Increased IL-6 Production by Monocytes and Keratinocytes in Patients with Psoriasis," J. Invest. Dermatol. 1991, 97, 27-33.

Nicholoff et al., "Recent Insights into the immunopathogenesis of psoriasis provide new therapeutic opportunities", J. Clin. Invest., 113; 1664-1675 (2004).

Nichols et al., "The lack of association between signs and symptoms in patients with dry eye disease", Cornea, vol. 23(8):762-770 (2004).

Nichols et al., "The repeatability of clinical measurements of dry eye", Cornea, vol. 23(3):272-85 (2004).

Nishimoto et. al., "Improvement in Castleman's disease by humanized anti-interleukin-6 receptor antibody theraphy," *Blood*, 2000, 95(1):56-61.

(56) References Cited

OTHER PUBLICATIONS

Nishio, et al., "Tyrosine kinase-dependent modulation by interferon-α of the ATP-sensitive K+ current in rabbit ventricular myocytes", FEBS Letters, (1999), 445, 87-91.
Nitta, et al., "Peptide-Titanium Complex as Catalyst for Asymmetric Addition of Hydrogen Cyanide to Aldehyde", J. Am. Chem. Soc., 1992, 114, 7969-75 (1992).
Norman, "Selective JAK1 inhibitor and selective Tyk2 inhibitor patents," *Expert Opinion*, Informa Healthcare. 2012, available at: <http://informahealthcare.com/doi/pdfplus/10.1517/13543776. 2012.723693>.
Norn, M., "Quantitative tear ferning. Clinical investigations", Acta Ophthalmol (Copenh), Jun. 1994;72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).
Office Action received for European Application No. 06 839 328.9 (Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 mailed Oct. 21, 2010.
Office Action, European Patent Office, mailed Nov. 6, 2009.
Office Action, Mexico, Patent Appl. No. MX/a/2008/007635 as received from foreign associate dated Jun. 15, 2010(1 page).
Office Action, Mexico, Patent Appl. No. MX/a/2008/007635 as received from foreign associate dated Nov. 13, 200 (4 pages).
Office Action/Examination Report received for Pakistan Application No. 211/2009 dated Jan. 18, 2010 (1 page).
Oguz, et al., "The height and radius of the tear meniscus and methods for examining these parameters", Cornea, 2000;19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Ecuador Patent Office, mailed Nov. 18, 2008 1 page letter from Foreign Associate enclosing the translation (5 pages) of the Opposition.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev., 17:1429-1450, 2003.
Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Patani, et al., "Bioisosterism: A Rational Approach in Drug Design", Chem. Rev., 1996, 96, 3147-3176.
Patrick, Graham L., "An Introduction to medical chemistry" *Oxford University Press Inc.*, New York, 1995 (31 pages) (cited in Opposition from India dated Nov. 12, 2012).
Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001) 78(1):30-36).
Pedranzini et al., "Pyridone 6, A Pan-Janus—Activated Kinase Inhibitor, Induces Growth Inhibition of Multiple Myeloma Cells," Cancer Res., 66(19):9714-9721 (2006).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Peters, K. G. et al., "Functional Significance of Tie2 Signaling in the Adult Vasculature", 2004, © The Endocrine Society (21 pages).
Pflugfelder, et al., "Evaluation of subjective assessments and objective diagnostic tests for diagnosing tear-film disorders known to cause ocular irritation", Cornea, 1998;17(1):38-56.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-108 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani, Naresh, et al. "Efficacy and safety of topical INCB018424, a selective Janus kinase 1 & 2 (JAK1&2) inhibitor in psoriasis." Journal of The American Academy of Dermatology. vol. 60. No. 3. 360 Park Avenue South, New York, NY 10010-1710 USA: Mosby-Elsevier, 2009.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).

(56) References Cited

OTHER PUBLICATIONS

Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, L., "Preformulation", Remington's Pharmaceutical Sciences, 17th ed., Mack Publishing Company, Easton, PA., 1985, Chapter 76, pp. 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, No. 288, vol. 3, pp. 1317-1326, p. 1321, compound 26.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).

Search Report in TW Application No. 100117866, dated Dec. 2014, 1 page.
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2,3-d]pyrimidine 2', 3'-Dideoxyribenucleosides Related to 2',3 '—Dideoxyadenosine and 2',3'-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (OPTION study): a double-blind, placebo-controlled, randomized trial", Lancet 371:987, 2008 (2008).
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., Blood, 2014, 123(24): 3832-3842.
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, dated Sep. 3, 2010 Pat. Appl. No. 200680052750.7 (8 pages).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., "The Relationship of Serum IL-6 Levels to Acute Graft-Versus-Host Disease and Hepatorenal Disease After Human Bone Marrow Transplantation," Transplantation, 1992, Abstract, 1 page.
Takahashi, et al., "Solvent-Free Reaction Using Pmospwonium Salts: Chlorination of Hydroxyheteroaromatics and dehydration of Primary Amides", Heterocycles 68: 1973-1979 (2006).

(56) References Cited

OTHER PUBLICATIONS

Takano et al., "Inflammatory cells in brush cytology samples correlate with the severity of corneal lesions in atopic keratoconjunctivitis", Br J Ophthalmol, 2004;88:1504-5.

Takemoto, et al. (1997). "Proliferation of adult T cell leukemia/lymphoma cells is associated with the constitutive activation of JAK/STAT proteins." Proc Natl Acad U S A, 94(25): 13897-902.

Tamura et al., "Involvement of Human Interleukin 6 in Experimental Cachexia Induced by a Human Uterine Cervical Carcinoma Xenograft," Clin. Cancer Res., Nov. 1995, 1: 1353-1358.

Tan, et al, "Racemization processes at a quaternary carbon center in the context of the asymmetric Michael reaction", Tetrahedron Lett., 42(30):5021-5023 (2001).

Tang et al., "Knowledge-based design of 7-azaindoles as selective B-Raf inhibitors", Bioorganic & Medicinal Chemistry Letters (2008), 18(16):4610-4614.

Tasian et al., "Understanding the biology of CRLF2-overexpressing acute lymphoblastic leukemia", Critical Reviews in Oncogenesis, (2011) vol. 16, No. 1-2, pp. 13-24.

Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).

Tefferi, Ayalew, "Primary myelofibrosis: 2012 update on diagnosis, risk stratification, and management", American Journal of Hematology, (Dec. 2011) vol. 86, No. 12, pp. 1017-1026.

Tefferi, et al., "Serious adverse events during ruxolitinib treatment discontinuation in patients with myelofibrosis", Mayo Clinic Proceedings, (Dec. 2011) vol. 86, No. 12, pp. 1188-1191.

Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.

Tiffany et al., Meniscometry using the Tearscope-plus (ARVO abstract). Invest Ophthalmol Vis Sci, (2001);42, s37 (1 page).

Tiffany, J., "Refractive index of meibomian and other lipids", Curr Eye Res, (1986);5:887-9.

Ting, et al., "The Synthesis of substituted bipiperidine amide compounds as CCR3 antagonists", Bioorg. Med. Chem. Lett., vol. 15, No. 5, 1 (2005) pp. 1375-1378.

Toyonaga, "Blockade of constitutively activated Janus kinase/signal transducer and activator of transcription-3 pathway inhibits growth of human pancreatic cancer", Cancer Lett. 201(1):107-16 (2003).

Trikha et al., "Targeted anti-interleukin-6 monoclonal antibody therapy for cancer: a review of the rationale and clinical evidence," Clinical Cancer Research, 2003, 9: 4653-4665.

Tsubota et al., "Brush cytology for the evaluation of dry-eye", Nippon Ganka Gakkai Zasshi, 1990a ;94:224-30; in Japanese with English abstract.

Tsubota et al., "Conjunctival brush cytology", Acta Cytol, (1990) vol. 34(2):233-5.

Tsubota et al., "Detection by brush cytology of mast cells and eosinophils in allergic and vernal conjunctivitis"; Cornea, (1991) vol. 10(6):525-31.

Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).

van Best et al., "Measurement of basal tear turnover using a standardized protocol", Graefe's Arch Clin Exp Ophthalmol, 1995; 233:1-7.

van Bijsterveld, O., "Diagnostic tests in the sicca syndrome", Arch Ophthalmol, 1969;82:10-14.

van Rhee et al., "Anti-Interleukin-6 Monoclonal man's Disease," J. Clin. Oncol., 2010, 28(23):3701-3708.

Vaillant et al., "Turbidity of pulpy fruit juice: A key factor for predicting cross-flow microfiltration performance," J Membrane Sci., 2008, 325:404-412.

Vanhoutte, Arthritis Rheum 64.10 (2012): S1051-1.

Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.

Vannucchi, A. et al, "Inhibitors of PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).

Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.

Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).

Verma, et al., "Jak family of kinases in cancer", Cancer and Metastasis Reviews, vol. 22, No. 4, 423-434, DOI: 10.1023/A:1023805715476 (2003).

Verstovsek, "Therapeutic Potential of JAK2 Inhibitors", Hematology Am Soc Hematol Educ Program, 2009:636-42.

Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).

Verstovsek, et al., Blood (ASH Annual Meeting Abstracts) 2007 110: Abstract 558.

Verstovsek, et al., Blood (ASH Annual Meeting Abstracts) 2009 114: Abstract 311.

Verstovsek, et al., Blood (ASH Annual Meeting Abstracts) 2010 116: Abstract 313.

Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.

Wagh, et al., "Polymers used in ocular dosage form and drug delivery systems", Asian J. Pharm., pp. 12-17 (Jan. 2008).

WebMD. "Diabetes Health Center." Available at: < http://diabetes.webmd.com/guide/diabetestreatment_care >. 3 pages, retrieved from the Internet May 28, 2013.

Webster's New World Medical Dictionary, Sjogren's syndrome, 2003, Wiley Publishing, printed fro http://www.credoreference.com/entry/webstermed/sjogren_s_syndrome, 2 pages.

Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).

Welch et al., "An approach to a more standardized method of evaluating tear film break-up time", Invest Ophthalmol Vis Sci, 2003; 2485/B324 (abstract only—2 pages).

White et al., "Human basic tear fluid osmolality. I. Importance of sample collection strategy", Acta Ophthalmol (Copenh), Aug;71(4):524-9, 1993.

(56) References Cited

OTHER PUBLICATIONS

Williams et al., "Carbohydrate Chemistry: Recent Advances", Chem. Rev. 81:589-636 (1981).
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wu et al., One-Pot Two-Step Microwave-Assisted Reaction in Construction 4,5-Disubstituted Pyrazolopyrimidines Organic Letters, 2003, 5(20), 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Ye et al., "The synthesis and the antitumor activity of 5,7-disubstituted pyrazolo [1,5-a] pyrimidines," Chinese J Med Chem., Feb. 28, 2007, 17(1):18-22.
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Yongjun et al., "Advances in research of tyrosine kinases inhibitor of vascular endothelial growth factor receptor," Chinese J New Drugs, Dec. 31, 2008, 17(7):544-550.
Younes, J. Clin. Oncol., 30(33):1461-1467 (2012).
Yu, et al., "Constitutive activation of the Janus kinase-STAT pathway in T lymphoma overexpressing the Lck protein tyrosine kinase", J Immunol. 159(11):5206-10 (1997).
Zheng, et al., "Discovery of INCB108201PF-4178903, a potent, selective, and orally bioavailable dual CCR2 and CCR5 antagonist", Bioorganic & Medical Chemistry Letters 21 (2011) 1442-45.
Zoppellaro, et al., "A Multifunctional High-Spin Biradical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase." Journal of Biological Chemistry, 274(26):18141-18144, 1999.

\* cited by examiner

N-(HETERO)ARYL-PYRROLIDINE DERIVATIVES OF PYRAZOL-4-YL-PYRROLO[2,3-D]PYRIMIDINES AND PYRROL-3-YL-PYRROLO[2,3-D]PYRIMIDINES AS JANUS KINASE INHIBITORS

CROSS REFERENCE TO RELATED APPLICATIONS

This application is a continuation of Ser. No. 12/784,916, filed May 21, 2010, which claims the benefit of U.S. Provisional Patent Application Ser. Nos. 61/180,622, filed May 22, 2009, and 61/225,092, filed Jul. 13, 2009, the disclosures of each of which are incorporated herein by reference in their entireties.

TECHNICAL FIELD

The present invention relates to N-(hetero)aryl-pyrrolidine derivatives of Formula I, as well as their compositions and methods of use, which are JAK inhibitors, such as selective JAK1 inhibitors, useful in the treatment of JAK-associated diseases including, for example, inflammatory and autoimmune disorders, as well as cancer.

BACKGROUND

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression. Thus far, oncogenic protein kinases represent one of the largest and most attractive groups of protein targets for cancer intervention and drug development.

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs.

Blocking signal transduction at the level of the JAK kinases holds promise for developing treatments for inflammatory diseases, autoimmune diseases, myeloproliferative diseases, and human cancers, to name a few. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including pyrrolopyridine and pyrrolopyrimidines, are reported in U.S. Application Pub. No. 2007/0135461, filed Dec. 12, 2006.

Thus, new or improved agents which inhibit kinases such as Janus kinases are continually needed for developing new and more effective pharmaceuticals to treat cancer and other diseases. The compositions and methods described herein are directed toward these needs and other ends.

SUMMARY

The present invention provides, inter alia, compounds of Formula I:

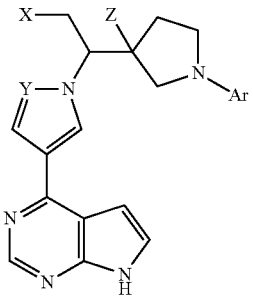

or pharmaceutically acceptable salts or N-oxides thereof; wherein:

X is cyano or halogen;

Y is CH or N;

Z is hydrogen, $C_{1-4}$ alkyl, $C_{1-4}$ fluorinated alkyl, or fluoro;

Ar is $C_{6-14}$ aryl, $C_{1-14}$ heteroaryl, $C_{7-14}$ fused cycloalkylaryl, $C_{6-14}$ fused heterocycloalkylaryl, $C_{2-14}$ fused cycloalkylheteroaryl, or $C_{2-14}$ fused heterocycloalkylheteroaryl, each of which is optionally substituted by 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, —$OR^a$, —$SR^a$, —$S(=O)R^b$, —$S(=O)_2R^b$, —$S(=O)NR^eR^f$, —$C(=O)R^b$, —$C(=O)OR^b$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^bS(=O)_2NR^eR^f$; wherein said $C_{1-6}$ alkyl, $C_{1-6}$haloalkyl, $C_{2-6}$ alkenyl, and $C_{2-6}$ alkynyl are each optionally substituted by 1, 2, 3, or 4 independently selected $R^{1a}$ groups; and wherein said $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, and $C_{1-13}$ heteroaryl-$C_{1-4}$-alkyl are each optionally substituted by 1, 2, 3, or 4 independently selected $R^2$ groups;

each $R^{1a}$ is independently selected from halogen, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each $R^2$ is independently selected from halogen, cyano, nitro, hydroxyl, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

or any $R^c$ and $R^d$, together with the moiety to which they are attached, can form a 3-, 4-, 5-, 6-, or 7-membered heterocycloalkyl ring, wherein said heterocycloalkyl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

each $R^x$ is independently selected from hydroxyl, $C_{1-4}$ alkoxy, $C_{1-4}$ haloalkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

provided that the valency of each atom in the optionally substituted moieties is not exceeded.

The present invention further provides pharmaceutical compositions, comprising a compound of Formula I as described herein, or a pharmaceutically acceptable salt or N-oxide thereof, and a pharmaceutically acceptable carrier.

The present invention also provides methods of modulating an activity of JAK1 comprising contacting JAK1 with a compound of Formula I as described herein, or a pharmaceutically acceptable salt or N-oxide thereof.

The present invention further provides methods of treating an autoimmune disease, a cancer, a myeloproliferative disorder, an inflammatory disease, or organ transplant rejection in a patient in need thereof, comprising administering to said patient a therapeutically effective amount of a compound of Formula I as described herein, or a pharmaceutically acceptable salt or N-oxide thereof.

The present invention also provides compounds of Formula I, or pharmaceutically acceptable salts or N-oxides thereof, as described herein for use in methods of treating autoimmune diseases, cancer, myeloproliferative disorders, inflammatory diseases, or organ transplant rejection.

The present invention further provides compounds of Formula I as described herein, or pharmaceutically acceptable salts or N-oxides thereof, for use in methods of modulating a JAK1.

The details of one or more embodiments of the invention are set forth in the accompanying drawings and the description below. Other features, objects, and advantages of the invention will be apparent from the description and drawings, and from the claims.

DETAILED DESCRIPTION

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

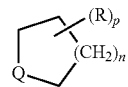

then it is understood that substituent R can occur p number of times on the ring, and R can be a different moiety at each occurrence. It is understood that each R group may replace any hydrogen atom attached to a ring atom, including one or both of the (CH$_2$) hydrogen atoms. Further, in the above example, should the variable Q be defined to include hydrogens, such as when Q is said to be CH$_2$, NH, etc., any floating substituent such as R in the above example, can replace a hydrogen of the Q variable as well as a hydrogen in any other non-variable component of the ring.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted. As used herein, the term "substituted" means that a hydrogen atom is removed and replaced by a substitutent. As used herein, the phrase "substituted with oxo" means that two hydrogen atoms are removed from a carbon atom and replaced by an oxygen bound by a double bond to the carbon atom. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 12, 1 to 8, 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, the term "$C_{n-m}$ alkylene", employed alone or in combination with other terms, refers to a divalent alkyl linking group having n to m carbon atoms. In some embodiments, the alkylene moiety contains 2 to 6, or 2 to 4 carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl", employed alone or in combination with other terms, refers to an alkyl group having one or more double carbon-carbon bonds and n to m carbon atoms. In some embodiments, the alkenyl moiety contains 2 to 6, or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkenylene", employed alone or in combination with other terms, refers to a divalent alkenyl group. In some embodiments, the alkenylene moiety contains 2 to 6, or 2 to 4 carbon atoms.

As used herein, "$C_{n-m}$ alkynyl", employed alone or in combination with other terms, refers to an alkyl group having one or more triple carbon-carbon bonds and n to m carbon atoms. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "$C_{n-m}$ alkynylene", employed alone or in combination with other terms, refers to a divalent alkynyl group. In some embodiments, the alkynylene moiety contains 2 to 6, or 2 to 4 carbon atoms.

As used herein, the term "$C_{n-m}$ alkoxy", employed alone or in combination with other terms, refers to a group of formula —O-alkyl, wherein the alkyl group has n to m carbon atoms. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "carboxy", employed alone or in combination with other terms, refers to a group of formula —C(=O)OH.

As used herein, the term "$C_{n-m}$-alkoxycarbonyl-($C_{n-m}$ alkyl)amino", employed alone or in combination with other terms, refers to a group of formula —N(alkyl)-C(=O)O(alkyl), wherein each alkyl independently has n to m carbon atoms.

As used herein, the term "$C_{n-m}$-alkoxycarbonylamino", employed alone or in combination with other terms, refers to a group of formula —NH—C(=O)O(alkyl), wherein the alkyl has n to m carbon atoms.

As used herein, the term "$C_{n-m}$ alkoxycarbonyl", employed alone or in combination with other terms, refers to a group of formula —C(=O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl", employed alone or in combination with other terms, refers to a group of formula —C(=O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino", employed alone or in combination with other terms, refers to a group of formula —NHC(=O)-alkyl, wherein the alkyl group has n to m carbon atoms. In some embodiments, the alkyl group has 1 to 6 or 1 to 4 carbon atoms.

As used herein, the term "di-$C_{n-m}$-alkylcarbonylamino", employed alone or in combination with other terms, refers to a group of formula —N(alkyl)C(=O)-alkyl, wherein each alkyl group independently has n to m carbon atoms. In some embodiments, each alkyl group independently has 1 to 6 or 1 to 4 carbon atoms.

As used herein, the term "amino" refers to a group of formula —NH$_2$.

As used herein, the term "$C_{n-m}$ alkylamino", employed alone or in combination with other terms, refers to a group of formula —NH(alkyl), wherein the alkyl group has n to m carbon atoms.

As used herein, the term "di-$C_{n-m}$-alkylamino", employed alone or in combination with other terms, refers to a group of formula —N(alkyl)$_2$, wherein each alkyl groups each has independently n to m carbon atoms. In some embodiments, each alkyl group independently has 1 to 6 or 1 to 4 carbon atoms.

As used herein, the term "carbamyl", employed alone or in combination with other terms, refers to a group of formula —C(=O)NH$_2$.

As used herein, the term "$C_{n-m}$ alkylcarbamyl", employed alone or in combination with other terms, refers to a group of formula —C(=O)—NH(alkyl), wherein the alkyl group has n to m carbon atoms. In some embodiments, the alkyl group has 1 to 6 or 1 to 4 carbon atoms.

As used herein, the term "di-$C_{n-m}$-alkylcarbamyl", employed alone or in combination with other terms, refers to a group of formula C(=O)—N(alkyl)$_2$, wherein each alkyl group independently has n to m carbon atoms. In some embodiments, each alkyl group independently has 1 to 6 or 1 to 4 carbon atoms.

As used herein, the term "$C_{n-m}$-alkylthio", employed alone or in combination with other terms, refers to a group of formula —S-alkyl, wherein the alkyl has n to m carbon atoms. In some embodiments, the alkyl group has 1 to 6 or 1 to 4 carbon atoms.

As used herein, the term "$C_{n-m}$-alkylsulfinyl", employed alone or in combination with other terms, refers to a group of formula —S(=O)-alkyl, wherein the alkyl has n to m carbon atoms. In some embodiments, the alkyl group has 1 to 6 or 1 to 4 carbon atoms.

As used herein, the term "$C_{n-m}$-alkylsulfonyl", employed alone or in combination with other terms, refers to a group of formula —S(=O)$_2$-alkyl, wherein the alkyl has n to m carbon atoms. In some embodiments, the alkyl group has 1 to 6 or 1 to 4 carbon atoms.

As used herein, the term "carbonyl", employed alone or in combination with other terms, refers to a —C(=O)— group, which is a divalent one-carbon moiety further bonded to an oxygen atom with a double bond.

As used herein, the term "cyano", employed alone or in combination with other terms, refers to a group of formula —CN, wherein the carbon and nitrogen atoms are bound together by a triple bond.

As used herein, the terms "halo" and "halogen", employed alone or in combination with other terms, refer to fluoro, chloro, bromo, and iodo.

As used herein, "$C_{n-m}$ haloalkoxy", employed alone or in combination with other terms, refers to a group of formula —O-haloalkyl, wherein the haloalkyl group has n to m carbon atoms. In some embodiments, the alkyl group has 1 to 6 or 1 to 4 carbon atoms. An example haloalkoxy group is —OCF$_3$.

As used herein, the term "$C_{n-m}$ haloalkyl", employed alone or in combination with other terms, refers to an alkyl group having from n to m carbon atoms and one halogen atom to 2x+1 halogen atoms which may be the same or different, where "x" is the number of carbon atoms in the alkyl group. In some embodiments, the halogen atoms are fluoro atoms. In some embodiments, the alkyl group has 1 to 6 or 1 to 4 carbon atoms. An example of a haloalkyl group is —CF$_3$.

As used herein, the term "$C_{n-m}$ fluorinated alkyl", employed alone or in combination with other terms, refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl.

As used herein, the term "$C_{n-m}$ cycloalkyl", employed alone or in combination with other terms, refers to a non-aromatic cyclic hydrocarbon moiety, which may optionally contain one or more alkenylene groups as part of the ring structure, and which has n to m ring member carbon atoms. Cycloalkyl groups can include mono- or polycyclic (e.g., having 2, 3, or 4 fused, bridged, or spiro rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as adamantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is adamantan-1-yl.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene groups as part of the ring structure, which has at least one heteroatom ring member independently selected from nitrogen, sulfur and oxygen, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 hetereoatoms independently selected from nitrogen, sulfur and oxygen. Also included in the definition of heterocycloalkyl are moieties that have one or more aromatic rings fused (i.e., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azadamantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized. In some embodiments, the heterocycloalkyl portion is a $C_{2-7}$ monocyclic heterocycloalkyl group.

As used herein, the term "$C_{n-m}$ heterocycloalkyl-$C_{o-p}$ alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. In some embodiments, aryl groups have from 6 to 14 carbon atoms, about 6 to 10 carbon atoms, or about 6 carbons atoms. In some embodiments, the aryl group is a monocyclic or bicyclic group.

As used herein, the term "$C_{n-m}$ aryl-$C_{o-p}$-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. In some embodiments, the heteroaryl group is a monocyclic or bicyclic group having 1, 2, 3, or 4 hetereoatoms independently selected from nitrogen, sulfur and oxygen. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. The carbon atoms or heteroatoms in the ring(s) of the heteroaryl group can be oxidized to form a carbonyl, or sulfonyl group (or other oxidized linkage) or a nitrogen atom can be quaternized, provided the aromatic nature of the ring is preserved. In some embodiments, the heteroaryl group has 5 to 10 carbon atoms.

As used herein, the term "$C_{n-m}$ heteroaryl-$C_{o-p}$-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 hetereoatoms independently selected from nitrogen, sulfur and oxygen. In some embodiments, the heteroaryl portion has 5 to 10 carbon atoms.

As used herein, the term "$C_{n-m}$ fused heterocycloalkylheteroaryl" refers to a moiety having a heteroaryl group fused to a heterocycloalkyl group, with n to m ring member carbon atoms in the moiety, wherein the moiety is attached to the nitrogen atom of the pyrrolidine ring of Formula I through the heteroaryl group. In some embodiments, the $C_{n-m}$ fused heterocycloalkylheteroaryl has 2-14, 3-14, 4-14, 5-14, 5-12, 5-10, or 6-9 carbon atoms. In some embodiments, the $C_{n-m}$ fused heterocycloalkylheteroaryl is 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, 2,3-dihydrofuro[2,3-b]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, or the like.

As used herein, the term "$C_{n-m}$ fused cycloalkylheteroaryl" refers to a moiety having a heteroaryl group fused to a cycloalkyl group, with n to m ring member carbon atoms in the moiety, wherein the moiety is attached to the nitrogen atom of the pyrrolidine ring of Formula I through the heteroaryl group. In some embodiments, the $C_{n-m}$ fused cycloalkylheteroaryl has 2-14, 3-14, 4-14, 5-14, 5-12, or 5-10 carbon atoms. In some embodiments, the $C_{n-m}$ fused cycloalkylheteroaryl is 6,7-dihydro-5H-cyclopenta[b]pyridin-2-yl or the like.

As used herein, the term "$C_{n-m}$ fused cycloalkylaryl" refers to a moiety having an aryl group fused to a cycloalkyl group, with n to m ring member carbon atoms in the moiety, wherein the moiety is attached to the nitrogen atom of the pyrrolidine ring of Formula I through the aryl group. In some embodiments, the $C_{n-m}$ fused cycloalkylaryl has 6-16, 6-15, 6-14, 6-13, 6-12, or 6-10 carbon atoms.

As used herein, the term "$C_{n-m}$ fused heterocycloalkylaryl" refers to a moiety having an aryl group fused to a heterocycloalkyl group, with n to m ring member carbon atoms in the moiety, wherein the moiety is attached to the nitrogen atom of the pyrrolidine ring of Formula I through the aryl group. In some embodiments, the $C_{n-m}$ fused heterocycloalkylaryl has 6-16, 6-15, 6-14, 6-13, 6-12, or 6-10 carbon atoms.

As used herein, the appearance of the term "bicyclic" before the name of a moiety indicates that the moiety has two fused rings.

As used herein, the appearance of the term "monocyclic" before the name of a moiety indicates that the moiety has a single ring.

Unless otherwise indicated herein, the point of attachment of a substituent is generally in the last portion of the name (e.g., arylalkyl is attached through the alkylene portion of the group).

As used herein, wherein Ar is indicated as "a thiazole ring", "a pyridine ring", "a pyridimine ring", etc., the ring can be attached at any position of the ring, provided that the valency of the atom at the point of attachment is not exceeded. By contrast, in some embodiments, the exact point of attachment is clearly indicated in the name (e.g., "thiazol-2-yl", "pyridin-2-yl", "pyridin-3-yl", "pyridin-4-yl", "pyridimin-2-yl" and "pyrimidin-4-yl"). For example, the point of attachment for "thiazol-2-yl" is the 2-position of the ring.

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The present invention provides, inter alia, a compound of Formula I:

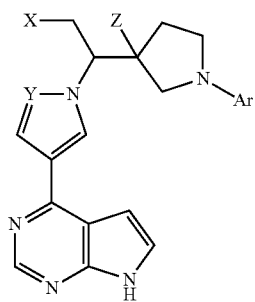

I or a pharmaceutically acceptable salt or N-oxide thereof; wherein:

X is cyano or halogen;

Y is CH or N;

Z is hydrogen, $C_{1-4}$ alkyl, $C_{1-4}$ fluorinated alkyl, or fluoro;

Ar is $C_{6-14}$ aryl, $C_{1-14}$ heteroaryl, $C_{7-14}$ fused cycloalkylaryl, $C_{6-14}$ fused heterocycloalkylaryl, $C_{2-14}$ fused cycloalkylheteroaryl, or $C_{2-14}$ fused heterocycloalkylheteroaryl, each of which is optionally substituted by 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, —$OR^a$, —$SR^a$, —$S(=O)R^b$, —$S(=O)_2R^b$, —$S(=O)NR^eR^f$, —$C(=O)R^b$, —$C(=O)OR^b$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^bS(=O)_2NR^eR^f$; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; and wherein said $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, and $C_{1-13}$ heteroaryl-$C_{1-4}$-alkyl are each optionally substituted by 1, 2, 3, or 4 independently selected $R^2$ groups;

each $R^{1a}$ is independently selected from halogen, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each $R^{2a}$ is independently selected from halogen, cyano, nitro, hydroxyl, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonyl-lamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

or any $R^c$ and $R^d$, together with the moiety to which they are attached, can form a 3-, 4-, 5-, 6-, or 7-membered heterocycloalkyl ring, wherein said heterocycloalkyl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;

each $R^x$ is independently selected from hydroxyl, $C_{1-4}$ alkoxy, $C_{1-4}$ haloalkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

It is understood that the valency of each atom in the optionally substituted moieties is not exceeded.

In some embodiments, Y is N. In some embodiments, Y is CH.

In some embodiments, X is cyano, fluoro, or chloro. In some embodiments, X is cyano or fluoro. In some embodiments, X is cyano. In some embodiments, X is chloro or fluoro. In some embodiments, X is fluoro.

In some embodiments, Z is hydrogen or fluoro. In some embodiments, Z is hydrogen. In some embodiments, Z is fluoro.

In some embodiments, Ar is selected from phenyl, $C_{1-6}$ monocyclic heteroaryl, $C_{1-9}$ bicyclic heteroeoaryl, bicyclic $C_{7-14}$ fused cycloalkylaryl, bicyclic $C_{6-14}$ fused heterocycloalkylaryl, bicyclic $C_{2-14}$ fused cycloalkylheteroaryl, and bicyclic $C_{2-14}$ fused heterocycloalkylheteroaryl; each of which is optionally substituted with 1, 2, 3, 4, 5, or 6 independently selected $R^1$ groups. In some embodiments, Ar is selected from phenyl, $C_{1-6}$ monocyclic heteroaryl, $C_{1-9}$ bicyclic heteroeoaryl, and bicyclic $C_{2-14}$ fused heterocycloalkylheteroaryl; each of which is optionally substituted with 1, 2, 3, 4, 5, or 6 independently selected $R^1$ groups. In some embodiments, Ar is phenyl, which is optionally substituted with 1, 2, 3, 4, 5, or 6 independently selected $R^1$ groups. In some embodiments, Ar is $C_{1-6}$ monocyclic heteroaryl, which is optionally substituted with 1, 2, 3, 4, 5, or 6 independently selected $R^1$ groups. In some embodiments, Ar is $C_{1-9}$ bicyclic heteroeoaryl, which is optionally substituted with 1, 2, 3, 4, 5, or 6 independently selected $R^1$ groups. In some embodiments, Ar is bicyclic $C_{2-14}$ fused heterocycloalkylheteroaryl, which is optionally substituted with 1, 2, 3, 4, 5, or 6 independently selected $R^1$ groups. In some embodiments, Ar is bicyclic $C_{2-14}$ fused cycloalkylheteroaryl, which is optionally substituted with 1, 2, 3, 4, 5, or 6 independently selected $R^1$ groups. In some embodiments, Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, and a quinoxaline ring; each of which is optionally substituted with 1, 2, 3, 4, 5, or 6 independently selected $R^1$ groups. In some embodiments, Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, and quinoxalin-2-yl; each of which is optionally substituted with 1, 2, 3, 4, 5, or 6 independently selected $R^1$ groups. In some embodiments, Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, a pyrrolo[2,3-b]pyridine ring, an oxazolo[4,5-b]pyridine ring, a 3-oxo-3,4-dihydropyrazine ring, and a quinoxaline ring; each of which is optionally substituted with 1, 2, 3, 4, 5, or 6 independently selected $R^1$ groups. In some embodiments, Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, and quinoxalin-2-yl; each of which is optionally substituted with 1, 2, 3, 4, 5, or 6 independently selected $R^1$ groups. In some embodiments, Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, a pyrrolo[2,3-b]pyridine ring, an oxazolo[4,5-b]pyridine ring, a 3-oxo-3,4-dihydropyrazine ring, a quinoxaline ring, a oxazolo[5,4-d]pyrimidine ring, a thieno[3,2-b]pyridine ring, a thieno[2,3-c]pyridine ring, a thiophene ring, a thiazolo[5,4-d]pyrimidine ring, a thieno[2,3-b]pyridine ring, a 2,3-dihydrofuro[2,3-b]pyridine ring, a 6,7-dihydro-5H-cyclopenta[b]pyridine ring, a furo[3,2-c]pyridine ring, a 2,3-dihydrothieno[3,2-e]pyridine ring, a S-oxo-2,3-dihydrothieno[3,2-c]pyridine ring, a S,S-dioxo-2,3-dihydrothieno[3,2-c]pyridine ring, a thieno[3,2-c]pyridine ring, and a 1H-pyrrolo[3,2-c]pyridine ring; each of which is optionally substituted with 1, 2, 3, 4, 5, or 6 independently selected $R^1$ groups. In some embodiments, Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-e]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-e]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected $R^1$ groups.

In some embodiments, each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, $C_{1-6}$ heteroaryl-$C_{1-4}$-alkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, —$NR^cC(=O)R^d$, and —$NR^cC(=O)OR^d$; wherein the $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; wherein the $C_{3-7}$ cycloalkyl, $C_{3-7}$ cycloalkyl-$C_{1-4}$-alkyl, $C_{2-6}$ heterocycloalkyl, $C_{2-6}$heterocycloalkyl-$C_{1-4}$-alkyl, phenyl, phenyl-$C_{1-4}$-alkyl, $C_{1-6}$heteroaryl, and $C_{1-6}$ heteroaryl-$C_{1-4}$-alkyl are each optionally substituted by 1, 2, 3, or 4 independently selected $R^{2a}$ groups. In some embodiments, each $R^1$ is independently selected from halogen, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, and —$NR^cC(=O)R^d$. In some embodiments, each $R^1$ is independently selected from $C_{1-6}$ alkyl, $C_{1-6}$haloalkyl, —$OR^a$, —$SR^a$, —$S(=O)R^b$, —$S(=O)_2R^b$, and —$NR^eR^f$. In some embodiments, each $R^1$ is independently selected from fluoro, bromo, chloro, cyano, hydroxyl, methyl, trifluoromethyl, methoxy, isopropylamino, dimethylamino, methylthio, methylsulfinyl, and methylsulfonyl.

In some embodiments, each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl. In some embodiments, each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{2-7}$ heterocycloalkyl, phenyl, and $C_{1-7}$ heteroaryl. In some embodiments, each $R^a$, $R^b$, $R^c$, $R^d$, $R^e$, and $R^f$ is independently selected from H, $C_{1-6}$ alkyl, and $C_{1-6}$ haloalkyl. In some embodiments, each $R^a$, $R^b$, $R^c$, $R^d$, $R^e$, and $R^f$ is independently selected from H and $C_{1-6}$ alkyl. In some embodiments, each $R^a$, $R^b$, $R^c$, $R^d$, $R^e$, and $R^f$ is independently selected from H and methyl.

In some embodiments:
each $R^{1a}$ is independently selected from fluoro, chloro, bromo, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino; and each $R^{2a}$ is independently selected from fluoro, chloro, bromo, cyano, nitro, hydroxyl, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino.

In some embodiments:

X is cyano or fluoro

Y is CH or N;

Z is hydrogen or fluoro;

Ar is selected from phenyl, $C_{1-6}$ monocyclic heteroaryl, $C_{1-9}$ bicyclic hetereoaryl, bicyclic $C_{7-14}$ fused cycloalkylaryl, bicyclic $C_{6-14}$ fused heterocycloalkylaryl, bicyclic $C_{2-14}$ fused cycloalkylheteroaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, $C_{1-6}$ heteroaryl-$C_{1-4}$-alkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, —$NR^cC(=O)R^d$, and —$NR^cC(=O)OR^d$; wherein the $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; wherein the $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^2$ groups;

each $R^{1a}$ is independently selected from fluoro, chloro, bromo, cyano, nitro, hydroxyl, $C_{1-4}$alkoxy, $C_{1-4}$haloalkoxy, $C_{1-4}$alkylthio, $C_{1-4}$alkylsulfinyl, $C_{1-4}$alkylsulfonyl, amino, $C_{1-4}$ alkylamino, and di-$C_{1-4}$-alkylamino;

each $R^{2a}$ is independently selected from fluoro, chloro, bromo, cyano, nitro, hydroxyl, $C_{1-4}$ alkyl, $C_{1-4}$haloalkyl, $C_{2-4}$ alkynyl, $C_{1-4}$alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$alkylamino, and di-$C_{1-4}$-alkylamino;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein the $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein the $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

each $R^x$ is independently selected from hydroxyl, $C_{1-4}$alkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$haloalkyl, $C_{1-4}$alkoxy, $C_{1-4}$haloalkoxy, amino, $C_{1-4}$alkylamino, and di-$C_{1-4}$-alkylamino.

In some embodiments:

X is cyano or fluoro;

Y is CH or N;

Z is hydrogen or fluoro;

Ar is selected from phenyl, $C_{1-6}$ monocyclic heteroaryl, $C_{1-9}$ bicyclic hetereoaryl, bicyclic $C_{7-14}$ fused cycloalkylaryl, bicyclic $C_{6-14}$ fused heterocycloalkylaryl, bicyclic $C_{2-14}$ fused cycloalkylheteroaryl, bicyclic $C_{2-14}$ fused cycloalkylheteroaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, $C_{1-6}$ heteroaryl-$C_{1-4}$-alkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, —$NR^cC(=O)R^d$, and —$NR^cC(=O)OR^d$; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; wherein said $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^2$ groups;

each $R^{1a}$ is independently selected from fluoro, chloro, bromo, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino;

each $R^{2a}$ is independently selected from fluoro, chloro, bromo, cyano, nitro, hydroxyl, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

each $R^x$ is independently selected from hydroxyl, $C_{1-4}$ alkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$haloalkyl, $C_{1-4}$ alkoxy, $C_{1-4}$ haloalkoxy, amino, $C_{1-4}$ alkylamino, and di-$C_{1-4}$-alkylamino.

In some embodiments:

X is cyano or fluoro;

Y is CH or N;

Z is hydrogen or fluoro;

Ar is selected from phenyl, $C_{1-6}$ monocyclic heteroaryl, $C_{1-9}$ bicyclic hetereoaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, $C_{1-6}$ heteroaryl-$C_{1-4}$-alkyl, —$OR^a$, —$SR^a$, —S(=O)$R^b$, —S(=O)$_2R^b$, —S(=O)$NR^eR^f$, —$NR^eR^f$, —C(=O)$R^b$, —C(=O)$OR^b$, —C(=O)$NR^eR^f$, —$NR^cC$(=O)$R^d$, and —$NR^cC$(=O)$OR^d$; wherein the $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; wherein the $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^2$ groups;

each $R^{1a}$ is independently selected from fluoro, chloro, bromo, cyano, nitro, hydroxyl, $C_{1-4}$alkoxy, $C_{1-4}$haloalkoxy, $C_{1-4}$alkylthio, $C_{1-4}$alkylsulfinyl, $C_{1-4}$alkylsulfonyl, amino, $C_{1-4}$ alkylamino, and di-$C_{1-4}$-alkylamino;

each $R^{2a}$ is independently selected from fluoro, chloro, bromo, cyano, nitro, hydroxyl, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$alkylthio, $C_{1-4}$ alkylsulfinyl, $C_{1-4}$ alkylsulfonyl, amino, $C_{1-4}$ alkylamino, and di-$C_{1-4}$-alkylamino;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein the $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein the $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

each $R^x$ is independently selected from hydroxyl, $C_{1-4}$alkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$ haloalkyl, $C_{1-4}$alkoxy, $C_{1-4}$haloalkoxy, amino, $C_{1-4}$alkylamino, and di-$C_{1-4}$-alkylamino.

In some embodiments:
X is cyano or fluoro;
Y is CH or N;
Z is hydrogen or fluoro;
Ar is selected from phenyl, $C_{1-6}$ monocyclic heteroaryl, $C_{1-9}$ bicyclic hetereoaryl, bicyclic $C_{2-14}$ fused cycloalkylheteroaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —S(=O)$R^b$, —S(=O)$_2R^b$, —S(=O)$NR^eR^f$, —$NR^eR^f$, —C(=O)$R^b$, —C(=O)$OR^b$, —C(=O)$NR^eR^f$, and —$NR^cC$(=O)$R^d$;

each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{3-7}$ cycloalkyl-$C_{1-4}$-alkyl, phenyl, phenyl-$C_{1-4}$-alkyl, $C_{1-7}$ heteroaryl, and $C_{1-7}$heteroaryl-$C_{1-4}$-alkyl.

In some embodiments:
X is cyano or fluoro;
Y is CH or N;
Z is hydrogen or fluoro;
Ar is selected from phenyl, $C_{1-6}$ monocyclic heteroaryl, $C_{1-9}$ bicyclic hetereoaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —S(=O)$R^b$, —S(=O)$_2R^b$, —S(=O)$NR^eR^f$, —$NR^eR^f$, —C(=O)$R^b$, —C(=O)$OR^b$, —C(=O)$NR^eR^f$, and —$NR^cC$(=O)$R^d$;

each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$heteroaryl-$C_{1-4}$-alkyl.

In some embodiments:
X is cyano or fluoro;
Y is CH or N;
Z is hydrogen or fluoro;
Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, and a quinoxaline ring; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —S(=O)$R^b$, —S(=O)$_2R^b$, —S(=O)$NR^eR^f$, —$NR^eR^f$, —C(=O)$R^b$, —C(=O)$OR^b$, —C(=O)$NR^eR^f$, and —$NR^cC$(=O)$R^d$; and each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{2-7}$ heterocycloalkyl, phenyl, and $C_{1-7}$ heteroaryl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, and quinoxalin-2-yl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —S(=O)$R^b$, —S(=O)$_2R^b$, and —$NR^eR^f$; and each $R^a$, $R^b$, $R^e$, and $R^f$ is independently selected from H, $C_{1-6}$ alkyl, and $C_{1-6}$ haloalkyl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, and quinoxalin-2-yl; each of which is optionally substituted with 1, 2, 3, 4, 5, or 6 independently selected $R^1$ groups;

each $R^1$ is independently selected from halogen, $C_{1-6}$ alkyl, $C_{1-6}$ haloalkyl, —$OR^a$, —$SR^a$, —$S(=O)R^b$, —$S(=O)_2R^b$, and —$NR^eR^f$; and each $R^a$, $R^b$, $R^e$, and $R^f$ is independently selected from H and $C_{1-6}$ alkyl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, and quinoxalin-2-yl; each of which is optionally substituted with 1, 2, 3, 4, 5, or 6 independently selected $R^1$ groups;

each $R^1$ is independently selected from halogen, $C_{1-6}$ alkyl, $C_{1-6}$ haloalkyl, —$OR^a$, —$SR^a$, —$S(=O)R^b$, —$S(=O)_2R^b$, and —$NR^eR^f$; and each $R^a$, $R^b$, $R^e$, and $R^f$ is independently selected from H and methyl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, and quinoxalin-2-yl; each of which is optionally substituted with 1, 2, 3, 4, 5, or 6 independently selected $R^1$ groups; and each $R^1$ is independently selected from fluoro, bromo, chloro, cyano, hydroxyl, methyl, trifluoromethyl, methoxy, isopropylamino, dimethylamino, methylthio, methylsulfinyl, and methylsulfonyl.

In some embodiments:

X is cyano or fluoro;

Y is CH or N;

Z is hydrogen or fluoro;

Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, a pyrrolo[2,3-b]pyridine ring, an oxazolo[4,5-b]pyridine ring, a 3-oxo-3,4-dihydropyrazine ring, and a quinoxaline ring;

each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, and —$NR^cC(=O)R^d$; and each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{2-7}$ heterocycloalkyl, phenyl, and $C_{1-7}$ heteroaryl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, and quinoxalin-2-yl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —$S(=O)R^b$, —$S(=O)_2R^b$, and —$NR^eR^f$; and each $R^a$, $R^b$, $R^c$, and $R^f$ is independently selected from H, $C_{1-6}$ alkyl, and $C_{1-6}$ haloalkyl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, pyrrolo[2,3-b]pyridin-6-yl, oxazolo[4,5-b]pyridin-2-yl, 3-oxo-3,4-dihydropyrazin-2-yl, quinolin-2-yl, and quinoxalin-2-yl; each of which is optionally substituted with 1, 2, 3, 4, 5, or 6 independently selected $R^1$ groups;

each $R^1$ is independently selected from halogen, $C_{1-6}$ alkyl, $C_{1-6}$ haloalkyl, —$OR^a$, —$SR^a$, —$S(=O)R^b$, —$S(=O)_2R^b$, and —$NR^eR^f$; and each $R^a$, $R^b$, $R^c$, and $R^f$ is independently selected from H and $C_{1-6}$ alkyl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, and quinoxalin-2-yl; each of which is optionally substituted with 1, 2, 3, 4, 5, or 6 independently selected R¹ groups;
each R¹ is independently selected from halogen, $C_{1-6}$ alkyl, $C_{1-6}$ haloalkyl, —OR$^a$, —SR$^a$, —S(=O)R$^b$, —S(=O)$_2$R$^b$, and —NR$^e$R$^f$; and
each R$^a$, R$^b$, R$^e$, and R$^f$ is independently selected from H and methyl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, and quinoxalin-2-yl; each of which is optionally substituted with 1, 2, 3, 4, 5, or 6 independently selected R¹ groups;
each R¹ is independently selected from fluoro, bromo, chloro, cyano, hydroxyl, methyl, trifluoromethyl, methoxy, isopropylamino, dimethylamino, methylthio, methylsulfinyl, and methylsulfonyl.

In some embodiments:
X is cyano or fluoro;
Y is CH or N;
Z is hydrogen or fluoro;
Ar is selected from phenyl, a thiazole ring, a pyridine ring, a pyridimine ring, a pyrazine ring, a benzo[d]oxazole ring, an oxazolo[4,5-c]pyridine ring, an oxazolo[5,4-b]pyridine ring, an oxazolo[5,4-d]pyrimidine ring, a 7H-pyrrolo[2,3-d]pyrimidine ring, a 2,3-dihydrothieno[2,3-b]pyridine ring, a S-oxo-2,3-dihydrothieno[2,3-b]pyridine ring, a S,S-dioxo-2,3-dihydrothieno[2,3-b]pyridine ring, a quinazoline ring, a quinoline ring, a pyrrolo[2,3-b]pyridine ring, an oxazolo[4,5-b]pyridine ring, a 3-oxo-3,4-dihydropyrazine ring, a quinoxaline ring, a oxazolo[5,4-d]pyrimidine ring, a thieno[3,2-b]pyridine ring, a thieno[2,3-c]pyridine ring, a thiophene ring, a thiazolo[5,4-d]pyrimidine ring, a thieno[2,3-b]pyridine ring, a 2,3-dihydrofuro[2,3-b]pyridine ring, a 6,7-dihydro-5H-cyclopenta[b]pyridine ring, a furo[3,2-c]pyridine ring, a 2,3-dihydrothieno[3,2-c]pyridine ring, a S-oxo-2,3-dihydrothieno[3,2-c]pyridine ring, a S,S-dioxo-2,3-dihydrothieno[3,2-c]pyridine ring, a thieno[3,2-c]pyridine ring, and a 1H-pyrrolo[3,2-c]pyridine ring; each of which is optionally substituted with 1, 2, 3, 4, 5, or 6 independently selected R¹ groups;
each R¹ is independently selected from halogen, cyano, nitro, $C_{1-6}$ alkyl, $C_{1-6}$ haloalkyl, —OR$^a$, —SR$^a$, —S(=O)R$^b$, —S(=O)$_2$R$^b$, —S(=O)NR$^e$R$^f$, —NR$^e$R$^f$, —C(=O)R$^b$, —C(=O)OR$^b$, —C(=O)NR$^e$R$^f$, and —NR$^c$C(=O)R$^d$; and
each R$^a$, R$^b$, R$^c$, R$^d$, R$^e$, and R$^f$ is independently selected from H, $C_{1-6}$ alkyl, $C_{1-6}$ haloalkyl, $C_{3-7}$ cycloalkyl, $C_{2-7}$ heterocycloalkyl, phenyl, and $C_{1-7}$ heteroaryl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, pyrrolo[2,3-b]pyridin-6-yl, oxazolo[4,5-b]pyridin-2-yl, 3-oxo-3,4-dihydropyrazin-2-yl, quinolin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected R¹ groups;
each R¹ is independently selected from halogen, cyano, nitro, $C_{1-6}$ alkyl, $C_{1-6}$ haloalkyl, —OR$^a$, —SR$^a$, —S(=O)R$^b$, —S(=O)$_2$R$^b$, and —NR$^e$R$^f$; and
each R$^a$, R$^b$, R$^e$, and R$^f$ is independently selected from H, $C_{1-6}$ alkyl, and $C_{1-6}$ haloalkyl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, pyrrolo[2,3-b]pyridin-6-yl, oxazolo[4,5-b]pyridin-2-yl, 3-oxo-3,4-dihydropyrazin-2-yl, quinolin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected R¹ groups;
each R¹ is independently selected from halogen, $C_{1-6}$ alkyl, $C_{1-6}$ haloalkyl, —OR$^a$, —SR$^a$, —S(=O)R$^b$, —S(=O)$_2$R$^b$, and —NR$^e$R$^f$; and
each R$^a$, R$^b$, R$^e$, and R$^f$ is independently selected from H and $C_{1-6}$ alkyl.

In some embodiments:
X is cyano or fluoro;
Y is CH or N;
Z is hydrogen or fluoro;
Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, pyrrolo[2,3-b]pyridin-6-yl, oxazolo[4,5-b]pyridin-2-yl, 3-oxo-3,4-dihydropyrazin-2-yl, quinolin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected $R^1$ groups;

each $R^1$ is independently selected from halogen, $C_{1-6}$ alkyl, $C_{1-6}$ haloalkyl, —$OR^a$, —$SR^a$, —$S(=O)R^b$, —$S(=O)_2R^b$, and —$NR^eR^f$; and each $R^a$, $R^b$, $R^e$, and $R^f$ is independently selected from H and methyl.

In some embodiments:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyridimin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected $R^1$ groups;

each $R^1$ is independently selected from fluoro, bromo, chloro, cyano, hydroxyl, methyl, trifluoromethyl, methoxy, isopropylamino, dimethylamino, methylthio, methylsulfinyl, and methylsulfonyl.

In some embodiments, the compound is a compound having formula Ia:

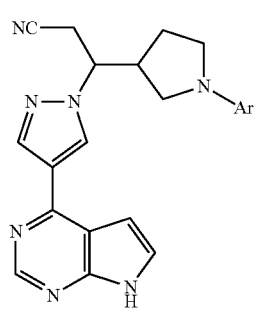

or a pharmaceutically acceptable salt or N-oxide thereof.

In some embodiments, the compound is a compound having formula Ib:

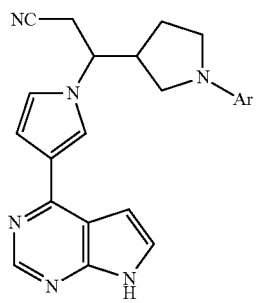

or a pharmaceutically acceptable salt or N-oxide thereof.

In some embodiments, the compound is a compound having formula Ic:

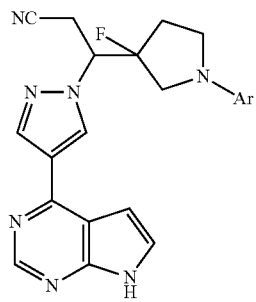

or a pharmaceutically acceptable salt or N-oxide thereof.

In some embodiments, the compound is a compound having Formula Id:

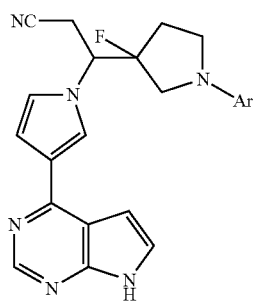

or a pharmaceutically acceptable salt or N-oxide thereof.

In some embodiments, the compound is a compound having Formula Ie:

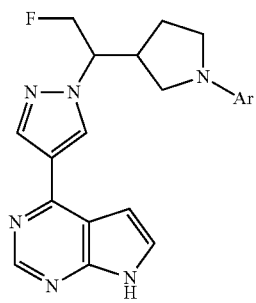

or a pharmaceutically acceptable salt or N-oxide thereof.

In some embodiments, the compound is a compound having formula If:
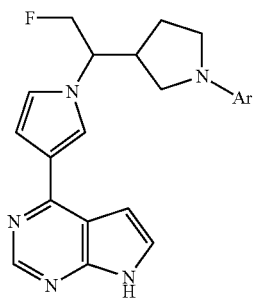
If
or a pharmaceutically acceptable salt or N-oxide thereof.
In some embodiments, the compound is a compound of Formula IIa, IIb, IIc, IId, IIe, IIf, IIg, IIh, IIi, IIj, IIm, IIn, or IIo:
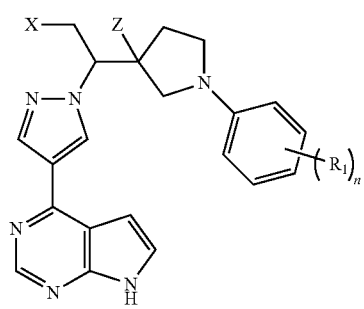
IIa
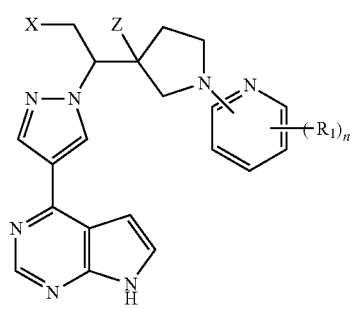
IIb
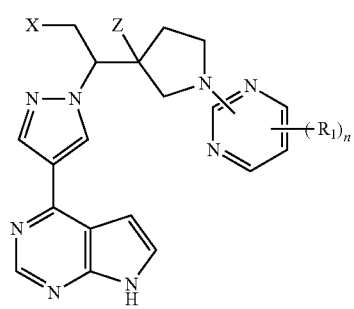
IIc
-continued
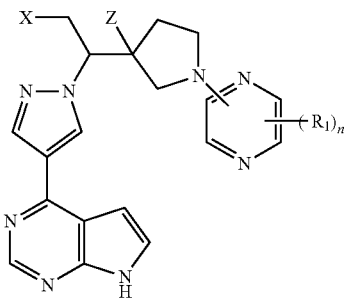
IId
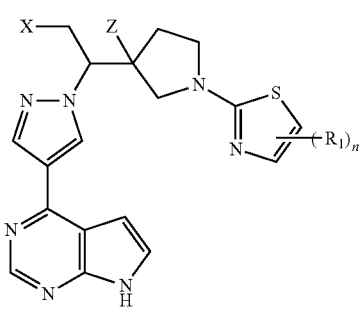
IIe
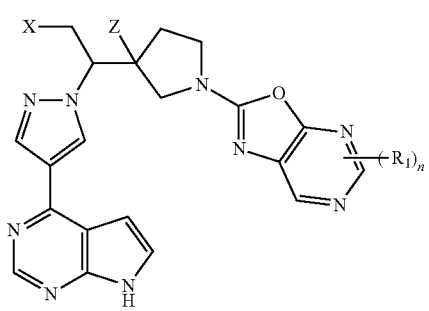
IIf
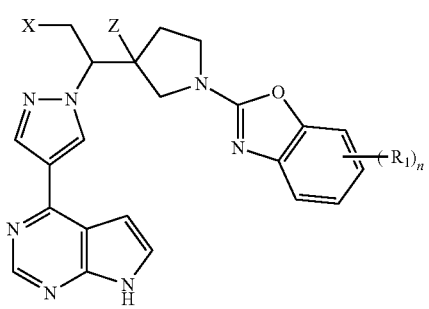
IIg
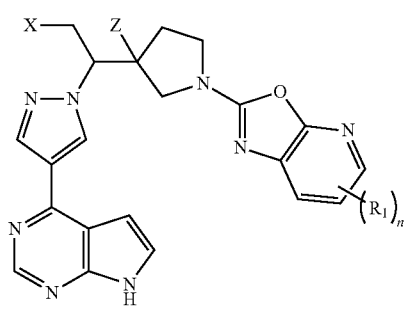
IIh

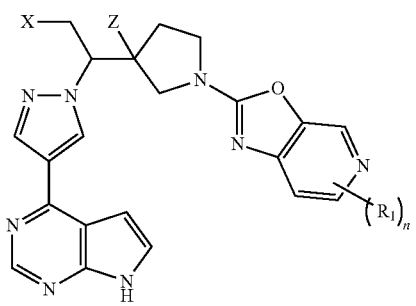

IIi

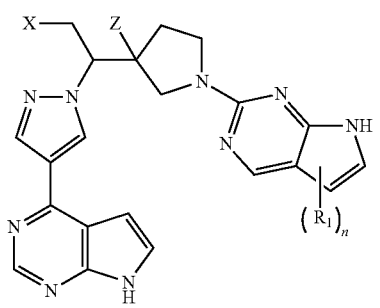

IIj

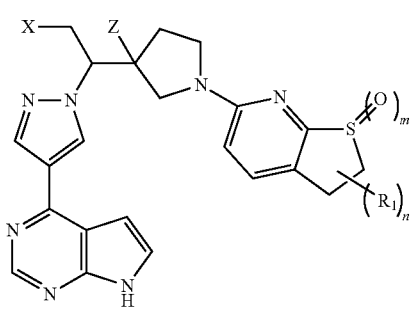

IIk

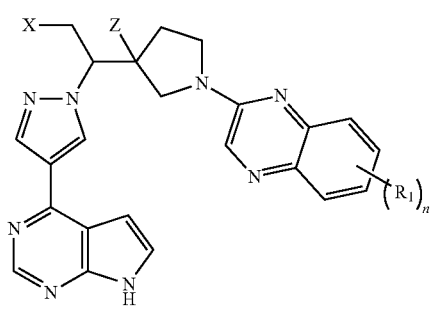

IIm

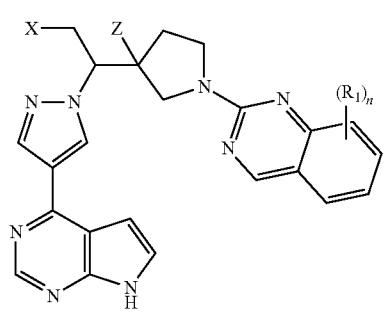

IIn

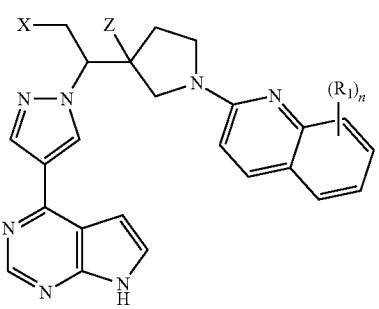

IIo or a pharmaceutically acceptable salt or N-oxide thereof, wherein each n is an integer selected from 0 to 5; and m is an integer selected from 0 to 2; provided that the valency of each atom in the optionally substituted moieties is not exceeded. Each of the preceding formulas can represent an individual embodiment. In some of the preceding embodiments, Z is hydrogen. In some of the preceding embodiments, Z is fluoro. In some of the preceding embodiments, X is cyano. In some of the preceding embodiments, X is fluoro. In some of the preceding embodiments, Z is hydrogen and X is cyano. In some of the preceding embodiments, Z is hydrogen and X is fluoro. In some of the preceding embodiments, Z is fluoro and X is cyano.

In some embodiments, the compound is a compound of Formula IIp, IIq, or IIr:

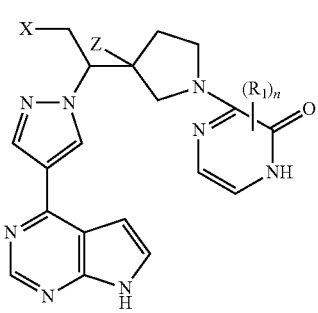

IIp

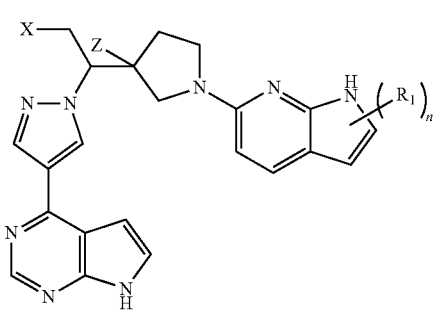

IIq

-continued

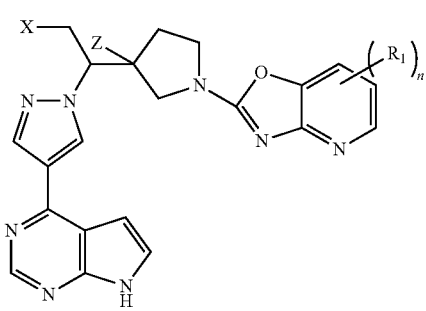

IIr or a pharmaceutically acceptable salt or N-oxide thereof, wherein each n is an integer selected from 0 to 5; provided that the valency of each atom in the optionally substituted moieties is not exceeded. Each of the preceding formulas can represent an individual embodiment. In some of the preceding embodiments, Z is hydrogen. In some of the preceding embodiments, Z is fluoro. In some of the preceding embodiments, X is cyano. In some of the preceding embodiments, X is fluoro. In some of the preceding embodiments, Z is hydrogen and X is cyano. In some of the preceding embodiments, Z is hydrogen and X is fluoro. In some of the preceding embodiments, Z is fluoro and X is cyano.

In some embodiments, the compound is a compound of Formula IIIa or IIIb:

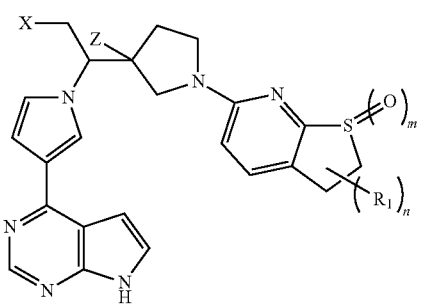

IIIa

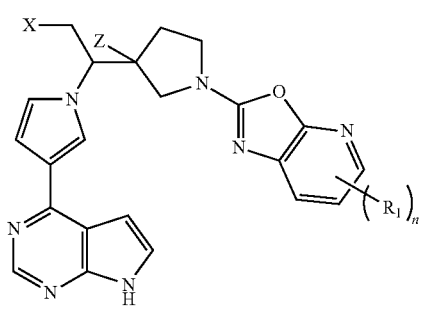

IIIb or a pharmaceutically acceptable salt or N-oxide thereof, wherein each n is an integer selected from 0 to 5; and m is an integer selected from 0 to 2; provided that the valency of each atom in the optionally substituted moieties is not exceeded. Each of the preceding formulas can represent an individual embodiment. In some of the preceding embodiments, m is 1 or 2. In some of the preceding embodiments, Z is hydrogen. In some of the preceding embodiments, Z is fluoro. In some of the preceding embodiments, X is cyano. In some of the preceding embodiments, X is fluoro. In some of the preceding embodiments, Z is hydrogen and X is cyano. In some of the preceding embodiments, Z is hydrogen and X is fluoro. In some of the preceding embodiments, Z is fluoro and X is cyano.

In some embodiments, Ar is optionally substituted with 1, 2, 3, or 4 independently selected $R^1$ groups. In some embodiments, Ar is optionally substituted with 1, 2, or 3 independently selected $R^1$ groups. In some embodiments, Ar is optionally substituted with 1 or 2 independently selected $R^1$ groups.

In some embodiments, the compound is selected from:
3-[1-(6-chloropyrazin-2-yl)pyrrolidin-3-yl]-3-[4-(7H-pyrrolo[2,3-d]pyrimidin-4-yl)-1H-pyrazol-1-yl]propanenitrile;
3-[1-(6-chloropyridin-2-yl)pyrrolidin-3-yl]-3-[4-(7H-pyrrolo[2,3-d]pyrimidin-4-yl)-1H-pyrazol-1-yl]propanenitrile;
3-[1-(2-chloropyrimidin-4-yl)pyrrolidin-3-yl]-3-[4-(7H-pyrrolo[2,3-d]pyrimidin-4-yl)-1H-pyrazol-1-yl]propanenitrile;
3-[1-(4-chloropyrimidin-2-yl)pyrrolidin-3-yl]-3-[4-(7H-pyrrolo[2,3-d]pyrimidin-4-yl)-1H-pyrazol-1-yl]propanenitrile;
3-[1-(4-bromo-1,3-thiazol-2-yl)pyrrolidin-3-yl]-3-[4-(7H-pyrrolo[2,3-d]pyrimidin-4-yl)-1H-pyrazol-1-yl]propanenitrile;
3-{1-[4-(dimethylamino)pyrimidin-2-yl]pyrrolidin-3-yl}-3-[4-(7H-pyrrolo[2,3-d]pyrimidin-4-yl)-1H-pyrazol-1-yl]propanenitrile;
3-{1-[4-(isopropylamino)pyrimidin-2-yl]pyrrolidin-3-yl}-3-[4-(7H-pyrrolo[2,3-d]pyrimidin-4-yl)-1H-pyrazol-1-yl]propanenitrile;
3-[1-(1,3-benzoxazol-2-yl)pyrrolidin-3-yl]-3-[4-(7H-pyrrolo[2,3-d]pyrimidin-4-yl)-1H-pyrazol-1-yl]propanenitrile;
3-[1-(5-chloro-1,3-benzoxazol-2-yl)pyrrolidin-3-yl]-3-[4-(7H-pyrrolo[2,3-d]pyrimidin-4-yl)-1H-pyrazol-1-yl]propanenitrile;
3-(1-[1,3]oxazolo[4,5-c]pyridin-2-ylpyrrolidin-3-yl)-3-[4-(7H-pyrrolo[2,3-d]pyrimidin-4-yl)-1H-pyrazol-1-yl]propanenitrile;
3-(1-[1,3]oxazolo[4,5-b]pyridin-2-ylpyrrolidin-3-yl)-3-[4-(7H-pyrrolo[2,3-d]pyrimidin-4-yl)-1H-pyrazol-1-yl]propanenitrile;
3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;
3-[1-(6-methyl[1,3]oxazolo[5,4-6]pyridin-2-yl)pyrrolidin-3-yl]-3-[4-(7H-pyrrolo[2,3-d]pyrimidin-4-yl)-1H-pyrazol-1-yl]propanenitrile;
3-[1-(6-fluoro[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile;
3-[4-(7H-pyrrolo[2,3-d]pyrimidin-4-yl)-1H-pyrazol-1-yl]-3-[1-(7H-pyrrolo[2,3-d]pyrimidin-2-yl)pyrrolidin-3-yl]propanenitrile;
3-[1-(7-methyl-7H-pyrrolo[2,3-d]pyrimidin-2-yl)pyrrolidin-3-yl]-3-[4-(7H-pyrrolo[2,3-d]pyrimidin-4-yl)-1H-pyrazol-1-yl]propanenitrile;
3-(1-[1,3]oxazolo[5,4-d]pyrimidin-2-ylpyrrolidin-3-yl)-3-[4-(7H-pyrrolo[2,3-d]pyrimidin-4-yl)-1H-pyrazol-1-yl]propanenitrile;
3-[1-(5-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;
3-[1-(4-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(7-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(5,7-difluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-{1-[2-(methylthio)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[2-(methylsulfinyl)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[2-(methylsulfonyl)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;

3-{1-[2-(methylsulfonyl)pyridin-4-yl]pyrrolidin-3-yl}-3-[4-(7H-pyrrolo[2,3-d]pyrimidin-4-yl)-1H-pyrazol-1-yl]propanenitrile;

3-[1-(1-oxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(1,1-dioxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-(3-fluoro-1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;

3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile;

3-[1-(1,1-dioxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile;

3-[1-(1-oxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile;

3-[1-(6-chloro-4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile;

3-[1-(4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile;

3-chloro-2-(3-{2-cyano-1-[4-(7H-pyrrolo[2,3-d]pyrimidin-4-yl)-1H-pyrazol-1-yl]ethyl}pyrrolidin-1-yl)isonicotinonitrile;

2-(3-{2-cyano-1-[4-(7H-pyrrolo[2,3-d]pyrimidin-4-yl)-1H-pyrazol-1-yl]ethyl}pyrrolidin-1-yl)pyridine-3,4-dicarbonitrile;

2-(3-{2-cyano-1-[4-(7H-pyrrolo[2,3-d]pyrimidin-4-yl)-1H-pyrazol-1-yl]ethyl}pyrrolidin-1-yl)-6-(methylthio)benzonitrile;

2-(3-{2-cyano-1-[4-(7H-pyrrolo[2,3-d]pyrimidin-4-yl)-1H-pyrazol-1-yl]ethyl}pyrrolidin-1-yl)-6-(methylsulfonyl)benzonitrile;

3-[1-(8-chloroquinolin-2-yl)pyrrolidin-3-yl]-3-[4-(7H-pyrrolo[2,3-d]pyrimidin-4-yl)-1H-pyrazol-1-yl]propanenitrile;

3-[1-(3-hydroxyquinoxalin-2-yl)pyrrolidin-3-yl]-3-[4-(7H-pyrrolo[2,3-d]pyrimidin-4-yl)-1H-pyrazol-1-yl]propanenitrile;

3-[1-(8-chloroquinazolin-2-yl)pyrrolidin-3-yl]-3-[4-(7H-pyrrolo[2,3-d]pyrimidin-4-yl)-1H-pyrazol-1-yl]propanenitrile;

3-[1-(6-chloro-1-oxidopyridin-2-yl)pyrrolidin-3-yl]-3-[4-(7H-pyrrolo[2,3-d]pyrimidin-4-yl)-1H-pyrazol-1-yl]propanenitrile;

3-[1-(8-fluoroquinazolin-2-yl)pyrrolidin-3-yl]-3-[4-(7H-pyrrolo[2,3-d]pyrimidin-4-yl)-1H-pyrazol-1-yl]propanenitrile;

3-[1-(5-bromo-1,3-thiazol-2-yl)pyrrolidin-3-yl]-3-[4-(7H-pyrrolo[2,3-d]pyrimidin-4-yl)-1H-pyrazol-1-yl]propanenitrile;

2-chloro-6-(3-{2-cyano-1-[4-(7H-pyrrolo[2,3-d]pyrimidin-4-yl)-1H-pyrazol-1-yl]ethyl}pyrrolidin-1-yl)benzonitrile;

3-(3-{2-cyano-1-[4-(7H-pyrrolo[2,3-d]pyrimidin-4-yl)-1H-pyrazol-1-yl]ethyl}pyrrolidin-1-yl)phthalonitrile;

2-(3-{2-cyano-1-[4-(7H-pyrrolo[2,3-d]pyrimidin-4-yl)-1H-pyrazol-1-yl]ethyl}pyrrolidin-1-yl)-4-(trifluoromethyl)nicotinonitrile;

3-(3-{2-cyano-1-[4-(7H-pyrrolo[2,3-d]pyrimidin-4-yl)-1H-pyrazol-1-yl]ethyl}pyrrolidin-1-yl)pyrazine-2-carbonitrile;

2-(3-{2-cyano-1-[4-(7H-pyrrolo[2,3-d]pyrimidin-4-yl)-1H-pyrazol-1-yl]ethyl}pyrrolidin-1-yl)benzonitrile;

2-(3-{2-cyano-1-[4-(7H-pyrrolo[2,3-d]pyrimidin-4-yl)-1H-pyrazol-1-yl]ethyl}pyrrolidin-1-yl)-6-methylbenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-fluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-methoxybenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-(trifluoromethyl)benzonitrile;

2-bromo-6-(3-{2-cyano-1-[4-(7H-pyrrolo[2,3-d]pyrimidin-4-yl)-1H-pyrazol-1-yl]ethyl}pyrrolidin-1-yl)benzonitrile;

2-(3-{2-cyano-1-[4-(7H-pyrrolo[2,3-d]pyrimidin-4-yl)-1H-pyrazol-1-yl]ethyl}pyrrolidin-1-yl)-3-fluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)isophthalonitrile;

6-(3-{2-cyano-1-[4-(7H-pyrrolo[2,3-d]pyrimidin-4-yl)-1H-pyrazol-1-yl]ethyl}pyrrolidin-1-yl)-2,3-difluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)-3,5,6-trifluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)nicotinonitrile;

3-chloro-5-(3-{2-cyano-1-[4-(7H-pyrrolo[2,3-d]pyrimidin-4-yl)-1H-pyrazol-1-yl]ethyl}pyrrolidin-1-yl)isonicotinonitrile;

3-(3-{2-cyano-1-[4-(7H-pyrrolo[2,3-d]pyrimidin-4-yl)-1H-pyrazol-1-yl]ethyl}pyrrolidin-1-yl)-2,5,6-trifluoroisonicotinonitrile;

3-{1-[3-fluoro-4-(trifluoromethyl)pyridin-2-yl]pyrrolidin-3-yl}-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-[1-(3,5,6-trifluoropyridin-2-yl)pyrrolidin-3-yl]propanenitrile;

3-(3-{2-cyano-1-[4-(7H-pyrrolo[2,3-d]pyrimidin-4-yl)-1H-pyrazol-1-yl]ethyl}pyrrolidin-1-yl)pyridine-2-carbonitrile;

2-chloro-6-(3-{2-cyano-1-[4-(7H-pyrrolo[2,3-d]pyrimidin-4-yl)-1H-pyrazol-1-yl]ethyl}pyrrolidin-1-yl)nicotinonitrile;

2-(3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine;

2-(3-(1-(4-(7H-pyrrolo[2,3-d]pyrimidin-4-yl)-1H-pyrazol-1-yl)-2-fluoro ethyl)pyrrolidin-1-yl)oxazolo[5,4-b]pyridine; and 3-[1-(1H-pyrrolo[2,3-b]pyridin-6-yl)pyrrolidin-3-yl]-3-[4-(7H-pyrrolo[2,3-d]pyrimidin-4-yl)-1H-pyrazol-1-yl]propanenitrile, or a pharmaceutically acceptable salt or N-oxide thereof.
In some embodiments, the compound is selected from:

5-(3-{2-cyano-1-[4-(7H-pyrrolo[2,3-d]pyrimidin-4-yl)-1H-pyrazol-1-yl]ethyl}pyrrolidin-1-yl)thieno[2,3-c]pyridine-4-carbonitrile;

5-(3-{2-cyano-1-[4-(7H-pyrrolo[2,3-d]pyrimidin-4-yl)-1H-pyrazol-1-yl]ethyl}pyrrolidin-1-yl)thieno[3,2-b]pyridine-6-carbonitrile;

2-(3-{2-cyano-1-[4-(7H-pyrrolo[2,3-d]pyrimidin-4-yl)-1H-pyrazol-1-yl]ethyl}pyrrolidin-1-yl)-4-hydroxythiophene-3-carbonitrile;

4-bromo-2-(3-{2-cyano-1-[4-(7H-pyrrolo[2,3-d]pyrimidin-4-yl)-1H-pyrazol-1-yl]ethyl}pyrrolidin-1-yl)thiophene-3-carbonitrile;

4-chloro-2-(3-{2-cyano-1-[4-(7H-pyrrolo[2,3-d]pyrimidin-4-yl)-1H-pyrazol-1-yl]ethyl}pyrrolidin-1-yl)thiophene-3-carbonitrile;

2-(3-{2-cyano-1-[4-(7H-pyrrolo[2,3-d]pyrimidin-4-yl)-1H-pyrazol-1-yl]ethyl}pyrrolidin-1-yl)thiophene-3,4-dicarbonitrile;

2-(3-{(1R)-2-fluoro-1-[4-(7H-pyrrolo[2,3-d]pyrimidin-4-yl)-1H-pyrazol-1-yl]ethyl}pyrrolidin-1-yl)thiophene-3,4-dicarbonitrile;

2-(3-{2-cyano-1-[3-(7H-pyrrolo[2,3-d]pyrimidin-4-yl)-1H-pyrrol-1-yl]ethyl}pyrrolidin-1-yl)thiophene-3,4-dicarbonitrile;

4-(3-{2-cyano-1-[4-(7H-pyrrolo[2,3-d]pyrimidin-4-yl)-1H-pyrazol-1-yl]ethyl}pyrrolidin-1-yl)-1,3-thiazole-5-carbonitrile;

5-(3-{2-fluoro-1-[3-(7H-pyrrolo[2,3-d]pyrimidin-4-yl)-1H-pyrrol-1-yl]ethyl}pyrrolidin-1-yl)-1,3-thiazole-4-carbonitrile;

4-(3-(1-(4-(7H-pyrrolo[2,3-d]pyrimidin-4-yl)-1H-pyrazol-1-yl)-2-cyanoethyl)pyrrolidin-1-yl)pyrimidine-5-carbonitrile;

4-(1-{2-fluoro-1-[1-(5-fluoro-2,3-dihydrothieno[2,3-b]pyridin-6-yl)pyrrolidin-3-yl]ethyl}-1H-pyrazol-4-yl)-7H-pyrrolo[2,3-d]pyrimidine;

4-(1-{2-fluoro-1-[1-(5-fluoro-1,1-dioxido-2,3-dihydrothieno[2,3-b]pyridin-6-yl)pyrrolidin-3-yl]ethyl}-1H-pyrazol-4-yl)-7H-pyrrolo[2,3-d]pyrimidine;

3-[1-(5-fluoro-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(6-bromo-3-fluoropyridin-2-yl)pyrrolidin-3-yl]-3-[4-(7H-pyrrolo[2,3-d]pyrimidin-4-yl)-1H-pyrazol-1-yl]propanenitrile;

3-[1-(5,6-difluoropyridin-2-yl)pyrrolidin-3-yl]-3-[4-(7H-pyrrolo[2,3-d]pyrimidin-4-yl)-1H-pyrazol-1-yl]propanenitrile;

3-{1-[6-chloro-3-fluoro-5-(hydroxymethyl)pyridin-2-yl]pyrrolidin-3-yl}-3-[4-(7H-pyrrolo[2,3-d]pyrimidin-4-yl)-1H-pyrazol-1-yl]propanenitrile;

3-(4-(7H-pyrrolo[2,3-d]pyrimidin-4-yl)-1H-pyrazol-1-yl)-3-(1-(5-amino-6-chloro-3-fluoropyridin-2-yl)pyrrolidin-3-yl)propanenitrile;

N-(2-(3-(1-(4-(7H-pyrrolo[2,3-d]pyrimidin-4-yl)-1H-pyrazol-1-yl)-2-cyano ethyl)pyrrolidin-1-yl)-6-chloro-5-fluoropyridin-3-yl)formamide;

3-{1-[6-(ethylsulfonyl)-3-fluoropyridin-2-yl]pyrrolidin-3-yl}-3-[4-(7H-pyrrolo[2,3-d]pyrimidin-4-yl)-1H-pyrazol-1-yl]propanenitrile;

3-[1-(6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile;

2-(3-{2-cyano-1-[4-(7H-pyrrolo[2,3-d]pyrimidin-4-yl)-1H-pyrazol-1-yl]ethyl}pyrrolidin-1-yl)-5-fluoro-4-(methoxymethyl)nicotinonitrile;

2-(3-{2-cyano-1-[4-(7H-pyrrolo[2,3-d]pyrimidin-4-yl)-1H-pyrazol-1-yl]ethyl}pyrrolidin-1-yl)-4-(methoxymethyl)nicotinonitrile;

4-(3-(1-(4-(7H-pyrrolo[2,3-d]pyrimidin-4-yl)-1H-pyrazol-1-yl)-2-cyanoethyl)pyrrolidin-1-yl)-6-methoxypyrimidine-5-carbonitrile;

3-(4-(7H-pyrrolo[2,3-d]pyrimidin-4-yl)-1H-pyrazol-1-yl)-3-(1-(6-(ethylsulfonyl)-3-fluoropyridin-2-yl)pyrrolidin-3-yl)propanenitrile;

2-(3-(1-(4-(7H-pyrrolo[2,3-d]pyrimidin-4-yl)-1H-pyrazol-1-yl)-2-cyanoethyl)pyrrolidin-1-yl)-4-methylnicotinonitrile;

3-{1-[3,5-difluoro-4-(methoxymethyl)pyridin-2-yl]pyrrolidin-3-yl}-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-[1-[1,3]thiazolo[5,4-d]pyrimidin-5-ylpyrrolidin-3-yl]propanenitrile;

2-(3-{2-cyano-1-[4-(7H-pyrrolo[2,3-d]pyrimidin-4-yl)-1H-pyrazol-1-yl]ethyl}pyrrolidin-1-yl)-4-(difluoromethyl)nicotinonitrile;

3-(4-(7H-pyrrolo[2,3-d]pyrimidin-4-yl)-1H-pyrazol-1-yl)-3-(1-(5-fluoro-2-methoxypyrimidin-4-yl)pyrrolidin-3-yl)propanenitrile;

3-(4-(7H-pyrrolo[2,3-d]pyrimidin-4-yl)-1H-pyrazol-1-yl)-3-(1-(3-amino-6-chloropyridin-2-yl)pyrrolidin-3-yl)propanenitrile;

4-(3-(1-(4-(7H-pyrrolo[2,3-d]pyrimidin-4-yl)-1H-pyrazol-1-yl)-2-cyanoethyl)pyrrolidin-1-yl)pyridazine-3-carbonitrile;

6-(3-(1-(4-(7H-pyrrolo[2,3-d]pyrimidin-4-yl)-1H-pyrazol-1-yl)-2-cyanoethyl)pyrrolidin-1-yl)-5-fluoronicotinonitrile;

2-(3-(1-(4-(7H-pyrrolo[2,3-d]pyrimidin-4-yl)-1H-pyrazol-1-yl)-2-cyanoethyl)pyrrolidin-1-yl)-5-fluoronicotinonitrile;

2-(3-(1-(4-(7H-pyrrolo[2,3-d]pyrimidin-4-yl)-1H-pyrazol-1-yl)-2-cyanoethyl)pyrrolidin-1-yl)-5-methylnicotinonitrile;

4-(3-(1-(4-(7H-pyrrolo[2,3-d]pyrimidin-4-yl)-1H-pyrazol-1-yl)-2-cyanoethyl)pyrrolidin-1-yl)-6-(difluoromethyl)pyrimidine-5-carbonitrile;

2-(3-(1-(4-(7H-pyrrolo[2,3-d]pyrimidin-4-yl)-1H-pyrazol-1-yl)-2-cyanoethyl)pyrrolidin-1-yl)-6-(difluoromethyl)benzonitrile;

2-(3-(1-(4-(7H-pyrrolo[2,3-d]pyrimidin-4-yl)-1H-pyrazol-1-yl)-2-cyanoethyl)pyrrolidin-1-yl)-6-(methoxymethyl)benzonitrile;

4-(3-(1-(3-(7H-pyrrolo[2,3-d]pyrimidin-4-yl)-1H-pyrrol-1-yl)-2-cyanoethyl)pyrrolidin-1-yl)pyridazine-3-carbonitrile;

2-(3-(1-(3-(7H-pyrrolo[2,3-d]pyrimidin-4-yl)-1H-pyrrol-1-yl)-2-cyanoethyl)pyrrolidin-1-yl)nicotinonitrile;

3-(3-(1-(3-(7H-pyrrolo[2,3-d]pyrimidin-4-yl)-1H-pyrrol-1-yl)-2-cyanoethyl)pyrrolidin-1-yl)pyrazine-2-carbonitrile;

4-(3-(1-(4-(7H-pyrrolo[2,3-d]pyrimidin-4-yl)-1H-pyrazol-1-yl)-2-fluoro ethyl)pyrrolidin-1-yl)pyridazine-3-carbonitrile;

3-(3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile;

2-(3-{2-fluoro-1-[4-(7H-pyrrolo[2,3-d]pyrimidin-4-yl)-1H-pyrazol-1-yl]ethyl}pyrrolidin-1-yl)nicotinonitrile;

4-(1-{1-[1-(1,1-dioxido-2,3-dihydrothieno[2,3-b]pyridin-6-yl)pyrrolidin-3-yl]-2-fluoroethyl}-1H-pyrazol-4-yl)-7H-pyrrolo[2,3-d]pyrimidine;

2-(3-(1-(4-(7H-pyrrolo[2,3-d]pyrimidin-4-yl)-1H-pyrazol-1-yl)-2-fluoro ethyl)pyrrolidin-1-yl)pyridine-3,4-dicarbonitrile;

3-(3-{2-fluoro-1-[4-(7H-pyrrolo[2,3-d]pyrimidin-4-yl)-1H-pyrazol-1-yl]ethyl}pyrrolidin-1-yl)phthalonitrile;

2-(3-{2-cyano-1-[4-(7H-pyrrolo[2,3-d]pyrimidin-4-yl)-1H-pyrazol-1-yl]ethyl}pyrrolidin-1-yl)-4-iodonicotinonitrile;

2-chloro-4-(3-{2-cyano-1-[4-(7H-pyrrolo[2,3-d]pyrimidin-4-yl)-1H-pyrazol-1-yl]ethyl}pyrrolidin-1-yl)nicotinonitrile;

4-(3-{2-cyano-1-[4-(7H-pyrrolo[2,3-d]pyrimidin-4-yl)-1H-pyrazol-1-yl]ethyl}pyrrolidin-1-yl)pyridine-2,3-dicarbonitrile;

3-[1-(2,6-dichloropyridin-3-yl)pyrrolidin-3-yl]-3-[4-(7H-pyrrolo[2,3-d]pyrimidin-4-yl)-1H-pyrazol-1-yl]propanenitrile;

5-(3-{2-fluoro-1-[4-(7H-pyrrolo[2,3-d]pyrimidin-4-yl)-1H-pyrazol-1-yl]ethyl}pyrrolidin-1-yl)-1,3-thiazole-4-carbonitrile;

2-(3-{2-cyano-1-[4-(7H-pyrrolo[2,3-d]pyrimidin-4-yl)-1H-pyrazol-1-yl]ethyl}pyrrolidin-1-yl)-4-(methylthio)nicotinonitrile;

2-(3-{2-cyano-1-[4-(7H-pyrrolo[2,3-d]pyrimidin-4-yl)-1H-pyrazol-1-yl]ethyl}pyrrolidin-1-yl)-4-(methylsulfonyl)nicotinonitrile;

3-{1-[3,5-difluoro-6-(methylthio)pyridin-2-yl]pyrrolidin-3-yl}-3-[4-(7H-pyrrolo[2,3-d]pyrimidin-4-yl)-1H-pyrazol-1-yl]propanenitrile;

3-{1-[3,5-difluoro-6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;

3-(1-{3,5-difluoro-6-[(2,2,2-trifluoroethyl)-sulfonyl]pyridin-2-yl}pyrrolidin-3-yl)-3-[4-(7H-pyrrolo[2,3-d]pyrimidin-4-yl)-1H-pyrazol-1-yl]propanenitrile;

4-[1-(1-{1-[3,5-difluoro-6-(methylsulfonyl)pyridin-2-yl]pyrrolidin-3-yl}-2-fluoro ethyl)-1H-pyrazol-4-yl]-7H-pyrrolo-[2,3-d]pyrimidine;

3-{1-[3-fluoro-6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;

3-{1-[2,5-difluoro-6-(methylsulfonyl)pyridin-3-yl]pyrrolidin-3-yl}-3-[4-(7H-pyrrolo[2,3-d]pyrimidin-4-yl)-1H-pyrazol-1-yl]propanenitrile 2-(3-{2-cyano-1-[4-(7H-pyrrolo[2,3-d]pyrimidin-4-yl)-1H-pyrazol-1-yl]ethyl}pyrrolidin-1-yl)-4-(1-fluoroethyl)nicotinonitrile;

3-(3-{2-cyano-1-[4-(7H-pyrrolo[2,3-d]pyrimidin-4-yl)-1H-pyrazol-1-yl]ethyl}pyrrolidin-1-yl)-6-(difluoromethyl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-(2,2-difluoroethyl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-(hydroxymethyl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-(methoxymethyl)pyrazine-2-carbonitrile;

6-bromo-3-(3-{2-cyano-1-[4-(7H-pyrrolo[2,3-d]pyrimidin-4-yl)-1H-pyrazol-1-yl]ethyl}pyrrolidin-1-yl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-ethynylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-ethylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile;

3-fluoro-5-(3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile;

3-{1-[2-(ethylsulfonyl)pyridin-4-yl]pyrrolidin-3-yl}-3-[3-(7H-pyrrolo[2,3-d]pyrimidin-4-yl)-1H-pyrrol-1-yl]propanenitrile;

5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile;

3-[1-(2-mercaptopyrimidin-4-yl)pyrrolidin-3-yl]-3-[4-(7H-pyrrolo[2,3-d]pyrimidin-4-yl)-1H-pyrazol-1-yl]propanenitrile;

N-[4-(3-{2-cyano-1-[4-(7H-pyrrolo[2,3-d]pyrimidin-4-yl)-1H-pyrazol-1-yl]ethyl}pyrrolidin-1-yl)pyrimidin-2-yl]-N,N-dimethylsulfonamide;

4-(3-{2-cyano-1-[4-(7H-pyrrolo[2,3-d]pyrimidin-4-yl)-1H-pyrazol-1-yl]ethyl}pyrrolidin-1-yl)-N-methylpyridine-2-carboxamide;

4-(3-{2-cyano-1-[4-(7H-pyrrolo[2,3-d]pyrimidin-4-yl)-1H-pyrazol-1-yl]ethyl}pyrrolidin-1-yl)-N,N-dimethylpyridine-2-carboxamide;

4-(3-{2-cyano-1-[4-(7H-pyrrolo[2,3-d]pyrimidin-4-yl)-1H-pyrazol-1-yl]ethyl}pyrrolidin-1-yl)-N-phenylpyridine-2-carboxamide;

3-[1-(2,3-dihydrofuro[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-(1-thieno[2,3-b]pyridin-6-ylpyrrolidin-3-yl)propanenitrile;

3-[1-(7,7-difluoro-6,7-dihydro-5H-cyclopenta[b]pyridin-2-yl)pyrrolidin-3-yl]-3-[4-(7H-pyrrolo[2,3-d]pyrimidin-4-yl)-1H-pyrazol-1-yl]propanenitrile;

3-[1-(7-fluoro-1,3-benzoxazol-2-yl)pyrrolidin-3-yl]-3-[3-(7H-pyrrolo[2,3-d]pyrimidin-4-yl)-1H-pyrrol-1-yl]propanenitrile;

3-[1-(7-bromo-1,3-benzoxazol-2-yl)pyrrolidin-3-yl]-3-[4-(7H-pyrrolo[2,3-d]pyrimidin-4-yl)-1H-pyrazol-1-yl]propanenitrile;

2-(3-{2-cyano-1-[4-(7H-pyrrolo[2,3-d]pyrimidin-4-yl)-1H-pyrazol-1-yl]ethyl}pyrrolidin-1-yl)-1,3-benzoxazole-7-carbonitrile;

3-[1-(7-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(7-methoxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-(4-(7H-pyrrolo[2,3-d]pyrimidin-4-yl)-1H-pyrazol-1-yl)-3-(1-(7-ethoxybenzo[d]oxazol-2-yl)pyrrolidin-3-yl)propanenitrile;

3-(4-(7H-pyrrolo[2,3-d]pyrimidin-4-yl)-1H-pyrazol-1-yl)-3-(1-(7-(difluoromethoxy)benzo[d]oxazol-2-yl)pyrrolidin-3-yl)propanenitrile;

3-[1-(4-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-{1-[7-(hydroxymethyl)-1,3-benzoxazol-2-yl]pyrrolidin-3-yl}-3-[4-(7H-pyrrolo[2,3-d]pyrimidin-4-yl)-1H-pyrazol-1-yl]propanenitrile;

6-(3-{2-cyano-1-[4-(7H-pyrrolo[2,3-d]pyrimidin-4-yl)-1H-pyrazol-1-yl]ethyl}pyrrolidin-1-yl)furo[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)furo[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile 1,1-dioxide;

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide;

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile;

6-(3-{2-cyano-1-[4-(7H-pyrrolo[2,3-d]pyrimidin-4-yl)-1H-pyrazol-1-yl]ethyl}pyrrolidin-1-yl)thieno[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)thieno[3,2-c]pyridine-7-carbonitrile;

6-(3-{2-cyano-1-[4-(7H-pyrrolo[2,3-d]pyrimidin-4-yl)-1H-pyrazol-1-yl]ethyl}pyrrolidin-1-yl)-1H-pyrrolo[3,2-c]pyridine-7-carbonitrile; and 6-((3S)-3-{2-fluoro-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide, or a pharmaceutically acceptable salt or N-oxide thereof.

In some embodiments, the compound is 6-(3-(1-(4-(7H-pyrrolo[2,3-d]pyrimidin-4-yl)-1H-pyrazol-1-yl)-2-cyanoethyl)pyrrolidin-1-yl)-2-chloro-5-fluoronicotinonitrile, or a pharmaceutically acceptable salt or N-oxide thereof.

In some embodiments, the compound is the trifluoroacetate or phosphate salt.

The present invention includes pharmaceutically acceptable salts and N-oxides of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds described herein may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include all isotopes of their constituent atoms. Isotopes include those atoms having the same atomic number but different mass numbers. For example, isotopes of hydrogen include tritium and deuterium.

The term, "compound" as used herein is meant to include all stereoisomers, tautomers, and isotopes of the structures depicted or chemical names provided, unless otherwise indicated.

All compounds, and pharmaceutically acceptable salts thereof, can be found together with other substances such as water and solvents (e.g. hydrates and solvates) or can be isolated.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt, or N-oxide thereof.

Methods

Compounds of the invention are JAK inhibitors, and the majority of the compounds of the invention are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio>1).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound, salt thereof, or N-oxide thereof, of the present invention or a pharmaceutical composition of any of the aforementioned. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity. In some embodiments, the JAK-associated disease is a JAK1-associated disease.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, as well as other JAK inhibitors, such as those reported in U.S. Ser. No. 11/637,545, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDS) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is primary myelofibrosis (PMF) or post polycythemia vera/essential thrombocythemia myelofibrosis (Post-PV/ET MF).

The present invention further provides methods of treating psoriasis or other skin disorders by administration of a topical formulation containing a compound of the invention.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", The Ocular Surface, 5(2), 75-92 April 2007. In some embodiments, the dry eye disorder is selected from aqueous tear-deficient dry eye (ADDE) or evaporative dry eye disorder, or appropriate combinations thereof.

In a further aspect, the present invention provides a method of treating conjunctivitis, uveitis (including chronic uveitis), chorioditis, retinitis, cyclitis, scleritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compound of the invention, as well as other JAK inhibitors such as those reported in U.S. Ser. No.

11/637,545, can be used to treat respiratory dysfunction or failure associated with viral infection, such as influenza and SARS.

In some embodiments, the present invention provides a compound of Formula I, pharmaceutically acceptable salt thereof, or N-oxide thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt or N-oxide thereof, for use in a method of modulating a JAK1. In some embodiments, the present invention also provides use of a compound of Formula I as described herein, or a pharmaceutically acceptable salt or N-oxide thereof, for the preparation of a medicament for use in a method of modulating a JAK1.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the compounds described herein for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, another JAK inhibitor, Bcr-Abl kinase inhibitor, Flt-3 kinase inhibitor, RAF kinase inhibitor, and FAK kinase inhibitor such as, for example, those described in WO 2006/056399. In some embodiments, the additional therapeutic agent is a tetracycline derivative (e.g., minocycline or doxycline).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the composition is for oral delivery. In further embodiments, the composition is for topical application.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds described herein can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt or N-oxide thereof, is administered as an ophthalmic composition. Accordingly, in some embodiments, the methods comprise administration of the compound, or pharmaceutically acceptable salt or N-oxide thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt or N-oxide thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt or N-oxide thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxypropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al., "Polymers used in ocular dosage form and drug delivery systems", *Asian J. Pharm.*, pages 12-17 (January 2008), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl) caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

The invention further provides a pharmaceutical formulation for topical skin application, comprising a therapeutically effective amount of a compound of the invention, or a pharmaceutically acceptable salt thereof.

In some embodiments, the pharmaceutical formulation comprises:

an oil-in-water emulsion; and a therapeutically effective amount of a compound of the invention, or a pharmaceutically acceptable salt thereof.

In some embodiments, the emulsion comprises water, an oil component, and an emulsifier component.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

In some embodiments, the oil component is present in an amount of about 10% to about 40% by weight of the formulation.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the formulation.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol). vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the oil component comprises a stiffening agent component.

In some embodiments, the stiffening agent component is present in an amount of about 2% to about 8% by weight of the formulation.

As used herein, the term "stiffening agent component" refers to a substance or mixture of substances that increases the viscosity and/or consistency of the formulation or improves the rheology of the formulation.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the oil component comprises an emollient component.

In some embodiments, the emollient component is present in an amount of about 5% to about 15% by weight of the formulation.

As used herein, the term "emollient component" refers to an agent that softens or soothes the skin or soothes an irritated internal surface.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the emollient component comprises one or more substances independently selected from light mineral oil, medium chain triglycerides, and dimethicone.

In some embodiments, the water is present in an amount of about 35% to about 65% by weight of the formulation.

In some embodiments, the emulsifier component is present in an amount of about 1% to about 9% by weight of the formulation.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the pharmaceutical formulation further comprises a stabilizing agent component.

In some embodiments, the stabilizing agent component is present in an amount of about 0.05% to about 5% by weight of the formulation.

As used herein, the term "stabilizing agent component" refers to a substance or mixture of substances that improves the stability of the pharmaceutical formulation and/or the compatibility of the components in the formulation. In some embodiments, the stabilizing agent component prevents agglomeration of the emulsion and stabilizes the droplets in the oil-in-water emulsion.

In some embodiments, the stabilizing agent component comprises one or more substances independently selected from polysaccharides.

In some embodiments, the stabilizing agent component comprises xanthan gum.

In some embodiments, the pharmaceutical formulation further comprises a solvent component.

In some embodiments, the solvent component is present in an amount of about 10% to about 35% by weight of the formulation.

As used herein, the term "solvent component" is a liquid substance or mixture of liquid substances capable of dissolving a compound of the invention or other substances in the formulation. In some embodiments, the solvent component is a liquid substance or mixture of liquid substances in which a compound of the invention, or a pharmaceutically acceptable salt thereof, has reasonable solubility.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the compound of the invention is present in an amount of about 0.5% to about 2.0% by weight of the formulation on a free base basis.

In some embodiments, the compound of the invention is present in an amount of about 0.5% by weight of the formulation on a free base basis.

In some embodiments, the compound of the invention is present in an amount of about 1% by weight of the formulation on a free base basis.

In some embodiments, the compound of the invention is present in an amount of about 1.5% by weight of the formulation on a free base basis.

In some embodiments, the compound of the invention is present in an amount selected from about 0.5, 0.6, 0.7, 0.8, 09, 1.0, 1.1, 1.2, 1.3, 1.4, 1.5, 1.6, 1.7, 1.8, 1.9, and 2.0% by weight of the formulation on a free base basis.

In some embodiments, the pharmaceutical formulation comprises: water; an oil component; an emulsifier component; a solvent component; a stabilizing agent component; and from about 0.5% to about 2.0% of a compound of the invention, or a pharmaceutically acceptable salt thereof, by weight of the formulation on a free base basis.

In some embodiments, the pharmaceutical formulation comprises:

from about 35% to about 65% of water by weight of the formulation;

from about 10% to about 40% of an oil component by weight of the formulation;

from about 1% to about 9% of an emulsifier component by weight of the formulation;

from about 10% to about 35% of a solvent component by weight of the formulation;

from about 0.05% to about 5% of a stabilizing agent component by weight of the formulation; and from about 0.5% to about 2.0% of a compound of the invention, or a pharmaceutically acceptable salt thereof, by weight of the formulation on a free base basis.

In some embodiments:

the oil component comprises one or more substances independently selected from petrolatums, fatty alcohols, mineral oils, triglycerides, and dimethicones;

the emulsifier component comprises one or more substances independently selected from glyceryl fatty esters and sorbitan fatty esters;

the solvent component comprises one or more substances independently selected from alkylene glycols and polyalkylene glycols; and the stabilizing agent component comprises one or more substances independently selected from polysaccharides.

In some embodiments:

the oil component comprises one or more substances independently selected from white petrolatum, cetyl alcohol, stearyl alcohol, light mineral oil, medium chain triglycerides, and dimethicone;

the emulsifier component comprises one or more substances independently selected from glyceryl stearate and polysorbate 20;

the solvent component comprises one or more substances independently selected from propylene glycol and polyethylene glycol; and the stabilizing agent component comprises xanthan gum.

In some embodiments, the pharmaceutical formulation comprises:

from about 35% to about 65% of water by weight of the formulation;

from about 2% to about 15% of an occlusive agent component by weight of the formulation;

from about 2% to about 8% of a stiffening agent component by weight of the formulation;

from about 5% to about 15% of an emollient component by weight of the formulation;

from about 1% to about 9% of an emulsifier component by weight of the formulation;

from about 0.05% to about 5% of a stabilizing agent component by weight of the formulation;

from about 10% to about 35% of a solvent component by weight of the formulation; and from about 0.5% to about 2.0% of a compound of the invention, or a pharmaceutically acceptable salt thereof, by weight of the formulation on a free base basis.

In some embodiments:

the occlusive agent component comprises a petrolatum;

the stiffening agent component comprises one or more substances independently selected from one or more fatty alcohols;

the emollient component comprises one or more substances independently selected from mineral oils and triglycerides;

the emulsifier component comprises one or more substances independently selected from glyceryl fatty esters and sorbitan fatty esters;

the stabilizing agent component comprises one or more substances independently selected from polysaccharides; and the solvent component comprises one or more substances independently selected from alkylene glycols and polyalkylene glycols.

In some embodiments:

the occlusive agent component comprises white petrolatum;

the stiffening agent component comprises one or more substances independently selected from cetyl alcohol and stearyl alcohol;

the emollient component comprises one or more substances independently selected from light mineral oil, medium chain triglycerides, and dimethicone;

the emulsifier component comprises one or more substances independently selected from glyceryl stearate and polysorbate 20;

the stabilizing agent component comprises xanthan gum; and the solvent component comprises one or more substances independently selected from propylene glycol and polyethylene glycol.

In some embodiments, the pharmaceutical formulation further comprises an antimicrobial preservative component.

In some embodiments, the antimicrobial preservative component is present in an amount of about 0.05% to about 3% by weight of the formulation.

As used herein, the phrase "antimicrobial preservative component" is a substance or mixtures of substances which inhibits microbial growth in the formulation.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the pharmaceutical formulation further comprises a chelating agent component.

As used herein, the phrase "chelating agent component" refers to a compound or mixtures of compounds that has the ability to bind strongly with metal ions.

In some embodiments, the chelating agent component comprises edetate disodium.

As used herein, "% by weight of the formulation" means the percent concentration of the component in the formulation is on weight/weight basis. For example, 1% w/w of component A=[(mass of component A)/(total mass of the formulation)]×100.

As used herein, "% by weight of the formulation on a free base basis" of a compound of the invention, or a pharmaceutically acceptable salt thereof" means that the % w/w is calculated based on the weight of the free base of the compound of the invention in the total formulation.

In some embodiments, the components are present in exactly the ranges specified (e.g., the term "about" is not present). In some embodiments, "about" means plus or minus 10% of the value.

As will be appreciated, some components of the pharmaceutical formulations described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

As used herein, the term "component" can mean one substance or a mixture of substances.

As used herein, the term "fatty acid" refers to an aliphatic acid that is saturated or unsaturated. In some embodiments, the fatty acid is a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula O-alkylene-. In some embodiments, the polyalkylene glycol is polyethylene glycol.

As used herein, the term, "sorbitan fatty ester" includes products derived from sorbitan or sorbitol and fatty acids and, optionally, poly(ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE(20) sorbitan monolaurate), 21 (POE(4) sorbitan monolaurate), 40 (POE (20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE (20) sorbitan monooleate), 81 (POE(5) sorbitan monooleate), and 85 (POE(20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula —O-alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

The oil-in-water cream formulations can be synthesized according using an overhead mixer with high and low shear mixing blades. For example, in some embodiments, the formulation can be synthesized by the following procedure.

1. An antimicrobial preservative phase can be prepared by mixing at least a portion of the antimicrobial preservative component with a portion of a solvent component.
2. Next, a stabilizing agent phase is prepared by mixing a stabilizing agent component with a portion of the solvent component.
3. An oil phase is then prepared by mixing an emollient component, an emulsifier component, an occlusive agent component, and a stiffening agent component. The oil phase is heated to 70-80° C. to melt and form a uniform mixture.
4. An aqueous phase is next prepared by mixing purified water, the remainder of the solvent component, and a chelating agent component. The phase is heated to 70-80° C.
5. The aqueous phase of step 4, antimicrobial preservative phase of step 1, and the compound of the invention, or a pharmaceutically acceptable salt thereof, are combined to form a mixture.
6. The stabilizing agent phase from step 2 was then added to the mixture from step 5.
7. The oil phase from step 3 is then combined under high shear mixing with the mixture from step 6 to form an emulsion.
8. Finally, additional antimicrobial preservative component may be then added to the emulsion from step 7. Mixing is continued, and then the product is cooled under low shear mixing.

Synthesis

Compounds of the invention, including salts and N-oxides thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

Compounds of Formula I, wherein X is cyano, can be made by methods analogous to that depicted in Scheme I. Accordingly, a protected pyrazol-4-yl-pyrrolo[2,3-d]pyrimidine or pyrrol-3-yl-pyrrolo[2,3-d]pyrimidine of formula (a) is reacted with a protected alkene of formula (b) in a Michael addition in the presence of a coupling agent. The protecting groups, $P^1$ and R, can be any appropriate protecting group, including, but not limited to, the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, $P^1$ is 2-(trimethylsilyl)ethoxymethyl (SEM). In some embodiments, the R protecting group is one that can be selectively removed in the presence of the $P^1$ protecting group. In some embodiments, the R protecting group is t-butoxycarbonyl (BOC) or benzyloxycarbonyl (Cbz). The coupling agent can be any appropriate coupling agent useful for Michael addition, including, but not limited to a tetraalkylammonium halide, tetraalkylammonium hydroxide, guanidine, amidine, hydroxide, alkoxide, silicate, alkali metal phosphate, oxide, tertiary amine, alkali metal carbonate, alkali metal bicarbonate, alkali metal hydrogen phosphate, phosphine, or alkali metal salt of a carboxylic acid. In some embodiments, the coupling agent is tetramethyl guanidine, 1,8-diazabicyclo[5.4.0]undec-7-ene, 1,5-diazabicyclo(4.3.0) non-5-ene, 1,4-diazabicyclo(2.2.2)octane, tert-butyl ammonium hydroxide, sodium hydroxide, potassium hydroxide, sodium methoxide, sodium ethoxide, tripotassium phosphate, sodium silicate, calcium oxide, triethylamine, sodium carbonate, potassium carbonate, sodium bicarbonate, potassium bicarbonate, potassium hydrogen phosphate, triphenyl phosphine, triethyl phosphine, potassium acetate, or potassium acrylate. In some embodiments, the coupling agent is 1,8-diazabicyclo[5.4.0]undec-7-ene (DBU). The Michael addition of the compounds of formulas (a) and (b) can be conducted in an appropriate solvent (e.g., acetonitrile).

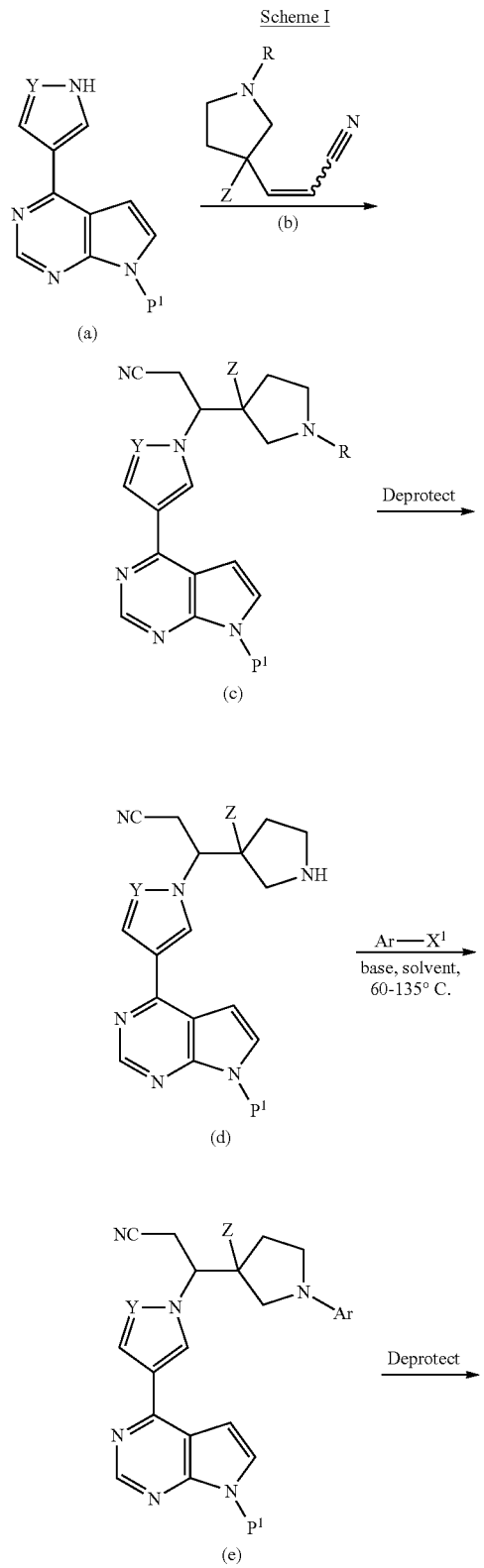

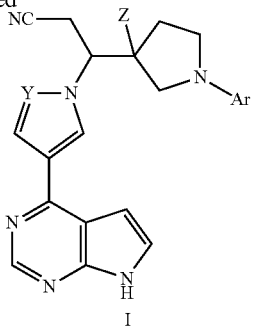

The Michael addition product (c) can then be deprotected to remove the R protecting group to form the pyrrolidine base (d). For example, when R is BOC, the protecting group can be removed through treatment with HCl in dioxane, while when R is Cbz, the protecting group can be removed under hydrogenation conditions (e.g., hydrogen gas in the presence of 10% palladium on carbon). The pyrrolidine base (d) can then be reacted with an aromatic moiety of formula Ar—$X^1$ to form the aryl-pyrrolidine of formula (e). Appropriate leaving groups for $X^1$, include, but are not limited to, chloro, bromo, fluoro, —$OSO_2CF_3$, and thio (SH). The reaction can be carried out in the presence of a base (such as a tertiary amine, e.g., diisopropylethylamine) in a solvent such as N-methylpyrrolidone (NMP), dioxane, or ethanol (EtOH) at an elevated temperature (e.g., 60 to 135° C.). The compound of formula (e) can then be deprotected to give the compound of Formula I.

Compounds of formula (a) may be formed by methods analogous to that depicted in Scheme II. Accordingly, Suzuki-coupling of a protected 4-chloro-pyrrolo[2,3-d]pyrimidine of formula (f) (wherein R" is hydrogen, alkyl or two R" join together with the oxygen and boron atoms to form a optionally substituted heterocycloalkyl ring such as a pinacol ring) with a protected or unprotected pyrrol-3-yl or pyrazol-4-yl boronic acid or ester of formula (g) (e.g., wherein R' is H or a protecting group) in the presence of a palladium catalyst (e.g., tetrakis(triphenylphosphine)palladium(0) or tetrakis(tri (o-tolylphosphine))palladium(0)) and a base (e.g., potassium carbonate) gives the desired starting material of formula (a) (see, e.g., Example 65 of US 20070135461, which is incorporated herein by reference in its entirety). The pyrrol-3-yl or pyrazol-4-yl boronic ester or acid can be protected with any appropriate protecting group. Similarly, the $P^1$ protecting group can be any appropriate protecting group (e.g., diethoxymethyl (DEM) or 2-(trimethylsilyl)ethoxymethyl (SEM)).

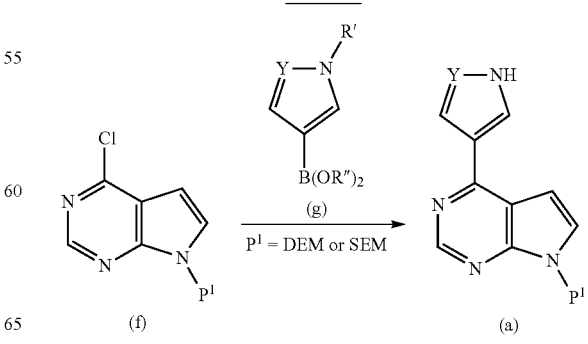

The alkene of formula (b) can be formed by reaction of the pyrrolidine aldehyde of formula (h) with a Horner-Wadsworth-Emmons reagent as shown in Scheme III. The R protecting group can be any of the protecting groups summarized above (e.g., BOC or Cbz).

Scheme III

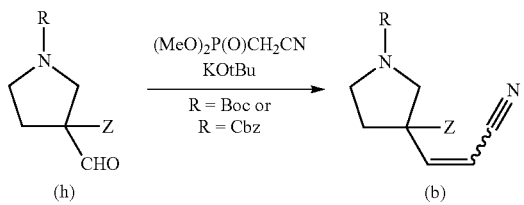

The Ar—X¹ compounds can be formed by methods known in the art. Compounds wherein Ar is a fused heterocycloalkyl (hetero)aryl group with a S-oxo or S,S-dioxo thioether moiety (v) or (vi) can be formed by methods analogous to those shown in Scheme IV. Accordingly, an appropriate di-chloro (hetero)arylaldehyde moiety (e.g., a compound of formula (i)) is reacted with a Wittig reagent to give an β-methoxyalkenyl moiety (e.g., a compound of formula (ii)), which can then be hydrolyzed and reduced to give a β-hydroxyethane moiety (e.g., a compound of formula (iii)). The hydroxyl group on the β-hydroxyethane moiety can then be converted to a thio group (e.g., a compound of formula (iv) and cyclized to form a thioether. The thioether can then be oxidized using an appropriate oxidizing agent (e.g., m-chloroperbenzoic acid, mCPBA) to give the S-oxothioether (e.g., a compound of formula (v)) and the S,S-dioxothioether (e.g., a compound of formula (vi)).

Scheme IV

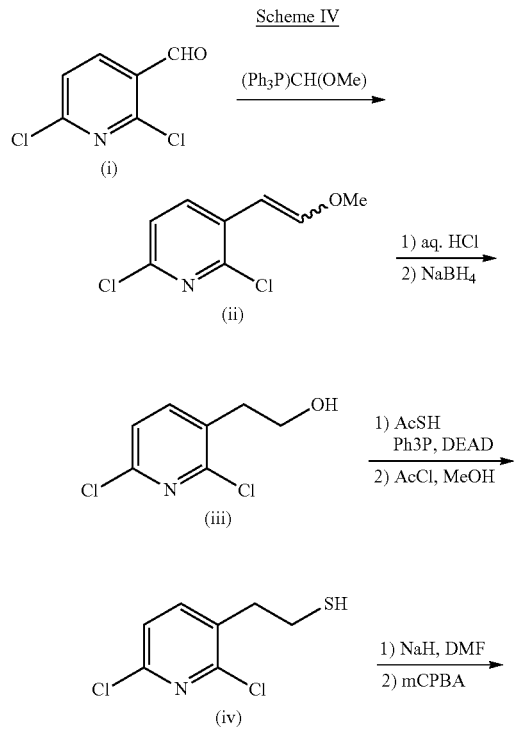

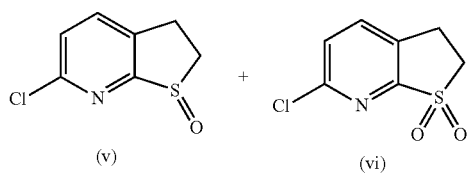

Certain compounds of formula Ar—X¹ wherein Ar is a fused heteroaryl or aryloxazole compound can be formed by methods analogous to that shown in Scheme V. Accordingly a 1-nitro-2-hydroxylaryl or heteroaryl moiety of formula (i) is reduced to give a 1-amino-2-hydroxylaryl or heteroaryl moiety of formula (ii), which can be cyclized to give the benzo[d]oxazole-2(3H)-thione compound of formula (iii). Certain compounds of formula (iii) can then be reacted to give the 2-chloro fused oxazole compound of formula (iv).

Scheme V

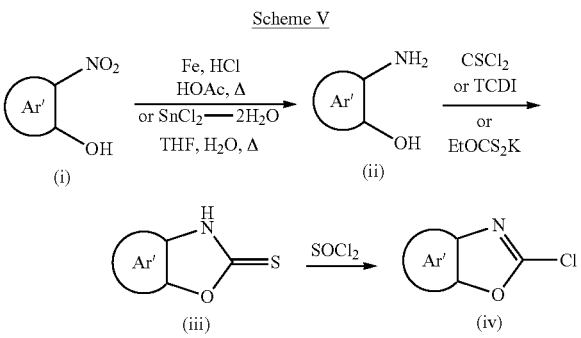

In some cases, the compound of formula (iii) can be reacted directly with the compound of formula (d) of Scheme I by methods analogous to those depicted in Scheme VI. Accordingly, the compound of formula (d) is reacted with the compound of formula (iii) in the presence of a base such as a tertiary amine (e.g., diisopropylethylamine) and a solvent (e.g., dioxane) at an elevated temperature (e.g., 70° C.), followed by treatment with silver nitrate in the presence of ammonium hydroxide and ethanol and deprotection to form the desired compound.

Scheme VI

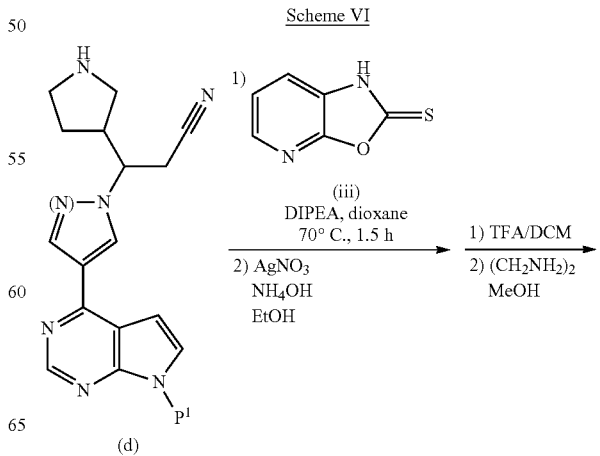

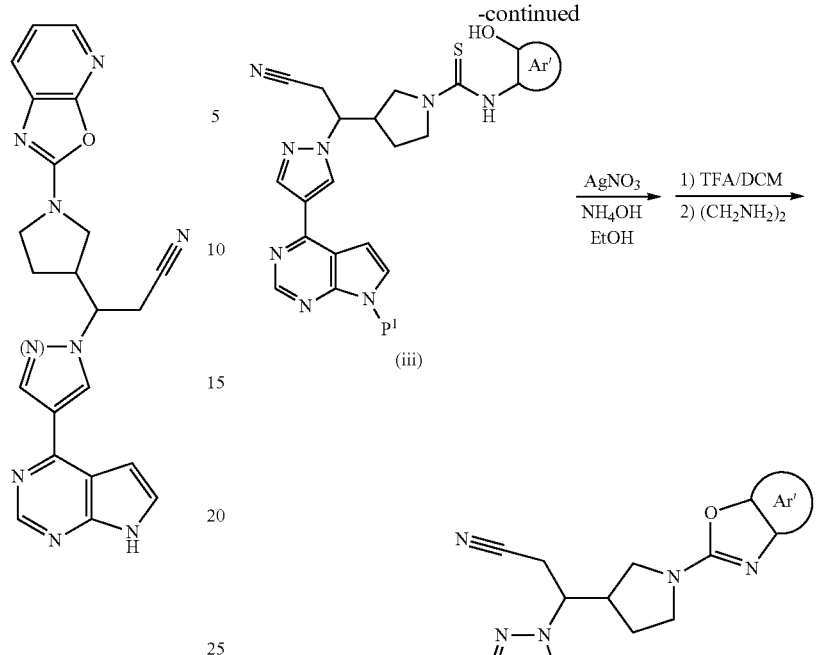

Alternatively, compounds of formula Ar—X¹ wherein Ar is a fused heteroaryl- or aryloxazole compound can be formed by methods analogous to that shown in Scheme VII. Accordingly, the compound of formula (i) is reacted with phenyl chlorothionocarbonate and pyridine, followed by reaction with the pyrrolidine core structure of formula (ii) to give the compound of formula (iii). The compound of formula (iii) can then be cyclized and deprotected to give the desired compound of formula (iv).

Compound of Formula I, wherein X is fluoro, can be made by the methods shown in Scheme VIII. Accordingly, a protected 3-carboxypyrrolidine (R is a protecting group) of formula 1 is reduced to give a methylol derivative of formula 2. The methylol derivative can then be oxidized via a Swern oxidation procedure to give the aldehyde of formula 3. The aldehyde can then be reacted with fluoromethylphenyl sulfone in the presence of lithium diisopropylamide (LDA) to give the compound of formula 4. The compound of formula 4 can then be reacted to remove the —SO₂Ph group to give the hydroxyl compound of formula 5. The hydroxyl group of the compound of formula 5 can be converted to a mesylate group (compound of formula 6), which can then be reacted with the protected pyrrolo[2,3-d]pyrimidine compound to give the compound of formula 7. The compound of formula 7 can then be deprotected to give a pyrrolidine base of formula 8. The compound of formula 8 can then be substituted for the compound of formula (d) in Scheme I, the compound of formula (d) in Scheme VI, or the compound of formula (ii) in Scheme VII to give the desired compound of Formula I. Alternatively, the hydroxyl compound of formula 5 of Scheme VIII can be formed by the process shown in Scheme IX.

Scheme VII

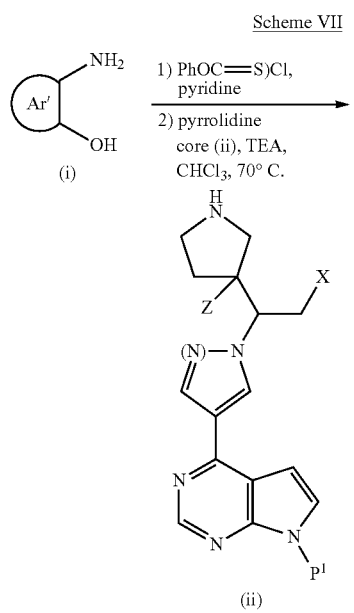

Scheme VIII

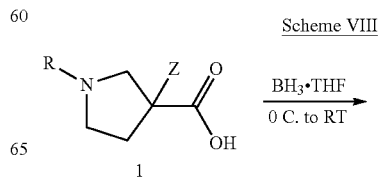

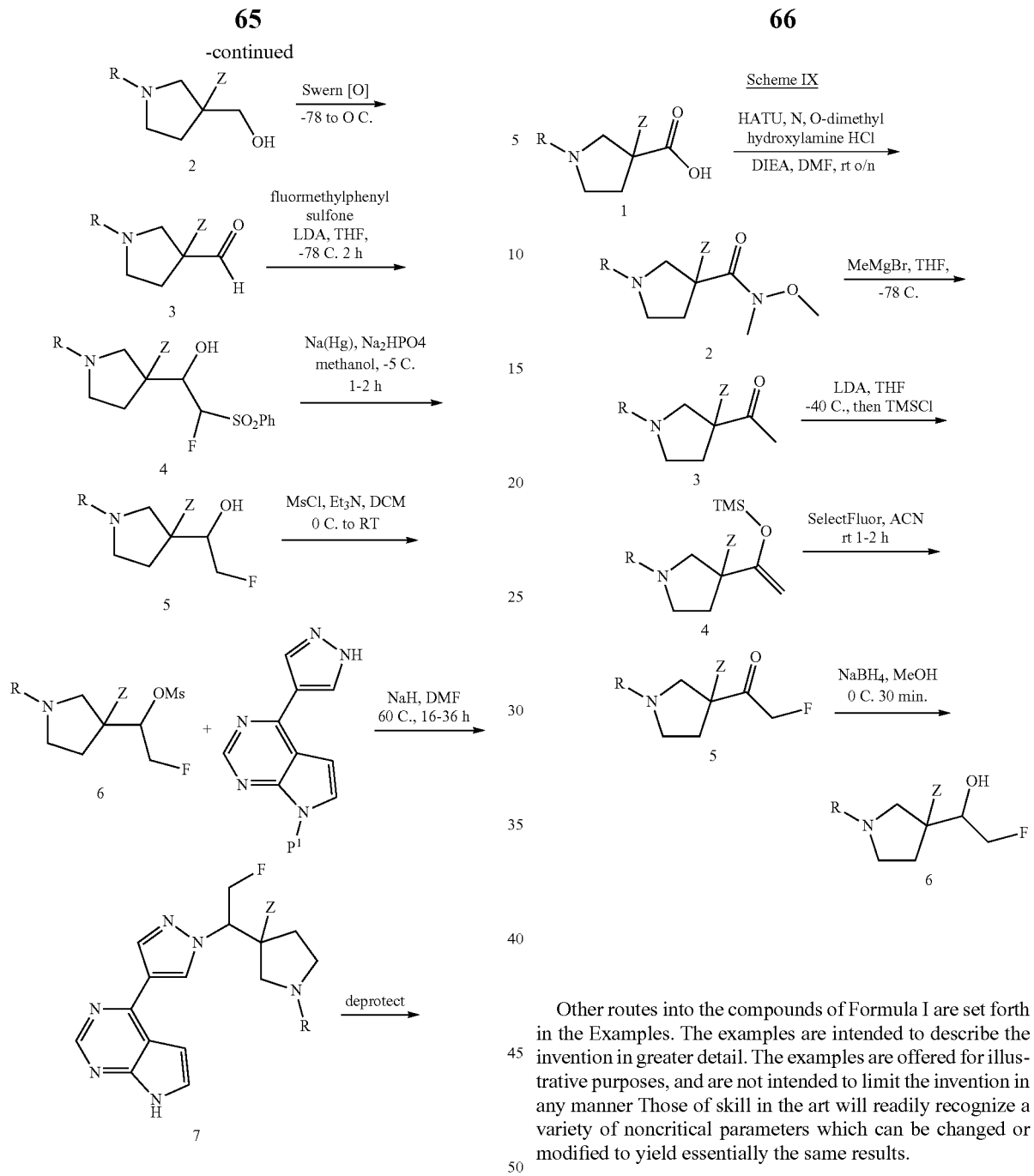

Other routes into the compounds of Formula I are set forth in the Examples. The examples are intended to describe the invention in greater detail. The examples are offered for illustrative purposes, and are not intended to limit the invention in any manner Those of skill in the art will readily recognize a variety of noncritical parameters which can be changed or modified to yield essentially the same results.

EXAMPLES

The following abbreviations are used throughout the text: NMP(N-methylpyrrolidone), EtOH (ethanol), HOAc (acetic acid), TFA (trifluoroacetic acid), DCM (methylene chloride or dichloromethane), MeOH (methanol), EDA (ethylenediamine), DIPEA (N,N-diisopropylethylamine), LDA (lithium diisopropylamide), MsCl (mesyl chloride), DMF (N,N-dimethylformamide), HATU (1-[Bis(dimethylamino)methylene]-1H-1,2,3-triazolo[4,5-b]pyridinium 3-oxide hexafluorophosphate), THF (tetrahydrofuran), LCMS (liquid chromatography-mass spectrometry), MS (mass spectrometry), HPLC (high performance liquid chromatography), LC (liquid chromatography), TMS (trimethylsilyl), MeCN or ACN (acetonitrile), IPA (isopropanol), EtOAc (ethyl acetate),

Example 1

3-[1-(6-chloropyrazin-2-yl)pyrrolidin-3-yl]-3-[4-(7H-pyrrolo[2,3-d]pyrimidin-4-yl)-1H-pyrazol-1-yl]propanenitrile (racemate of a single diastereomer)

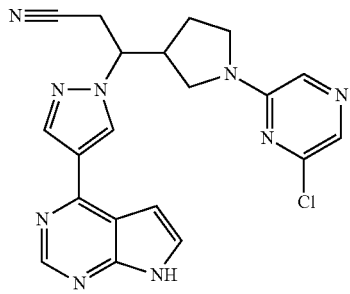 [SMILES: N#CCC(C1CCN(c2cncc(Cl)n2)C1)n1cc(-c2ncnc3[nH]ccc23)cn1]

Step 1. benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate Benzyl 3-[2-cyanovinyl]pyrrolidine-1-carboxylate (4.3 g, 0.017 mol, mixture of E and Z isomers prepared as described in WO 2007/070514 Ex. 742) was dissolved in acetonitrile (270 mL). 1,8-Diazabicyclo[5.4.0]undec-7-ene (5.02 mL, 0.0336 mol) was added, followed by 4-(1H-pyrazol-4-yl)-7-{[2-(trimethylsilyl)ethoxy]methyl}-7H-pyrrolo[2,3-d]pyrimidine (5.6 g, 0.017 mol, prepared as described in WO 2007/070514, Ex. 65). The mixture was stirred at RT overnight. The solvent was removed by rotary evaporation, and the residue was redissolved in ethyl acetate. The solution was washed successively with 1N HCl, water, saturated sodium bicarbonate, and brine, dried over sodium sulfate and concentrated in vacuo. The product was purified by flash column chromatography on silica gel, eluting with a gradient of 0-100% ethyl acetate in hexanes to afford diastereomer 1 (first to elute) (3.5 g, 36%) and diastereomer 2 (second to elute) (2.5 g, 25%). LCMS (M+H)$^+$: 572.2.

Step 2. 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile Benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (3.5 g, 6.1 mmol) (diastereomer 1 from Example 1, Step 1) was dissolved in 100 mL methanol, and a catalytic amount of 10% Pd—C was added. The mixture was shaken under 50 psi of hydrogen for 24 h. The mixture was then filtered and the solvent removed in vacuo. The product was used without further purification. LCMS (M+H)$^+$: 438.2.

Step 3. 3-[1-(6-chloropyrazin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (150 mg, 0.27 mmol) and 2,6-dichloropyrazine (49.0 mg, 0.329 mmol) in ethanol (1.2 mL), and N,N-diisopropylethylamine (96 μL, 0.55 mmol) was heated in a sealed vial in an oil bath held at 85° C. for one h. Flash column chromatography on silica gel, eluting with a gradient from 0-100% ethyl acetate in hexanes afforded product (49 mg, 27%). LCMS (M+H)$^+$: 550.0.

Step 4. 3-[1-(6-chloropyrazin-2-yl)pyrrolidin-3-yl]-3-[4-(7H-pyrrolo[2,3-d]pyrimidin-4-yl)-1H-pyrazol-1-yl]propanenitrile 3-[1-(6-Chloropyrazin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (15 mg, 0.027 mmol) was dissolved in DCM (1 mL), and 0.2 ml TFA was added. The mixture was stirred for 2 h, then concentrated. The residue was dissolved in MeOH (1 mL), and 0.2 ml EDA was added. Purification by preparative-HPLC/MS (C18 column eluting with a gradient of ACN/H$_2$O containing 0.15% NH$_4$OH) afforded product (7 mg, 61%). $^1$H NMR (400 MHz, CD$_3$OD): δ 8.66 (s, 2H), 8.41 (s, 1H), 7.77 (s, 1H), 7.67 (s, 1H), 7.50 (d, 1H), 6.93 (d, 1H), 4.85-4.76 (m, 1H), 3.86 (dd, 1H), 3.61-3.54 (m, 1H), 3.43-3.16 (m, 4H), 3.11-2.99 (m, 1H), 1.89-1.81 (m, 2H); LCMS (M+H)$^+$: 420.0.

Example 2

3-[1-(6-chloropyridin-2-yl)pyrrolidin-3-yl]-3-[4-(7H-pyrrolo[2,3-d]pyrimidin-4-yl)-1H-pyrazol-1-yl]propanenitrile (two different enantiomers isolated)

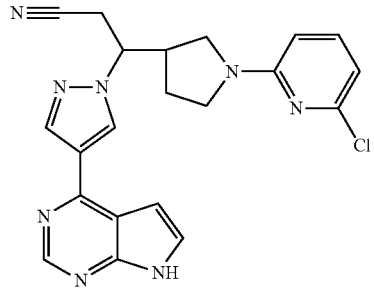 [SMILES: N#CCC(C1CCN(c2cccc(Cl)n2)C1)n1cc(-c2ncnc3[nH]ccc23)cn1]

Step 1. 3-[1-(6-chloropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (150 mg, 0.27 mmol, from Example 1, Step 2) and 2,6-dichloropyridine (48.7 mg, 0.329 mmol) in NMP (1.6 mL) and N,N-diisopropylethylamine (96 microL, 0.55 mmol) was heated to 135° C. for 20 min in the microwave. Purification by flash column chromatography on silica gel, eluting with a gradient from 0-80% ethyl acetate in hexanes, afforded the title product (28 mg, 18%). $^1$H NMR (400 MHz, CDCl$_3$): δ 8.85 (s, 1H), 8.36 (s, 1H), 8.36 (s, 1H), 7.41 (d, 1H), 7.37 (dd, 1H), 6.79 (d, 1H), 6.57 (d, 1H), 6.22 (d, 1H), 5.68 (s, 2H), 4.45 (dt, 1H), 3.91 (dd, 1H), 3.57-3.46 (m, 3H), 3.39-3.29 (m, 2H), 3.24 (dd, 1H), 3.13-3.01 (m, 1H), 3.01 (dd, 1H), 1.98-1.88 (m, 1H), 1.82-1.69 (m, 1H), 0.95-0.88 (m, 2H), −0.06 (s, 9H); LCMS (M+H)$^+$: 549.1.

DMSO (dimethylsulfoxide), tBu (tert-butyl), SEM (2-(trimethylsilyl)ethoxymethyl), h (hour or hours), and min (minute or minutes).

This racemic product was separated into its enantiomers by chiral HPLC (Chiral Technologies Chiralcel OJ-H, 5μ, 30×250 mm, 45% EtOH/Hexanes, 20 mL/min) to afford enantiomer 1 (first to elute, retention time 40.7 min) and enantiomer 2 (second to elute, retention time 51.6 min), which were deprotected separately in Step 2.

Step 2a. 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile (enantiomer 1)

3-[1-(6-Chloropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (enantiomer 1 from Step 1) was stirred in a solution containing 1:1 TFA/DCM (2 mL) for 2 h, and then concentrated. The residue was dissolved in 1 mL MeOH, and 0.2 mL EDA was added. Purification via preparative-HPLC/MS (C18 column eluting with a gradient of ACN/H$_2$O containing 0.15% NH$_4$OH) afforded product. $^1$H NMR (400 MHz, CDCl$_3$): δ 9.44 (br s, 1H), 8.84 (s, 1H), 8.37 (s, 2H), 7.39 (dd, 1H), 7.38 (dd, 1H), 6.79 (dd, 1H), 6.58 (d, 1H), 6.22 (d, 1H), 4.46 (dt, 1H), 3.92 (dd, 1H), 3.55-3.48 (m, 1H), 3.39-3.31 (m, 2H), 3.25 (dd, 1H), 3.13-3.02 (m, 1H), 3.02 (dd, 1H), 2.00-1.88 (m, 1H), 1.84-1.71 (m, 1H); LCMS (M+H)$^+$: 419.1.

Step 2b. 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile (enantiomer 2)

Performed as in Step 2a, using enantiomer 2 from Step 1: $^1$H NMR (400 MHz, CDCl$_3$): 9.59 (br s, 1H), 8.84 (s, 1H), 8.37 (s, 2H), 7.40 (dd, 1H), 7.38 (dd, 1H), 6.79 (dd, 1H), 6.58 (d, 1H), 6.22 (d, 1H), 4.46 (dt, 1H), 3.92 (dd, 1H), 3.55-3.48 (m, 1H), 3.39-3.31 (m, 2H), 3.25 (dd, 1H), 3.14-3.02 (m, 1H), 3.02 (dd, 1H), 1.99-1.90 (m, 1H), 1.83-1.72 (m, 1H); LCMS (M+H)$^+$: 419.1.

Example 3

3-[1-(2-chloropyrimidin-4-yl)pyrrolidin-3-yl]-3-[4-(7H-pyrrolo[2,3-d]pyrimidin-4-yl)-1H-pyrazol-1-yl]propanenitrile (two different enantiomers isolated)

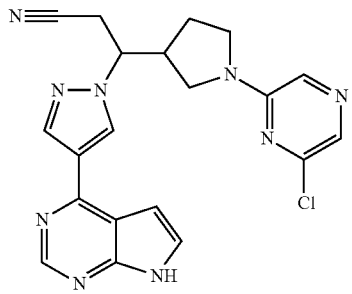 [SMILES: N#CCC(C1CCN(c2cncc(Cl)n2)C1)n1cc(-c2ncnc3[nH]ccc23)cn1]

Step 1. 3-[1-(2-chloropyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile and 3-(1-(4-chloropyrimidin-2-yl)pyrrolidin-3-yl)-3-(4-(7-((2-(trimethylsilyl)ethoxy)methyl)-7H-pyrrolo[2,3-d]pyrimidin-4-yl)-1H-pyrazol-1-yl)propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (181 mg, 0.331 mmol, prepared as in Example 1, Step 2) and 2,4-dichloropyrimidine (59 mg, 0.40 mmol) in 1,4-dioxane (1.1 mL) and N,N-diisopropylethylamine (115 microL) was heated to 70° C. for 110 min. The mixture was concentrated, then purified by flash column chromatography on silica gel, eluting with 0-5% methanol in DCM to afford two regioisomeric products. The reaction was repeated on the same scale, substituting ethanol (1.1 mL) for 1,4-dioxane and was heated to 80° C. for 1 h. The products of this run were chromatographed similarly and combined with the products of the previous run.

3-[1-(2-Chloropyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile: $^1$H NMR (500 MHz, d$_6$-DMSO, 90° C.): δ 8.81 (s, 1H), 8.76 (s, 1H), 8.40 (s, 1H), 8.02 (d, 1H), 7.71 (d, 1H), 7.04 (d, 1H), 6.45 (d, 1H), 5.65 (s, 2H), 4.85 (dt, 1H), 3.80 (br s, 1H), 3.61-3.57 (m, 2H), 3.53 (br s, 1H), 3.42-3.25 (m, 4H), 3.03-2.90 (m, 1H), 1.83-1.69 (m, 2H), 0.89-0.84 (m, 2H), −0.07 (s, 9H); LCMS (M+H)$^+$: 550.1.

Separation of 3-[1-(2-chloropyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile by chiral HPLC (Chiral Technologies Chiralpak IA, 5μ, 20×250 mm, 40% EtOH/Hexanes, 10 mL/min) afforded enantiomer 1 (first to elute, retention time 26.5 min), 42 mg, 9%; and enantiomer 2 (second to elute, retention time 32.7 min), 37 mg, 8%.

Separation of the isomer [3-(1-(4-chloropyrimidin-2-yl)pyrrolidin-3-yl)-3-(4-(7-((2-(trimethylsilyl)ethoxy)methyl)-7H-pyrrolo[2,3-d]pyrimidin-4-yl)-1H-pyrazol-1-yl)propanenitrile] by chiral HPLC (Chiral Technologies Chiralcel OJ-H, 5μ, 30×250 mm, 45% EtOH/Hexanes, 22 mL/min) afforded enantiomer 1 (first to elute, retention time 32.6 min), 12 mg, 2.6%; and enantiomer 2 (second to elute, retention time 39.6 min), 12 mg, 2.6%.

Step 2a. 3-[1-(2-chloropyrimidin-4-yl)pyrrolidin-3-yl]-3-[4-(7H-pyrrolo[2,3-d]pyrimidin-4-yl)-1H-pyrazol-1-yl]propanenitrile (enantiomer 1)

3-[1-(2-Chloropyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (42 mg, 0.076 mmol, Example 3, Step 1, enantiomer 1) was dissolved in 3 mL of 20% TFA/DCM. The mixture was stirred for 2 h, then concentrated. The residue was dissolved in MeOH (2 mL), and 0.3 mL EDA was added. Following completion of the deprotection reaction, preparative-HPLC/MS (C18 column eluting with a gradient of ACN/H$_2$O containing 0.15% NH$_4$OH) was used to purify the product (18 mg, 56%). $^1$H NMR (400 MHz, d$_6$-DMSO): δ 12.13 (br s, 1H), 8.87 (s, 1H), 8.68 (s, 1H), 8.43 (s, 1H), 8.08 (d, 0.5H), 8.02 (d, 0.5H), 7.61 (d, 1H), 6.99 (d, 1H), 6.51-6.45 (m, 1H), 4.86-4.78 (m, 1H), 3.90-2.81 (m, 7H), 1.79-1.58 (m, 2H); LCMS (M+H)$^+$: 420.0.

Step 2b. 3-[1-(2-chloropyrimidin-4-yl)pyrrolidin-3-yl]-3-[4-(7H-pyrrolo[2,3-d]pyrimidin-4-yl)-1H-pyrazol-1-yl]propanenitrile (enantiomer 2)

Enantiomer 2 of 3-[1-(2-chloropyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile from Example 3, Step 1 (37 mg) was deprotected and purified as described in step 2a (17 mg, 60%). $^1$H NMR (400 MHz, d$_6$-DMSO): δ 12.13 (br s, 1H), 8.87 (s, 1H), 8.68 (s, 1H), 8.43 (s, 1H), 8.08 (d, 0.5H), 8.02 (d, 0.5H), 7.61 (dd, 1H), 6.99 (d, 1H), 6.48 (dd, 1H), 4.87-4.78 (m, 1H), 3.88-2.78 (m, 7H), 1.79-1.56 (m, 2H); LCMS (M+H)$^+$: 420.0.

Example 4a

3-[1-(4-chloropyrimidin-2-yl)pyrrolidin-3-yl]-3-[4-(7H-pyrrolo[2,3-d]pyrimidin-4-yl)-1H-pyrazol-1-yl]propanenitrile (one enantiomer isolated)

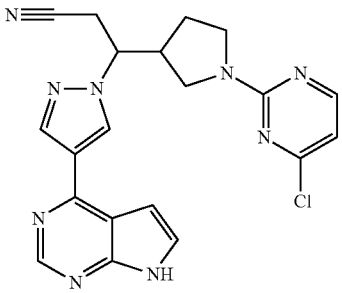 [SMILES: N#CCC(C1CCN(c2nccc(Cl)n2)C1)n1cc(-c2ncnc3[nH]ccc23)cn1]

3-[1-(4-chloropyrimidin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (12 mg, 0.022 mmol, enantiomer 1 from Example 3, Step 1) was dissolved in 20% TFA/DCM (2 mL). The mixture was stirred for 2 h, then concentrated. The residue was dissolved in MeOH (2 mL), and 0.3 mL EDA was added. Following complete reaction, preparative-HPLC/MS (C18 column eluting with a gradient of ACN/H$_2$O containing 0.15% NH$_4$OH) was used to purify the product (6 mg, 65%). $^1$H NMR (400 MHz, CDCl$_3$): δ 10.03 (br s, 1H), 8.85 (s, 1H), 8.39 (s, 1H), 8.38 (s, 1H), 8.18 (d, 1H), 7.41 (dd, 1H), 6.79 (dd, 1H), 6.56 (d, 1H), 4.47 (dt, 1H), 4.00 (dd, 1H), 3.81-3.73 (m, 1H), 3.52-3.44 (m, 1H), 3.38 (dd, 1H), 3.26 (dd, 1H), 3.10 (dq, 1H), 3.00 (dd, 1H), 1.97-1.89 (m, 1H), 1.82-1.70 (m, 1H); LCMS (M+H)$^+$: 420.0.

Example 4b

3-[1-(4-chloropyrimidin-2-yl)pyrrolidin-3-yl]-3-[4-(7H-pyrrolo[2,3-d]pyrimidin-4-yl)-1H-pyrazol-1-yl]propanenitrile (one enantiomer isolated)

Enantiomer 2 of 3-[1-(4-chloropyrimidin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile from Example 3, Step 1 (12 mg) was deprotected and purified in the same manner as described for Example 4a (8 mg, 87%). $^1$H NMR (400 MHz, CDCl$_3$): δ 10.24 (br s, 1H), 8.86 (s, 1H), 8.39 (s, 1H), 8.38 (s, 1H), 8.18 (d, 1H), 7.45-7.41 (m, 1H), 6.82-6.78 (m, 1H), 6.56 (d, 1H), 4.47 (dt, 1H), 4.00 (dd, 1H), 3.82-3.73 (m, 1H), 3.54-3.44 (m, 1H), 3.42-3.34 (m, 1H), 3.26 (dd, 1H), 3.16-3.05 (m, 1H), 3.04-2.96 (m, 1H), 1.98-1.88 (m, 1H), 1.82-1.70 (m, 1H); LCMS (M+H)$^+$: 420.0.

Example 5

3-[1-(4-bromo-1,3-thiazol-2-yl)pyrrolidin-3-yl]-3-[4-(7H-pyrrolo[2,3-d]pyrimidin-4-yl)-1H-pyrazol-1-yl]propanenitrile trifluoroacetate

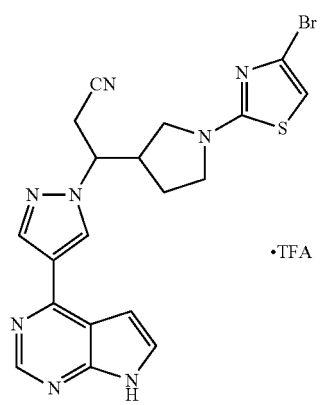 [SMILES: N#CCC(C1CCN(c2nc(Br)cs2)C1)n1cc(-c2ncnc3[nH]ccc23)cn1]

Step 1. 3-[1-(4-bromo-1,3-thiazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (151 mg, 0.345 mmol, from Example 1, Step 2) and 2,4-dibromo-1,3-thiazole (126 mg, 0.518 mmol) in NMP (0.50 mL), and N,N-diisopropylethylamine (0.12 mL) was heated to 135° C. in the microwave for 50 min. The product was purified by flash column chromatography on silica gel, eluting with a gradient from 0-60% ethyl acetate in hexanes to afford product as a white solid (66 mg, 32%). $^1$H NMR (400 MHz, CDCl$_3$): δ 8.85 (s, 1H), 8.36 (s, 1H), 8.35 (s, 1H), 7.42 (d, 1H), 6.79 (d, 1H), 6.38 (s, 1H), 5.68 (s, 2H), 4.47 (dt, 1H), 3.89 (dd, 1H), 3.57-3.52 (m, 2H), 3.51-3.33 (m, 1H), 3.22 (dd, 1H), 3.20-3.10 (m, 1H), 2.96 (dd, 1H), 2.04-1.77 (m, 2H), 0.95-0.90 (m, 2H), −0.06 (s, 9H); LCMS (M+H)$^+$: 599.0, 601.0.

Step 2. 3-[1-(4-bromo-1,3-thiazol-2-yl)pyrrolidin-3-yl]-3-[4-(7H-pyrrolo[2,3-d]pyrimidin-4-yl)-1H-pyrazol-1-yl]propanenitrile trifluoroacetate 3-[1-(4-Bromo-1,3-thiazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (10.0 mg, 0.0167 mmol) was dissolved in 20% TFA/DCM and stirred for 2 h. The solvents were evaporated, The residue was redissolved in 1 mL MeOH, and 0.2 mL of EDA was added. After the reaction was determined complete, preparative-HPLC/MS (C18 column eluting with a gradient of ACN/H$_2$O containing 0.1% TFA) was used to purify the product, which was obtained as the trifluoroacetate salt (6 mg). $^1$H NMR (400 MHz, d$_6$-DMSO): δ 12.63 (br s, 1H), 9.00 (br s, 1H), 8.84 (br s, 1H), 8.55 (br s, 1H), 7.91 (br s, 1H), 7.79 (br s, 1H), 7.15 (br s, 1H), 4.96-4.79 (m, 1H), 4.01-3.94 (m, 1H), 3.70-3.64 (m, 1H), 3.54-3.19 (m, 4H), 3.09-2.90 (m, 1H), 1.82-1.61 (m, 2H); LCMS (M+H)$^+$: 469.0, 470.9.

Example 6

3-{1-[4-(dimethylamino)pyrimidin-2-yl]pyrrolidin-3-yl}-3-[4-(7H-pyrrolo[2,3-d]pyrimidin-4-yl)-1H-pyrazol-1-yl]propanenitrile

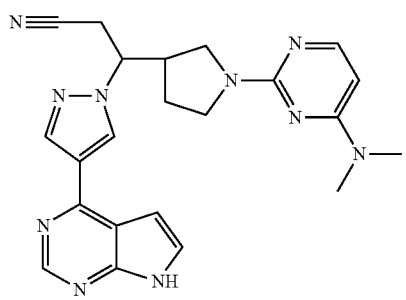 [SMILES: CN(C)c1ccnc(N2CCC(C(CC#N)n3cc(-c4ncnc5[nH]ccc45)cn3)C2)n1]

3-[1-(4-Chloropyrimidin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (11 mg, 0.020 mmol, racemic, from Example 3, Step 1) was mixed with 2.0 M of dimethylamine in THF (0.10 mL). The mixture was heated to 70° C. for 1.5 h and then concentrated. The crude product was deprotected by stirring in a solution of 1:1 TFA/DCM for 1.5 h. After removal of the solvent in vacuo, the residue was dissolved in methanol, and 0.2 mL of EDA was added. The product was purified via preparative-HPLC/MS (C18 column eluting with a gradient of ACN/H$_2$O containing 0.15% NH$_4$OH). $^1$H NMR (400 MHz, CDCl$_3$): δ 9.72 (br s, 1H), 8.85 (s, 1H), 8.38 (s, 1H), 8.37 (s, 1H), 7.91 (d, 1H), 7.39 (dd, 1H), 6.80 (dd, 1H), 5.82 (d, 1H), 4.44 (dt, 1H), 3.96 (dd, 1H), 3.74 (ddd, 1H), 3.45 (dddd, 1H), 3.39 (dd, 1H), 3.25 (dd, 1H), 3.05 (s, 6H), 2.98 (dd, 1H), 1.91-1.82 (m, 1H), 1.74-1.63 (m, 1H); LCMS (M+H)$^+$: 429.1.

Example 7

3-{1-[4-(isopropylamino)pyrimidin-2-yl]pyrrolidin-3-yl}-3-[4-(7H-pyrrolo[2,3-d]pyrimidin-4-yl)-1H-pyrazol-1-yl]propanenitrile 3-[1-(4-Chloropyrimidin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (7 mg, 0.01 mmol; racemic, from Example 3, Step 1) was mixed with 2-propanamine (0.011 mL, 0.127 mmol) in 0.1 mL THF. The mixture was heated to 70° C. over four days. Following removal of the solvent, the product was deprotected by stirring in a solution of 1:1 TFA/DCM for 1.5 h, followed by evaporation of solvent, and subsequent stirring with 0.2 mL EDA in methanol. Preparative-HPLC/MS (C18 column eluting with a gradient of ACN/H$_2$O containing 0.15% NH$_4$OH) was used to purify the product (1 mg, 18%). LCMS (M+H)$^+$: 443.2.

Example 9

3-[1-(1,3-benzoxazol-2-yl)pyrrolidin-3-yl]-3-[4-(7H-pyrrolo[2,3-d]pyrimidin-4-yl)-1H-pyrazol-1-yl]propanenitrile (two different enantiomers isolated)

Step 1. Separation of enantiomers of diastereomer 1 of benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate Benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (4.2 g, 7.3 mmol, from Example 1, Step 1, diastereomer 1) was separated into its enantiomers via chiral HPLC (Chiral Technologies Chiralcel OJ-H, 5μ, 30×250 mm, 45% EtOH/Hexanes, 20 mL/min) to afford 1.6 g of enantiomer 1 (first to elute, retention time 46.1 min) and 1.6 g of enantiomer 2 (second to elute, retention time 57.5 min). Each was deprotected separately according to the following procedure in Step 2.

Step 2a. 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (enantiomer 1)

Benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (1.6 g, 2.8 mmol, enantiomer 1, from Step 1) was dissolved in methanol (60 mL), and a catalytic amount of 10% Pd—C was added. The mixture was shaken under hydrogen (50 psi) for 3.5 h. The mixture was filtered and the solvent removed by rotary evaporation to afford product (1 g, 80%). LCMS (M+H)$^+$: 438.2.

Step 2b. 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (enantiomer 2)

Deprotection of enantiomer 2 (from Step 1) of benzyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (1.6 g, 2.8 mmol) was performed as described in step 2a, except the hydrogenation proceeded for 4 h. LCMS (M+H)$^+$: 438.1.

Step 3a. 3-[1-(1,3-benzoxazol-2-yl)pyrrolidin-3-yl]-3-[4-(7H-pyrrolo[2,3-d]pyrimidin-4-yl)-1H-pyrazol-1-yl]propanenitrile (enantiomer 1)

3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (10.0 mg, 0.0228 mmol, enantiomer 1, from Step 2a) and 2-chlorobenzoxazole (4.2 mg, 0.027 mmol) were dissolved in 1,4-dioxane (0.20 mL), and N,N-Diisopropylethylamine (8.0 microL, 0.046 mmol) was added. The mixture was heated to 70° C. for 1.5 h. The solvent was removed in vacuo and the residue was sequentially stirred with 50% TFA/DCM for 1.5 h, concentrated, and stirred with 0.3 mL EDA in methanol for 30 min. Purification via preparative-HPLC/MS (C18 column eluting with a gradient of ACN/H$_2$O containing 0.15% NH$_4$OH) afforded product. $^1$H NMR (400 MHz, d$_6$-DMSO): δ 12.13 (br s, 1H), 8.89 (s, 1H), 8.68 (s, 1H), 8.43 (s, 1H), 7.61 (d, 1H), 7.39 (d, 1H), 7.26 (d, 1H), 7.13 (t, 1H), 7.02-6.95 (m, 2H), 4.86 (dt, 1H), 3.87 (dd, 1H), 3.68-3.60 (m, 1H), 3.53-3.29 (m, 4H), 3.03-2.91 (m, 1H), 1.78-1.64 (m, 2H); LCMS (M+H)$^+$: 425.1.

Step 3b. 3-[1-(1,3-benzoxazol-2-yl)pyrrolidin-3-yl]-3-[4-(7H-pyrrolo[2,3-d]pyrimidin-4-yl)-1H-pyrazol-1-yl]propanenitrile (enantiomer 2)

3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (10.0 mg, 0.0228 mmol; enantiomer 2, from step 2b) and 2-chlorobenzoxazole (4.2 mg, 0.027 mmol) were dissolved in 1,4-dioxane (0.20 mL) and N,N-diisopropylethylamine (8.0 microL, 0.046 mmol) was added. The mixture was heated to 70° C. for 1.5 h. The solvent was removed in vacuo and the residue was sequentially stirred with 50% TFA/DCM for 1.5 h, concentrated, and stirred with 0.3 mL EDA in methanol for 30 min. Purification via preparative-HPLC/MS (C18 column eluting with a gradient of ACN/H$_2$O containing 0.15% NH$_4$OH) afforded product. $^1$H NMR (400 MHz, d$_6$-DMSO): δ 12.13 (br s, 1H), 8.89 (s, 1H), 8.68 (s, 1H), 8.43 (s, 1H), 7.61 (d, 1H), 7.39 (d, 1H), 7.26 (dd, 1H), 7.13 (dt, 1H), 7.01-6.96 (m, 2H), 4.86 (dt, 1H), 3.87 (dd, 1H), 3.68-3.61 (m, 1H), 3.53-3.28 (m, 4H), 3.03-2.91 (m, 1H), 1.79-1.64 (m, 2H); LCMS (M+H)$^+$: 425.0.

Example 10

3-[1-(5-chloro-1,3-benzoxazol-2-yl)pyrrolidin-3-yl]-3-[4-(7H-pyrrolo[2,3-d]pyrimidin-4-yl)-1H-pyrazol-1-yl]propanenitrile (one enantiomer isolated)

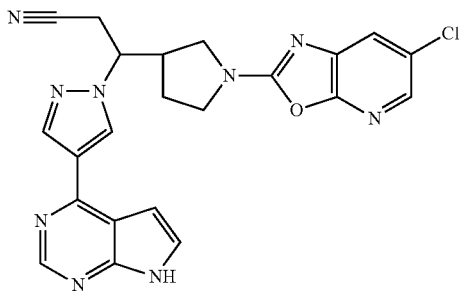 [SMILES: N#CCC(C1CCN(c2nc3cc(Cl)cnc3o2)C1)n1cc(-c2ncnc3[nH]ccc23)cn1]

To a solution of 5-chloro-1,3-benzoxazole-2-thiol (0.50 g, 2.7 mmol, Aldrich) in toluene (10 mL) was added thionyl chloride (0.59 mL, 8.1 mmol) followed by a drop of DMF. The reaction was heated to reflux for 30 min and the solvent removed in vacuo. A portion of this crude product (17 mg) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (20.0 mg, 0.0457 mmol; enantiomer 2 from Example 9, Step 2b) were dissolved in 1,4-dioxane (0.40 mL) and N,N-diisopropylethylamine (16 microL, 0.091 mmol) was added. The mixture was heated to 70° C. for 1.5 h. The solvent was removed in vacuo and the residue was sequentially stirred with 50% TFA/DCM for 1.5 h, concentrated, then stirred with 0.3 mL EDA in methanol for 30 min. Purification via preparative-HPLC/MS (C18 column eluting with a gradient of ACN/H$_2$O containing 0.15% NH$_4$OH) afforded product. $^1$H NMR (400 MHz, d$_6$-DMSO): δ 12.13 (br s, 1H), 8.88 (s, 1H), 8.68 (s, 1H), 8.43 (s, 1H), 7.60 (d, 1H), 7.41 (d, 1H), 7.31 (d, 1H), 7.02-6.97 (m, 2H), 4.86 (dt, 1H), 3.86 (dd, 1H), 3.68-3.59 (m, 1H), 3.54-3.28 (m, 4H), 3.03-2.90 (m, 1H), 1.77-1.67 (m, 2H); LCMS (M+H)$^+$: 459.0, 461.0.

Example 11

3-(1-[1,3]oxazolo[4,5-c]pyridin-2-ylpyrrolidin-3-yl)-3-[4-(7H-pyrrolo[2,3-d]pyrimidin-4-yl)-1H-pyrazol-1-yl]propanenitrile (one enantiomer isolated)

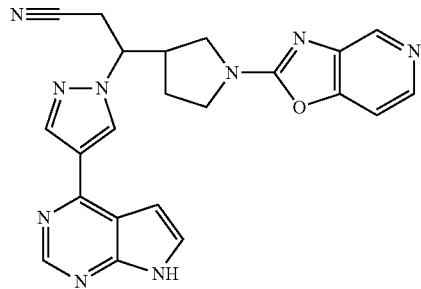 [SMILES: N#CCC(C1CCN(c2nc3cnccc3o2)C1)n1cc(-c2ncnc3[nH]ccc23)cn1]

A solution of 3-aminopyridin-4-ol (0.250 g, 2.27 mmol, Bosche Scientific) and potassium O-ethyl dithiocarbonate (0.400 g, 2.50 mmol) in ethanol (1 mL) was heated to reflux. When the reaction was determined complete, it was cooled to ambient temperature and partitioned between 1N HCl and ethyl acetate. The organic layer was washed with water, dried over sodium sulfate, decanted and concentrated. This crude product was dissolved in toluene (6 mL) and thionyl chloride (0.365 mL, 5.01 mmol) followed by DMF (3 microL) was added. The mixture was heated to reflux for 1 h, cooled and the solvent removed in vacuo. A portion of this crude product (14 mg) was dissolved in 1,4-dioxane (0.40 mL), along with 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (20.0 mg, 0.0457 mmol, enantiomer 2 from Example 9, Step 2b), and N,N-diisopropylethylamine (16 microL, 0.091 mmol) was added. The mixture was heated to 70° C. for 1.5 h. The solvent was removed in vacuo and the residue was sequentially stirred with 50% TFA/DCM for 1.5 h, concentrated, and stirred with 0.3 mL EDA in methanol for 30 min. Purification via preparative-HPLC/MS (C18 column eluting with a gradient of ACN/H$_2$O containing 0.15% NH$_4$OH) afforded product. $^1$H NMR (400 MHz, d$_6$-DMSO): δ 8.89 (s, 1H), 8.68 (s, 1H), 8.44 (s, 1H), 8.11 (dd, 1H), 7.72 (dd, 1H), 7.60 (d, 1H), 6.99 (d, 1H), 6.96 (dd, 1H), 4.88 (dt, 1H), 3.90 (dd, 1H), 3.71-3.63 (m, 1H), 3.58-3.30 (m, 4H), 3.04-2.93 (m, 1H), 1.80-1.66 (m, 2H); LCMS (M+H)$^+$: 426.1.

Example 12

3-(1-[1,3]oxazolo[4,5-b]pyridin-2-ylpyrrolidin-3-yl)-3-[4-(7H-pyrrolo[2,3-d]pyrimidin-4-yl)-1H-pyrazol-1-yl]propanenitrile (one enantiomer isolated)

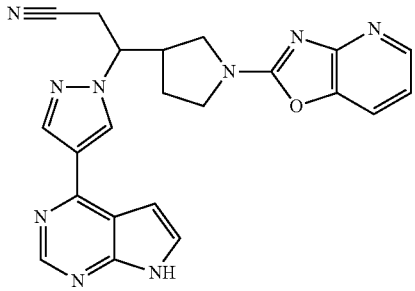 [SMILES: N#CCC(C1CCN(c2nc3ncccc3o2)C1)n1cc(-c2ncnc3[nH]ccc23)cn1]

A solution of 2-aminopyridin-3-ol (0.250 g, 2.27 mmol, Aldrich) and potassium O-ethyl dithiocarbonate (0.400 g, 2.50 mmol) in ethanol (1 mL) was heated to 120° C. in the microwave for 10 min. The reaction mixture was partitioned between 1N HCl and ethyl acetate. The organic layer was washed with water, dried over sodium sulfate, decanted and concentrated. This crude product was dissolved in toluene (6 mL) and thionyl chloride (0.365 mL, 5.01 mmol) followed by DMF (3 microL) was added. The mixture was heated to reflux for 1 h, cooled and the solvent removed in vacuo. A portion of this crude product (14 mg) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (20.0 mg, 0.0457 mmol; enantiomer 2, from Example 9, Step 2b) were dissolved in 1,4-dioxane (0.40 mL), and N,N-diisopropylethylamine (16 microL, 0.091 mmol) was added. The mixture was heated to 70° C. for 1.5 h. The solvent was removed in vacuo and the residue was sequentially stirred with 50% TFA/DCM for 1.5 h, concentrated, and stirred with 0.3 mL EDA in methanol for 30 min. Purification via preparative-HPLC/MS (C18 column eluting with a gradient of ACN/H$_2$O containing 0.15% NH$_4$OH) afforded product. $^1$H NMR (400 MHz, d$_6$-DMSO): δ 12.08 (br s, 1H), 8.89 (s, 1H), 8.68 (s, 1H), 8.44 (s, 1H), 8.11 (dd, 1H), 7.72 (dd, 1H), 7.60 (d, 1H), 6.99 (d, 1H), 6.96 (dd, 1H), 4.88 (dt, 1H), 3.90 (dd, 1H), 3.72-3.63 (m, 1H), 3.58-3.31 (m, 4H), 3.04-2.92 (m, 1H), 1.80-1.66 (m, 2H); LCMS (M+H)$^+$: 426.1.

Example 13a 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile (one enantiomer isolated)

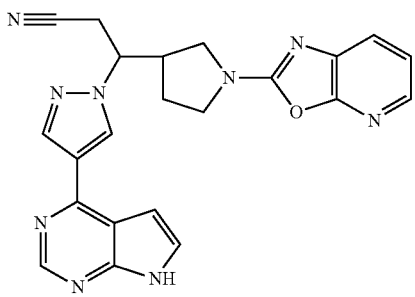

To a solution of 3-aminopyridin-2-ol (0.500 g, 4.54 mmol, 3B Scientific) in THF (4 mL) was added thiocarbonyldiimidazole (1.21 g, 6.81 mmol). After the reaction was determined complete, the THF was removed in vacuo. The product was partitioned between ethyl acetate and 1N HCl sufficient to adjust the pH to 4-5. The aqueous portion was extracted two further times with ethyl acetate. The combined extracts were washed with brine, dried over sodium sulfate, decanted and concentrated. A suspension of oxazolo[5,4-b]pyridine-2(1H)-thione (0.65 g, 4.3 mmol) prepared in this manner in toluene (13 mL) was treated with thionyl chloride (0.94 mL, 12.9 mmol) and a drop of DMF. The reaction was heated to reflux for 1 h, and the solvent was then removed by rotary evaporation. This crude product (0.018 g) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.020 g, 0.046 mmol, enantiomer 2 from Example 9, Step 2b) in 1,4-dioxane (0.2 mL) containing N,N-diisopropylethylamine (32 microL, 0.183 mmol) was heated to 70° C. for 1.5 h. Upon cooling, the product was purified by applying to a plug of silica, first eluting with ethyl acetate, then with methanol. The methanol eluent was concentrated to afford about 30 mg of crude material with desired as the major component. The product was deprotected by sequentially stirring with 20% TFA in DCM for 2 h, evaporation of solvent, then stirring with EDA in methanol. Purification via preparative-HPLC/MS (C18 column eluting with a gradient of ACN/H$_2$O containing 0.15% NH$_4$OH) afforded product (5 mg, 25%). $^1$H NMR (400 MHz, d$_6$-DMSO): δ 11.97 (br s, 1H), 8.82 (s, 1H), 8.61 (s, 1H), 8.37 (s, 1H), 7.79 (dd, 1H), 7.56-7.52 (m, 2H), 7.12 (dd, 1H), 6.92 (d, 1H), 4.80 (dt, 1H), 3.82 (dd, 1H), 3.63-3.54 (m, 1H), 3.50-3.24 (m, 4H), 2.97-2.85 (m, 1H), 1.73-1.61 (m, 2H); LCMS (M+H)$^+$: 426.1.

Example 13b 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile (one enantiomer isolated)

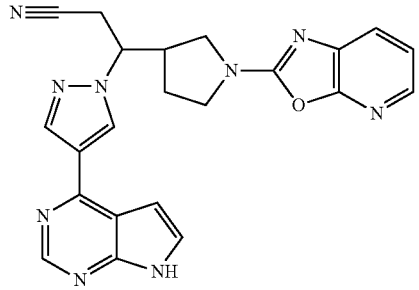 [SMILES: N#CCC(C1CCN(c2nc3cccnc3o2)C1)n1cc(-c2ncnc3[nH]ccc23)cn1]

To a solution of 3-aminopyridin-2-ol (0.500 g, 4.54 mmol, 3B Scientific) in THF (4 mL) was added thiocarbonyldiimidazole (1.21 g, 6.81 mmol). After the reaction was determined complete, the THF was removed in vacuo. The product was partitioned between ethyl acetate and 1N HCl sufficient to adjust the pH to 4-5. The aqueous portion was extracted two further times with ethyl acetate. The combined extracts were washed with brine, dried over sodium sulfate, decanted and concentrated. A suspension of oxazolo[5,4-b]pyridine-2(1H)-thione (0.65 g, 4.3 mmol) prepared in this manner in toluene (13 mL) was treated with thionyl chloride (0.94 mL, 12.9 mmol) and a drop of DMF. The reaction was heated to reflux for 1 h, and the solvent was then removed by rotary evaporation. This crude product (0.018 g) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.020 g, 0.046 mmol, enantiomer 1 from Example 9, step 2a) in 1,4-dioxane (0.2 mL) containing N,N-diisopropylethylamine (32 microL, 0.183 mmol) was heated to 70° C. for 1.5 h and then solvent evaporated. Deprotected by stirring with 20% TFA/DCM for 2 h, followed by evaporation and stirring with EDA (0.3 mL) in methanol for 1 h. Purified by preparative-HPLC/MS (C18 column eluting with a gradient of ACN/H$_2$O containing 0.15% NH$_4$OH) to afford product (5 mg, 25%). $^1$H NMR (400 MHz, d$_6$-DMSO): δ 12.10 (br s, 1H), 8.89 (s, 1H), 8.68 (s, 1H), 8.43 (s, 1H), 7.85 (dd, 1H), 7.62-7.59 (m, 2H), 7.19 (dd, 1H), 6.99 (dd, 1H), 4.87 (dt, 1H), 3.89 (dd, 1H), 3.69-3.61 (m, 1H), 3.57-3.30 (m, 4H), 3.03-2.91 (m, 1H), 1.78-1.68 (m, 2H); LCMS (M+H)$^+$: 426.1.

Example 13c 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile (one enantiomer isolated)

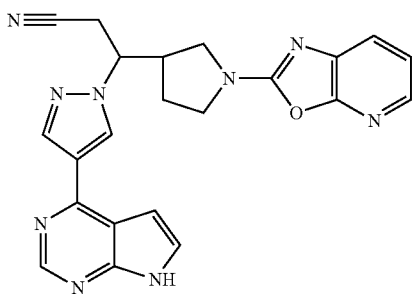

Step 1. 3-(1-[1,3]oxazolo[5,4-b]pyridin-2-ylpyrrolidin-3-yl)-3-[4-(7-{[2-(trimethylsilyl)ethoxy]methyl}-7H-pyrrolo[2,3-d]pyrimidin-4-yl)-1H-pyrazol-1-yl]propanenitrile Oxazolo[5,4-b]pyridine-2(1H)-thione (1.17 g, 7.68 mmol, prepared as in Example 33, Step 4) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (2.80 g, 6.40 mmol from Example 15, Step 3) in 1,4-dioxane (30 mL) was heated to 70° C. for 2 h. The solvent was removed in vacuo. The crude product was reconstituted in ethanol (40 mL) and treated with silver nitrate (3 g, 15 mmol) and aqueous ammonium hydroxide (6 mL) portionwise over the course of 20 h. Into the reaction was added water, 1N NaOH and brine. Insoluble material was removed by filtration. The layers of the filtrate were separated. The aqueous portion was extracted with three portions of ethyl acetate. The extracts were dried over sodium sulfate, decanted and concentrated. The crude product was purified by flash column chromatography on silica gel, eluting with 10% MeOH/DCM to afford the product as an off-white foam (2.84 g, 80%). $^1$H NMR (300 MHz, CDCl$_3$): δ 8.83 (s, 1H), 8.37 (s, 1H), 8.36 (s, 1H), 7.92 (dd, 1H), 7.57 (dd, 1H), 7.40 (d, 1H), 7.13 (dd, 1H), 6.78 (d, 1H), 5.67 (s, 2H), 4.52 (dt, 1H), 4.05 (dd, 1H), 3.82 (ddd, 1H), 3.67-3.44 (m, 4H), 3.25 (dd, 1H), 3.24-3.09 (m, 1H), 2.98 (dd, 1H), 2.06-1.74 (m, 2H), 0.97-0.88 (m, 2H), −0.06 (s, 9H); LCMS (M+H)$^+$: 556.1.

Step 2. 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile 3-(1-[1,3]Oxazolo[5,4-b]pyridin-2-ylpyrrolidin-3-yl)-3-[4-(7-{[2-(trimethylsilyl)ethoxy]methyl}-7H-pyrrolo[2,3-d]pyrimidin-4-yl)-1H-pyrazol-1-yl]propanenitrile (5.35 g, 9.63 mmol, prepared by the method of Step 1) was stirred in a 2:1 mixture of DCM and TFA (60 mL) for 6 h. The solvents were removed by rotary evaporation. The crude residue was dissolved in methanol (50 mL) containing EDA (5.15 mL, 77.0 mmol) and was stirred overnight. After removal of solvent, the product was purified by flash column chromatography on silica gel, eluting with a gradient from 0-15% MeOH/DCM (3.59 g, 88%). $^1$H NMR (300 MHz, CDCl$_3$): δ 8.72 (s, 1H), 8.40 (s, 1H), 8.34 (s, 1H), 7.89 (dd, 1H), 7.54 (dd, 1H), 7.36 (d, 1H), 7.12 (dd, 1H), 6.75 (d, 1H), 4.56 (dt, 1H), 4.01 (dd, 1H), 3.80 (ddd, 1H), 3.60 (ddd, 1H), 3.48 (dd, 1H), 3.26 (dd, 1H), 3.21-3.06 (m, 1H), 3.02 (dd, 1H), 2.03-1.76 (m, 2H); LCMS (M+H)$^+$: 426.1.

Example 14

3-[1-(6-methyl[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile (one enantiomer isolated)

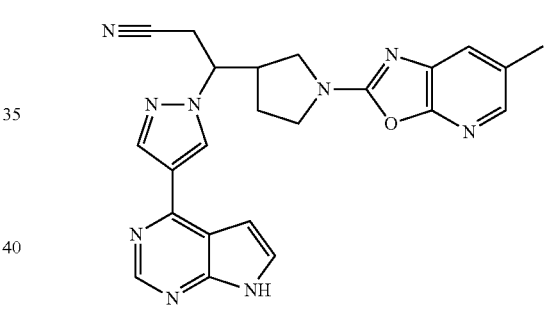

Step 1.
6-methyl[1,3]oxazolo[5,4-b]pyridine-2(1H)-thione

3-Amino-5-methylpyridin-2-ol (0.21 g, 1.7 mmol) was dissolved in THF (5 mL), and 1,1'-thiocarbonyldiimidazole (0.48 g, 2.7 mmol) was added. The mixture was stirred at RT for 20 min. The reaction was diluted with water, treated with 1N HCl to adjust the pH to the range of 4-5. The product was then extracted with ethyl acetate, the extracts were washed with brine, and dried over sodium sulfate, filtered and concentrated to afford the product, used without further purification in the following step. LCMS (M+H)$^+$: m/z=167.0.

Step 2.
2-chloro-6-methyl[1,3]oxazolo[5,4-b]pyridine

To a solution of 6-methyl[1,3]oxazolo[5,4-b]pyridine-2(1H)-thione (0.23 g, 1.4 mmol) in toluene (6.0 mL) was added thionyl chloride (0.36 mL, 5.0 mmol), followed by a catalytic drop of DMF. The mixture was then heated to reflux for 1 h. The reaction mixture was cooled and the solvent removed in vacuo. LCMS (M+H)$^+$: 168.9, 170.9.

Step 3. 3-[1-(6-methyl[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (20.0 mg, 0.0457 mmol, enantiomer 2, from Example 9, step 2b) and 2-chloro-6-methyl[1,3]oxazolo[5,4-b]pyridine (15.4 mg, 0.0914 mmol) were dissolved in 1,4-dioxane (0.40 mL), and N,N-diisopropylethylamine (16 microL, 0.091 mmol) was added. The mixture was heated to 70° C. for 1.5 h. The mixture was concentrated, then sequentially stirred with 50% TFA/DCM for 1.5 h, concentrated, and stirred with 0.3 mL EDA in methanol for 30 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.11 (br s, 1H), 8.88 (s, 1H), 8.68 (s, 1H), 8.43 (s, 1H), 7.66 (dd, 1H), 7.60 (d, 1H), 7.42 (dd, 1H), 6.98 (d, 1H), 4.86 (dt, 1H), 3.87 (dd, 1H), 3.67-3.60 (m, 1H), 3.55-3.30 (m, 4H), 3.02-2.90 (m, 1H), 2.30 (s, 3H), 1.77-1.67 (m, 2H); LCMS (M+H)$^+$: 440.1.

Example 15

3-[1-(6-fluoro[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile (one enantiomer isolated)

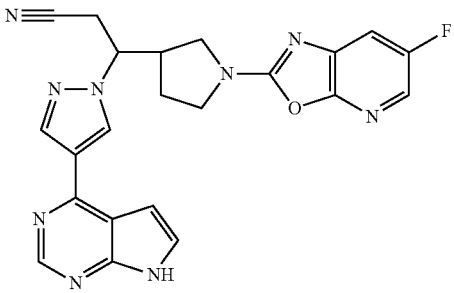 [SMILES: N#CCC(C1CCN(c2nc3cc(F)cnc3o2)C1)n1cc(-c2ncnc3[nH]ccc23)cn1]

Step 1. tert-butyl 3-[2-cyanovinyl]pyrrolidine-1-carboxylate

To a solution of 1.00 M of potassium tert-butoxide in THF (190 mL, 0.19 mol) at 0° C. was added a solution of diethyl cyanomethylphosphonate (30.0 mL, 0.185 mol) in THF (400 mL) drop-wise. The bath was removed and the reaction was warmed to RT over the course of approximately two h. The mixture was re-cooled to 0° C. and a solution of tert-butyl 3-formylpyrrolidine-1-carboxylate (35.00 g, 0.1757 mol, Adesis) in THF (300 mL) was added drop-wise. The bath was removed and the reaction was allowed to warm to ambient temperature and stir for 16 h. The mixture was then diluted with ethyl acetate and water, the aqueous solution was extracted with two further portions of ethyl acetate, the combined extracts were washed with brine, dried over sodium sulfate, filtered and concentrated. The product was used without further purification in the following step (39 g, 100%). $^1$H NMR (300 MHz, CDCl$_3$): δ 6.65 (dd, 1H, trans), 6.38 (t, 1H, cis), 5.41 (dd, 1H, trans), 5.37 (dd, 1H, cis), 4.30-2.68 (m, 10H), 2.21-2.00 (m, 2H), 1.84-1.65 (m, 2H), 1.45 (s, 9H), 1.45 (s, 9H).

Step 2. tert-butyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate To a solution of tert-butyl 3-[2-cyanovinyl]pyrrolidine-1-carboxylate (39 g, 180 mmol) and 4-(1H-pyrazol-4-yl)-7-{[2-(trimethylsilyl)ethoxy]methyl}-7H-pyrrolo[2,3-d]pyrimidine (55 g, 180 mmol, prepared as described in WO 2007/070514, Ex. 65) in acetonitrile (500 mL) was added 1,8-diazabicyclo[5.4.0]undec-7-ene (26 mL) and the reaction was stirred for three days. The majority of the solvent was removed by rotary evaporation prior to partition of the reaction mixture between saturated sodium bicarbonate solution and ethyl acetate. The product was extracted with a further two portions of ethyl acetate. The combined extracts were dried over sodium sulfate, decanted and concentrated. Flash column chromatography (on 2.5 Kg silica gel) using 7.5% isopropanol/25% ethyl acetate/67.5% hexanes as eluent afforded 27.73 g of pure diastereomer 1 (first to elute). Recolumn of mixed fractions, eluting with a gradient from 5% isopropanol/5% ethyl acetate/90% hexanes to 10% isopropanol/50% ethyl aceate/40% hexanes afforded 9.84 g additional product (diastereomer 1). The enantiomers were separated by chiral HPLC (Chiral Technologies Chiralcel OD-H, 5μ, 30×250 mm, 20% EtOH/Hexanes, 22 mL/min). Desired enantiomer 2 (second to elute, retention time 22.9 min) was collected (17.3 g, 18%). $^1$H NMR (300 MHz, CDCl$_3$): δ 8.84 (s, 1H), 8.34 (s, 1H), 8.33 (s, 1H), 7.40 (d, 1H), 6.78 (d, 1H), 5.67 (s, 2H), 4.37 (dt, 1H), 3.76-2.80 (m, 9H), 1.85-1.52 (m, 2H), 1.45 (s, 9H), 0.95-0.87 (m, 2H), −0.07 (s, 9H); LCMS (M+H)$^+$: 538.1.

Step 3. 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile To a solution of tert-butyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (8.9 g, 16 mmol) (from Step 2, diastereomer 1, enantiomer 2) in 1,4-dioxane (200 mL) was added 4 M of hydrogen chloride in 1,4-dioxane (32 mL, 130 mmol) and the reaction was stirred for 16 h. The solvent was removed in vacuo. The residue was partitioned between 500 mL 1N NaOH and ethyl acetate. The layers were separated, and the aqueous layer was extracted with ethyl acetate four times. The combined extracts were washed with brine, dried over sodium sulfate, decanted and concentrated to afford product as a yellow solid (7.12 g, 98%). $^1$H NMR (300 MHz, CDCl$_3$): δ 8.84 (s, 1H), 8.34 (s, 1H), 8.33 (s, 1H), 7.39 (d, 1H), 6.79 (d, 1H), 5.67 (s, 2H), 4.38 (dt, 1H), 3.57-3.49 (m, 2H), 3.26 (dd, 1H), 3.13 (dd, 1H), 2.98-2.77 (m, 4H), 2.73 (dd, 1H), 1.83-1.70 (m, 1H), 1.55-1.38 (m, 1H), 0.95-0.87 (m, 2H), −0.07 (s, 9H); LCMS (M+H)$^+$: 438.1.

Step 4. 3-amino-5-fluoropyridin-2-ol

A mixture of 5-fluoro-3-nitropyridin-2-ol (73 mg, 0.46 mmol; prepared according to procedure reported in WO 2006/114706) and iron (130 mg, 2.3 mmol), in ethanol (1.0 mL), acetic acid (0.76 mL), water (0.38 mL) and c. HCl (1 drop) was heated to 100° C. for 20 min. After cooling to RT, the solution was diluted with water (10 mL), filtered, and the filtrate was concentrated. The residue was then treated with saturated sodium bicarbonate solution to near pH 7, and the product was extracted with 6×40 mL of 20% isopropanol/DCM. The extracts were dried over sodium sulfate, filtered and concentrated and the product was used without further purification in the following step. LCMS (M+H)+: 129.0.

Step 5. 3-[1-(6-fluoro[1,3]oxazolo[5,4-b]pyridin-2-yl)pyrrolidin-3-yl]-3-[4-(7H-pyrrolo[2,3-]pyrimidin-4-yl)-1H-pyrazol-1-yl]propanenitrile 3-Amino-5-fluoropyridin-2-ol (24 mg, 0.19 mmol) was dissolved in THF (0.66 mL), and carbonothioic dichloride (21 microL, 0.28 mmol) was added drop-wise. The mixture was stirred at RT for two h, then solvent was removed in vacuo to give a dark brown oil. 1,4-dioxane (0.50 mL) and N,N-diisopropylethylamine (98 microL, 0.56 mmol) was added, followed by 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (41 mg, 0.094 mmol, single enantiomer, from step 3). The mixture was stirred at 60° C. for 16 h to produce the desired pyridyl oxazole as well as thiourea. Solvent was removed in vacuo and the mixture was deprotected by stirring sequentially in a solution of 1:1 TFA/DCM for 1.5 h, evaporation of solvent, and stirring in a solution of 0.4 mL of EDA in 1.5 mL of methanol for 30 min. The product was purified by preparative-HPLC/MS (C18 column eluting with a gradient of ACN/$H_2O$ containing 0.15% $NH_4OH$). $^1H$ NMR (400 MHz, $d_6$-DMSO): δ 12.11 (br s, 1H), 8.88 (s, 1H), 8.67 (s, 1H), 8.43 (s, 1H), 7.81 (dd, 1H), 7.61-7.57 (m, 2H), 6.98 (d, 1H), 4.87 (dt, 1H), 3.88 (dd, 1H), 3.67-3.29 (m, 5H), 3.03-2.91 (m, 1H), 1.81-1.69 (m, 2H); LCMS (M+H)+: 444.0.

Example 16

3-[4-(7H-pyrrolo[2,3-d]pyrimidin-4-yl)-1H-pyrazol-1-yl]-3-[1-(7H-pyrrolo[2,3-d]pyrimidin-2-yl)pyrrolidin-3-yl]propanenitrile (one enantiomer isolated)

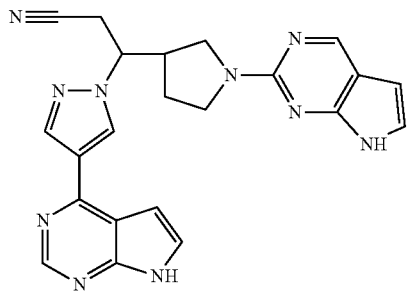 [SMILES: N#CCC(C1CCN(c2ncc3cc[nH]c3n2)C1)n1cc(-c2ncnc3[nH]ccc23)cn1]

3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (21 mg, 0.048 mmol from Example 15, Step 3) and 2-chloro-7H-pyrrolo[2,3-d]pyrimidine (16 mg, 0.058 mmol, prepared as reported in *Bioorganic and Medicinal Chemistry Letters*, 16(22), 5778-5783; 2006) were dissolved in NMP (0.1 mL), and N,N-diisopropylethylamine (41 microL, 0.23 mmol) was added. The mixture was heated to 135° C. for 40 min in the microwave. The mixture was concentrated, treated with 1:1 TFA/DCM for 2 h, concentrated again, and stirred in a solution of methanol (1 mL) containing 0.2 mL EDA for 30 min. The product was purified via preparative-HPLC/MS (C18 column eluting with a gradient of ACN/$H_2O$ containing 0.15% $NH_4OH$). $^1H$ NMR (400 MHz, $d_6$-DMSO): δ 12.12 (br s, 1H), 11.32 (s, 1H), 8.88 (s, 1H), 8.69 (s, 1H), 8.57 (s, 1H), 8.43 (s, 1H), 7.61 (d, 1H), 7.04 (dd, 1H), 7.00 (d, 1H), 6.30 (d, 1H), 4.84 (dt, 1H), 3.86 (dd, 1H), 3.68-3.60 (m, 1H), 3.46-3.22 (m, 4H), 2.97-2.84 (m, 1H), 1.77-1.58 (m, 2H); LCMS (M+H)+: 425.1.

Example 17

3-[1-(7-methyl-7H-pyrrolo[2,3-d]pyrimidin-2-yl)pyrrolidin-3-yl]-3-[4-(7H-pyrrolo[2,3-d]pyrimidin-4-yl)-1H-pyrazol-1-yl]propanenitrile (one enantiomer isolated)

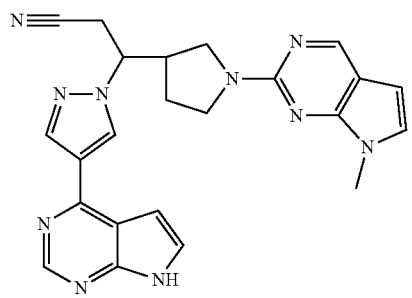 [SMILES: Cn1ccc2cnc(N3CCC(C(CC#N)n4cc(-c5ncnc6[nH]ccc56)cn4)C3)nc21]

Step 1.
2-chloro-7-methyl-7H-pyrrolo[2,3-d]pyrimidine

To a solution of 2-chloro-7H-pyrrolo[2,3-d]pyrimidine (27 mg, 0.16 mmol, prepared as reported in *Bioorganic and Medicinal Chemistry Letters*, 16(22), 5778-5783 (2006)) in DMF (0.15 mL) was added potassium carbonate (67 mg, 0.48 mmol), followed by methyl iodide (10 microL, 0.16 mmol). The mixture was stirred in a sealed vial at RT for 3 h. The reaction was diluted with DCM and acetonitrile, filtered and concentrated. The product was purified by flash column chromatography on silica gel, eluting with 0-50% ethyl acetate in hexanes to afford product as a white solid (13 mg, 47%). LCMS (M+H)+: 167.9, 169.9.

Step 2. 3-[1-(7-methyl-7H-pyrrolo[2,3-d]pyrimidin-2-yl)pyrrolidin-3-yl]-3-[4-(7H-pyrrolo[2,3-d]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (26 mg, 0.060 mmol; from Example 15, Step 3) and 2-chloro-7-methyl-7H-pyrrolo[2,3-d]pyrimidine (12.0 mg, 0.0716 mmol) were dissolved in NMP (0.050 mL) and N,N-diisopropylethylamine (42 microL, 0.24 mmol) was added. The mixture was heated to 135° C. for 60 min in the microwave. After removal of solvent, the residue was stirred sequentially in 1:1 TFA/DCM for 1.5 h, concentrated, then in a solution in 1.0 mL methanol containing 0.2 mL EDA for 30 min. The product was purified via preparative-HPLC/MS (C18 column eluting with a gradient of ACN/$H_2O$ containing 0.15% $NH_4OH$). $^1H$ NMR (400 MHz, $d_6$-DMSO): δ 12.13 (br s, 1H), 8.89 (s, 1H), 8.69 (s, 1H), 8.55 (s, 1H), 8.43 (s, 1H), 7.61 (d, 1H), 7.08 (d, 1H), 7.00 (d, 1H), 6.33 (d, 1H), 4.84 (dt, 1H), 3.91 (dd, 1H), 3.67 (dd, 1H), 3.62 (s, 3H), 3.46-3.27 (m, 4H), 2.96-2.84 (m, 1H), 1.77-1.59 (m, 2H); LCMS (M+H)+: 439.1.

Example 18

3-(1-[1,3]oxazolo[5,4-d]pyrimidin-2-ylpyrrolidin-3-yl)-3-[4-(7H-pyrrolo[2,3-d]pyrimidin-4-yl)-1H-pyrazol-1-yl]propanenitrile (one enantiomer isolated)

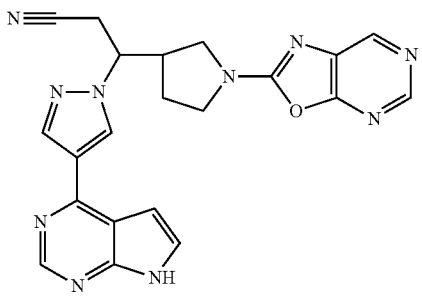 [SMILES: N#CCC(C1CCN(c2nc3cncnc3o2)C1)n1cc(-c2ncnc3[nH]ccc23)cn1]

Step 1. 5-aminopyrimidin-4-ol

To a degassed mixture of 5-amino-6-chloropyrimidin-4-ol (227 mg, 1.56 mmol, Matrix) and triethylamine (1.09 mL, 7.80 mmol) in ethanol (15.0 mL) was added 10% palladium on carbon (51 mg) and the mixture was shaken under 50 psi hydrogen for two h. The mixture was filtered and concentrated to give product. LCMS (M+H)$^+$: 112.1.

Step 2. 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}-N-(4-hydroxypyrimidin-5-yl)pyrrolidine-1-carbothioamide 5-Aminopyrimidin-4-ol (52.4 mg, 0.203 mmol) was dissolved in pyridine (0.55 mL) and phenyl chlorothionocarbonate (33 microL, 0.24 mmol) was added. The mixture was stirred at RT for one h. The reaction was diluted with DCM and washed with water and brine, the organic phase was dried over sodium sulfate and concentrated. The residue was dissolved in chloroform (1.7 mL), and triethylamine (141 microL, 1.01 mmol) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (75 mg, 0.17 mmol; from Example 15, Step 3) were added. The mixture was stirred for 30 min at 70° C. The solvents were removed in vacuo and the product was purified by preparative-HPLC/MS (C18 column eluting with a gradient of ACN/H$_2$O containing 0.15% NH$_4$OH) (15 mg, 15%). LCMS (M+H)$^+$: 591.1.

Step 3. 3-(1-[1,3]oxazolo[5,4-d]pyrimidin-2-ylpyrrolidin-3-yl)-3-[4-(7H-pyrrolo[2,3-d]pyrimidin-4-yl)-1H-pyrazol-1-yl]propanenitrile A solution of 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}-N-(4-hydroxypyrimidin-5-yl)pyrrolidine-1-carbothioamide (15 mg, 0.025 mmol) in ethanol (0.50 mL), was treated with silver nitrate (17.2 mg, 0.10 mmol) and ammonium hydroxide solution (24 microL). The mixture was then heated to 60° C. for one h. Following complete reaction, the mixture was diluted with acetonitrile, filtered and concentrated. The residue was stirred sequentially with 1:1 TFA/DCM for 1.5 h, concentrated, then with 1.0 mL MeOH containing 0.2 mL EDA for 30 min. The product was purified via preparative-HPLC/MS (C18 column eluting with a gradient of ACN/H$_2$O containing 0.15% NH$_4$OH). LCMS (M+H)$^+$: 427.0.

Example 19

3-[1-(5-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile (one enantiomer isolated)

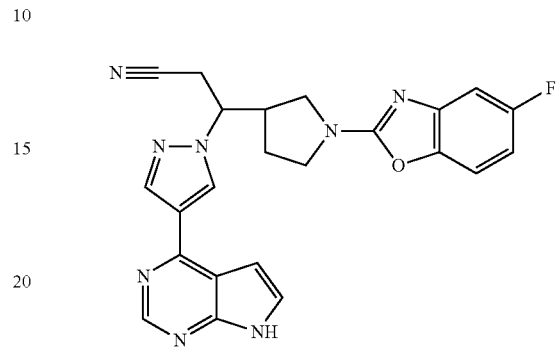

2-Amino-4-fluorophenol (24 mg, 0.19 mmol, Matrix) was dissolved in THF (0.67 mL), and carbonothioic dichloride (21 microL, 0.28 mmol) was added. The mixture was stirred at RT for two h, then concentrated to give a dark brown oil. The residue was redissolved in 1,4-dioxane (0.50 mL) and N,N-diisopropylethylamine (98 microL, 0.56 mmol) was added, followed by 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (41.0 mg, 0.0937 mmol, from Example 15, Step 3). The mixture was stirred at 70° C. for 1.5 h, then at 80° C. for 2.5 h. The mixture was concentrated. The crude product was deprotected by stirring sequentially in a mixture of 1:1 TFA/DCM for 1.5 h, then concentrated and stirred with 0.3 mL EDA in 1.5 mL methanol for 30 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.12 (br s, 1H), 8.88 (s, 1H), 8.68 (s, 1H), 8.43 (s, 1H), 7.61 (d, 1H), 7.38 (dd, 1H), 7.09 (dd, 1H), 6.99 (d, 1H), 6.78 (ddd, 1H), 4.86 (dt, 1H), 3.86 (dd, 1H), 3.67-3.59 (m, 1H), 3.53-3.28 (m, 4H), 3.02-2.90 (m, 1H), 1.78-1.66 (m, 2H); LCMS (M+H)$^+$: 443.0.

Example 20

3-[1-(4-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile (one enantiomer isolated)

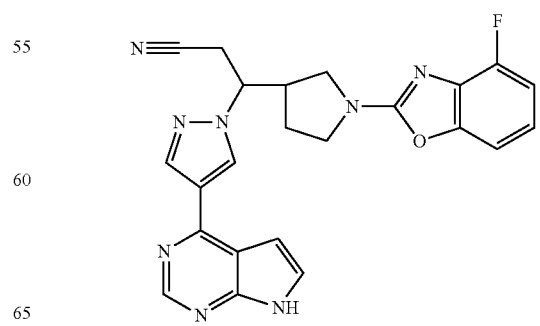

Step 1. 2-amino-3-fluorophenol

Stannous chloride, dihydrate (0.724 g, 3.18 mmol) was added to a solution of 3-fluoro-2-nitrophenol (0.100 g, 0.636 mmol, SynQuest) in THF (5.0 mL), and water (5.0 mL) and the mixture was heated to 80° C. for 40 min. Upon cooling to RT, the reaction was diluted with ethyl acetate and saturated sodium bicarbonate solution. The mixture was then filtered to remove the insoluble material and the layers were separated. The aqueous layer was extracted with ethyl acetate three times. The extracts were washed with brine, dried over sodium sulfate, decanted and concentrated to afford product which was used without further purification (65 mg, 80%). LCMS (M+H)$^+$: 128.0.

Step 2. 3-[1-(4-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile A solution of 2-amino-3-fluorophenol (24 mg, 0.19 mmol) in THF (0.67 mL) was treated with carbonothioic dichloride (21 microL, 0.28 mmol). The mixture was stirred at RT for two h and the solvent was removed in vacuo. The residue was dissolved in 1,4-dioxane (0.50 mL) and N,N-diisopropylethylamine (98 microL, 0.56 mmol) was added, followed by 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (41.0 mg, 0.0937 mmol; from Example 15, Step 3). The mixture was stirred at 60° C. overnight and then concentrated. The crude product was stirred sequentially in a solution of 1:1 TFA/DCM for 1.5 h, concentrated, and in a solution of 0.3 mL EDA in 1.5 mL of methanol for 30 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.13 (br s, 1H), 8.89 (s, 1H), 8.68 (s, 1H), 8.43 (s, 1H), 7.61 (d, 1H), 7.28 (dd, 1H), 7.06-6.95 (m, 3H), 4.86 (dt, 1H), 3.88 (dd, 1H), 3.69-3.61 (m, 1H), 3.56-3.31 (m, 4H), 3.03-2.91 (m, 1H), 1.79-1.66 (m, 2H); LCMS (M+H)$^+$: 443.1.

Example 21

3-[1-(7-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile (one enantiomer isolated)

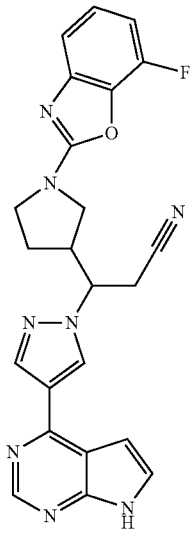 [SMILES: N#CCC(C1CCN(c2nc3cccc(F)c3o2)C1)n1cc(-c2ncnc3[nH]ccc23)cn1]

Step 1. 2-amino-6-fluorophenol

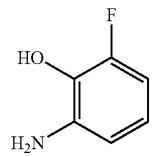

To 2-fluoro-6-nitrophenol (SynQuest) (2.4 g, 15 mmol) in THF (70 mL), and water (70 mL) was added tin dichloride (14.6 g, 76.4 mmol). The mixture was then heated at 80° C. for 2 h. The THF was removed in vacuo. A solution of sat'd NaHCO$_3$ was added, followed by EtOAc. Insoluble material was removed by filtration. The layers of the filtrate were separated and the aqueous portion was extracted with ethyl acetate three times. The combined extracts were washed with brine, dried over sodium sulfate, filtered through a plug of silica gel and concentrated. The product was purified by silica gel chromatography, eluting with 0-60% ethyl acetate in hexanes (230 mg, 12%).

$^1$H NMR (300 MHz, CD$_3$OD): δ 6.56 (ddd, 1H), 6.51 (ddd, 1H), 6.41 (ddd, 1H); $^{19}$F NMR (300 MHz, CD$_3$OD): δ −141.27 (dd, 1F); LCMS (M+H)$^+$: 128.1.

Step 2. 7-fluorobenzo[d]oxazole-2(3H)-thione

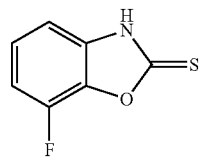 [SMILES: Fc1cccc2[nH]c(=S)oc12]

To a solution of 2-amino-6-fluorophenol (8.2 g, 64 mmol) in THF (100 mL) at 0° C. was added carbonothioic dichloride (6.15 mL, 80.6 mmol) drop-wise. The reaction was warmed to RT and stirred for 16 h. The THF was evaporated in vacuo and the residue was partitioned between water and ethyl acetate. The extract was washed with brine, dried over sodium sulfate, decanted and concentrated. The product was used without further purification.

$^1$H NMR (500 MHz, d$_6$-DMSO): δ 14.1 (br s, 1H), 7.28 (ddd, 1H), 7.17 (ddd, 1H), 7.06 (dd, 1H); $^{13}$C NMR (500 MHz, d$_6$-DMSO): δ 180.12 (s), 144.43 (d), 134.88 (d), 134.17 (d), 126.15 (d), 110.80 (d), 106.85 (d); LCMS (M+H)$^+$: 169.9.

Step 3. 3-[7-(7-fluoro-1,3-benzoxazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile

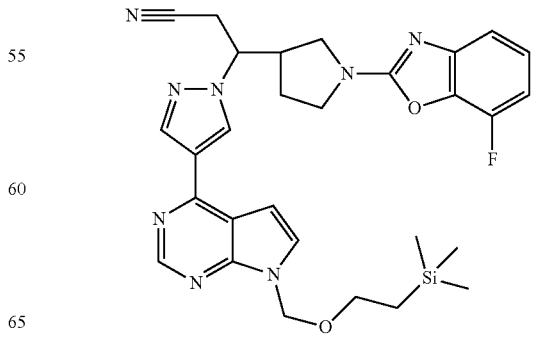

3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (1.0 g, 2.3 mmol, prepared as in Example 15, Step 3) was added to a mixture of 7-fluorobenzo[d]oxazole-2(3H)-thione (0.773 g, 4.57 mmol) and N,N-diisopropylethylamine (1.59 mL, 9.14 mmol) in 1,4-dioxane (12 mL). The mixture was heated to 60° C. for 16 h, then to 80° C. for 1.5 h. The dioxane was removed in vacuo and replaced with ethanol (12 mL). Silver Nitrate (0.776 g, 4.57 mmol) and ammonium hydroxide solution (29% in water, 1.35 mL) were added, and the mixture was stirred for 16 h. The reaction was diluted with water and ethyl acetate and filtered to remove insoluble material. The layers were separated and the organic was washed with water and brine, dried over sodium sulfate, filtered and concentrated. The product was purified by flash column chromatography, eluting first with 0-100% ethyl acetate/hexanes followed by a gradient from 0-5% methanol in ethyl acetate (1.0 g, 76%).

$^1$H NMR (300 MHz, CDCl$_3$): δ 8.85 (s, 1H), 8.37 (s, 2H), 7.41 (d, 1H), 7.16-7.05 (m, 2H), 6.84-6.76 (m, 2H), 5.68 (s, 2H), 4.51 (dt, 1H), 4.10-4.01 (m, 1H), 3.87-3.78 (m, 1H), 3.68-3.45 (m, 4H), 3.32-3.10 (m, 2H), 2.99 (dd, 1H), 2.07-1.80 (m, 2H), 0.97-0.88 (m, 2H), −0.06 (s, 9H); LCMS (M+H)$^+$: 573.1.

Step 4. 3-[7-(7-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile 3-[1-(7-Fluoro-1,3-benzoxazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (1.0 g, 1.7 mmol) was dissolved in DCM (33 mL) and TFA (8.3 mL) was added. The mixture was stirred at RT for 5 h and the solvents were removed in vacuo. The residue was dissolved in methanol (33 mL), and EDA (2.2 mL, 0.033 mol) was added. After stirring for 1 h, the mixture was concentrated in vacuo. The product was purified by flash column chromatography eluting with 0-5% methanol in ethyl acetate (500 mg, 65%).

$^1$H NMR (400 MHz, d$_6$-DMSO): δ 12.13 (br s, 1H), 8.89 (s, 1H), 8.68 (s, 1H), 8.43 (s, 1H), 7.60 (d, 1H), 7.16-7.09 (m, 2H), 6.99 (d, 1H), 6.91 (ddd, 1H), 4.86 (dt, 1H), 3.89 (dd, 1H), 3.70-3.62 (m, 1H), 3.57-3.30 (m, 4H), 3.03-2.91 (m, 1H), 1.79-1.66 (m, 2H); LCMS (M+H)$^+$: 443.1.

Where desired, the final product can be purified further by HPLC/MS (C18 eluting with a gradient of ACN/H$_2$O containing 0.15% NH$_4$OH), frozen and lyophilized to afford the parent compound. Further, the compound can be converted to the phosphoric acid salt by the following procedure: the free base was dissolved in refluxing 3:1 MeOH:CH$_2$Cl$_2$ at a concentration of approximately 27 mg/mL. One equivalent of H$_3$PO$_4$ dissolved in a small amount of IPA was added. The heating was discontinued and the mixture cooled to RT, then the solvent volume was reduced by rotary evaporation until the mixture became cloudy. The mixture was then stirred at RT over 3 days. The solid was isolated by filtration and then dried under vacuum at 50-60° C. overnight.

Example 22

3-[1-(5,7-difluoro-1,3-benzoxazol-2-yl)pyrrolidin-3-yl]-3-[4-(7H-pyrrolo[2,3-d]pyrimidin-4-yl)-1H-pyrazol-1-yl]propanenitrile (one enantiomer isolated)

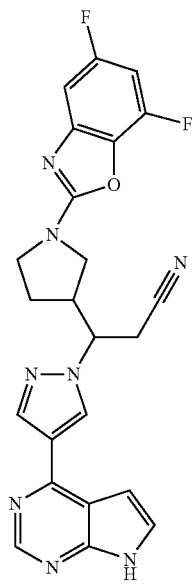 [SMILES: N#CCC(C1CCN(c2nc3cc(F)cc(F)c3o2)C1)n1cc(-c2ncnc3[nH]ccc23)cn1]

Prepared according to the method of Example 20, Step 2, starting with 2-amino-4,6-difluorophenol (Apollo Scientific), with the exception that the substitution was carried out at 60° C. overnight, then at 80° C. for 3 h: $^1$H NMR (400 MHz, d$_6$-DMSO): δ 8.88 (s, 1H), 8.67 (s, 1H), 8.43 (s, 1H), 7.60 (d, 1H), 7.00 (dd, 1H), 6.98 (d, 1H), 6.93 (dt, 1H), 4.86 (dt, 1H), 3.88 (dd, 1H), 3.68-3.60 (m, 1H), 3.58-3.30 (m, 4H), 3.03-2.90 (m, 1H), 1.80-1.67 (m, 2H); LCMS (M+H)$^+$: 461.0.

Example 23

3-{1-[2-(methylthio)pyrimidin-4-yl]pyrrolidin-3-yl}-3-[4-(7H-pyrrolo[2,3-d]pyrimidin-4-yl)-1H-pyrazol-1-yl]propanenitrile (one enantiomer isolated)

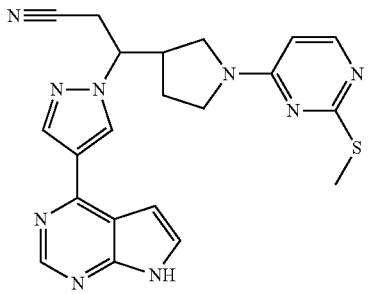 [SMILES: CSc1nccc(N2CCC(C(CC#N)n3cc(-c4ncnc5[nH]ccc45)cn3)C2)n1]

A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (51 mg, 0.12 mmol; from Example 15, Step 3) and 4-chloro-2-(methylthio)pyrimidine (22.5 mg, 0.140 mmol, Aldrich) in 1,4-dioxane (0.20 mL), and containing N,N-diisopropylethylamine (40 microL, 0.233 mmol) was heated to 70° C. for one h. The mixture was concentrated and deprotected by stirring sequentially in 1:1 TFA/DCM for 1.5 h, concentrated, then with 0.3 mL EDA in 1.5 mL methanol for 30 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.12 (br s, 1H), 8.87 (s, 1H), 8.69 (s, 1H), 8.43 (s, 1H), 8.00 (br s, 1H), 7.61 (d, 1H), 6.99 (d, 1H), 6.19 (br s, 1H), 4.81 (dt, 1H), 3.94-2.32 (10H), 1.74-1.57 (m, 2H); LCMS (M+H)$^+$: 432.0.

Example 24

3-{1-[2-(methylsulfinyl)pyrimidin-4-yl]pyrrolidin-3-yl}-3-[4-(7H-pyrrolo[2,3-d]pyrimidin-4-yl)-1H-pyrazol-1-yl]propanenitrile (one enantiomer isolated)

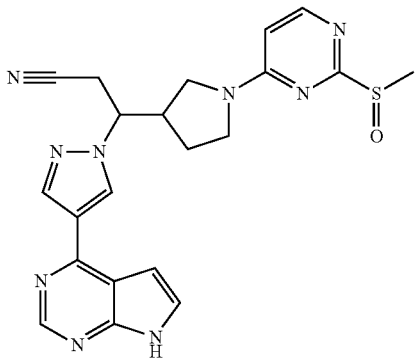 [SMILES: CS(=O)c1nccc(N2CCC(C(CC#N)n3cc(-c4ncnc5[nH]ccc45)cn3)C2)n1]

3-{1-[2-(Methylthio)pyrimidin-4-yl]pyrrolidin-3-yl}-3-[4-(7H-pyrrolo[2,3-d]pyrimidin-4-yl)-1H-pyrazol-1-yl]propanenitrile (6.1 mg, 0.014 mmol, from Example 23) was dissolved in DCM (1.0 mL) and cooled to −10° C. m-Chloroperbenzoic acid (3.2 mg, 0.014 mmol) in DCM was added drop-wise. The mixture was slowly warmed to RT over 3 h. The product was purified via preparative-HPLC/MS (C18 column eluting with a gradient of ACN/H$_2$O containing 0.15% NH$_4$OH). $^1$H NMR (400 MHz, d$_6$-DMSO): δ 12.13 (br s, 1H), 8.87 (s, 1H), 8.68 (s, 1H), 8.43 (s, 1H), 8.30 (d, 0.5H), 8.24 (dd, 0.5H), 7.61 (d, 1H), 6.98 (d, 1H), 6.54 (br t, 1H), 4.88-4.80 (m, 1H), 3.96-2.82 (m, 7H), 2.80 (s, 1.5H), 2.73 (d, 1.5H), 1.81-1.58 (m, 2H); LCMS (M+H)$^+$: 448.0.

Example 25

3-{1-[2-(methylsulfonyl)pyrimidin-4-yl]pyrrolidin-3-yl}-3-[4-(7H-pyrrolo[2,3-d]pyrimidin-4-yl)-1H-pyrazol-1-yl]propanenitrile (one enantiomer isolated)

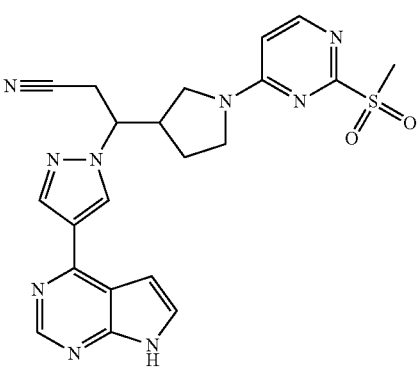 [SMILES: CS(=O)(=O)c1nccc(N2CCC(C(CC#N)n3cc(-c4ncnc5[nH]ccc45)cn3)C2)n1]

To a solution of m-chloroperbenzoic acid (8.2 mg, 0.036 mmol) in DCM (1.2 mL) at −5° C. was added 3-{1-[2-(methylthio)pyrimidin-4-yl]pyrrolidin-3-yl}-3-[4-(7H-pyrrolo[2,3-d]pyrimidin-4-yl)-1H-pyrazol-1-yl]propanenitrile (7.5 mg, 0.017 mmol, from Example 23) in DCM (0.6 mL), drop-wise. The mixture was allowed to warm slowly to 0° C., then the bath was removed and the mixture was stirred at RT for 50 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.14 (br s, 1H), 8.88 (d, 1H), 8.68 (s, 1H), 8.43 (s, 1H), 8.34 (d, 0.5H), 8.28 (d, 0.5H), 7.63-7.59 (m, 1H), 6.99 (dd, 1H), 6.69 (dd, 1H), 4.89-4.80 (m, 1H), 3.96-3.30 (6H), 3.32 (s, 1.5H), 3.25 (s, 1.5H), 3.02-2.84 (m, 1H), 1.82-1.59 (m, 2H); LCMS (M+H)$^+$: 464.0.

Example 26

3-{1-[6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile (one enantiomer isolated)

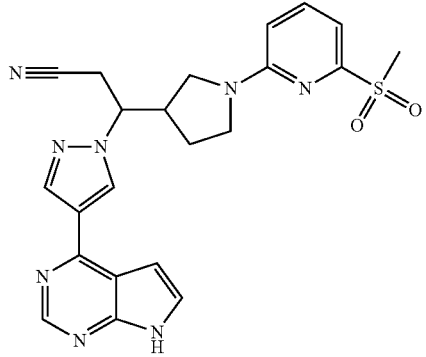 [SMILES: CS(=O)(=O)c1cccc(N2CCC(C(CC#N)n3cc(-c4ncnc5[nH]ccc45)cn3)C2)n1]

Step 1. 2-chloro-6-(methylsulfonyl)pyridine m-Chloroperbenzoic acid (326 mg, 1.46 mmol) in DCM (35 mL) was cooled to −5° C. 2-chloro-6-(methylthio)pyridine (101 mg, 0.633 mmol, prepared according to the method reported in *J. Org. Chem.*, 67(1), 234-237; 2002) in DCM (5.0 mL) was added drop-wise. The mixture was allowed to warm to 0° C. slowly, then the bath was removed and the mixture reached RT and was stirred for a further 2 h. The reaction solution was then washed with saturated NaHCO$_3$, brine, dried over sodium sulfate, filtered and concentrated to afford product (120 mg, 99%). $^1$H NMR (400 MHz, CDCl$_3$): δ 8.03 (dd, 1H), 7.94 (t, 1H), 7.59 (dd, 1H), 3.26 (s, 3H); LCMS (M+H)$^+$: 191.9, 194.0.

Step 2. 3-{1-[6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (21 mg, 0.048 mmol; from Example 15, Step 3) and 2-chloro-6-(methylsulfonyl)pyridine (10 mg, 0.053 mmol) in ethanol (0.050 mL) and N,N-diisopropylethylamine (17 microL, 0.096 mmol) was heated in a sealed vial by means of an oil bath held at 120° C. for 4 h. The mixture was cooled and concentrated. The crude product was deprotected by stirring sequentially in 1:1 TFA/DCM for 1.5 h, then concentrated and stirred with 0.2 mL EDA in 1.5 mL methanol for 30 min. The product was purified via preparative-HPLC/MS (C18 column eluting with a gradient of ACN/H$_2$O containing 0.15% NH$_4$OH). $^1$H NMR (400 MHz, d$_6$-DMSO): δ 12.10 (br s, 1H), 8.88 (s, 1H), 8.69 (s, 1H), 8.44 (s, 1H), 7.76 (dd, 1H), 7.61 (d, 1H), 7.13 (d, 1H), 6.99 (d, 1H), 6.74 (d, 1H), 4.84 (dt, 1H), 3.83-3.71 (m, 1H), 3.60-3.48 (m, 1H), 3.42 (dd, 1H), 3.38-3.24 (m, 3H), 3.21 (s, 3H), 3.00-2.87 (m, 1H), 1.75-1.61 (m, 2H); LCMS (M+H)$^+$: 463.0.

Example 27

3-[1-[2-(methylsulfonyl)pyridin-4-yl]pyrrolidin-3-yl]-3-[4-(7H-pyrrolo[2,3-d]pyrimidin-4-yl)-1H-pyrazol-1-yl]propanenitrile (one enantiomer isolated)

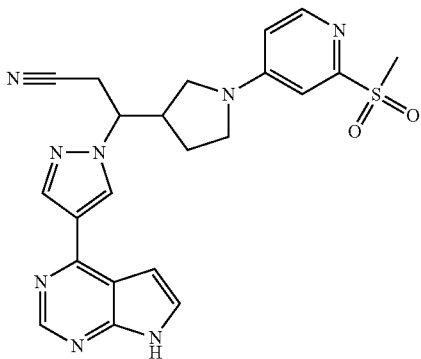 [SMILES: CS(=O)(=O)c1cc(N2CCC(C(CC#N)n3cc(-c4ncnc5[nH]ccc45)cn3)C2)ccn1]

Prepared according to the method of Example 26, using 4-chloro-2-(methylthio)pyridine (prepared according to the procedure reported in *Tetrahedron*, 62(26), 6166-6171, 2006) as starting material in Step 1 and the modification to Step 2 that the substitution reaction was carried out at 120° C. for 1 h. $^1$H NMR (400 MHz, d$_6$-DMSO): δ 12.11 (br s, 1H), 8.88 (s, 1H), 8.69 (s, 1H), 8.44 (s, 1H), 8.24 (d, 1H), 7.61 (d, 1H), 7.04 (br s, 1H), 6.98 (d, 1H), 6.70-6.65 (m, 1H), 4.87-4.77 (m, 1H), 3.70-3.61 (m, 1H), 3.50-3.22 (m, 5H), 3.19 (s, 3H), 3.06-2.89 (m, 1H), 1.77-1.64 (m, 2H); LCMS (M+H)$^+$: 463.1.

Example 28

3-[1-(1-oxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile (one enantiomer isolated)

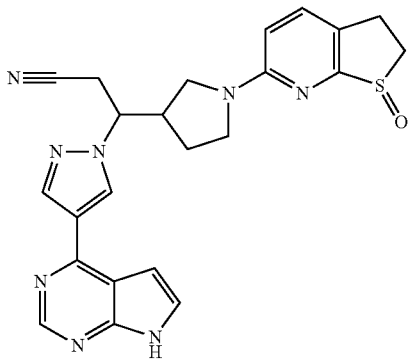 [SMILES: N#CCC(C1CCN(c2ccc3c(n2)S(=O)CC3)C1)n1cc(-c2ncnc3[nH]ccc23)cn1]

Step 1. 2,6-dichloro-3-[2-methoxyvinyl]pyridine

To a solution of (methoxymethyl)(triphenyl)phosphonium chloride (9.97 g, 29.1 mmol) in THF (80 mL) at 0° C. under an atmosphere of nitrogen was added 1.0 M of potassium tert-butoxide in THF (29.1 mL, 29.1 mmol). After stirring for 30 min, a solution of 2,6-dichloronicotinaldehyde (3.01 g, 17.1 mmol, Aldrich) in THF (22 mL) was added drop-wise. The resulting solution was stirred at 0° C. for 20 min, then at RT for 1 h.

The reaction was quenched by the addition of water and the product was extracted with three portions of ethyl acetate. The combined organic extracts were washed with brine, dried over Na$_2$SO$_4$, filtered and concentrated. The crude product was purified by flash column chromatography on silica gel, eluting with a gradient from 0-10% ethyl acetate in hexanes to afford the product as a mixture of olefin isomers (3.1 g, 80%). $^1$H NMR, a 1:1 mixture of olefin isomers (300 MHz, CDCl$_3$): δ 8.34 (d, 1H), 7.60 (d, 1H), 7.19 (d, 1H), 7.17 (d, 1H), 7.04 (d, 1H), 6.36 (d, 1H), 5.94 (d, 1H), 5.53 (d, 1H), 3.83 (s, 3H), 3.75 (s, 3H); LCMS (M+H)$^+$: 204.0.

Step 2. 2-(2,6-dichloropyridin-3-yl)ethanol 2,6-dichloro-3-[2-methoxyvinyl]pyridine (3.1 g, 14 mmol) was dissolved in THF (41 mL), and 4.0 M of hydrogen chloride in water (12 mL) was added. The mixture was heated at reflux for 3 h. The reaction was cooled to RT and the solvents were removed in vacuo. The residue was dissolved in ethyl acetate, washed with saturated NaHCO$_3$, brine, dried over sodium sulfate and concentrated to afford a light yellow oil. The crude product was dissolved in methanol (51 mL) and was cooled to 0° C. Sodium borohydride (0.517 g, 13.7 mmol) was added and the reaction stirred for 30 min at this temperature. The mixture was quenched by the addition of saturated ammonium chloride, the methanol was removed by rotary evaporation, then the remaining aqueous solution was extracted with ethyl acetate three times. The combined extracts were dried over sodium sulfate and concentrated. The product was purified by flash column chromatography on silica gel, eluting with a gradient from 0-50% ethyl acetate in hexanes to afford a colorless oil (1.47 g, 56%). $^1$H NMR (300 MHz, CDCl$_3$): δ 7.62 (d, 1H), 7.23 (d, 1H), 3.92 (q, 2H), 2.97 (t, 2H), 1.55 (t, 1H); LCMS (M+H)$^+$: 192.0.

Step 3. 2-(2,6-dichloropyridin-3-yl)ethanethiol

To a solution of 2-(2,6-dichloropyridin-3-yl)ethanol (0.500 g, 2.60 mmol) and triphenylphosphine (1.02 g, 3.90 mmol) in THF (20 mL) at 0° C. was added diethyl azodicarboxylate (615 microL, 3.90 mmol). After 10 min, thioacetic acid (279 microL, 3.90 mmol) was added. The mixture was stirred for two h at RT. The reaction was diluted with hexanes and the white precipitate was filtered off. The filtrate was concentrated and the resulting crude thioacetate was purified by flash column chromatography on silica gel, eluting with a gradient from 0-10% ethyl acetate in hexanes. $^1$H NMR (300 MHz, CDCl$_3$): δ 7.96 (d, 1H), 7.24 (d, 1H), 3.13 (dd, 2H), 2.98 (dd, 2H), 2.34 (s, 3H); LCMS (M+H)$^+$: 250.0.

The thioacetate was stirred overnight in a solution of acetyl chloride (4 eq.) in methanol (20 mL). The solvent was removed in vacuo to afford the product as a viscous oil (320 mg, 59%). $^1$H NMR (300 MHz, CDCl$_3$): δ 7.57 (d, 1H), 7.24 (d, 1H), 3.01 (t, 2H), 2.82 (q, 2H), 1.39 (t, 1H); LCMS (M+H)$^+$: 208.0.

Step 4. 6-chloro-2,3-dihydrothieno[2,3-b]pyridine 1-oxide and 6-chloro-2,3-dihydrothieno[2,3-b]pyridine 1,1-dioxide 2-(2,6-dichloropyridin-3-yl)ethanethiol (0.25 g, 0.85 mmol) was dissolved in DMF (8.7 mL). The solution was degassed by passing a stream of nitrogen through the solution for 15 min. The solution was then cooled to 0° C. and sodium hydride (60% in mineral oil, 68 mg, 1.7 mmol) was added and the reaction was stirred at this temperature for 1.5 h. The reaction was quenched by the addition of water (80 mL) and the product was extracted with ethyl acetate (100 mL). The organic layer was washed with water (3×), brine (1×), dried over sodium sulfate and concentrated. The product was purified by flash column chromatography on silica gel, eluting with a gradient from 0-30% ethyl acetate in hexanes to afford product as a light yellow oil (150 mg, 92%). LCMS (M+H)$^+$: 172.0.

m-Chloroperbenzoic acid (110 mg, 0.49 mmol) in DCM (5.0 mL) was added to a solution of 6-chloro-2,3-dihydrothieno[2,3-b]pyridine (71 mg, 0.38 mmol) in DCM (21 mL) at 0° C. The clear solution was allowed to reach RT and stir for one h. The mixture was quenched with saturated $Na_2S_2O_3$ solution followed by saturated $NaHCO_3$ solution. The organic layer was washed with water, brine, dried over sodium sulfate and concentrated. The product was purified by flash column chromatography on silica gel, eluting with a gradient of 0-100% ethyl acetate in hexanes to afford sulfone (17 mg, 22% yield), followed by a change in eluent to 5% methanol in ethyl acetate to afford sulfoxide (29 mg, 41% yield).

6-chloro-2,3-dihydrothieno[2,3-b]pyridine 1-oxide: $^1$H NMR (300 MHz, $CDCl_3$): δ 7.80 (d, 1H), 7.45 (d, 1H), 3.91-3.76 (m, 1H), 3.46-3.28 (m, 3H); LCMS (M+H)$^+$: 188.1.

6-chloro-2,3-dihydrothieno[2,3-b]pyridine 1,1-dioxide: $^1$H NMR (400 MHz, $CDCl_3$): δ 7.75 (d, 1H), 7.53 (d, 1H), 3.56 (t, 2H), 3.36 (t, 2H); LCMS (M+H)$^+$: 204.0.

Step 5. 3-[1-(1-oxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (21 mg, 0.048 mmol; from Example 15, Step 3) and 6-chloro-2,3-dihydrothieno[2,3-b]pyridine 1-oxide (10.0 mg, 0.0533 mmol) were dissolved in ethanol (0.050 mL) and N,N-Diisopropylethylamine (17 microL, 0.1 mmol). The mixture was heated in a sealed vial by means of an oil bath held at 120° C. for 5.5 h. The mixture was concentrated. The residue was dissolved in a mixture of 1:1 TFA/DCM, stirred for 1.5 h, then concentrated again. The residue was dissolved in 1.5 mL methanol containing 0.2 mL EDA and was stirred for 30 min. The product was purified via preparative-HPLC/MS (C18 column eluting with a gradient of ACN/$H_2O$ containing 0.15% $NH_4OH$). $^1$H NMR (400 MHz, $d_6$-DMSO): δ 12.04 (br s, 1H), 8.81 (s, 1H), 8.69 (s, 1H), 8.62 (s, 1H), 8.36 (s, 1H), 7.63 (dd, 1H), 7.53 (d, 1H), 6.92 (d, 1H), 6.56 (dd, 1H), 4.81-4.76 (m, 1H), 3.75-3.67 (m, 1H), 3.49-2.78 (10H), 1.72-1.55 (m, 2H); LCMS (M+H)$^+$: 459.1.

Example 29

3-[1-(2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile (one enantiomer isolated)

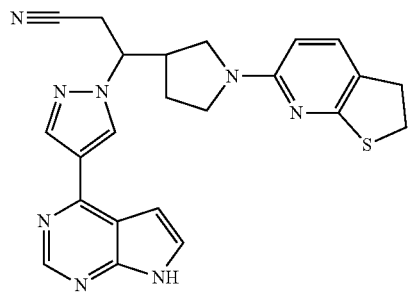 [SMILES: N#CCC(C1CCN(c2ccc3c(n2)SCC3)C1)n1cc(-c2ncnc3[nH]ccc23)cn1]

To a solution of 3-[1-(1-oxido-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (36 mg, 0.061 mmol, prepared as in Example 28) in isopropyl alcohol (1.0 mL) was added indium (21 mg, 0.18 mmol) and 2,2-dimethylpropanoyl chloride (45 microL, 0.37 mmol). The mixture was stirred at RT for 3 h. The reaction was diluted with saturated $Na_2CO_3$ solution, extracted thrice with DCM and the combined extracts were concentrated to dryness. The residue was dissolved in a mixture of 1:1 TFA/DCM and was stirred for 1.5 h, and then solvents were removed in vacuo. The residue was stirred in a mixture of 1.5 mL methanol and 0.2 mL EDA for 30 min. The product was purified via preparative-HPLC/MS (C18 column eluting with a gradient of ACN/$H_2O$ containing 0.15% $NH_4OH$). $^1$H NMR (400 MHz, $d_6$-DMSO): 12.11 (br s, 1H), 8.87 (s, 1H), 8.69 (s, 1H), 8.42 (s, 1H), 7.61 (d, 1H), 7.29 (d, 1H), 6.99 (d, 1H), 6.04 (d, 1H), 4.79 (dt, 1H), 3.67 (dd, 1H), 3.44-3.25 (m, 5H), 3.23-3.14 (m, 2H), 3.13-3.06 (dd, 2H), 2.92-2.80 (m, 1H), 1.75-1.56 (m, 2H); LCMS (M+H)$^+$: 443.2.

Example 30

3-[1-(1,1-dioxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile (one enantiomer isolated)

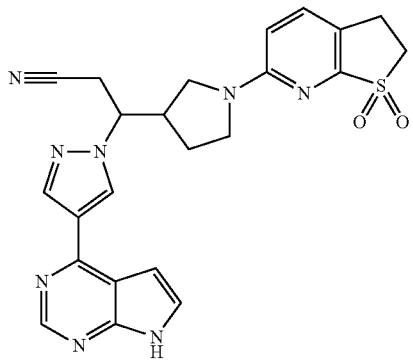 [SMILES: N#CCC(C1CCN(c2ccc3c(n2)S(=O)(=O)CC3)C1)n1cc(-c2ncnc3[nH]ccc23)cn1]

Prepared as in Example 28, Step 5 using 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (21 mg, 0.048 mmol; from Example 15, Step 3) and 6-chloro-2,3-dihydrothieno[2,3-b]pyridine 1,1-dioxide (10.7 mg, 0.0528 mmol, from Example 28, Step 4) in ethanol (0.050 mL) and N,N-diisopropylethylamine (17 microL, 0.1 mmol) with the exception that the substitution reaction time was 2.5 h. $^{1}$H NMR (400 MHz, CDCl$_{3}$): δ 8.88 (s, 1H), 8.69 (s, 1H), 8.43 (s, 1H), 7.68 (d, 1H), 7.61 (d, 1H), 6.99 (d, 1H), 6.74 (d, 1H), 4.84 (dt, 1H), 3.78 (dd, 1H), 3.58-3.22 (m, 7H), 3.11 (dd, 2H), 2.98-2.86 (m, 1H), 1.78-1.61 (m, 2H); LCMS (M+H)$^{+}$: 475.0.

Example 31

3-(3-fluoro-1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile (four stereoisomers isolated)

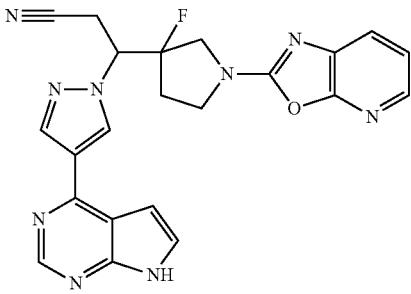 [SMILES: N#CCC(n1cc(-c2ncnc3[nH]ccc23)cn1)C1(F)CCN(c2nc3cccnc3o2)C1]

Step 1. tert-butyl 3-[2-cyanovinyl]-3-fluoropyrrolidine-1-carboxylate

To a solution of 1.00 M of potassium tert-butoxide in THF (6.4 mL, 6.4 mmol) at 0° C. was added a solution of diethyl cyanomethylphosphonate (1.01 mL, 6.27 mmol) in THF (10 mL) drop-wise. The bath was removed and the reaction was warmed to RT and stirred for 30 min. The mixture was re-cooled to 0° C. and a solution of tert-butyl 3-fluoro-3-formylpyrrolidine-1-carboxylate (1.29 g, 5.94 mmol, prepared as described in US2007/0037853) in THF (10 mL) was added drop-wise. The reaction was stirred overnight with warming to RT. The reaction mixture was diluted with ethyl acetate and water, the aqueous solution was extracted with ethyl acetate three times and the combined extracts were washed with brine, dried over sodium sulfate, filtered and concentrated. Flash column chromatography, eluting with a gradient from 0-60% ethyl acetate in hexanes afforded cis- and trans-olefins, combined and used in the subsequent step (950 mg, 66%).

$^{1}$H NMR trans-olefin (300 MHz, CDCl$_{3}$): δ 6.66 (dd, 1H), 5.78 (d, 1H), 3.81-3.30 (m, 4H), 2.27-1.94 (m, 2H), 1.43 (s, 9H).

$^{19}$F NMR trans-olefin (300 MHz, CDCl$_{3}$): δ −158.3 (m, 1F).

$^{1}$H NMR cis-olefin (300 MHz, CDCl$_{3}$): δ 6.45 (ddd, 1H), 5.56 (dd, 1H), 3.92-3.34 (m, 4H), 2.44-2.02 (m, 2H), 1.44 (s, 9H).

$^{19}$F NMR cis-olefin (300 MHz, CDCl$_{3}$): δ −151.9 (m, 1F).

Step 2. tert-butyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}-3-fluoropyrrolidine-1-carboxylate tert-Butyl 3-[2-cyanovinyl]-3-fluoropyrrolidine-1-carboxylate (0.95 g, 4.0 mmol) (as a mixture of olefin isomers) and 4-(1H-pyrazol-4-yl)-7-{[2-(trimethylsilyl)ethoxy]methyl}-7H-pyrrolo[2,3-d]pyrimidine (1.2 g, 4.0 mmol, prepared as described in WO 2007/070514, Ex. 65, or US2007/135461) in acetonitrile (10 mL) were treated with 1,8-diazabicyclo[5.4.0]undec-7-ene (0.59 mL, 4.0 mmol) and stirred at RT for 30 min. Solvent was removed in vacuo and the residue was purified by flash column chromatography on silica gel, eluting with a gradient of 5% IPA/5% ethyl acetate/90% hexanes to 10% IPA/50% ethyl acetate/40% hexanes. Diastereomer 1 (first to elute) (0.92 g, 42%), and diastereomer 2 (second to elute) (0.91 g, 41%). $^{1}$H NMR diastereomer 1 (400 MHz, CDCl$_{3}$): δ 8.86 (s, 1H), 8.39 (s, 1H), 8.34 (s, 1H), 7.42 (d, 1H), 6.81-6.78 (m, 1H), 5.68 (s, 2H), 4.93-4.81 (m, 1H), 3.84-3.34 (m, 7H), 3.08 (dt, 1H), 2.37-2.13 (m, 1H), 1.93 (dt, 1H), 1.45 (s, 9H), 0.95-0.89 (m, 2H), −0.06 (s, 9H); $^{19}$F NMR diastereomer 1 (400 MHz, CDCl$_{3}$): −158.8 (m, 1F); LCMS (M+H)$^{+}$: 556.2. $^{1}$H NMR diastereomer 2 (400 MHz, CDCl$_{3}$): δ 8.86 (s, 0.5H), 8.85 (s, 0.5H), 8.39 (s, 0.5H), 8.37 (s, 0.5H), 8.35 (s, 0.5H), 8.30 (s, 0.5H), 7.44-7.40 (m, 1H), 6.81-6.77 (m, 1H), 5.68 (s, 2H), 4.87 (ddd, 1H), 3.83-3.38 (m, 6H), 3.34 (dd, 1H), 3.17 (dd, 1H), 2.34-2.18 (m, 1H), 2.07-1.79 (m, 1H), 1.42 (s, 9H), 0.96-0.88 (m, 2H), −0.06 (s, 9H); $^{19}$F NMR diastereomer 2 (400 MHz, CDCl$_{3}$): δ −157.6 (m, 1F); LCMS (M+H)$^{+}$: 556.2.

Step 3a. 3-(3-fluoropyrrolidin-3-yl)-3-[4-(7-{[2-(trimethylsilyl)ethoxy]methyl}-7H-pyrrolo[2,3-d]pyrimidin-4-yl)-1H-pyrazol-1-yl]propanenitrile To a solution of tert-butyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}-3-fluoropyrrolidine-1-carboxylate (0.200 g, 0.360 mmol) (diastereomer 1 from Step 2) in 1,4-dioxane (10 mL) was added 4.0 M of Hydrogen chloride in 1,4-dioxane (0.70 mL, 2.8 mmol) and stirred at RT until the reaction was complete. The solvent was removed in vacuo. The residue was partitioned between 1N NaOH and ethyl acetate, the layers were separated and the aqueous portion was extracted with an additional three portions of ethyl acetate. The combined extracts were washed with brine, dried over sodium sulfate, decanted and concentrated. The product was used without further purification. LCMS (M+H)$^{+}$: 456.0.

Step 3b. 3-(3-fluoropyrrolidin-3-yl)-3-[4-(7-{[2-(trimethylsilyl)ethoxy]methyl}-7H-pyrrolo[2,3-d]pyrimidin-4-yl)-1H-pyrazol-1-yl]propanenitrile The procedure described for Step 3a was followed, using tert-butyl 3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}-3-fluoropyrrolidine-1-carboxylate (0.480 g, 0.864 mmol) (diastereomer 2 from Step 2). LCMS (M+H)$^{+}$: 456.0.

Step 4a. 3-(3-fluoro-1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile A solution of oxazolo[5,4-b]pyridine-2(1H)-thione (0.042 g, 0.27 mmol, from Example 33, Step 4) and 3-(3-fluoropyrrolidin-3-yl)-3-[4-(7-{[2-(trimethylsilyl)ethoxy]methyl}-7H-pyrrolo[2,3-d]pyrimidin-4-yl)-1H-pyrazol-1-yl]propanenitrile (0.100 g, 0.219 mmol, from Step 3a) in 1,4-dioxane (2 mL) containing N,N-diisopropylethylamine (153 microL, 0.878 mmol) was heated to 70° C. for 2 h. The cooled reaction mixture was concentrated in vacuo. The residue was reconstituted in ethanol (2 mL) and the resulting suspension was treated with silver nitrate (0.149 g, 0.878 mmol) and aqueous ammonium hydroxide (0.5 mL) and stirred at RT overnight. Water and 1N NaOH were added into the reaction which was then stirred for 15 min and subsequently filtered. The filtrate was extracted with ethyl acetate thrice and the combined extracts were washed with brine, dried over sodium sulfate, filtered and concentrated. The product was deprotected by stirring with 25% TFA/DCM for 3 h, followed by evaporation of the solvents and stirring the residue with excess EDA in methanol. When the deprotection step was complete, the product was purified via preparative-HPLC/MS (C18 column eluting with a gradient of ACN/H$_2$O containing 0.15% NH$_4$OH) to afford the purified racemate (20 mg, 20%), a portion of which was separated into its enantiomers by chiral HPLC (Phenomenex Lux-cellulose-1 column, 5μ, 20×250 mm, 70% EtOH/Hexanes, 8 mL/min) to afford enantiomer 1 (first to elute, retention time 26.9 min) and enantiomer 2 (second to elute, retention time 31.7 min) $^1$H NMR (300 MHz, d$_6$-DMSO): δ 12.11 (br s, 1H), 8.90 (s, 1H), 8.70 (s, 1H), 8.46 (s, 1H), 7.90 (dd, 1H), 7.66 (dd, 1H), 7.63 (d, 1H), 7.22 (dd, 1H), 7.02 (d, 1H), 5.43 (ddd, 1H), 4.14-3.55 (m, 5H), 3.50 (dd, 1H), 2.50-2.25 (m, 1H), 1.88-1.73 (m, 1H); $^{19}$F NMR (300 MHz, d$_6$-DMSO): δ −159.6; LCMS (M+H)$^+$: 444.0.

Step 4b. 3-(3-fluoro-1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile The procedure described for Step 4a was followed, using the product of Step 3b. The product was subjected to chiral HPLC to separate the enantiomers (Phenomenex Lux-cellulose-1 column, 5μ, 20×250 mm, 60% EtOH/Hexanes, 10 mL/min) to afford enantiomer 1 (first to elute, retention time 18.0 min) and enantiomer 2 (second to elute, retention time 25.7 min). $^1$H NMR (300 MHz, d$_6$-DMSO): δ 12.12 (br s, 1H), 8.92 (s, 1H), 8.72 (s, 1H), 8.49 (s, 1H), 7.87 (dd, 1H), 7.63 (d, 1H), 7.61 (dd, 1H), 7.19 (dd, 1H), 7.03 (d, 1H), 5.44 (ddd, 1H), 4.12-3.30 (m, 6H), 2.54-2.26 (m, 2H); $^{19}$F NMR (300 MHz, d$_6$-DMSO): δ −160.2; LCMS (M+H)$^+$: 444.0.

Example 32

3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile (two enantiomers and one diasteromer isolated)

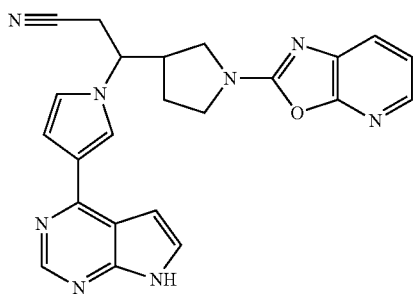

Step 1. tert-butyl 3-(2-cyano-1-{3-[7-(diethoxymethyl)-7H-pyrrolo[2,3-d]pyrimidin-4-yl]-1H-pyrrol-1-yl}ethyl)pyrrolidine-1-carboxylate A solution of tert-butyl 3-[2-cyanovinyl]pyrrolidine-1-carboxylate (0.480 g, 2.16 mmol, prepared as in Example 15, Step 1) and 7-(diethoxymethyl)-4-(1H-pyrrol-3-yl)-7H-pyrrolo[2,3-d]pyrimidine (0.72 g, 2.2 mmol, prepared as in WO 2007/070514 Ex. 500) in acetonitrile (5 mL) was treated with 1,8-diazabicyclo[5.4.0]undec-7-ene (0.323 mL, 2.16 mmol) and stirred for 5 days. The solvent was removed by rotary evaporation and the product was purified by flash column chromatography on silica gel, eluting with a gradient from 50-90% ethyl acetate in hexanes to afford separated diastereomers. Diastereomer 1 (first to elute): 279 mg, 25%. Diastereomer 2 (second to elute): 352 mg, 32%.

$^1$H NMR (300 MHz, CDCl$_3$) diastereomer 1: δ 8.78 (s, 1H), 7.68 (t, 1H), 7.53 (d, 1H), 6.98 (dd, 1H), 6.91 (t, 1H), 6.83 (d, 1H), 6.77 (s, 1H), 4.12-4.03 (m, 1H), 3.80-3.63 (m, 3H), 3.60-3.38 (m, 3H), 3.34-3.20 (m, 1H), 3.17-3.05 (m, 1H), 2.89 (d, 2H), 2.91-2.78 (m, 1H), 1.89-1.76 (m, 1H), 1.68-1.52 (m, 1H), 1.47 (s, 9H), 1.23 (t, 6H); LCMS (M+H)$^+$: 509.1.

$^1$H NMR (300 MHz, CDCl$_3$) diastereomer 2: δ 8.78 (s, 1H), 7.65 (br s, 1H), 7.53 (br d, 1H), 7.00-6.79 (m, 3H), 6.77 (s, 1H), 4.17-4.05 (m, 1H), 3.79-3.28 (m, 7H), 3.09-2.80 (m, 4H), 2.27-2.13 (m, 1H), 1.79-1.60 (m, 1H), 1.44-1.34 (m, 9H), 1.23 (t, 6H); LCMS (M+H)$^+$: 509.1.

Step 2a. 3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile To a solution of tert-butyl 3-(2-cyano-1-{3-[7-(diethoxymethyl)-7H-pyrrolo[2,3-d]pyrimidin-4-yl]-1H-pyrrol-1-yl}ethyl)pyrrolidine-1-carboxylate (0.060 g, 0.12 mmol, diastereomer 1 from Step 1) in 1,4-dioxane (2 mL) was added 4.00 M of hydrogen chloride in 1,4-dioxane (0.24 mL, 0.94 mmol). The reaction was stirred for 16 h. The solvent was removed by rotary evaporation and the globally deprotected product, 3-pyrrolidin-3-yl-3-[3-(7H-pyrrolo[2,3-d]pyrimidin-4-yl)-1H-pyrrol-1-yl]propanenitrile, was used without further purification. LCMS (M+H)$^+$: 307.1.

To a solution of 3-aminopyridin-2-ol (2.00 g, 18.2 mmol, 3B Scientific) in THF (40 mL) was added thiophosgene (1.52 mL, 20 mmol). Water was added and the pH adjusted to 4-5. The product was extracted with ethyl acetate, dried over sodium sulfate and concentrated. The solid material was triturated with ether overnight, and the product was filtered off and air dried. (6.25 g, 41.1 mmol) of oxazolo[5,4-b]pyridine-2(1H)-thione prepared in this manner was mixed with toluene (100 mL) and was treated with thionyl chloride (9.0 mL, 120 mmol) and a few drops of DMF. The reaction was heated to reflux for 1 h. Upon cooling to RT and standing overnight, a precipitate formed which was isolated by filtration and air dried. This crude product (23 mg) and 3-pyrrolidin-3-yl-3-[3-(7H-pyrrolo[2,3-d]pyrimidin-4-yl)-1H-pyrrol-1-yl]propanenitrile (0.036 g) in 1,4-dioxane (0.6 mL) containing N,N-diisopropylethylamine (82 microL, 0.47 mmol) was heated to 70° C. for 2 h. Solvent was removed in vacuo. The residue was reconstituted in ethanol (0.8 mL) and the resulting suspension was treated with silver nitrate (0.040 g, 0.23 mmol) and ammonium hydroxide solution (36 microL). After stirring for 16 h, the reaction was worked up by partition between water and ethyl acetate. The layers were separated and the aqueous portion was extracted with ethyl acetate three times. The combined extracts were dried over sodium sulfate, filtered and concentrated. The product was purified via preparative-HPLC/MS (C18 column eluting with a gradient of ACN/H$_2$O containing 0.15% NH$_4$OH). A portion of this product was purified by chiral HPLC (Chiral Technologies Chiralpak IA, 5μ, 20×250 mm, eluted with 45% EtOH/Hexanes) to afford enantiomer 1 (first to elute, retention time 47.0 min) and enantiomer 2 (second to elute, retention time 53.4 min).
¹H NMR (300 MHz, d₆-DMSO) enantiomer 1: δ 11.97 (br s, 1H), 8.61 (s, 1H), 8.01 (dd, 1H), 7.87 (dd, 1H), 7.62 (dd, 1H), 7.51 (d, 1H), 7.20 (dd, 1H), 7.16 (dd, 1H), 6.96-6.90 (m, 2H), 4.57 (dt, 1H), 3.85 (dd, 1H), 3.71-3.60 (m, 1H), 3.53-3.23 (m, 4H), 2.99-2.83 (m, 1H), 1.76-1.56 (m, 2H); LCMS (M+H)⁺: 425.1.
¹H NMR (300 MHz, d₆-DMSO) enantiomer 2: δ 11.97 (br s, 1H), 8.61 (s, 1H), 8.01 (dd, 1H), 7.87 (dd, 1H), 7.62 (dd, 1H), 7.51 (d, 1H), 7.20 (dd, 1H), 7.16 (dd, 1H), 6.97-6.93 (m, 2H), 4.59 (dt, 1H), 3.86 (dd, 1H), 3.73-3.62 (m, 1H), 3.56-3.24 (m, 4H), 3.01-2.85 (m, 1H), 1.75-1.61 (m, 2H); LCMS (M+H)⁺: 425.1.

Step 2b. 3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile The procedure for Step 2a was followed, using diastereomer 2 from Step 1 as starting material to afford product as the racemate. ¹H NMR (400 MHz, d₆-DMSO): δ 11.97 (br s, 1H), 8.61 (s, 1H), 8.00 (dd, 1H), 7.81 (dd, 1H), 7.53 (dd, 1H), 7.50 (dd, 1H), 7.17-7.13 (m, 2H), 6.96 (dd, 1H), 6.93 (dd, 1H), 4.60 (dt, 1H), 3.80-3.73 (m, 1H), 3.65-3.56 (m, 1H), 3.47 (dd, 1H), 3.39-3.23 (m, 3H), 3.05-2.94 (m, 1H), 2.31-2.20 (m, 1H), 1.98-1.88 (m, 1H); LCMS (M+H)⁺: 425.0.

Example 33

3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile phosphate (one enantiomer converted to the salt form)

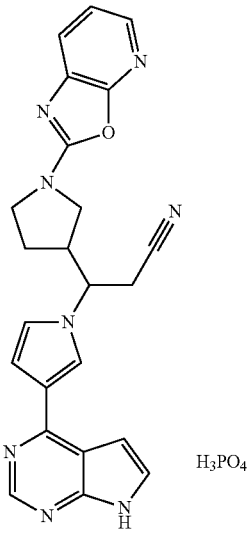

Step 1. 4-(1H-pyrrol-3-yl)-7-{[2-(trimethylsilyl)ethoxy]methyl}-7H-pyrrolo[2,3-d]pyrimidine A mixture of 4-chloro-7-{[2-(trimethylsilyl)ethoxy]methyl}-7H-pyrrolo[2,3-d]pyrimidine (12.9 g, 45.4 mmol) (prepared as in WO 2007/070514, Example 65) and [1-(triisopropylsilyl)-1H-pyrrol-3-yl]boronic acid (Frontier Scientific) (10.4 g, 38.9 mmol) and sodium carbonate (4.36 g, 41.2 mmol) in 1,2-dimethoxyethane (100 mL) and water (35 mL) was degassed by purging with a stream of nitrogen for 20 min. Tetrakis(triphenylphosphine)palladium(0) (2.25 g, 1.94 mmol) was then added and the reaction was heated to reflux for 9 h. As the coupling reaction proceeded, the TIPS protecting group was also slowly removed. At the time the reaction was stopped, starting materials were nearly consumed, however the TIPS deprotection was not complete. The solvent was removed by rotary evaporation and the product was purified by flash column chromatography on silica gel, eluting with a gradient from 10-50% ethyl acetate in hexanes. TIPS protected material was also collected (3.8 g, 21%), in addition to the desired 4-(1H-pyrrol-3-yl)-7-{[2-(trimethylsilyl)ethoxy]methyl}-7H-pyrrolo[2,3-d]pyrimidine (7 g, 57%). ¹H NMR (300 MHz, CDCl₃): δ 8.93 (br s, 1H), 8.84 (s, 1H), 7.73-7.69 (m, 1H), 7.33 (d, 1H), 7.04-7.00 (m, 1H), 6.94 (dd, 1H), 6.85 (d, 1H), 5.66 (s, 2H), 3.55 (m, 2H), 0.92 (m, 2H), −0.06 (s, 9H). LCMS (M+H)⁺: 315.2.

Step 2. tert-butyl 3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate To a mixture of 4-(1H-pyrrol-3-yl)-7-{[2-(trimethylsilyl)ethoxy]methyl}-7H-pyrrolo[2,3-d]pyrimidine (7.69 g, 24.4 mmol) and tert-butyl 3-[2-cyanovinyl]pyrrolidine-1-carboxylate as a mixture of olefin isomers (5.70 g, 25.7 mmol, prepared as in Example 15, Step 1) in acetonitrile (70 mL) was added 1,8-diazabicyclo[5.4.0]undec-7-ene (3.66 mL, 24.4 mmol) and the reaction was stirred overnight. The volume was then reduced by half in vacuo and the reaction was heated to 60° C. for 4.5 h. The solvent was removed by rotary evaporation. The product was purified by flash column chromatography on silica gel, eluting with a gradient initially from 0-65% B in A, (A: 5% isopropanol/5% ethyl acetate/90% hexanes, B: 10% isopropanol/50% ethyl acetate/40% hexanes), until second diastereomer started eluting, then quickly raised to 90% B in A. The first diastereomer to elute (diastereomer 1) was collected (4.45 g, 34%). ¹H NMR (400 MHz, CDCl₃) diastereomer 1: δ 8.82 (s, 1H), 7.70-7.68 (m, 1H), 7.35 (d, 1H), 7.00 (dd, 1H), 6.92 (t, 1H), 6.84 (d, 1H), 5.66 (s, 2H), 4.13-4.04 (m, 1H), 3.80-3.65 (m, 1H), 3.57-3.38 (m, 3H), 3.33-3.20 (m, 1H), 3.16-3.05 (m, 1H), 2.93-2.80 (m, 3H), 1.89-1.78 (m, 1H), 1.63-1.52 (m, 1H), 1.47 (s, 9H), 0.92 (m, 2H), −0.06 (s, 9H); LCMS (M+H)⁺: 537.3. ¹H NMR (500 MHz, d₆-DMSO, 90° C.) diastereomer 2: δ 8.69 (s, 1H), 7.92 (t, 1H), 7.62 (d, 1H), 7.09 (t, 1H), 6.99 (d, 1H), 6.94 (dd, 1H), 5.63 (s, 2H), 4.47 (dt, 1H), 3.58 (m, 2H), 3.43 (ddd, 1H), 3.30 (dd, 1H), 3.28-3.22 (m, 1H), 3.19 (dd, 1H), 3.11 (dd, 1H), 2.94 (dd, 1H), 2.87-2.77 (m, 1H), 2.13-2.04 (m, 1H), 1.73 (dq, 1H), 1.34 (s, 9H), 0.86 (m, 2H), −0.07 (s, 9H); LCMS (M+H)⁺: 537.3.

Step 3. 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile To a solution of tert-butyl 3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate (4.45 g, 8.29 mmol) (diastereomer 1 from Step 2) in 1,4-dioxane (50 mL) was added 4 M of hydrogen chloride in 1,4-dioxane (31 mL). The reaction was stirred for 16 h. The product was filtered off and rinsed with a small amount of dioxane. The wet solid was dissolved in and partitioned between 1N NaOH and ethyl acetate. The aqueous portion was extracted an additional two times with ethyl acetate. The combined extracts were washed with brine, dried over sodium sulfate, decanted and concentrated (3.6 g, 99%). $^1$H NMR (300 MHz, CDCl$_3$): δ 8.81 (s, 1H), 7.69 (dd, 1H), 7.34 (d, 1H), 6.98 (dd, 1H), 6.92 (dd, 1H), 6.85 (d, 1H), 5.66 (s, 2H), 4.15-4.03 (m, 1H), 3.53 (m, 2H), 3.28 (dd, 1H), 2.95 (t, 2H), 2.86 (d, 2H), 2.82-2.61 (m, 2H), 1.89-1.73 (m, 1H), 1.50-1.35 (m, 1H), 0.91 (m, 2H), –0.06 (s, 9H); (M+H)$^+$: 437.3.

Step 4. oxazolo[5,4-b]pyridine-2(1H)-thione

Preparation similar to that referenced in *J. Org. Chem.* 1995, 60(17), 5721-5725. To a mixture of 3-aminopyridin-2-ol (3B Scientific Corporation) (10.12 g, 91.9 mmol) in THF (200 mL) at 0° C. in an ice bath was added carbonothioic dichloride (7.71 mL, 101 mmol) drop-wise. The reaction was stirred at RT for 3 h. Water was added and the pH was adjusted to the range of 4-5. The product was obtained by extraction with ethyl acetate. The extracts were dried over sodium sulfate, filtered and concentrated. The product was used without further purification. $^1$H NMR (300 MHz, d$_6$-DMSO): δ 14.08 (br s, 1H), 8.14 (d, 1H), 7.67 (d, 1H), 7.35 (dd, $^1$H); (M+H)$^+$: 152.9.

Step 5. 3-(1-[1,3]oxazolo[5,4-b]pyridin-2-ylpyrrolidin-3-yl)-3-[3-(7-{[2-(trimethylsilyl)ethoxy]methyl}-7H-pyrrolo[2,3-d]pyrimidin-4-yl)-1H-pyrrol-1-yl]propanenitrile A mixture of 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (1.2 g, 2.7 mmol, from Step 3) and oxazolo[5,4-b]pyridine-2(1H)-thione (0.50 g, 3.3 mmol) in 1,4-dioxane (20 mL) and N,N-diisopropylethylamine (0.96 mL, 5.5 mmol) was heated to 70° C. for 2 h. The solvent was evaporated and replaced with ethanol (20 mL) and silver nitrate (1.4 g, 8.2 mmol) and ammonium hydroxide solution (3.8 mL) were added. The reaction was stirred for 16 h. Water, 1N NaOH and ethyl acetate were added into the reaction and the solids were filtered off, rinsing with ethyl acetate, and the layers of the filtrate were separated. The aqueous layer was extracted with three further portions of ethyl acetate. The combined extracts were washed with brine, dried over sodium sulfate, decanted and concentrated. The product was purified by flash column chromatography on silica gel, eluting with a gradient from 0-10% ethyl acetate in hexanes (930 mg, 61%). $^1$H NMR (300 MHz, CDCl$_3$): δ 8.83 (s, 1H), 7.96 (dd, 1H), 7.73 (t, 1H), 7.60 (dd, 1H), 7.36 (d, 1H), 7.15 (dd, 1H), 7.03 (dd, 1H), 6.96 (t, 1H), 6.85 (d, 1H), 5.67 (s, 2H), 4.27-4.17 (m, 1H), 4.09 (dd, 1H), 3.91-3.81 (m, 1H), 3.70-3.60 (m, 1H), 3.55 (m, 2H), 3.52-3.45 (m, 1H), 3.17-3.04 (m, 1H), 2.98 (d, 2H), 2.12-2.00 (m, 1H), 1.91-1.74 (m, 1H), 0.92 (m, 2H), –0.06 (s, 9H); LCMS (M+H)$^+$: 555.2.

Step 6. 3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile phosphate A solution of racemic 3-(1-[1,3]oxazolo[5,4-b]pyridin-2-ylpyrrolidin-3-yl)-3-[3-(7-{[2-(trimethylsilyl)ethoxy]methyl}-7H-pyrrolo[2,3-d]pyrimidin-4-yl)-1H-pyrrol-1-yl]propanenitrile (0.93 g, 1.7 mmol, produced in Step 5) in DCM (30 mL) and TFA (10 mL) was stirred for 2.5 h. The solvents were evaporated and the residue was stirred with ammonium hydroxide solution in methanol for 16 h. The solvent was again evaporated. The residue was partitioned between water and 10% IPA in CHCl$_3$. The layers were separated and the aqueous portion was extracted two further times with 10% IPA in CHCl$_3$. The extracts were dried over sodium sulfate, decanted and concentrated. The enantiomers were separated by chiral HPLC (Phenomenex Lux-cellulose-1, 5μ, 20×250 mm, 80% ethanol/hexanes, 10 mL/min), to provide enantiomer 1 (first to elute, retention time 19.3 min), and enantiomer 2 (second to elute, retention time 24.1 min). Enantiomer 1 was obtained by removal of solvent in vacuo, in the amount of 314 mg. This product was dissolved in hot isopropanol and one equivalent of phosphoric acid was added. There was immediate formation of a precipitate and the mixture was allowed to cool slowly to ambient temperature, with stirring. The product was isolated by filtration and was air dried, then dried further at 60° C. under vacuum (289 mg, 33%). $^1$H NMR (300 MHz, d$_6$-DMSO): δ 11.97 (s, 1H), 8.61 (s, 1H), 8.01 (t, 1H), 7.87 (dd, 1H), 7.62 (dd, 1H), 7.52 (dd, 1H), 7.20 (dd, 1H), 7.16 (t, 1H), 6.97-6.92 (m, 2H), 4.59 (dt, 1H), 3.87 (dd, 1H), 3.72-3.62 (m, 1H), 3.56-3.40 (m, 3H), 3.30 (dd, 1H), 3.00-2.85 (m, 1H), 1.75-1.63 (m, 2H); LCMS (M+H)$^+$: 425.1.

Example 34

3-[1-(1,1-dioxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile (two enantiomers isolated)

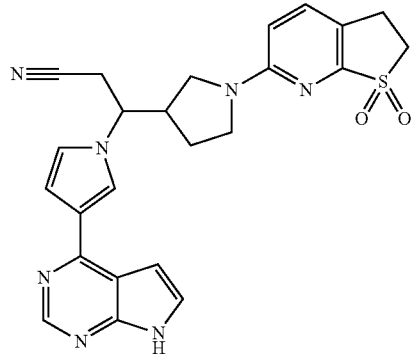 [SMILES: N#CCC(C1CCN(c2ccc3c(n2)S(=O)(=O)CC3)C1)n1ccc(-c2ncnc3[nH]ccc23)c1]

3-Pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (80 mg, 0.18 mmol, from Example 33, Step 3) and 6-chloro-2,3-dihydrothieno[2,3-b]pyridine 1,1-dioxide (37 mg, 0.18 mmol, prepared as described in Example 28, Step 4) were dissolved in ethanol (190 microL) and N,N-diisopropylethylamine (64 microL, 0.37 mmol). In a sealed vial, the mixture was heated in an oil bath held at 120° C. for 3 h. The mixture was then concentrated in vacuo. The product was purified by flash column chromatography, eluting with a gradient from 0-5% Methanol in Ethyl acetate to afford racemic product. This material was separated by chiral HPLC (Chiral Technologies Chiralpak AD-H, 5μ, 20×250 mm, eluting with 80% EtOH/Hexanes, 8 mL/min) to afford enantiomer 1 (first to elute, retention time 35.0 min) and enantiomer 2 (second to elute, retention time 55.6 min).

After removal of solvent in vacuo, each enantiomer was deprotected separately by stirring sequentially in a mixture of 1:1 TFA/DCM for 1 h, removal of solvent, then stirring in methanol (1.5 mL) containing EDA (0.2 mL) for 30 min. Preparative-HPLC/MS (C18 column eluting with a gradient of ACN/H$_2$O containing 0.15% NH$_4$OH) was used to purify the products.

Enantiomer 1: (6 mg, 6%). $^1$H NMR (400 MHz, d$_6$-DMSO): δ 11.96 (br s, 1H), 8.61 (s, 1H), 8.01 (t, 1H), 7.69 (d, 1H), 7.51 (d, 1H), 7.16 (dd, 1H), 6.96-6.93 (m, 2H), 6.75 (d, 1H), 4.56 (dt, 1H), 3.76 (dd, 1H), 3.57-3.22 (m, 7H), 3.15-3.08 (m, 2H), 2.94-2.81 (m, 1H), 1.71-1.63 (m, 2H); LCMS (M+H)$^+$: 474.1.

Enantiomer 2: (4 mg, 4%). $^1$H NMR (400 MHz, d$_6$-DMSO): δ 11.96 (br s, 1H), 8.61 (s, 1H), 8.01 (t, 1H), 7.69 (d, 1H), 7.51 (d, 1H), 7.16 (dd, 1H), 6.96-6.93 (m, 2H), 6.75 (d, 1H), 4.56 (dt, 1H), 3.76 (dd, 1H), 3.57-3.22 (m, 7H), 3.15-3.08 (m, 2H), 2.94-2.81 (m, 1H), 1.71-1.63 (m, 2H); LCMS (M+H)$^+$: 474.1.

Example 35

3-[1-(1-oxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile

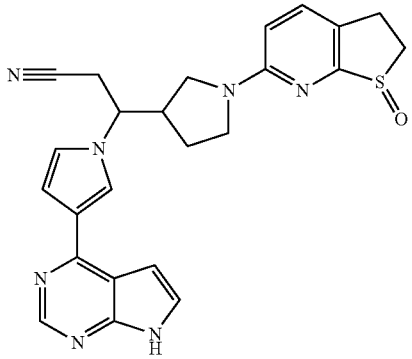 [SMILES: N#CCC(C1CCN(c2ccc3c(n2)S(=O)CC3)C1)n1ccc(-c2ncnc3[nH]ccc23)c1]

A mixture of 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (26 mg, 0.053 mmol, from Example 33, Step 3) and 6-chloro-2,3-dihydrothieno[2,3-b]pyridine 1-oxide (10.0 mg, 0.0533 mmol, prepared as described in Example 28, Step 4) in ethanol (56 microL) and N,N-diisopropylethylamine (19 microL) was heated to 120° C. for 1.5 h in the microwave. The mixture was concentrated in vacuo. The crude mixture was dissolved in 1:1 TFA/DCM, stirred for 1.5 h, and then concentrated again. The residue was then dissolved in methanol (1.5 mL) and EDA (0.2 mL) was added. After stirring for 30 min, preparative-HPLC/MS (C18 column eluting with a gradient of ACN/H$_2$O containing 0.15% NH$_4$OH) was used to purify the product (3 mg, 12%). $^1$H NMR (400 MHz, d$_6$-DMSO): δ 11.96 (br s, 1H), 8.61 (s, 1H), 8.02-8.00 (m, 1H), 7.71 (d, 1H), 7.51 (d, 1H), 7.16 (t, 1H), 6.96-6.92 (m, 2H), 6.64 (d, 1H), 4.56 (ft, 1H), 3.75 (dd, 1H), 3.56-2.98 (m, 9H), 2.94-2.82 (m, 1H), 1.73-1.61 (m, 2H); LCMS (M+H)$^+$: 458.1.

Example 36

±3-[1-(6-chloro-4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile trifluoroacetate

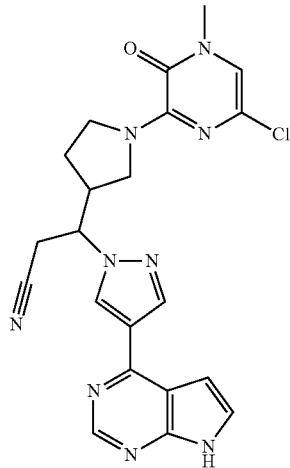 [SMILES: Cn1cc(Cl)nc(N2CCC(C(CC#N)n3cc(-c4ncnc5[nH]ccc45)cn3)C2)c1=O]

Step 1. 3,5-dichloro-1-methylpyrazin-2(1H)-one (Methylamino)acetonitrile hydrochloride (2.55 g, 23.9 mmol) was dissolved in chloroform in a 1-neck round-bottom flask (38.93 mL, 486.5 mmol) and oxalyl chloride (6.07 mL, 71.8 mmol) was added. The reaction was heated to reflux overnight and was transferred into a different flask, and the solvent removed by rotary evaporation. The reaction was chromatographed on silica gel using 1:1 EtOAc/hexanes to give the product. Mass spec: [M+1]: 179. $^1$H NMR (CDCl$_3$): 7.25 (s, 1H), 3.60 (s, 3H).

Step 2. ±3-[7-(6-chloro-4-methyl-3-oxo-3,4-dihydropyrazin-2-yl)pyrrolidin-3-yl]-3-[4-(7-{[2-(trimethylsilyl)ethoxy]methyl}-7H-pyrrolo[2,3-c]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (50.00 mg, 0.1142 mmol, prepared as in Example 15, Steps 1-3, omitting the chiral separation performed in Step 2) was mixed with 3,5-dichloro-1-methylpyrazin-2(1H)-one (32.00 mg, 0.1788 mmol) and was dissolved in 1,4-dioxane (0.5 mL). The reaction was heated at 100° C. for 2 h at which time LCMS analysis showed mainly product. The residues were chromatographed on silica gel using EtOAc and 5% MeOH/EtOAc to give the product. Mass spec: [M+1]: 580.

Step 3. ±3-[7-(6-chloro-4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile trifluoroacetate The product from step 2 was dissolved in DCM (0.50 mL) in a 1-neck round-bottom flask, and TFA (0.30 mL, 3.9 mmol)

was added. The reaction was stirred at 25° C. for 1 h, and the solvent removed by rotary evaporation. The residue was dissolved in methanol (2.00 mL) and 16 M of ammonia in water (0.30 mL, 4.9 mmol) was added. The mixture was stirred for 1 h, and the solvent removed by rotary evaporation. The product was isolated by preparative HPLC-MS using a Waters Fraction-Linx instrument and a 19 mm×100 mm Sunfire C18 column; eluting with a gradient of ACN/H$_2$O (0.1% TFA), 30 mL/min; Mass spec: [M+1]: 450. $^1$H NMR (CD$_3$OD): δ 8.95 (s, 1H), 8.87 (s, 1H), 8.54 (s, 1H), 7.83 (d, 1H), 7.25 (d, 1H), 6.77 (s, 1H), 4.83 (m, 1H), 3.60-4.2 (m, 4H), 3.35 (s, 3H), 3.40 (m, 1H), 3.20 (m, 1H), 2.94 (m, 1H), 1.76 (m, 2H).

Example 37

±3-[1-(4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile trifluoroacetate

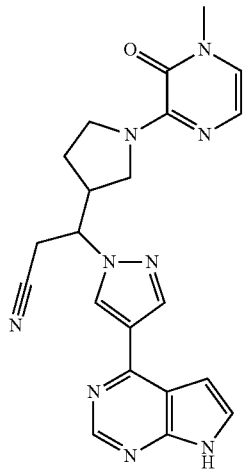 [SMILES: Cn1ccnc(N2CCC(C(CC#N)n3cc(-c4ncnc5[nH]ccc45)cn3)C2)c1=O]

Step 1. ±3-[1-(4-methyl-3-oxo-3,4-dihydropyrazin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile 3-[1-(6-Chloro-4-methyl-3-oxo-3,4-dihydropyrazin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (from Example 36, 27 mg, 0.046 mmol) was dissolved in isopropyl alcohol (1.00 mL) and methanol (1.00 mL) with sodium bicarbonate (12 mg, 0.14 mmol) in a 1-neck round-bottom flask. 10% Palladium on carbon (10:90, palladium:carbon black, 15.0 mg, 0.0141 mmol) was added. The reaction was stirred under an atmosphere of hydrogen overnight at which time LCMS analysis showed a 1:1 mixture of starting material and product. Into the reaction was added an additional 10% palladium on carbon (10:90, palladium:carbon black, 15.0 mg, 0.0141 mmol) and was stirred under an atmosphere of hydrogen for 48 h at which time LCMS analysis showed no starting material present. The reaction was filtered, and the solvent removed by rotary evaporation. The residue was used in the next reaction without purification. Mass spec: [M+1]: 546

Step 2. ±3-[1-(4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile trifluoroacetate The product from step 1 was dissolved in DCM (0.50 mL) in a 1-neck round-bottom flask, and TFA (0.30 mL, 3.9 mmol) was added. The reaction was stirred at 25° C. for 2 h, and the solvent removed by rotary evaporation. The residue was dissolved in methanol (2.00 mL) and 16 M of ammonia in water (0.30 mL, 4.9 mmol) was added and was stirred for 2 h. The solvent was then removed by rotary evaporation. The product was isolated by preparative HPLC-MS using a Waters Fraction-Linx instrument and a 19 mm×100 mm Sunfire C18 column; eluting with a gradient of ACN/H$_2$O (0.1% TFA), 30 mL/min; detector set at m/z 415; to give the product as the TFA salt. Mass spec: [M+1]: 416; $^1$H NMR (CD$_3$OD): δ 8.94 (s, 1H), 8.86 (s, 1H), 8.54 (s, 1H), 7.82 (d, 1H), 7.23 (d, 1H), 6.88 (d, 1H), 6.68 (d, 1H), 4.90 (m, 1H), 3.70-4.5 (m, 4H), 3.43 (s, 3H), 3.40 (m, 1H), 3.20 (m, 1H), 3.10 (m, 1H), 1.88 (m, 2H).

Example 38

±3-chloro-2-(3-{2-cyano-1-[4-(7H-pyrrolo[2,3-d]pyrimidin-4-yl)-1H-pyrazol-1-yl]ethyl}pyrrolidin-1-yl)isonicotinonitrile trifluoroacetate

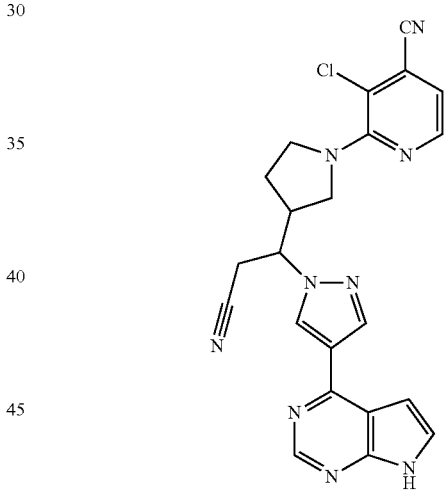

Step 1. 2,3-dichloroisonicotinaldehyde

N,N-Diisopropylamine (1.14 mL, 8.11 mmol) was dissolved in THF in a 1-neck round-bottom flask (15.00 mL, 184.9 mmol). The solution was then cooled at −78° C. and 1.60 M of n-butyllithium in hexane (4.64 mL, 7.43 mmol) was added. The reaction was allowed to warm at 0° C. and was re-cooled to −78° C. Into the reaction was added 2,3-dichloropyridine (1.00 g, 6.76 mmol) in THF (5.00 mL, 61.6 mmol). The reaction was then stirred at −78° C. for 2 h and DMF (1.046 mL, 13.51 mmol) was added and was stirred at −78° C. for 30 min and was allowed to warm to 0° C. TLC analysis (20% EtOAc/hexanes) showed no starting material present. LCMS analysis showed M+1+CH$_3$OH peak. NMR analysis showed an aldehyde proton, although most of the product had solidified and the NMR is more indicative of the composition of the non-crystallized material. The reaction was chromatographed on silica gel using 25% EtOAc/hexanes to give the product. $^1$H NMR (CDCl$_3$): δ 10.49 (s, 1H), 8.49 (d, 1H), 7.67 (d, 1H).

Step 2. 2,3-dichloroisonicotinaldehyde oxime 2,3-Dichloroisonicotinaldehyde (0.50 g, 2.8 mmol) was dissolved in methanol (10.0 mL, 247 mmol) with Potassium bicarbonate (0.35 g, 3.5 mmol) in a 1-neck round-bottom flask, and hydroxylamine hydrochloride (0.22 g, 3.2 mmol) was added The reaction was stirred at 25° C. for 2 days. LCMS analysis showed no starting material and the two oxime isomers mainly. The reaction mixture was partitioned between EtOAc and water and EtOAc extract was washed with brine, dried (MgSO$_4$), and stripped in vacuo. The product was used in the next reaction without further purification. Mass spec: [M+1]: 191;

Step 3. 2,3-dichloroisonicotinonitrile 2,3-Dichloroisonicotinaldehyde oxime (0.617 g, 0.00323 mol) was dissolved in pyridine (6.0 mL, 0.074 mol) in a 1-neck round-bottom flask. Methanesulfonyl chloride (1.0 mL, 0.013 mol) was added drop-wise, and the reaction was heated at 60° C. for 2 h. After cooling, the reaction was extracted with ethyl acetate and the organic extracts were washed with water, 0.5 N HCl, saturated NaCl solution, dried (MgSO$_4$) and stripped in vacuo. The residue was chromatographed on silica gel using 20% EtOAc/hexanes to give the product. $^1$H NMR (CDCl$_3$): δ 8.48 (d, 1H), 7.53 (d, 1H).

Step 4. ±3-chloro-2-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)isonicotinonitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (100.00 mg, 0.22851 mmol, prepared as in Example 15, Steps 1-3, omitting the chiral separation performed in Step 2) was mixed with 2,3-dichloroisonicotinonitrile (57.99 mg, 0.3352 mmol) and then was dissolved in NMP (0.60 mL, 6.2 mmol). The reaction was heated at 130° C. for 2 h at which time LCMS analysis showed mainly product. The residues were chromatographed on silica gel using EtOAc and 5% MeOH/EtOAc to give the product. Mass spec: [M+1]: 574.

Step 5. ±3-chloro-2-(3-{2-cyano-1-[4-(7H-pyrrolo[2,3-d]pyrimidin-4-yl)-1H-pyrazol-1-yl]ethyl}pyrrolidin-1-yl)isonicotinonitrile trifluoroacetate 3-Chloro-2-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)isonicotinonitrile (25.00 g, 43.54 mmol) was dissolved in DCM (0.50 mL, 7.8 mmol) in a 1-neck round-bottom flask, and TFA (0.30 mL, 3.9 mmol) was added. The reaction was stirred at 25° C. for 1 h, and the solvent was removed by rotary evaporation. The residue was dissolved in methanol (2.00 mL, 49.4 mmol) and 16 M of ammonia in water (0.30 mL, 4.9 mmol) was added. The mixture was stirred for 1 h, and the solvent was removed by rotary evaporation. The product was isolated by preparative HPLC-MS using a Waters Fraction-Linx instrument and a 19 mm×100 mm Sunfire C18 column; eluting with a gradient of ACN/H$_2$O (0.1% TFA), 30 mL/min; detector set at m/z 443 to give the product as the TFA salt. Mass spec: [M+1]: 444; $^1$H NMR (CD$_3$OD): δ 8.96 (s, 1H), 8.87 (s, 1H), 8.54 (s, 1H), 8.16 (d, 1H), 7.84 (d, 1H), 7.25 (d, 1H), 6.96 (d, 1H), 4.83 (m, 1H), 3.70-4.00 (m, 4H), 3.40 (m, 1H), 3.20 (m, 1H), 3.00 (m, 1H), 1.80 (m, 2H).

Example 39

±2-(3-{2-cyano-1-[4-(7H-pyrrolo[2,3-d]pyrimidin-4-yl)-1H-pyrazol-1-yl]ethyl}pyrrolidin-1-yl)pyridine-3,4-dicarbonitrile trifluoroacetate

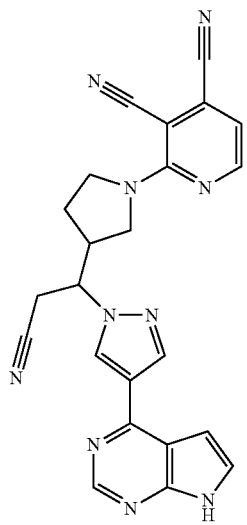 [SMILES: N#CCC(C1CCN(c2nccc(C#N)c2C#N)C1)n1cc(-c2ncnc3[nH]ccc23)cn1]

Step 1. ±2-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyridine-3,4-dicarbonitrile 3-Chloro-2-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)isonicotinonitrile (65.0 mg, 0.113 mmol, from Example 38, Step 4) was dissolved in NMP (0.8 mL, 8 mmol) in a 1-neck round-bottom flask, and zinc cyanide (39.9 mg, 0.340 mmol) and zinc (22.2 mg, 0.340 mmol) was added. The reaction was degassed and bis(tri-t-butylphosphine)palladium (28.9 mg, 0.0566 mmol) was added and the reaction was heated at 130° C. for 100 min at which time LCMS analysis showed that it was mainly a 1:1 mixture of product and dechlorinated starting material. The reaction was filtered and the product was isolated by preparative HPLC-MS using a Waters Fraction-Linx instrument and a 19 mm×100 mm Sunfire C18 column; eluting with a gradient of ACN/H$_2$O (0.1% TFA), 30 mL/min; detector set at m/z 564; Mass spec: [M+1] m/z: 565.

Step 2. ±2-(3-{2-cyano-1-[4-(7H-pyrrolo[2,3-d]pyrimidin-4-yl)-1H-pyrazol-1-yl]ethyl}pyrrolidin-1-yl)pyridine-3,4-dicarbonitrile trifluoroacetate The product from step 1 was dissolved in DCM (0.50 mL, 7.8 mmol) in a 1-neck round-bottom flask, and TFA (0.30 mL, 3.9 mmol) was added. The reaction was stirred at 25° C. for 2 h, and the solvent was removed by rotary evaporation. The residue was dissolved in methanol (2.00 mL, 49.4 mmol) and 16 M of ammonia in water (0.30 mL, 4.9 mmol) was added. The mixture was then stirred for 2 h, and the solvent was removed by rotary evaporation. The residue was purified by prep. The product was isolated by preparative HPLC-MS using a Waters Fraction-Linx instrument and a 19 mm×100 mm Sunfire C18 column; eluting with a gradient of ACN/H$_2$O (0.1% TFA), 30 mL/min; detector set at m/z 434; to give the product as the TFA salt. Mass spec: [M+1]: 435; $^1$H NMR (CD$_3$OD): δ 9.00 (s, 1H), 8.90 (s, 1H), 8.56 (s, 1H), 8.44 (d, 1H), 7.90 (d, 1H), 7.29 (d, 1H), 6.99 (d, 1H), 4.91 (m, 1H), 4.11 (m, 1H), 3.9 (m, 1H), 3.75 (m, 2H), 3.40 (m, 1H), 3.30 (m, 1H), 3.05 (m, 1H), 1.89 (m, 2H).

Example 40

±2-(3-{2-cyano-1-[4-(7H-pyrrolo[2,3-d]pyrimidin-4-yl)-1H-pyrazol-1-yl]ethyl}pyrrolidin-1-yl)-6-(methylthio)benzonitrile

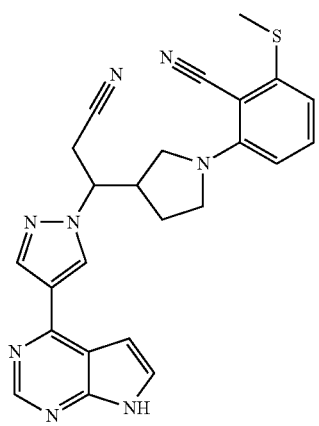 [SMILES: CSc1cccc(N2CCC(C(CC#N)n3cc(-c4ncnc5[nH]ccc45)cn3)C2)c1C#N]

Step 1. 2-fluoro-6-(methylthio)benzonitrile

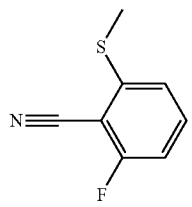

To a 0° C. solution of 2,6-difluorobenzonitrile (0.20 g, 1.4 mmol) in DMF (2 mL, 20 mmol) was added sodium methyl mercaptide (0.13 g, 1.7 mmol). The reaction was allowed to warm to RT and was stirred overnight. It was then filtered and purified by LCMS (C18 column eluting with a gradient of ACN/H$_2$O containing 0.15% NH$_4$OH at 5 mL/min) to give 41 mg pale yellow solid (17% yield). $^1$H NMR (400 MHz, CDCl$_3$): δ 7.55 (1H, m); 7.07 (1H, m); 6.96 (1H, t); 2.59 (3H, s). LCMS (M+1): 168.

Step 2. 2-(3-{2-cyano-1-[4-(7H-pyrrolo[2,3-d]pyrimidin-4-yl)-1H-pyrazol-1-yl]ethyl}pyrrolidin-1-yl)-6-(methylthio)benzonitrile A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.075 g, 0.17 mmol, prepared as in Example 15, Steps 1-3, omitting the chiral separation performed in Step 2), 2-fluoro-6-(methylthio)benzonitrile (0.040 g, 0.24 mmol) and N,N-diisopropylethylamine (60 microL, 0.3 mmol) in 1-butyl-3-methyl-1H-imidazol-3-ium fluoride/trifluoroborane (1:1) (0.15 g, 0.66 mmol) was heated at 120° C. for 3.2 h, then at 150° C. for 2 h. It was purified by LCMS (C18 column eluting with a gradient of ACN/H$_2$O containing 0.15% NH$_4$OH at 5 mL/min) to give 30 mg 2-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(methylthio)benzonitrile (A, 30% yield). LCMS (M+1): 585.

5 mg A was stirred in 1 mL DCE and 1 mL TFA for 1 h. It was concentrated and the residue was stirred in 50 uL EDA and 1 mL MeOH for 1 h. The reaction was purified by LCMS (C18 column eluting with a gradient ACN/H$_2$O containing 0.15% NH$_4$OH at 5 mL/min) gave 3.5 mg white solid. $^1$H NMR (400 MHz, DMSO): δ 12.1 (1H, br); 8.85 (1H, s); 8.65 (1H, s); 8.0 (1H, s); 7.6 (1H, m); 7.18 (1H, m); 6.98 (1H, m); 6.6 (2H, m); 4.81 (1H, m); 3.68 (1H, m); 3.6-3.2 (5H, m); 2.9 (1H, m); 2.5 (3H, s); 1.62 (2H, br). LCMS (M+1): 455.

Example 41

±2-(3-{2-cyano-1-[4-(7H-pyrrolo[2,3-d]pyrimidin-4-yl)-1H-pyrazol-1-yl]ethyl}pyrrolidin-1-yl)-6-(methylsulfonyl)benzonitrile

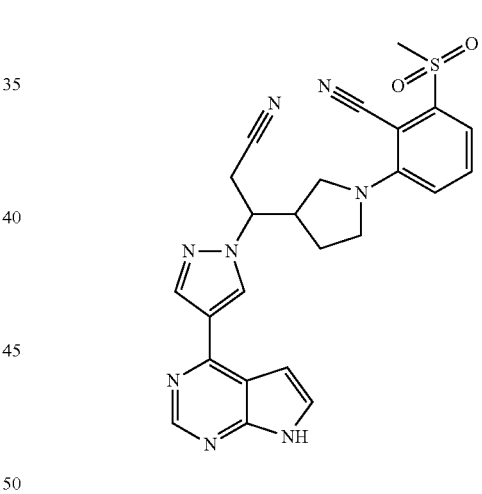

A solution of 15 mg A (from Example 40, step 2, 26 mmol) and m-chloroperbenzoic acid (0.018 g, 0.080 mmol) in DCM (1 mL, 20 mmol) was stirred for 1.5 h. MeOH and DMF were added. The mixture was purified by LCMS to give 5 mg white solid. The compound was then deprotected to remove the SEM group. It was stirred in 1 mL DCE and 1 mL TFA for 1 h. It was concentrated and the residue was stirred in 50 uL EDA and 1 mL MeOH for 1 h. The reaction was purified by LCMS (C18 column eluting with a gradient ACN/H$_2$O containing 0.15% NH$_4$OH at 5 mL/min) and gave 4.1 mg white solid. $^1$H NMR (400 MHz, DMSO): δ 12.13 (1H, s); 8.88 (1H, s); 8.68 (1H, s); 8.41 (1H, s); 7.61 (1H, m); 7.6 (1H, m); 7.35 (1H, m); 7.19 (1H, m); 6.98 (1H, m); 4.82 (1H, m); 3.67 (1H, m); 3.6-3.2 (5H, m); 2.92 (1H, m); 2.5 (3H, s); 1.63 (2H, m). LCMS (M+1): 487.

Example 42

±3-[1-(8-chloroquinolin-2-yl)pyrrolidin-3-yl]-3-[4-(7H-pyrrolo[2,3-d]pyrimidin-4-yl)-1H-pyrazol-1-yl]propanenitrile

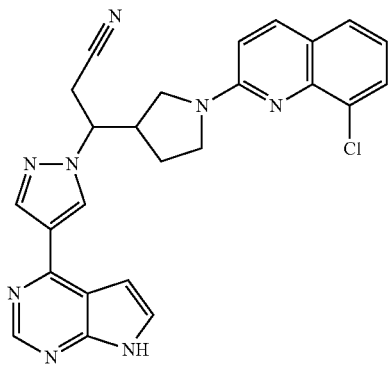 [SMILES: N#CCC(C1CCN(c2ccc3cccc(Cl)c3n2)C1)n1cc(-c2ncnc3[nH]ccc23)cn1]

A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.020 g, 0.000046 mol, prepared as in Example 15, Steps 1-3, omitting the chiral separation performed in Step 2) and 2,8-dichloroquinoline (0.020 g, 0.00010 mol) in ethanol (0.020 mL, 0.00034 mol) and N,N-diisopropylethylamine (20.0 microL, 0.000115 mol) was heated at 120° C. for 1.3 h. The crude was purified by LCMS (C18 column eluting with a gradient ACN/H$_2$O containing 0.15% NH$_4$OH at 5 mL/min) to give 16 mg. LCMS (M+1): 599.

The compound was then deprotected to remove the SEM group. It was stirred in 1 mL DCE and 1 mL TFA for 1 h. It was concentrated and the residue was stirred in 50 μL EDA and 1 mL MeOH for 1 h. The reaction was purified by LCMS (C18 column eluting with a gradient ACN/H$_2$O containing 0.15% NH$_4$OH at 5 mL/min) to give 9.7 mg (45% yield). $^1$H NMR (400 MHz, DMSO): δ 12.1 (1H, br); 8.9 (1H, s); 8.68 (1H, s); 8.42 (1H, s); 8.15 (1H, d); 7.65 (2H, m); 7.6 (1H, m); 7.15 (1H, t); 7.0 (1H, m); 6.95 (1H, d); 4.85 (1H, m); 3.85 (1H, br); 3.75 (1H, br); 3.45 (2H, m); 3.40-3.26 (2H, m); 2.98 (1H, m); 1.7 (2H, br). LCMS (M+1): 469.

Examples 43-46 in the table below were prepared by the general method of Example 42, with the exception that for Example 45, the starting material used was a single enantiomer of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile, prepared by the method of Example 15, Steps 1-3. Additionally, for Examples 43 and 44, the final product was purified by LCMS (C18 column eluting with a gradient of ACN/H$_2$O containing 0.1% TFA) to afford the trifluoroacetate salt of the parent compound.

| Ex. | Structure | Name | Salt form | MS (M + H) |
|---|---|---|---|---|
| 43 | 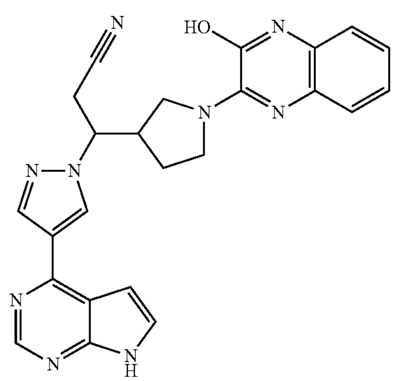 [SMILES: N#CCC(C1CCN(c2nc3ccccc3nc2O)C1)n1cc(-c2ncnc3[nH]ccc23)cn1] | 3-[1-(3-hydroxyquinoxalin-2-yl)pyrrolidin-3-yl]-3-[4-(7H-pyrrolo[2,3-d]pyrimidin-4-yl)-1H-pyrazol-1-yl]propanenitrile trifluoroacetate salt | 2TFA | 452 |
| 44 | 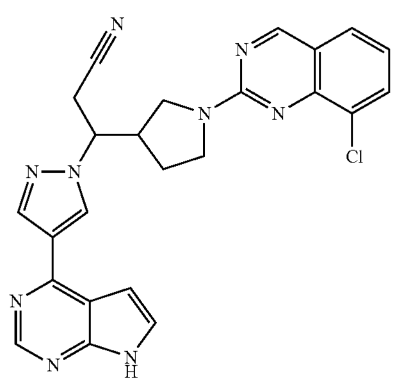 | 3-[1-(8-chloroquinazolin-2-yl)pyrrolidin-3-yl]-3-[4-(7H-pyrrolo[2,3-d]pyrimidin-4-yl)-1H-pyrazol-1-yl]propanenitrile trifluoroacetate salt | 2TFA | 470 |

-continued

| Ex. | Structure | Name | Salt form | MS (M + H) |
|---|---|---|---|---|
| 45 | 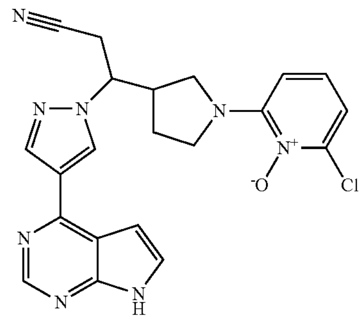 | 3-[1-(6-chloro-1-oxidopyridin-2-yl)pyrrolidin-3-yl]-3-[4-(7H-pyrrolo[2,3-d]pyrimidin-4-yl)-1H-pyrazol-1-yl]propanenitrile | — | 435 |
| 46 | 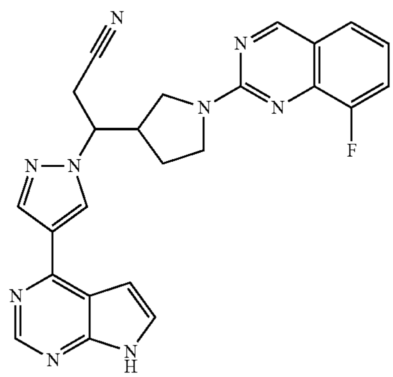 [SMILES: N#CCC(C1CCN(c2ncc3cccc(F)c3n2)C1)n1cc(-c2ncnc3[nH]ccc23)cn1] | 3-[1-(8-fluoroquinazolin-2-yl)pyrrolidin-3-yl]-3-[4-(7H-pyrrolo[2,3-d]pyrimidin-4-yl)-1H-pyrazol-1-yl]propanenitrile | — | 454 |

| Ex. No. | $^1$H NMR |
|---|---|
| 43 | (DMSO-d6): δ 8.9 (1H, s); 8.68 (1H, s); 8.60 (1H, s); 7.95 (1H, m); 7.6 (1H, m); 7.29 (1H, br); 7.06 (1H, m); 7.00 (1H, m); 7.0 (2H, br); 4.80 (1H, m); 3.4-2.8 (7H, br); 1.6 (2H, br) |
| 44 | (DMSO-d6): δ 12.2 (1H, br); 9.23 (1H, m); 9.01 (1H, s); 8.82 (1H, s); 8.55 (1H, s); 7.87 (1H, m); 7.79 (2H, m); 7.20 (1H, m); 7.19 (1H, m); 4.95 (1H, m); 4.0 (1H, m); 3.79 (1H, m); 3.6-3.3 (4H, br); 2.97 (1H, m); 1.75 (2H, br) |
| 45 | (DMSO-d6): δ 12.1 (1H, br); 8.90 (1H, s); 8.68 (1H, s); 8.41 (1H, s); 7.60 (1H, m); 7.18 (2H, m); 7.0 (1H, m); 6.81 (1H, m); 4.79 (1H, m); 3.7 (2H, m); 3.50 (2H, m); 3.25 (2H, m); 2.81 (1H, m); 1.6 (2H, br) |
| 46 | (DMSO-d6): δ 12.1 (1H, br); 9.23 (1H, br); 8.89 (1H, s); 8.65 (1H, s); 8.41 (1H, s); 7.64 (1H, m); 7.58 (2H, m); 7.18 (1H, m); 6.99 (1H, m); 4.87 (1H, m); 4.0 (1H, m); 3.77 (1H, m); 3.5-3.3 (4H, br); 2.95 (1H, m); 1.7 (2H, br) |

Example 47

(3S)-3-[(3S)-1-(5-bromo-1,3-thiazol-2-yl)pyrrolidin-3-yl]-3-[4-(7H-pyrrolo[2,3-d]pyrimidin-4-yl)-1H-pyrazol-1-yl]propanenitrile trifluoroacetate

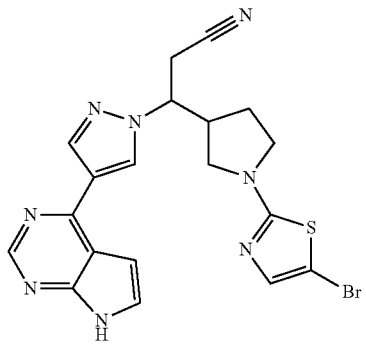 [SMILES: N#CCC(C1CCN(c2ncc(Br)s2)C1)n1cc(-c2ncnc3[nH]ccc23)cn1]

(3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (175 mg, 0.400 mmol; from Example 15, step 3) (free base) and 2,5-dibromo-1,3-thiazole (290 mg, 1.2 mmol) were mixed in isopropyl alcohol (2.2 mL, 29 mmol). 4-Methylmorpholine (130 microL, 1.2 mmol) was then added. The mixture was heated at 80° C. After 16 h, LCMS showed reaction, M+H 599/601. The intermediate was isolated by prep HPLC-MS using a Waters Fraction-Linx instrument and a 30 mm×100 mm Sunfire C18 column; 37% CH$_3$CN—H$_2$O (0.1% TFA), 0.5 min, 6 min gradient to 54%; 60 mL/min; retention time 5.6 min. The compound was then freeze dried to give 101 mg. The compound was then deprotected using TFA followed by NH$_4$OH. The deprotection generally involved the following: The compound was dissolved in DCM (1 mL) at 21° C., and TFA (1 mL) was added. The reaction mixture was then stirred for 1 h. The solution was concentrated to remove TFA. The residue was dissolved in acetonitrile or methanol (1 mL), and 15.0 M of ammonium hydroxide in water (0.25 mL) added. The solution was stirred at 21° C. for 2-18 h. After LCMS showed the deprotection was complete, the solution was concentrated by rotary evaporation. The product was isolated by prep HPLCMS using a Waters Fraction-Linx instrument and a 19 mm×100 mm Sunfire C18 column; 30 mL/min; 12% CH₃CN—H₂O (0.1% TFA), 0.5 min, gradient to 30% at 6 min; detector set at m/z 471; retention time, 5.5 min (3 runs). The compound was then freeze-dried to give the TFA salt (47 mg). $^1$H NMR (400 MHz, DMSO-D₆): δ 12.8 (s, 1H); 9.03 (s, 1H); 8.87 (s, 1H); 8.56 (s, 1H); 7.84 (s, 1H); 7.18 (s, 1H); 7.17 (s, 1H); 4.88 (m, 1H); 3.64 (m, 1H); 3.22-3.42 (m, 5H); 2.96 (m, 1H); 1.71 (m, 2H); LCMS (M+H)$^+$: 469.

Example 48

2-chloro-6-((3S)-3-{(1S)-2-cyano-1-[4-(7H-pyrrolo[2,3-d]pyrimidin-4-yl)-1H-pyrazol-1-yl]ethyl}pyrrolidin-1-yl)benzonitrile trifluoroacetate

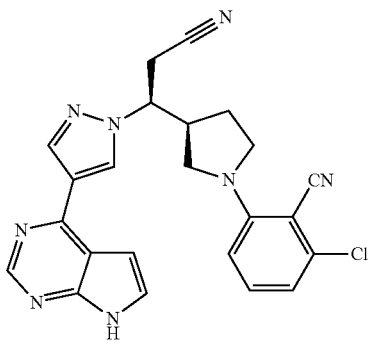 [SMILES: N#CC[C@@H]([C@H]1CCN(c2cccc(Cl)c2C#N)C1)n1cc(-c2ncnc3[nH]ccc23)cn1]

A solution of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (92 mg, 0.21 mmol; from Example 15, step 3), NMP (1.5 mL, 16 mmol), 4-methylmorpholine (69 microL, 0.63 mmol) and 2-chloro-6-fluorobenzonitrile (65 mg, 0.42 mmol) was heated at 90° C. for 50 min in a microwave reactor. LCMS showed about 80% complete reaction, and showed the expected, [M+H] 573. The intermediate was isolated by preparative HPLCMS using a Waters Fraction-Linx instrument and a 30 mm×100 mm Sunfire C18 column; 49% CH₃CN—H₂O (0.1% TFA), 0.5 min, to 67% at 6 min; 60 mL/min; retention time 5.3 min. The solvent was then removed by rotary evaporation. The compound was then deprotected using TFA followed by NH₄OH (see general procedure for Example 47). The product was isolated by prep LCMS using a Waters Fraction-Linx instrument and a 19 mm×100 mm Sunfire C18 column; 30 mL/min; 29% CH₃CN—H₂O (0.1% TFA), 0.5 min, gradient to 47% at 6 min; retention time 5.1 min. The compound was freeze-dried to give the TFA salt, 24 mg, a white solid. $^1$H NMR (400 MHz, DMSO-D6): δ 12.8 (s, 1H); 8.99 (s, 1H); 8.82 (s, 1H); 8.53 (s, 1H); 7.77 (s, 1H); 7.37 (t, 1H); 7.12 (s, 1H); 6.86 (d, 1H); 6.74 (d, 1H); 4.87 (m, 1H); 3.21-3.74 (m, 6H); 2.91 (m, 1H); 1.66 (m, 2H); LCMS (M+H)$^+$: 443.

Example 49

3-((3S)-3-{(1S)-2-cyano-1-[4-(7H-pyrrolo[2,3-d]pyrimidin-4-yl)-1H-pyrazol-1-yl]ethyl}pyrrolidin-1-yl)phthalonitrile trifluoroacetate

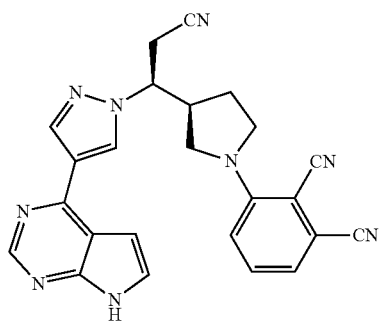 [SMILES: N#CC[C@@H]([C@H]1CCN(c2cccc(C#N)c2C#N)C1)n1cc(-c2ncnc3[nH]ccc23)cn1]

2-Bromo-6-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)benzonitrile (20.0 mg, 0.0324 mmol, prepared in a manner similar to that described in Example 48) was stirred in NMP (0.75 mL, 7.8 mmol). Zinc cyanide (57.0 mg, 0.486 mmol) was then added. Tetrakis(triphenylphosphine)palladium(0) (37.4 mg, 0.0324 mmol) was next added, and the solution was flushed with nitrogen (subsurface). The vial was then sealed and heated at 150° C. for 20 min in a microwave reactor. The reaction was worked up with 5% NaHCO₃ and EtOAc and filtered. The intermediate was isolated by preparative LCMS using a Waters Fraction-Linx instrument and a 30 mm×100 mm Sunfire C18 column; 46% CH₃CN—H₂O (0.1% TFA), 0.5 min, to 64% at 6 min; 60 mL/min; detector set at m/z 564; retention time 5.3 min. The solvent was then removed by rotary evaporation. The compound was then deprotected using TFA followed by NH₄OH (see general procedure for Example 47). The product was isolated by prep LCMS using a Waters Fraction-Linx instrument and a 19 mm×100 mm Sunfire C18 column; 24% CH₃CN—H₂O (0.1% TFA), 0.5 min, to 42% at 6 min; 30 mL/min; retention time 5.5 min. freeze-dried to give a white solid TFA salt. LCMS (M+H)$^+$: 434.1. $^1$H NMR (300 MHz, DMSO-d₆): δ 12.4 (s, 1H); 8.93 (s, 1H); 8.75 (s, 1H); 8.48 (s, 1H); 7.69 (s, 1H); 7.55 (dd, 1H); 7.25 (d, 1H); 7.10 (d, 1H); 7.05 (s, 1H); 4.86 (m, 1H); 3.2-3.8 (m, 6H); 2.93 (m, 1H); 1.69 (m, 2H).

Example 50

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(trifluoromethyl)nicotinonitrile trifluoroacetate

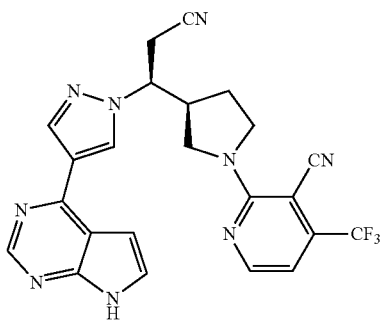 [SMILES: N#CC[C@@H]([C@H]1CCN(c2nccc(C(F)(F)F)c2C#N)C1)n1cc(-c2ncnc3[nH]ccc23)cn1]

6-Chloro-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(trifluoromethyl)nicotinonitrile (7.0 mg, 0.011 mmol, prepared in a manner similar to described in Example 51) was dissolved in methanol (1.0 mL, 25 mmol), and 6 mg 10% Pd/C added. Stirred at 21 C. A balloon containing hydrogen was attached to the flask for 0.5 h. LCMS showed the desired [M+H] 608, amine byproduct, [M+H] 612, other over-reduction byproducts, and a trace of remaining starting material. The product was isolated by preparative HPLC-MS using a Waters Fraction-Linx instrument and a 19 mm×100 mm Sunfire C18 column; 51% $CH_3CN$—$H_2O$ (0.1% TFA), to 69% at 6 min; 30 mL/min; detector set at m/z 608; retention time, 5.0 min. The compound was then deprotected using TFA followed by $NH_4OH$ (see general procedure for Example 47). The product was isolated by preparative HPLC-MS using a Waters Fraction-Linx instrument and a 19 mm×100 mm Sunfire C18 column; 30% $CH_3CN$—$H_2O$ (0.1% TFA), to 48% at 6 min; 30 mL/min; retention time, 4.1 min. LCMS (M+H)$^+$: 478.

Example 51

3-((3S)-3-{(1S)-2-cyano-1-[4-(7H-pyrrolo[2,3-d]pyrimidin-4-yl)-1H-pyrazol-1-yl]ethyl}pyrrolidin-1-yl)pyrazine-2-carbonitrile trifluoroacetate

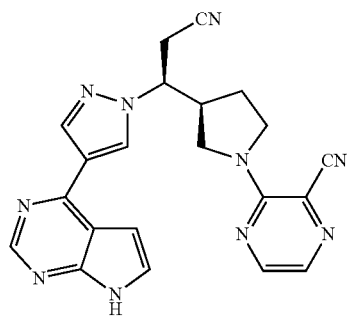 [SMILES: N#CC[C@@H]([C@H]1CCN(c2nccnc2C#N)C1)n1cc(-c2ncnc3[nH]ccc23)cn1]

(3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (38 mg, 0.087 mmol; from Example 15, step 3) was dissolved in NMP (0.7 mL, 7 mmol) and N,N-diisopropylethylamine (3.0E1 microL, 0.17 mmol). 3-chloropyrazine-2-carbonitrile (18 mg, 0.13 mmol) was added. The solution was stirred at 80° C. for 20 min (or 21° C. for 16 h). LCMS showed fairly clean conversion to the expected intermediate, and showed [M+H]: 541. The intermediate was isolated by preparative HPLC-MS using a Waters Fraction-Linx instrument and a 30 mm×100 mm Sunfire C18 column; 44% $CH_3CN$—$H_2O$ (0.1% TFA), 0.5 min; 6 min gradient to 62%; 60 mL/min; retention time, 4.9 min. The solvent was then removed by rotary evaporation. The compound was then deprotected using TFA followed by $NH_4OH$ (see general procedure for Example 47). The product was isolated by prep LCMS using a Waters Fraction-Linx instrument and a 19 mm×100 mm Sunfire C18 column; 30 mL/min; 20% $CH_3CN$—H2O (0.1% TFA), 0.5 min, gradient to 38% at 6 min freeze-dried to give a yellow solid TFA salt. $^1$H NMR (400 MHz, DMSO-d6): δ 12.7 (s, 1H); 9.01 (s, 1H); 8.83 (s, 1H); 8.54 (s, 1H); 8.36 (d, 1H); 7.95 (d, 1H); 7.79 (s, 1H); 7.14 (s, 1H); 4.89 (m, 1H); 3.92 (m, 1H); 3.80 (m, 1H); 3.61 (m, 2H); 3.40 (m, 1H); 3.29 (m, 1H); 2.91 (m, 1H); 1.71 (m, 2H); LCMS (M+H)$^+$: 411.

Examples 52-69

The examples in the table below were made by procedures analogous to those for producing Examples 47-51.

| Ex. | Structure | Name | M + H |
|---|---|---|---|
| 52 | 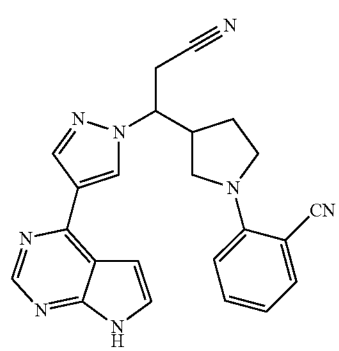 [SMILES: N#CCC(C1CCN(c2ccccc2C#N)C1)n1cc(-c2ncnc3[nH]ccc23)cn1] | 2-(3-{2-cyano-1-[4-(7H-pyrrolo[2,3-d]pyrimidin-4-yl)-1H-pyrazol-1-yl]ethyl}pyrrolidin-1-yl)benzonitrile trifluoroacetate salt | 409 |

| Ex. | Structure | Name | M + H |
|---|---|---|---|
| 53 | 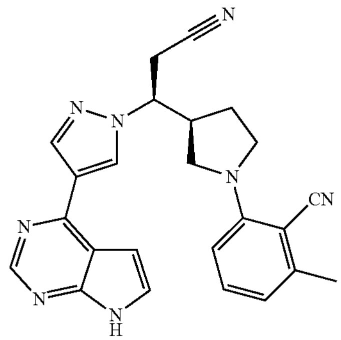 [SMILES: Cc1cccc(N2CC[C@H]([C@H](CC#N)n3cc(-c4ncnc5[nH]ccc45)cn3)C2)c1C#N] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-methylbenzonitrile trifluoroacetate salt | 423 |
| 54 | 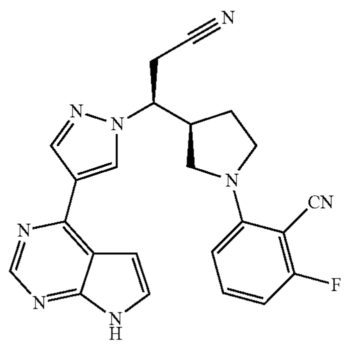 [SMILES: N#CC[C@@H]([C@H]1CCN(c2cccc(F)c2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-fluorobenzonitrile trifluoroacetate salt | 427 |
| 55 | 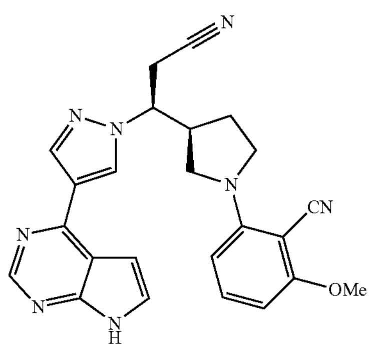 [SMILES: COc1cccc(N2CC[C@H]([C@H](CC#N)n3cc(-c4ncnc5[nH]ccc45)cn3)C2)c1C#N] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-methoxybenzonitrile trifluoroacetate salt | 439 |
| 56 | 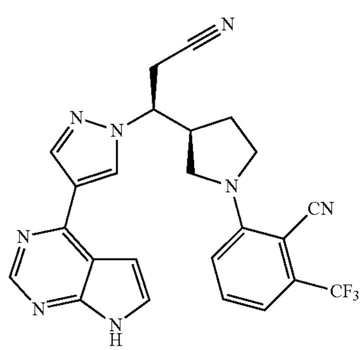 [SMILES: N#CC[C@@H]([C@H]1CCN(c2cccc(C(F)(F)F)c2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(trifluoromethyl)benzonitrile trifluoroacetate salt | 477 |

-continued

| Ex. | Structure | Name | M + H |
|---|---|---|---|
| 57 | 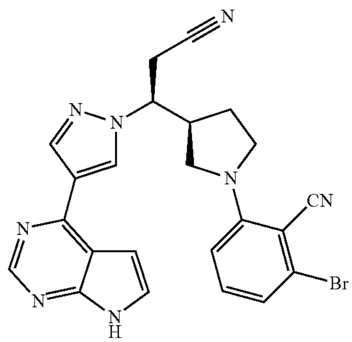 [SMILES: N#CC[C@@H]([C@H]1CCN(c2cccc(Br)c2C#N)C1)n1cc(-c2ncnc3[nH]ccc23)cn1] | 2-bromo-6-((3S)-3-{(1S)-2-cyano-1-[4-(7H-pyrrolo[2,3-d]pyrimidin-4-yl)-1H-pyrazol-1-yl]ethyl}pyrrolidin-1-yl)benzonitrile trifluoroacetate salt | 487 |
| 58 | 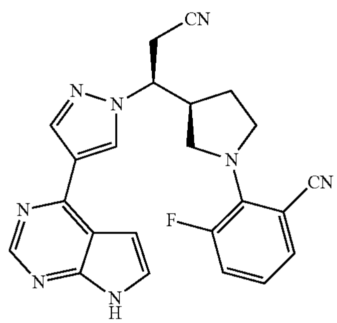 [SMILES: N#CC[C@@H]([C@H]1CCN(c2c(F)cccc2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-3-fluorobenzonitrile trifluoroacetate salt | 427 |
| 59 | 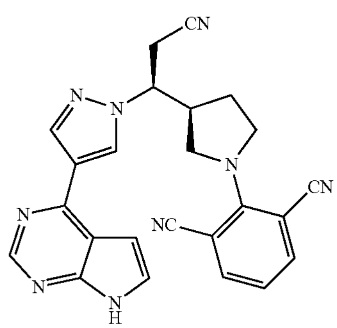 [SMILES: N#CC[C@@H]([C@H]1CCN(c2c(C#N)cccc2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)isophthalonitrile trifluoroacetate salt | 434 |
| 60 | 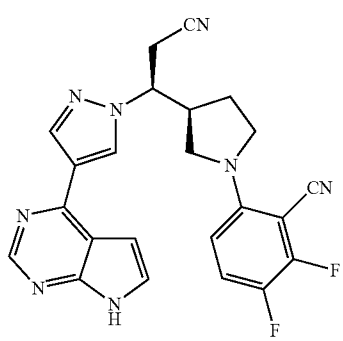 [SMILES: N#CC[C@@H]([C@H]1CCN(c2ccc(F)c(F)c2C#N)C1)n1cc(-c2ncnc3[nH]ccc23)cn1] | 6-((3S)-3-{(1S)-2-cyano-1-[4-(7H-pyrrolo[2,3-d]pyrimidin-4-yl)-1H-pyrazol-1-yl]ethyl}pyrrolidin-1-yl)-2,3-difluorobenzonitrile trifluoroacetate salt | 445 |

-continued

| Ex. | Structure | Name | M + H |
|---|---|---|---|
| 61 | 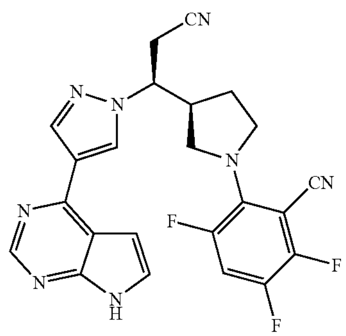 [SMILES: N#CC[C@@H]([C@H]1CCN(c2c(F)cc(F)c(F)c2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-3,5,6-trifluorobenzonitrile trifluoroacetate salt | 463 |
| 62 | 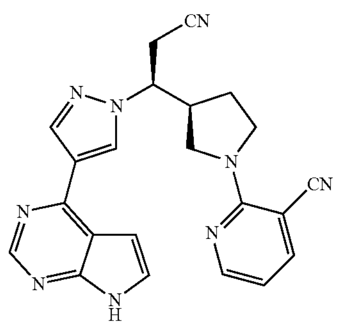 [SMILES: N#CC[C@@H]([C@H]1CCN(c2ncccc2C#N)C1)n1cc(-c2ncnc3[nH]ccc23)cn1] | 2-((3S)-3-{(1S)-2-cyano-1-[4-(7H-pyrrolo[2,3-d]pyrimidin-4-yl)-1H-pyrazol-1-yl]ethyl}pyrrolidin-1-yl)nicotinonitrile trifluoroacetate salt | 410 |
| 63 | 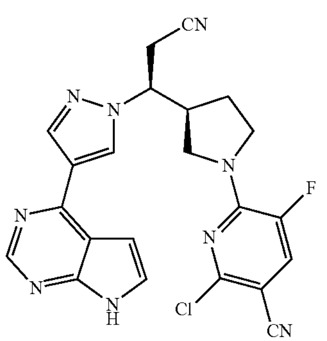 [SMILES: N#CC[C@@H]([C@H]1CCN(c2nc(Cl)c(C#N)cc2F)C1)n1cc(-c2ncnc3[nH]ccc23)cn1] | 6-((S)-3-((S)-1-(4-(7H-pyrrolo[2,3-d]pyrimidin-4-yl)-1H-pyrazol-1-yl)-2-cyanoethyl)pyrrolidin-1-yl)-2-chloro-5-fluoronicotinonitrile trifluoroacetate salt | 462 |
| 64 | 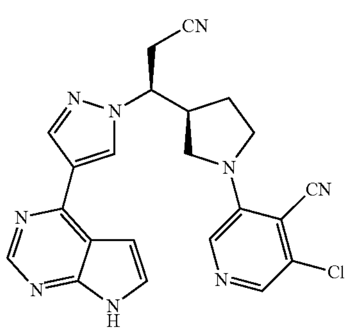 [SMILES: N#CC[C@@H]([C@H]1CCN(c2cncc(Cl)c2C#N)C1)n1cc(-c2ncnc3[nH]ccc23)cn1] | 3-chloro-5-((3S)-3-{(1S)-2-cyano-1-[4-(7H-pyrrolo[2,3-d]pyrimidin-4-yl)-1H-pyrazol-1-yl]ethyl}pyrrolidin-1-yl)isonicotinonitrile trifluoroacetate salt | 444 |

| Ex. | Structure | Name | M + H |
|---|---|---|---|
| 65 | 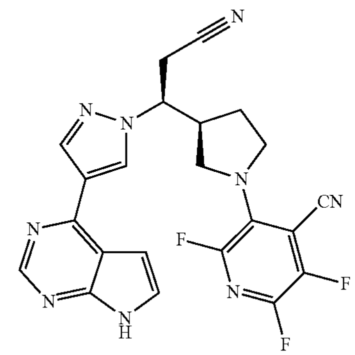 [SMILES: N#CC[C@@H]([C@H]1CCN(c2c(F)nc(F)c(F)c2C#N)C1)n1cc(-c2ncnc3[nH]ccc23)cn1] | 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-2,5,6-trifluoroisonicotinonitrile trifluoroacetate salt | 464 |
| 66 | 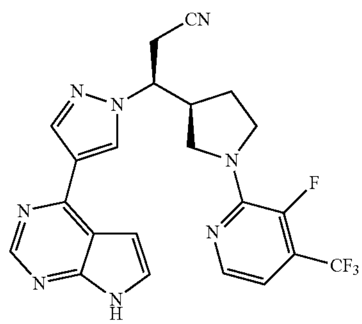 [SMILES: N#CC[C@@H]([C@H]1CCN(c2nccc(C(F)(F)F)c2F)C1)n1cc(-c2ncnc3[nH]ccc23)cn1] | (3S)-3-{(3S)-1-[3-fluoro-4-(trifluoromethyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate salt | 471 |
| 67 | 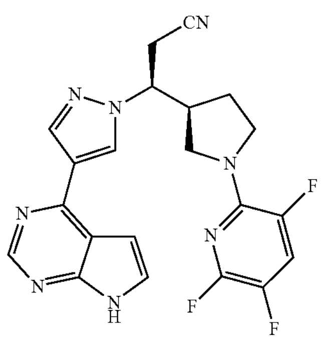 [SMILES: N#CC[C@@H]([C@H]1CCN(c2nc(F)c(F)cc2F)C1)n1cc(-c2ncnc3[nH]ccc23)cn1] | (3S)-3-[4-(7H-pyrrolo[2,3-d]pyrimidin-4-yl)-1H-pyrazol-1-yl]-3-[(3S)-1-(3,5,6-trifluoropyridin-2-yl)pyrrolidin-3-yl]propanenitrile trifluoroacetate salt | 439 |
| 68 | 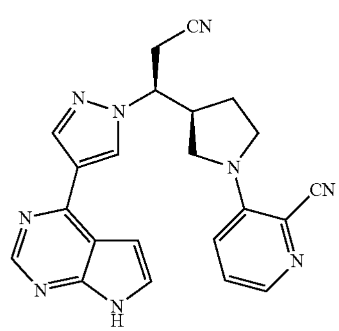 [SMILES: N#CC[C@@H]([C@H]1CCN(c2cccnc2C#N)C1)n1cc(-c2ncnc3[nH]ccc23)cn1] | 3-((3S)-3-{(1S)-2-cyano-1-[4-(7H-pyrrolo[2,3-d]pyrimidin-4-yl)-1H-pyrazol-1-yl]ethyl}pyrrolidin-1-yl)pyridine-2-carbonitrile trifluoroacetate salt | 410 |

| Ex. | Structure | Name | M + H |
|---|---|---|---|
| 69 | 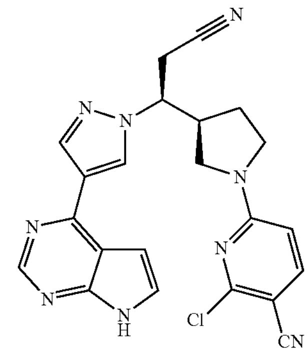 [SMILES: N#CC[C@@H]([C@H]1CCN(c2ccc(C#N)c(Cl)n2)C1)n1cc(-c2ncnc3[nH]ccc23)cn1] | 2-chloro-6-((3S)-3-{(1S)-2-cyano-1-[4-(7H-pyrrolo[2,3-d]pyrimidin-4-yl)-1H-pyrazol-1-yl]ethyl}pyrrolidin-1-yl)nicotinonitrile trifluoroacetate salt | 444 |

| Ex. | ¹H NMR |
|---|---|
| 54 | ¹H NMR (300 MHz, DMSO-D6): δ 12.6 (s, 1H); 9.00 (s, 1H); 8.83 (s, 1H); 8.54 (s, 1H); 7.78 (s, 1H); 7.42 (m, 1H); 7.14 (s, 1H); 6.59 (m, 2H); 4.88 (m, 1H); 3.73 (m, 1H); 3.22-3.69 (m, 5H); 2.93 (m, 1H); 1.69 (m, 2H) |
| 56 | ¹H NMR (400 MHz, DMSO-D6): δ 12.6 (s, 1H); 8.98 (s, 1H); 8.80 (s, 1H); 8.52 (s, 1H); 7.75 (s, 1H); 7.56 (t, 1H); 7.12 (m, 3H); 4.88 (m, 1H); 3.75 (m, 1H); 3.59 (m, 3H); 3.39 (m, 1H); 3.29 (m, 1H); 2.92 (m, 1H); 1.68 (m, 2H) |
| 57 | ¹H NMR (300 MHz, DMSO-D6): δ 12.5 (s, 1H); 8.96 (s, 1H); 8.79 (s, 1H); 8.51 (s, 1H); 7.74 (s, 1H); 7.30 (t, 1H); 7.10 (s, 1H); 7.03 (d, 1H); 6.80 (d, 1H); 4.86 (m, 1H); 3.71 (m, 1H); 3.21-3.64 (m, 5H); 2.91 (m, 1H); 1.67 (m, 2H) |
| 58 | ¹H NMR (300 MHz, DMSO-D6): δ 12.5 (s, 1H); 8.97 (s, 1H); 8.79 (s, 1H); 8.50 (s, 1H); 7.73 (s, 1H); 7.37 (m, 2H); 7.10 (s, 1H); 6.81 (td, 1H); 4.87 (m, 1H); 3.5-4.0 (m, 4H); 3.30 (m, 2H); 2.87 (m, 1H); 1.63 (m, 2H) |
| 59 | ¹H NMR (300 MHz, DMSO-D6): δ 12.5 (s, 1H); 8.95 (s, 1H); 8.78 (s, 1H); 8.50 (s, 1H); 7.82 (d, 2H); 7.72 (s, 1H); 7.08 (s, 1H); 6.83 (t, 1H); 4.94 (m, 1H); 4.02 (m, 1H); 3.88 (m, 3H); 3.31 (m, 2H); 2.92 (m, 1H); 1.77 (m, 1H); 1.64 (m, 1H) |
| 60 | ¹H NMR (300 MHz, DMSO-D6): δ 12.7 (s, 1H); 9.01 (s, 1H); 8.84 (s, 1H); 8.54 (s, 1H); 7.79 (s, 1H); 7.37 (m, 1H); 7.15 (s, 1H); 6.65 (m, 1H); 4.90 (m, 1H); 3.87 (m, 1H); 3.74 (m, 3H); 3.32 (m, 2H); 2.86 (m, 1H); 1.63 (m, 2H) |
| 61 | ¹H NMR (300 MHz, DMSO-D6): δ 12.6 (s, 1H); 8.99 (s, 1H); 8.82 (s, 1H); 8.52 (s, 1H); 7.82 (m, 1H); 7.77 (s, 1H); 7.15 (s, 1H); 4.88 (m, 1H); 3.81 (m, 1H); 3.66 (m, 3H); 3.32 (m, 2H); 2.86 (m, 1H); 1.65 (m, 2H) |
| 62 | ¹H NMR (300 MHz, DMSO-D6): δ 12.7 (s, 1H); 9.03 (s, 1H); 8.86 (s, 1H); 8.56 (s, 1H); 8.31 (dd, 1H); 7.94 (dd, 1H); 7.82 (s, 1H); 7.18 (s, 1H); 6.70 (dd, 1H); 4.90 (m, 1H); 3.91 (m, 1H); 3.78 (m, 1H); 3.60 (m, 2H); 3.35 (m, 2H); 2.89 (m, 1H); 1.70 (m, 2H) |
| 63 | ¹H NMR (300 MHz, DMSO-D6): δ 12.5 (s, 1H); 8.97 (s, 1H); 8.80 (s, 1H); 8.51 (s, 1H); 8.00 (d, 1H); 7.74 (s, 1H); 7.10 (s, 1H); 4.86 (m, 1H); 3.92 (m, 1H); 3.71 (m, 1H); 3.54 (m, 2H); 3.35 (m, 2H); 2.85 (m, 1H); 1.64 (m, 2H) |
| 64 | ¹H NMR (400 MHz, DMSO-D6): δ 12.6 (s, 1H); 9.00 (s, 1H); 8.84 (s, 1H); 8.54 (s, 1H); 8.17 (s, 1H); 7.97 (s, 1H); 7.79 (s, 1H); 7.14 (s, 1H); 4.88 (m, 1H); 3.84 (m, 1H); 3.71 (m, 1H); 3.62 (m, 2H); 3.40 (m, 1H); 3.29 (m, 1H); 2.94 (m, 1H); 1.75 (m, 1H); 1.63 (m, 1H) |
| 67 | ¹H NMR (400 MHz, DMSO-D6): δ 12.6 (s, 1H); 8.98 (s, 1H); 8.81 (s, 1H); 8.51 (s, 1H); 7.97 (m, 1H); 7.76 (s, 1H); 7.12 (s, 1H); 4.84 (m, 1H); 3.75 (m, 1H); 3.57 (m, 1H); 3.26-3.45 (m, 4H); 2.83 (m, 1H); 1.61 (m, 2H) |
| 68 | ¹H NMR (400 MHz, DMSO-D6): δ 12.7 (s, 1H); 9.02 (s, 1H); 8.84 (s, 1H); 8.55 (s, 1H); 7.96 (d, 1H); 7.80 (s, 1H); 7.43 (dd, 1H); 7.23 (d, 1H); 7.15 (s, 1H); 4.88 (m, 1H); 3.72 (m, 1H); 3.45-3.65 (m, 3H); 3.40 (m, 1H); 3.28 (m, 1H); 2.93 (m, 1H); 1.68 (m, 2H) |
| 69 | ¹H NMR of SEM protected intermediate (500 MHz, DMSO-D6, recorded at 90 C): δ 8.89 (s, 1H); 8.84 (s, 1H); 8.46 (s, 1H); 7.86 (d, 1H); 7.82 (d, 1H); 7.12 (d, 1H); 6.51 (d, 1H); 5.67 (s, 2H); 4.87 (m, 1H); 3.82 (m, 1H); 3.59 (t, 2H); 3.55 (br m, 1H); 3.42 (m, 1H); 3.38 (m, 1H); 3.36 (m, 1H); 3.29 (m, 1H); 2.98 (m, 1H); 1.78 (m, 2H); 0.86 (t, 2H); −0.07 (s, 9H)<br>¹H NMR (300 MHz, DMSO-D6): δ 12.6 (s, 1H); 8.99 (s, 1H); 8.83 (s, 1H); 8.53 (s, 1H); 7.90 (m, 1H); 7.78 (s, 1H); 7.13 (s, 1H); 6.51 (m, 1H); 4.87 (m, 1H); 3.22-3.94 (m, 6H); 2.91 (m, 1H); 1.69 (m, 2H) |

Example 70

2-((3S)-3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine phosphoric acid salt

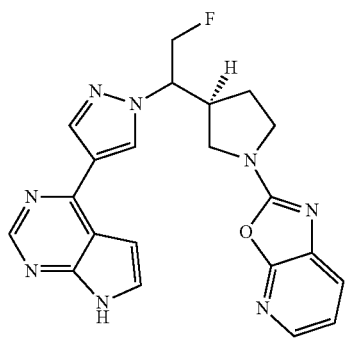 [SMILES: FCC([C@H]1CCN(c2nc3cccnc3o2)C1)n1cc(-c2ncnc3[nH]ccc23)cn1]

Step 1. tert-butyl (3S)-3-(hydroxymethyl)pyrrolidine-1-carboxylate

A solution of (3S)-1-(tert-butoxycarbonyl)pyrrolidine-3-carboxylic acid (Chem-Impex; 2.5 g, 12 mmol) in THF (54 mL) was cooled to 0° C. and 1.0 M of $BH_3$ in THF (14 mL, 14 mmol) was slowly added. The reaction was allowed to warm to ambient temperature and was stirred for 4 h, at which time LCMS analysis showed complete reduction to alcohol. The solution was cooled to 0° C. and quenched by careful addition of 1N HCl. EtOAc was added and the phases were separated, the aqueous phase was extracted with additional EtOAc. The combined organic phase was washed with sat'd $NaHCO_3$, then sat'd NaCl, dried over $MgSO_4$ and reduced in vacuo to leave the crude product as a colorless oil, 2.15 g. $^1$H NMR (300 MHz, $CDCl_3$): δ 3.7-3.2 (m, 5H), 3.1 (m, 1H), 2.4 (m, 1H), 1.95 (m, 1H), 1.7 (s, 2H), 1.45 (s, 9H). MS (EI): 146.0 (M-tBu+2H), 128.1 (M-OtBu).

Step 2: tert-butyl (3S)-3-formylpyrrolidine-1-carboxylate

Oxalyl chloride (1.4 mL, 16 mmol) was dissolved in DCM (28 mL) and this solution was cooled to –78° C., then DMSO (1.8 mL, 26 mmol) was added. To this was then added a solution of tert-butyl (3S)-3-(hydroxymethyl)pyrrolidine-1-carboxylate (2.15 g, 10.7 mmol) in DCM (28 mL), followed in 20 min by addition of 4-methylmorpholine (5.9 mL, 53 mmol). The reaction was held at –78° C. for 20 min, then warmed to 0° C. for 1 h, at which time tlc analysis showed complete oxidation to aldehyde. The reaction was quenched by addition of water and $CHCl_3$, the phases were separated and the aqueous phase was extracted with additional $CHCl_3$. The combined organic phase was washed with water, then 1N HCl, then sat'd $NaHCO_3$, sat'd NaCl, dried over $MgSO_4$ and reduced in vacuo to leave the crude product which was used without further purification, 2.1 g. $^1$H NMR (300 MHz, $CDCl_3$): δ 9.68 (s, 1H), 3.68 (m, 1H), 3.50 (m, 1H), 3.37 (m, 2H), 3.0 (m, 1H), 2.13 (m, 2H), 1.42 (s, 9H). MS (EI): 144.1 (M-tBu+2H), 126.0 (M-OtBu).

Step 3: tert-butyl (3S)-3-[2-fluoro-1-hydroxy-2-(phenylsulfonyl)ethyl]pyrrolidine-1-carboxylate N,N-Diisopropylamine (1.62 mL, 11.59 mmol) was added to THF (9.89 mL) and this solution was cooled to –78° C., then 1.60 M of n-butyllithium in hexane (6.59 mL, 10.54 mmol) was added. The reaction was held at –78° C. for 5 min, then warmed to 0° C. for 15 min, then cooled back to –78° C. To this was added a solution of fluoromethyl phenyl sulfone (2.02 g, 11.59 mol) in THF (14 mL), the reaction was held for 20 min, then a solution of tert-butyl (3S)-3-formylpyrrolidine-1-carboxylate (2.1 g, 10.0 mmol) in THF (14 mL) was added. The reaction was held at –78° C. for 1.5 h, at which time LCMS analysis indicated complete reaction. The reaction was quenched at –78° C. by addition of sat'd $NH_4Cl$ solution and extracted into EtOAc. The phases were separated and the organic phase was washed with water, then sat'd NaCl, and dried over $MgSO_4$. The solvent was removed in vacuo and the residue was purified (120 g prepacked $SiO_2$ cartridge, 85 mL/min, gradient from 0-65% EtOAc/hexanes over 25 min) to obtain the desired product, 2.96 g. $^1$H NMR (300 MHz, $CDCl_3$): δ 7.91 (m, 2H), 7.75 (m, 1H), 7.66 (m, 2H), 5.06 (m, 0.5H), 4.91 (m, 0.5H), 4.31 (m, 1H), 3.51 (m, 2H), 3.24 (m, 2H), 2.99 (m, 1H), 2.54 (m, 1H), 1.92 (m, 2H), 1.42 (s, 9H). MS (EI): 318.1 (M-tBu+2H), 300.0 (M-OtBu), 274.1 (M-BOC+H).

Step 4: tert-butyl (3S)-3-(2-fluoro-1-hydroxyethyl)pyrrolidine-1-carboxylate tert-Butyl (3S)-3-[2-fluoro-1-hydroxy-2-(phenylsulfonyl)ethyl]pyrrolidine-1-carboxylate (2.96 g, 7.93 mmol) was dissolved in $CH_3OH$ (290 mL) and $Na_2HPO_4$ (6.8 g, 48 mmol) was added, the reaction was cooled to –5° C. and sodium-mercury amalgam (10% Na) (11 g, 48 mmol) was added. The reaction was held at –5° C. for 1 to 3 h at which time LCMS analysis indicated complete reaction. Stirring was discontinued and the solids were allowed to settle. The supernatant methanolic phase was decanted and the solid residue was rinsed with methanol, the combined methanol phase was kept at 0° C. The pH was adjusted to neutral by careful addition of 1N HCl, then the solution was reduced in vacuo, keeping the temperature below 15° C. The residue was partitioned between sat' d NaCl and EtOAc, the phases were separated and the aqueous phase was extracted again with EtOAc. The combined EtOAc phase was dried over $MgSO_4$ and reduced in vacuo to give the crude product, 1.8 g, which was carried forward without further purification. MS (EI): 178.0 (M-tBu+2H), 160.0 (M-OtBu).

Step 5: tert-butyl (3S)-3-{2-fluoro-1-[(methylsulfonyl)oxy]ethyl}pyrrolidine-1-carboxylate A solution of tert-butyl (3S)-3-(2-fluoro-1-hydroxyethyl)pyrrolidine-1-carboxylate (1.80 g, 7.72 mmol) in DCM (35 mL) was cooled to 0° C. and methanesulfonyl chloride (657 microL, 8.49 mmol) was added followed by $Et_3N$ (2.15 mL, 15.4 mmol), the reaction was held at 0° C. for 1 h at which time LCMS analysis indicated complete reaction. The reaction mixture was partitioned between water and $CHCl_3$, the phases were separated and the aqueous phase was extracted with additional $CHCl_3$. The combined organic phase was washed with 1N HCl, sat'd $NaHCO_3$, water, then sat'd NaCl, dried over $MgSO_4$ and reduced in vacuo to leave the crude product, which was purified (120 g prepacked $SiO_2$ cartridge, 85 mL/min, hexanes for 2 min, then gradient from 0-70% EtOAc/hexanes over 12 min, held at 70% EtOAc/hexanes for 10 min, product was visualized on tlc plate with $KMnO_4$ stain) to give the desired product, 1.6 g. $^1$H NMR (300 MHz, $CDCl_3$): δ 4.9-4.4 (m, 3H), 3.50 (m, 2H), 3.22 (m, 2H), 3.09 (s, 3H), 2.50 (m, 1H), 2.2-1.7 (m, 2H), 1.43 (s, 9H). $^{19}$F NMR (300 MHz, $CDCl_3$): δ –226.39 (td, J=49.5, 17.4 Hz), –227.34

(td, J=47.3, 19.0 Hz), −227.59 (td, J=47.3, 19.5 Hz). MS (EI): 256.0 (M-tBu+2H), 238.0 (M-OtBu).

Step 6: tert-butyl (3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate To 4-(1H-pyrazol-4-yl)-7-{[2-(trimethylsilyl)ethoxy]methyl}-7H-pyrrolo[2,3-d]pyrimidine (1.71 g, 5.41 mmol, prepared as described in WO 2007/070514) was added sodium hydride (60% in mineral oil, 60%, 247 mg, 6.17 mmol) followed by DMF (4.1 mL). After gas evolution ceased, a solution of tert-butyl (3S)-3-{2-fluoro-1-[(methylsulfonyl)oxy]ethyl}pyrrolidine-1-carboxylate (1.6 g, 5.1 mmol) in DMF (17.1 mL) was added and the reaction was heated to 60° C. for 16 to 36 h. The reaction was cooled to ambient temperature and partitioned between water and EtOAc, the phases were separated and the aqueous phase was extracted with additional EtOAc. The combined organic phase was washed with water, then sat'd NaCl, dried over MgSO$_4$ and reduced in vacuo to leave the crude product. The mixture was separated (120 g prepacked SiO$_2$ cartridge, 85 mL/min, solvent A=92/5/3 hexanes/EtOAc/IPA, solvent B=49/45/6 hexanes/EtOAc/IPA. Eluted with gradient from 0-40% B over 20 min, and held at 40% B for 10 min. Mixed fractions were recombined and purified by same manner to give the desired (first eluting) isomer, 0.8 g. $^1$H NMR (300 MHz, CDCl$_3$): δ 8.91 (s, 1H), 8.374 (s, 1H), 8.367 (s, 1H), 7.46 (d, 1H, J=3.68 Hz), 6.86 (d, 1H, J=3.78 Hz), 5.74 (s, 2H), 5.0-4.6 (m, 2H), 4.4 (m, 1H), 4.1 (m, 1H), 3.76 (m, 1H), 3.60 (m, 2H), 3.54 (m, 1H), 3.25 (m, 2H), 2.92 (m, 1H), 1.9-1.6 (m, 1H), 1.52 (s, 9H), 0.97 (m, 2H). $^{19}$F NMR (300 MHz, CDCl$_3$): δ −225.12 (td, J=49.5, 19.0 Hz), −225.52 (td, J=49.5, 19.8 Hz). MS (EI): 531.2 (M+H).

Step 7: 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine tert-Butyl (3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidine-1-carboxylate (800.0 mg, 1.507 mmol) was dissolved in THF (12 mL), then 12.0 M HCl (1.40 mL, 16.7 mmol) was added. The reaction was allowed to stir at ambient temperature for 16 h at which time LCMS analysis indicated complete BOC deprotection. The reaction was neutralized by addition of sat'd NaHCO$_3$, followed by solid NaHCO$_3$ until pH was basic. The reaction solution was extracted with EtOAc, the phases were separated and the aqueous phase was washed with additional EtOAc. The combined organic phase was washed with water, then sat'd NaCl, dried over MgSO$_4$ and reduced in vacuo to leave the crude product. MS (EI): 431.2 (M+H).

Step 8: 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)[1,3]oxazolo[5,4-b]pyridine

[1,3]oxazolo[5,4-b]pyridine-2(1H)-thione (233 mg, 1.53 mmol, prepared as in Example 33, Step 4) and 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (550 mg, 1.3 mmol) were mixed in 1,4-dioxane (6.0 mL) and the reaction was heated to 70° C. for 2 h at which point LCMS analysis indicated complete reaction to the intermediate hydroxypyridinyl thiourea. The reaction was cooled to ambient temperature and was concentrated in vacuo, then EtOH (7.4 mL) was added and the mixture was stirred well until the thiourea was suspended freely in the solvent. This mixture was then treated with AgNO$_3$ (434 mg, 2.55 mmol) and NH$_4$OH (790 microL, 11.5 mmol), and the reaction was stirred at ambient temperature for 16 h at which point LCMS analysis indicated complete conversion to the desired product. The reaction was filtered through a plug of Celite on a sintered glass funnel and rinsed with dioxane (20 mL) and EtOAc (20 mL). The filtrate was reduced in vacuo and the residue was partitioned between water and EtOAc, the phases were separated and the aqueous phase was extracted with additional EtOAc. The combined organic phase was washed with water, then sat'd NaCl, dried over MgSO$_4$ and reduced in vacuo to leave the crude product which was purified (40 g prepacked SiO$_2$ cartridge, 40 mL/min, DCM for 3 min, then isocratic elution with 5% MeOH/DCM for 15 min) to recover the product, 592 mg. MS (EI): 549.2 (M+H).

Step 9: 2-((3S)-3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine trifluoroacetate To 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)[1,3]oxazolo[5,4-b]pyridine (592 mg, 1.07 mmol) was added DCM (5.0 mL) and TFA (5.0 mL). The reaction was stirred at ambient temperature for 1 h, then the solvents were removed in vacuo and methanol (5.0 mL) and NH$_4$OH (5.0 mL) were added. After 30 min LCMS analysis indicated complete removal of SEM group. The solvents were removed in vacuo and the residual material was purified by reverse phase preparative LCMS on a Waters FractionLynx system using mass directed fractionation (column Waters SunFire C18, 5 μM particle size, 30×100 mm, mobile phase A: water (0.1% TFA), B: acetonitrile (0.1% TFA), gradient 17-37% B over 5 min, flow rate 60 mL/min), the product was isolated as a tris-TFA salt, 455 mg. $^1$H NMR (300 MHz, CD$_3$OD): δ 8.97 (s, 1H), 8.90 (s, 1H), 8.55 (s, 1H), 7.88 (d, 1H, J=3.88 Hz), 7.86 (dd, 1H, J=5.40, 1.45 Hz), 7.58 (dd, 1H, J=7.64, 1.38 Hz), 7.31 (d, 1H, J=3.58 Hz), 7.20 (dd, 1H, J=7.83, 4.90 Hz), 5.09 (m, 1H), 5.0-4.8 (m, 2H), 4.02 (m, 1H), 3.76 (m, 1H), 3.61 (m, 2H), 3.15 (m, 1H), 1.96 (m, 2H). MS (EI): 419.1 (M+H).

Step 10: 2-((3S)-3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine phosphate 2-((3S)-3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine tris-trifluoroacetate (455 mg, 0.60 mmol) was partitioned between sat'd NaHCO$_3$ and 3:1 CHCl$_3$/IPA, the phases were separated and the aqueous phase was extracted with additional solvent. The combined organic phase was washed with sat'd NaCl, dried over MgSO$_4$ and reduced in vacuo to leave the free base. To this material was added IPA (10 mL) and EtOH (3 mL) and the reaction was heated to 90° C. under a reflux condenser until complete dissolution occurred. A solution of H$_3$PO$_4$ (61 mg, 0.63 mmol) in 200 microL IPA was then added, and the reaction was removed from the oil bath and allowed to stand and cool. Upon cooling a solid was precipitated, and this was collected by filtration. The solids were dried in vacuo to give the product as the phosphate salt, 204 mg. $^1$H NMR (300 MHz, DMSO-d$_6$): δ 12.1 (bs, 1H), 8.80 (s, 1H), 8.65 (s, 1H), 8.38 (s, 1H), 7.84 (dd, 1H, J=5.22, 1.32 Hz), 7.58 (m, 2H), 7.17 (dd, 1H, J=7.63, 5.15 Hz), 6.96 (m, 1H), 5.00 (m, 1H), 4.81 (m, 2H), 3.88 (m, 1H), 3.65 (m, 1H), 3.47 (m, 2H), 2.95 (m, 1H), 1.72 (m, 2H). $^{19}$F NMR (300 MHz, DMSO-d$_6$): δ −223.176 (td, J=46.1, 15.9 Hz). MS (EI): 419.1 (M+H).

Scheme 1. The carboxylic acid 1 was reduced to alcohol 2 by action of borane, which was subsequently oxidized via a Swern oxidation to the corresponding aldehyde 3. The anion of fluoromethyl phenyl sulfone was added to 3 to give the intermediate 4, which was desulfonylated under reductive conditions using sodium amalgam to give the fluoroalcohol 5. This compound was then converted to mesylate 6, which was added to the anion of the pyrazole core, the resulting diastereomers were separated by silica gel chromatography to give the desired single isomer of the N—BOC pyrrolidine derivative 7. This was cleanly deprotected under acidic conditions to give the advanced intermediate 8, which underwent reaction with the indicated oxazolopyridine-2-thiol in a two-step procedure, followed by a two-step deprotection procedure to give the final product 9 in good yield and high diastereomeric excess.

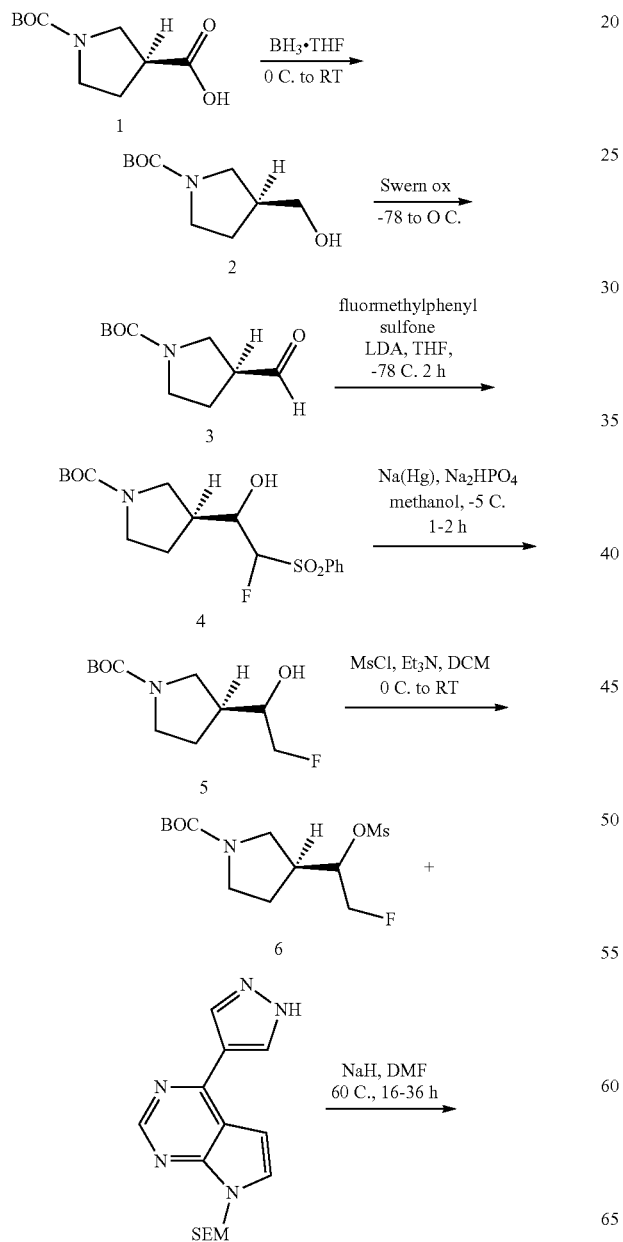

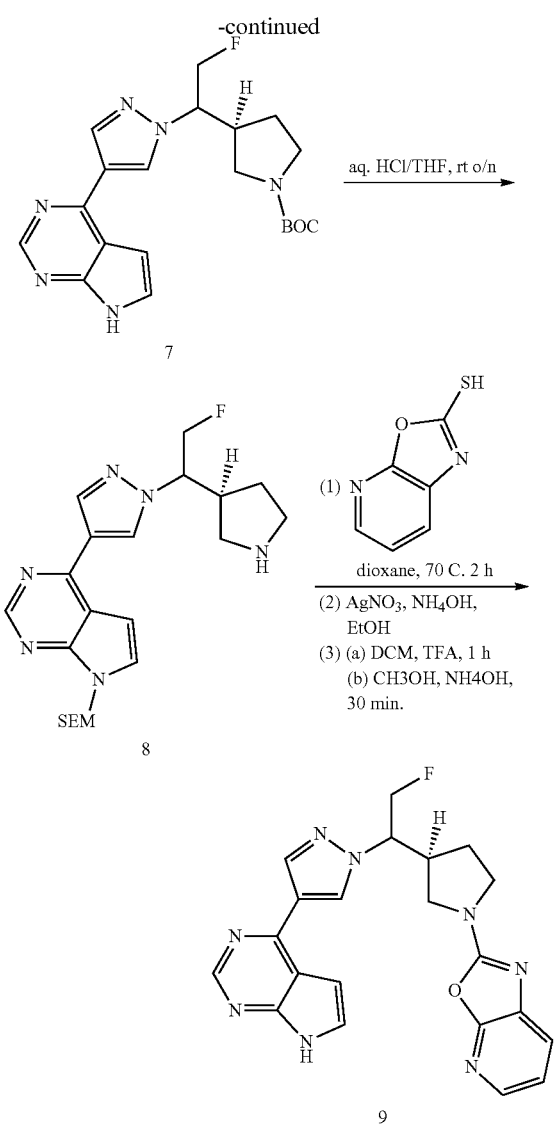

Example 71

2-((3R)-3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine phosphoric acid salt

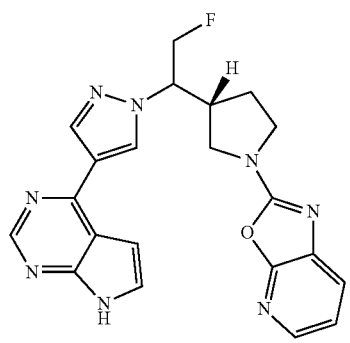 [SMILES: FCC([C@@H]1CCN(c2nc3cccnc3o2)C1)n1cc(-c2ncnc3[nH]ccc23)cn1]

This example can be prepared by following steps 1-10 for Example 70, substituting (3R)-1-(tert-butoxycarbonyl)pyrrolidine-3-carboxylic acid for the (S) isomer in step 1. All following steps are carried out analogously. ¹H NMR (300 MHz, DMSO-d₆): δ 12.1 (bs, 1H), 8.80 (s, 1H), 8.65 (s, 1H), 8.38 (s, 1H), 7.84 (dd, 1H, J=5.22, 1.32 Hz), 7.58 (m, 2H), 7.17 (dd, 1H, J=7.63, 5.15 Hz), 6.96 (m, 1H), 5.00 (m, 1H), 4.81 (m, 2H), 3.88 (m, 1H), 3.65 (m, 1H), 3.47 (m, 2H), 2.95 (m, 1H), 1.72 (m, 2H). ¹⁹F NMR (300 MHz, DMSO-d₆): δ −223.176 (td, J=46.1, 15.9 Hz). MS (EI): 419.1 (M+H).

Example 72

2-(3-(1-(4-(7H-pyrrolo[2,3-d]pyrimidin-4-yl)-1H-pyrazol-1-yl)-2-fluoroethyl)pyrrolidin-1-yl)oxazolo[5,4-b]pyridine trifluoroacetate

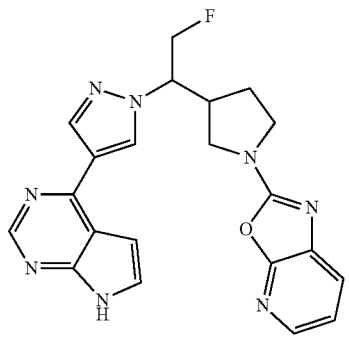 [SMILES: FCC(C1CCN(c2nc3cccnc3o2)C1)n1cc(-c2ncnc3[nH]ccc23)cn1]

The racemic product above can be prepared by following steps 1-9 for Example 70, utilizing racemic 1-(tert-butoxycarbonyl)pyrrolidine-3-carboxylic acid in step 1. Alternatively, the following sequence may be used to access the racemic product.

Step 1: tert-butyl 3-{[methoxy(methyl)amino]carbonyl}pyrrolidine-1-carboxylate

To 1-(tert-butoxycarbonyl)pyrrolidine-3-carboxylic acid (1.0 g, 4.6 mmol) was added DMF (26 mL) followed by N,N,N',N'-tetramethyl-O-(7-azabenzotriazol-1-yl)uronium hexafluorophosphate (2.6 g, 7.0 mmol) and N,N-diisopropylethylamine (3.9 mL, 22 mmol). N,O -Dimethylhydroxylamine HCl (910 mg, 9.3 mmol) was then added and the reaction was stirred at ambient temperature for 16 h at which point LCMS and tlc indicated complete conversion to the Weinreb amide. The reaction mixture was partitioned between water and EtOAc, the phases were separated and the aqueous phase was extracted with additional EtOAc. The combined organic phase was washed with water, then sat'd NaCl, dried over MgSO₄ and reduced in vacuo to leave the crude product, which was then purified by column chromatography (40 g prepacked SiO₂ cartridge, 40 mL/min, gradient from 0-90% EtOAc/hexanes over 20 min) to give the desired product, 1.05 g. ¹H NMR (300 MHz, CDCl₃): δ 3.71 (s, 3H), 3.7-3.3 (m, 5H), 3.20 (s, 3H), 2.1 (m, 2H), 1.45 (s, 9H). MS (EI): 203.1 (M-tBu+2H), 185.1 (M-OtBu).

Step 2: tert-butyl 3-acetylpyrrolidine-1-carboxylate

A solution of tert-butyl 3-{[methoxy(methyl)amino]carbonyl}pyrrolidine-1-carboxylate (1.00 g, 3.87 mmol) in THF (11 mL) was cooled to −78° C., then 3.0 M CH₃MgBr in ether (3.87 mL, 11.6 mmol) was added. The reaction was held at −78° C. for 1.5 h, then warmed to 0° C. for 1 h, at which point thin layer chromatography analysis indicated complete conversion to ketone. The reaction was quenched with sat'd NH₄Cl and extracted with EtOAc. The phases were separated and the aqueous phase was extracted with additional EtOAc. The combined organic phase was washed with sat'd NaCl, dried over MgSO₄, and reduced in vacuo to leave the crude product, which was used directly in the next reaction. ¹H NMR (300 MHz, CDCl₃): δ 3.6-3.4 (m, 3H), 3.33 (s, 1H), 3.12 (m, 1H), 2.20 (s, 3H), 2.06 (m, 2H), 1.45 (s, 9H). MS (EI): 158.1 (M-tBu+2H), 140.1 (M-OtBu).

Step 3: tert-butyl 3-{1-[(trimethylsilyl)oxy]vinyl}pyrrolidine-1-carboxylate

N,N-Diisopropylamine (631 microL, 4.50 mmol) was added to THF (4.2 mL) and this solution was cooled to −78° C., then 1.60 M n-butyllithium in hexane (2.81 mL, 4.50 mmol) was added. The reaction was held at −78° C. for 5 min, then warmed to 0° C. for 15 min, then cooled back to −78° C. To this was added a solution of tert-butyl 3-acetylpyrrolidine-1-carboxylate (800 mg, 3.75 mmol) in THF (10 mL). This was held at −40° C. for 20 min, then TMSCl (714 microL, 5.63 mmol) was added. The reaction was warmed from −40° C. to −10° C. over 1.5 h, then the reaction was cooled back to −40° C., quenched by addition of sat'd NaHCO₃ and extracted into EtOAc. The phases were separated and the aqueous phase was extracted with additional EtOAc. The combined organic phase was washed with water followed by 0.1N HCl solution until pH of aqueous wash is acidic. The organic phase was then washed twice with water, then sat'd NaCl, dried over MgSO₄ and reduced in vacuo to leave the crude product, 1.01 g. ¹H NMR (300 MHz, CDCl₃): δ 3.95 (s, 1H), 3.91 (s, 1H), 3.40 (m, 2H), 3.20 (m, 2H), 2.72 (m, 1H), 1.90 (m, 2H), 1.30 (s, 9H), 0.05 (m, 9H). MS (EI): 230.1 (M-tBu+2H).

Step 4: tert-butyl 3-(fluoroacetyl)pyrrolidine-1-carboxylate

To a solution of tert-butyl 3-{1-[(trimethylsilyl)oxy]vinyl}pyrrolidine-1-carboxylate (847 mg, 2.97 mmol) in CH₃CN (26 mL) was added SelectFluor® (1.38 g, 3.88 mmol). The mixture was stirred at ambient temperature for 1.5 h at which point LCMS analysis indicated conversion to fluoromethyl ketone. The reaction mixture was partitioned between sat'd NaHCO₃ and EtOAc, the phases were separated and the aqueous phase was extracted with additional EtOAc. The combined organic phase was washed with water, then sat'd NaCl, dried over MgSO₄ and reduced in vacuo to leave the crude product. The product was purified (40 g prepacked SiO₂ cartridge, 40 mL/min, gradient from 0-80% EtOAc/hexanes over 20 min) to recover the fluoromethyl ketone, 351 mg. ¹H NMR (300 MHz, CDCl₃): δ 4.89 (d, 2H, J=47.4 Hz), 3.35-3.15 (m, 5H), 2.10 (m, 2H), 1.45 (s, 9H). MS (EI): 176.0 (M-tBu+2H), 158.1 (M-OtBu).

Step 5: tert-butyl 3-(2-fluoro-1-hydroxyethyl)pyrrolidine-1-carboxylate

A solution of tert-butyl 3-(fluoroacetyl)pyrrolidine-1-carboxylate (245 mg, 1.06 mmol) in CH₃OH (0.61 mL) was cooled to 0° C., and NaBH₄ (28 mg, 0.74 mmol) was added. The reaction was stirred at 0° C. for 30 min, then a sample was withdrawn and quenched into 0.1N HCl/EtOAc and subsequent tlc analysis indicated complete reduction of ketone.

The reaction was quenched by addition of 0.1 N HCl and EtOAc, the phases were separated and the aqueous phase was extracted with additional EtOAc. The combined organic phase was washed with sat'd NaHCO$_3$, then sat'd NaCl, dried over MgSO$_4$ and reduced in vacuo to leave the crude product, 240 mg, which was carried forward without further purification. MS (EI): 178.0 (M-tBu+2H), 160.0 (M-OtBu).

The synthesis is completed by following the remaining steps shown for Example 70.

Scheme 2. The carboxylic acid 1 was converted to the Weinreb amide 2, which then was treated with methyl Grignard to give a good yield of methyl ketone 3. The ketone was converted to the silyl enol ether 4, which then reacted with Selectfluor® to give fluoromethyl ketone 5. Reduction of 5 with sodium borohydride gave the fluoroalcohol 6, which was subsequently taken on to form the racemic fluoromethylpyrrolidine compounds by procedures illustrated in Scheme 1.

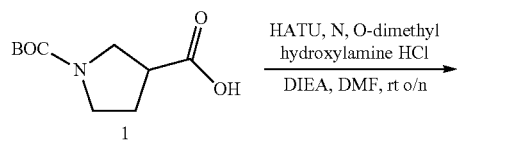

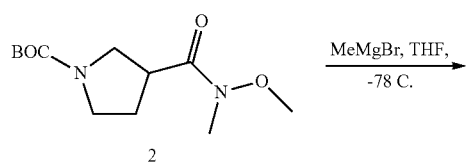

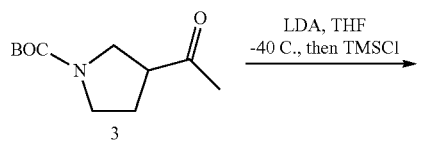

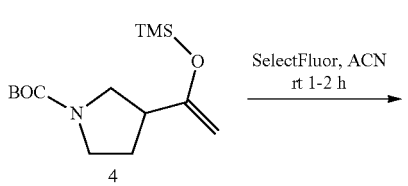

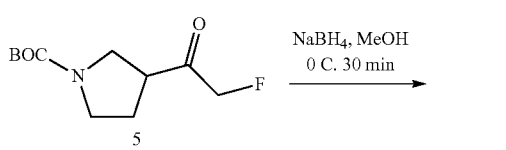

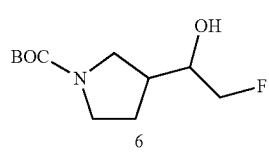

Example 73

3-(1-(1H-pyrrolo[2,3-b]pyridin-6-yl)pyrrolidin-3-yl)-3-(4-(7H-pyrrolo[2,3-d]pyrimidin-4-yl)-1H-pyrazol-1-yl)propanenitrile trifluoroacetate

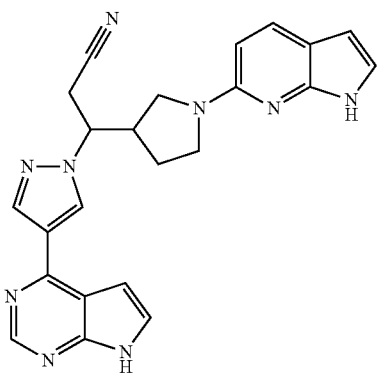 [SMILES: N#CCC(C1CCN(c2ccc3cc[nH]c3n2)C1)n1cc(-c2ncnc3[nH]ccc23)cn1]

Step 1: 3-(1-(1H-pyrrolo[2,3-b]pyridin-6-yl)pyrrolidin-3-yl)-3-(4-(7-((2-(trimethylsilyl)ethoxy)methyl)-7H-pyrrolo[2,3-d]pyrimidin-4-yl)-1H-pyrazol-1-yl) propanenitrile 1H-Pyrrolo[2,3-b]pyridine-7-oxide hemihydrate (31 mg, 0.22 mmol, Sigma-Aldrich) was suspended in CH$_3$CN (0.4 mL) and dimethyl sulfate (25 microL, 0.27 mmol) was added. The reaction was heated to 55° C. at which point the solution became homogeneous. The reaction was held at 55° C. for 16 h. To the solution was then added 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (98 mg, 0.22 mmol, prepared as in Example 15, Steps 1-3, omitting the chiral separation performed in Step 2) and 2,2,6,6-tetramethylpiperidine (75 microL, 0.45 mmol). The reaction was then heated to 50° C. for 4 h at which point LCMS analysis indicated complete reaction. The reaction was cooled to ambient temperature and partitioned between water and EtOAc, the phases were separated and the aqueous phase was extracted with additional EtOAc. The combined organic phase was washed with water, then sat'd NaCl, dried over MgSO$_4$ and reduced in vacuo to leave the crude product. This was purified (4 g prepacked SiO$_2$ cartridge, 20 mL/min, gradient from 0-100% EtOAc/hexanes over 16 min) to recover the product, 31 mg. MS (EI): 554.2 (M+H).

Step 2: 3-[7-(1H-pyrrolo[2,3-b]pyridin-6-yl)pyrrolidin-3-yl]-3-[4-(7H-pyrrolo[2,3-d]pyrimidin-4-yl)-1H-pyrazol-1-yl]propanenitrile trifluoroacetate To 3-1-(1H-pyrrolo[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (31 mg, 0.056 mmol) was added DCM (500 microL) and TFA (500 microL). The reaction was stirred at ambient temperature for 1 h, then the solvents were removed and methanol (500 microL) and NH$_4$OH (500 microL) were added. After 30 min, LCMS analysis indicated complete removal of SEM group. The solvents were removed in vacuo and the residual material was purified by reverse phase preparative LCMS on a Waters FractionLynx system using mass directed fractionation (column Waters SunFire C18, 5 microM particle size, 19×100 mm, mobile phase A: water (0.1% TFA), B: acetonitrile (0.1% TFA), flow rate 30 mL/min, to afford the product as a TFA salt. ¹H NMR (300 MHz, DMSO-d₆): δ 12.61 (bs, 1H), 11.10 (bs, 1H), 8.97 (s, 1H), 8.78 (s, 1H), 8.50 (s, 1H), 7.79 (d, 1H, J=8.2 Hz), 7.73 (m, 1H), 7.10 (m, 1H), 6.97 (m, 1H), 6.31 (d, 1H, J=8.8 Hz), 6.24 (m, 1H), 4.84 (m, 1H), 3.72 (m, 1H), 3.48 (m, 1H), 3.4-3.2 (m, 4H), 2.90 (m, 1H), 1.67 (m, 2H). MS (EI): 424.0 (M+H).

Scheme 3. Pyrrolopyridine 1 was treated with dimethyl sulfate to form the intermediate 7-methoxy pyrrolopyridine 2, which was not isolated, but directly reacted with the pyrrolidine core 3 to give the advanced intermediate 4. The SEM protecting group was removed in a two-step procedure to give the desired target 5.

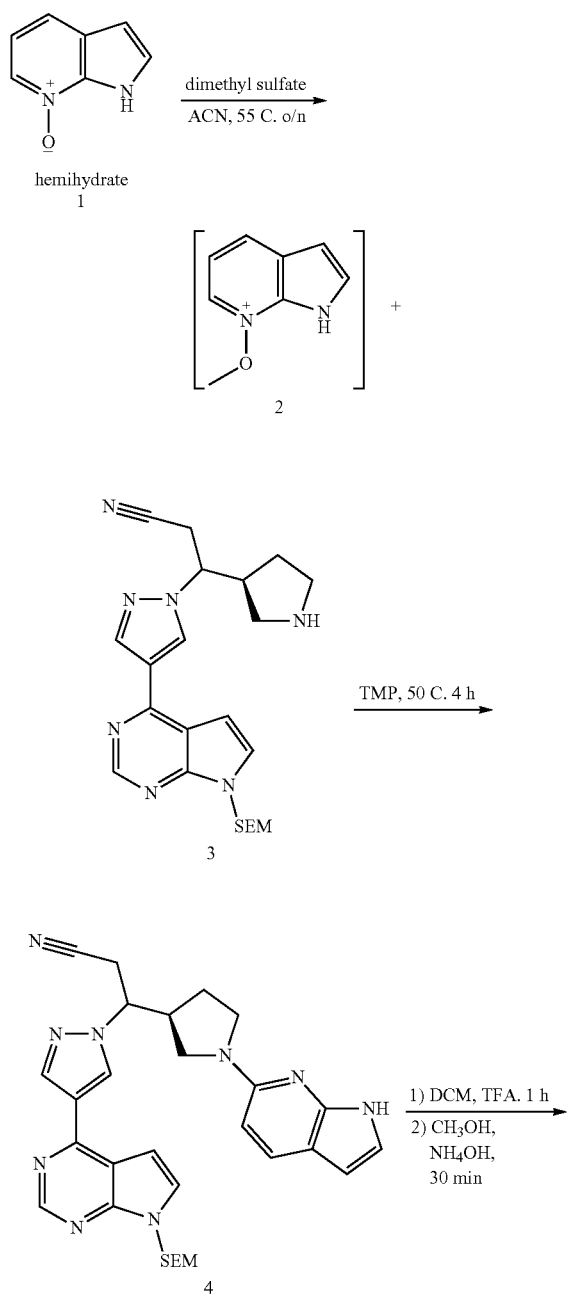

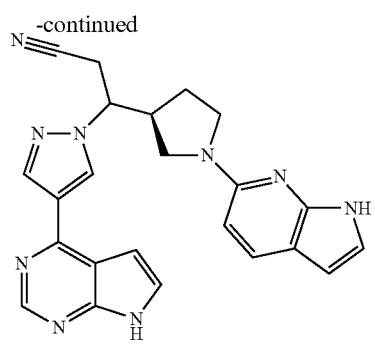

Example 74

5-((3S)-3-{(1S)-2-cyano-1-[4-(7H-pyrrolo[2,3-d]pyrimidin-4-yl)-1H-pyrazol-1-yl]ethyl}pyrrolidin-1-yl)thieno[2,3-c]pyridine-4-carbonitrile

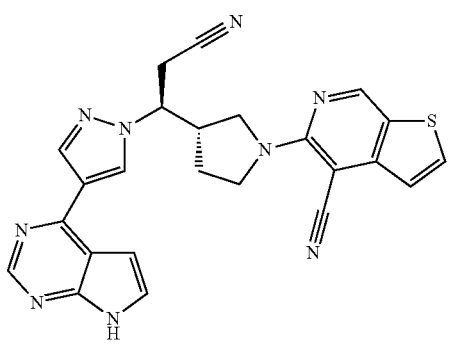 [SMILES: N#CC[C@@H]([C@H]1CCN(c2ncc3sccc3c2C#N)C1)n1cc(-c2ncnc3[nH]ccc23)cn1]

Step 1. 5-chlorothieno[2,3-c]pyridine-4-carbonitrile

To a mixture of 3-thienylacetonitrile (1.16 g, 9.42 mmol), phosphoryl chloride (10.1 g, 65.9 mmol) was added DMF (2.2 mL, 28 mmol). The resulting mixture was heated at 100° C. for 2.5 h. Hydroxylamine hydrochloride (1.28 g, 18.4 mmol) was added portion-wise and stirred for another 20 min. The reaction solution was cooled to RT and the resulting precipitate was filtered and washed with acetone to give the desired product as white solid (26% yield). LCMS (M+H)⁺: 194.9.

Step 2. 5-((3S)-3-{(1S)-2-cyano-1-[4-(7H-pyrrolo[2,3-d]pyrimidin-4-yl)-1H-pyrazol-1-yl]ethyl}pyrrolidin-1-yl)thieno[2,3-c]pyridine-4-carbonitrile A mixture of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (from Example 15, step 3; 18 mg, 0.041 mmol), 5-chlorothieno[2,3-c]pyridine-4-carbonitrile (18 mg, 0.095 mmol) and DIPEA (20 μL, 0.1 mmol) in ethanol (0.09 mL) was heated to reflux for 2.5 h. It was purified by LCMS (Sunfire C18 column 19×100 mm), eluting with a gradient of acetonitrile/water containing 0.1% TFA, at flow rate 30 mL/min) to give 7 mg pale yellow solid (30% yield). LCMS (M+1): 596.0.

The above pale yellow solid (7 mg) was stirred in 0.5 mL DCM and 0.5 mL TFA for 1 h. The mixture was concentrated and the residue was stirred in 50 uL EDA and 1 mL MeOH for 1 h. The reaction solution was purified by LCMS (C18 column 19×100 mm) eluting with a gradient ACN/H₂O containing 0.15% NH₄OH at 30 mL/min) to give the desired product as white solid (1.6 mg, 8% yield). LCMS (M+H)⁺: 466.1.

Example 75

5-((3S)-3-{(1S)-2-cyano-1-[4-(7H-pyrrolo[2,3-d]pyrimidin-4-yl)-1H-pyrazol-1-yl]ethyl}pyrrolidin-1-yl)thieno[3,2-b]pyridine-6-carbonitrile

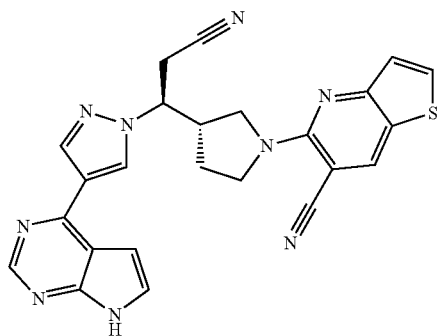 [SMILES: N#CC[C@@H]([C@H]1CCN(c2nc3ccsc3cc2C#N)C1)n1cc(-c2ncnc3[nH]ccc23)cn1]

Step 1. 3-acetylthiophene oxime

To a solution of 1-(3-thienyl)ethanone (1.49 g, 11.8 mmol) in ethanol (43 mL) and water (13 mL), N-hydroxyamine hydrochloride (1.96 g, 28.2 mmol) and sodium acetate (2.32 g, 28.3 mmol) were added sequentially. The resulting solution was refluxed for 1 h, then 100 mL cold water was added and resultant precipitate was collected to yield the desired product as white powder (816 mg, 49%). LCMS (M+H)⁺: 142.0.

Step 2. 5-chlorothieno[3,2-b]pyridine-6-carbonitrile

To a solution of 3-acetylthiophene oxime (0.816 g, 5.78 mmol) in ether (20 mL) was added phosphoryl chloride (5.2 mL, 56 mmol) drop-wise at 10° C. over 20 min. The resulting mixture was stirred at 10° C. for 2 h. DMF (1.1 mL, 14.5 mmol) was then added drop-wise and the mixture was heated to boil off the ether. Heating was continued until all the ether had been removed and temperature of the reaction mixture reached 110° C. The reaction mixture was heated at 110° C. for 1 h. Hydroxylamine hydrochloride (0.800 g, 11.5 mmol) was added portion-wise over 15 min and stirred for another 20 min. The reaction solution was cooled to RT and the resulting mixture was poured into a mixture of 40 g of ice and 60 g of water with stirring. The yellow precipitate which formed was collected by filtration and dried to give the desired product (449 mg, 40%). LCMS (M+H)⁺: 195.0.

Step 3. 5-((3S)-3-{(1S)-2-cyano-1-[4-(7H-pyrrolo[2,3-d]pyrimidin-4-yl)-1H-pyrazol-1-yl]ethyl}pyrrolidin-1-yl)thieno[3,2-b]pyridine-6-carbonitrile A mixture of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (18 mg, 0.041 mmol; from Example 15, step 3), 5-chlorothieno[3,2-b]pyridine-6-carbonitrile (18 mg, 0.095 mmol) and DIPEA (20 μL, 0.1 mmol) in ethanol (0.1 mL) was heated to reflux for 2.5 h. It was purified by LCMS (Sunfire C18 column 19×100 mm), eluting with a gradient of acetonitrile/water containing 0.1% TFA, at flow rate 30 mL/min) to give 7 mg yellow solid (30% yield). LCMS (M+1): 596.2.

The yellow solid (7 mg) was stirred in 1 mL DCM and 1 mL TFA for 1 h. It was concentrated and the residue was stirred in 50 μL EDA and 1 mL MeOH for 1 h. The reaction solution was purified by LCMS (C18 column 19×100 mm) eluting with a gradient ACN/H₂O containing 0.15% NH₄OH at 30 mL/min) to give the desired product as white solid (2.0 mg, 10% yield). LCMS (M+H)⁺: 466.0.

Example 76

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-hydroxythiophene-3-carbonitrile

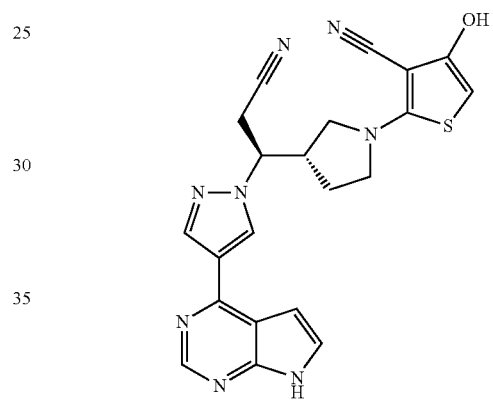

Step 1. 2,4-dibromo-3-methylthiophene

A suspension of zinc (1.94 g, 29.7 mmol) in acetic acid (5.20 mL, 91.4 mmol), water (14.0 mL) and THF (2.0 mL) was brought to a gentle reflux, and then the heat was removed. 2,3,5-tribromo-4-methylthiophene (from TCI; 10.0 g, 29.9 mmol) in THF (1.0 mL) was then added drop-wise at such a rate that the reaction mixture kept refluxing. After the addition was complete, the mixture was refluxed overnight, and then cooled to RT and extracted with ethyl acetate. The organic extract was washed with water, saturated NaHCO₃, and brine, dried over Na₂SO₄ and concentrated. Distillation of the crude product under high vacuum gave the desired product as colorless liquid (4 g, 52%). ¹H NMR (300 MHz, CDCl₃): δ 7.22 (s, 1H), 2.20 (s, 3H).

Step 2. 2,4-dibromo-3-(bromomethyl)thiophene

A suspension of 2,4-dibromo-3-methylthiophene (1.89 g, 7.38 mmol) and N-bromosuccinimide (1.42 g, 7.98 mmol) and 2,2'-azobis(isobutyronitrile) (from Aldrich 10.3 mg, 0.0626 mmol) in carbon tetrachloride (15.4 mL) was heated to 80° C. for 2 h. The reaction suspension was cooled to RT. The precipitate was filtered and washed with small amount of DCM. The filtrate was concentrated to give a solid. The crude material was used in the next step without purification.

Step 3. (2,4-dibromo-3-thienyl)methyl acetate

To a solution of 2,4-dibromo-3-(bromomethyl)thiophene (2.47 g, 7.38 mmol) in DMF (20 mL) was added sodium acetate (3.02 g, 36.9 mmol). The mixture was heated at 110° C. for 3 h. The reaction solution was cooled to RT and diluted with ethyl acetate and water. The aqueous layer was extracted with ethyl acetate once. The combined organic extracts were washed with water, brine and dried over $Na_2SO_4$, filtered and concentrated. The residue was purified by silica gel column (0% to 10% ethyl acetate/hexanes) to give the desired product as clear oil (1.89 g, 81%). $^1$H NMR (300 MHz, $CD_3OD$): δ 7.57 (s, 1H), 5.06 (s, 2H), 2.05 (s, 3H); LCMS (M+Na)$^+$: 336.7.

Step 4. (2,4-dibromo-3-thienyl)methanol

To a solution of (2,4-dibromo-3-thienyl)methyl acetate (1.89 g, 6.02 mmol) in acetonitrile (10 mL) and water (10 mL) was added 50% NaOH in water (50:50, water:sodium hydroxide, 0.651 mL, 18.0 mmol). The resulting solution was stirred at RT overnight. The reaction solution was diluted with 2 N $H_2SO_4$ and ethyl acetate. The aqueous layer was extracted with ethyl acetate once. The combined organic extracts were washed with brine, dried over $Na_2SO_4$, filtered and concentrated. The residue was purified on a silica gel column (0% to 15% ethyl acetate/hexanes) to give the desired product as a white solid (1.46 g, 89%). LCMS (M+H–$H_2O$)$^+$: 254.9.

Step 5. 2,4-dibromothiophene-3-carbaldehyde

To a solution of (2,4-dibromo-3-thienyl)methanol (1.46 g, 5.37 mmol) in DCM (50 mL) was added Dess-Martin periodinane (2.5 g, 5.9 mmol). The reaction solution was stirred at RT for 2 h. The reaction solution was diluted with ether and saturated $NaHCO_3$. After stirring for 1 h, the reaction mixture was filtered through a pad of Celite. The aqueous layer was extracted with ethyl acetate once. The combined organic extracts were washed with brine, dried over $Na_2SO_4$, filtered and concentrated in vacuo to give the desired product (1.45 g, 100%). The crude product was used in the next step without further purification

Step 6. 2,4-dibromothiophene-3-carbaldehyde oxime

To a solution of 2,4-dibromothiophene-3-carbaldehyde (1.45 g, 5.37 mmol) in ethanol (19.5 mL) and water (5.9 mL) was added N-hydroxyamine hydrochloride (0.410 g, 5.91 mmol) and sodium acetate (0.617 g, 7.52 mmol) sequentially. The resultant solution was refluxed for 1 h. The organic solvent was removed in vacuo and the solution was diluted with water. The resultant precipitate was collected and dried under vacuum to give the desired product as white solid (1.38 g, 90%). LCMS (M+H)$^+$: 285.8.

Step 7. 2,4-dibromothiophene-3-carbonitrile

To a solution of 2,4-dibromothiophene-3-carbaldehyde oxime (1.37 g, 4.81 mmol) in pyridine (15 mL) was added methanesulfonyl chloride (1.5 mL, 19 mmol). It was heated at 60° C. for 2 h. The reaction solution was diluted with ethyl acetate and saturated $CuSO_4$ solution. The organic layer was washed with $CuSO_4$ twice, followed by 1 N HCl solution and brine, dried over $Na_2SO_4$, filtered and concentrated. The residue was purified by silica gel column (0-10% ethyl acetate/hexanes) to give the desired product as white solid (1.18 g, 92%). $^1$H NMR (300 MHz, $CD_3OD$): δ 7.73 (s, 1H).

Step 8. 4-bromo-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile A mixture of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (122 mg, 0.279 mmol; from Example 15, step 3), 2,4-dibromothiophene-3-carbonitrile (83.0 mg, 0.311 mmol) and DIPEA (53.4 µL, 0.307 mmol) in 1-butyl-3-methyl-1H-imidazol-3-ium tetrafluoroborate (315 mg) was heated at 120° C. for 2 h. The reaction solution was cooled to RT and diluted with ethyl acetate and water. The aqueous layer was extracted with ethyl acetate. The extracts were washed with brine, dried over $Na_2SO_4$, filtered and concentrated. The residue was purified with silica gel column to give the desired product as a yellow solid (88 mg, 50%). LCMS (M+H)$^+$: 623.0, 625.1.

Step 9. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-hydroxythiophene-3-carbonitrile To a solution of 4-bromo-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile (16.1 mg, 0.0258 mmol) in DCM (0.50 mL) was added TFA (0.50 mL). The reaction solution was stirred at RT for 2 h and the solvent was removed in vacuo. The residue was dissolved in methanol (1 mL) and treated with (100 mL, 1.50 mmol). The reaction solution was stirred for 1 h and diluted with EDA methanol and purified by LCMS (C18 column 19×100 mm) eluting with a gradient ACN/$H_2O$ containing 0.15% $NH_4OH$ at 30 mL/min to give the desired product as white solid (5.7 mg, 51%). LCMS (M+H)$^+$: 431.1.

Example 77

4-bromo-2-((3S)-3-{(1S)-2-cyano-1-[4-(7H-pyrrolo[2,3-d]pyrimidin-4-yl)-1H-pyrazol-1-yl]ethyl}pyrrolidin-1-yl)thiophene-3-carbonitrile

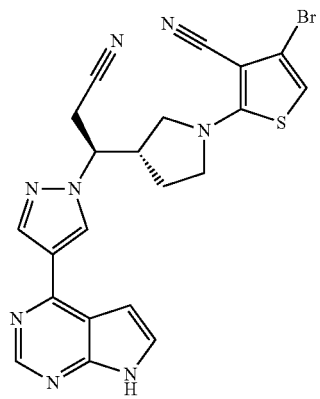 [SMILES: N#CC[C@@H]([C@H]1CCN(c2scc(Br)c2C#N)C1)n1cc(-c2ncnc3[nH]ccc23)cn1]

To a stirred suspension of 4-bromo-2-((3S)-3-{(1S)-2-cyano-1-[4-(7-{[2-(trimethylsilyl)ethoxy]methyl}-7H-pyrrolo

[2,3-d]pyrimidin-4-yl)-1H-pyrazol-1-yl]ethyl}pyrrolidin-1-yl)thiophene-3-carbonitrile (from example 76, step 8; 24.2 mg, 0.039 mmol) in acetonitrile (0.2 mL) at RT was added boron trifluoride etherate (12.3 mL, 0.097 mmol). The resulting clear brown solution was stirred for 2 h. The reaction solution was diluted with methanol (0.5 mL) and treated with EDA (50 mL, 0.75 mmol). The reaction solution was stirred for 1 h and diluted with methanol and purified with preparative LCMS (C18 column 19×100 mm eluting with a gradient ACN/H$_2$O containing 0.15% NH$_4$OH at 30 mL/min) to give the desired product (5.3 mg, 27%). $^1$H NMR (300 MHz, DMSO-D6): δ 12.1 (s, 1H); 8.86 (s, 1H); 8.67 (s, 1H); 8.42 (s, 1H); 7.59 (d, 1H); 6.97 (d, 1H); 6.75 (s, 1H); 4.84 (m, 1H); 3.72-3.20 (m, 6H); 2.96 (m, 1H); 1.74 (m, 2H); LCMS (M+H)$^+$: 493.0, 495.0.

Example 78

4-chloro-2-038)-3-{(1S)-2-cyano-1-[4-(7H-pyrrolo[2,3-d]pyrimidin-4-yl)-1H-pyrazol-1-yl]ethyl}pyrrolidin-1-yl)thiophene-3-carbonitrile

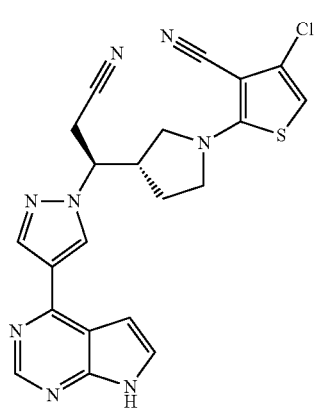 [SMILES: N#CC[C@@H]([C@H]1CCN(c2scc(Cl)c2C#N)C1)n1cc(-c2ncnc3[nH]ccc23)cn1]

Step 1. 4-chloro-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile To a solution of 4-bromo-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile (from example 76, step 8; 21 mg, 0.034 mmol) in pyridine (100 μL) was added cuprous monochloride (16.7 mg, 0.168 mmol). The resultant mixture was heated at 120° C. overnight. The reaction solution was diluted with methanol and purified with preparative LCMS (Sunfire C18 column 19×100 mm eluting with a gradient ACN/H$_2$O containing 0.1% TFA at 30 mL/min) to give the desired product (3.2 mg, 16%). LCMS (M+H)$^+$: 579.2.

Step 2. 4-chloro-2-((3S)-3-{(1S)-2-cyano-1-[4-(7H-pyrrolo[2,3-d]pyrimidin-4-yl)-1H-pyrazol-1-yl]ethyl}pyrrolidin-1-yl)thiophene-3-carbonitrile This compound was prepared according to the procedure of Example 77, using 4-chloro-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile as the starting material. LCMS (M+H)$^+$: 449.1.

Example 79

2-((3S)-3-{(1S)-2-cyano-1-[4-(7H-pyrrolo[2,3-d]pyrimidin-4-yl)-1H-pyrazol-1-yl]ethyl}pyrrolidin-1-yl)thiophene-3,4-dicarbonitrile

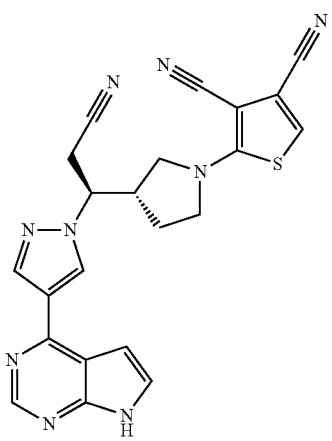 [SMILES: N#CC[C@@H]([C@H]1CCN(c2scc(C#N)c2C#N)C1)n1cc(-c2ncnc3[nH]ccc23)cn1]

Step 1. 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3,4-dicarbonitrile To a solution of 4-bromo-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile (from example 76, step 8; 30.0 mg, 0.0481 mmol) in NMP (0.4 mL) was added zinc cyanide (28.2 mg, 0.240 mmol). tetrakis(triphenylphosphine)palladium(0) (13.9 mg, 0.012 mmol) and the solution was flushed with nitrogen. The solution was heated at 150° C. for 15 min in a microwave reactor. The reaction solution was diluted with methanol and purified by preparative LCMS (Sunfire C18 column 19×100 mm eluting with a gradient ACN/H$_2$O containing 0.1% TFA at 30 mL/min) to give the desired product (8.3 mg, 30%). LCMS (M+H)$^+$: 570.2.

Step 2. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)thiophene-3,4-dicarbonitrile This compound was prepared according to the procedure of Example 77, using 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3,4-dicarbonitrile as the starting material. $^1$H NMR (300 MHz, DMSO-D6): δ 12.06 (s, 1H); 8.81 (s, 1H); 8.62 (s, 1H);

8.36 (s, 1H); 7.59 (s, 1H); 7.54 (d, 1H); 6.92 (d, 1H); 4.80 (m, 1H); 3.69-3.16 (m, 6H); 2.96 (m, 1H); 1.72 (m, 2H); LCMS (M+H)+: 440.1.

Example 80

2-((3S)-3-{2-fluoro-1-[4-(7H-pyrrolo[2,3-d]pyrimidin-4-yl)-1H-pyrazol-1-yl]ethyl}pyrrolidin-1-yl)thiophene-3,4-dicarbonitrile

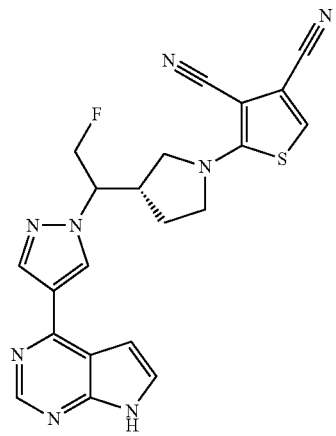 [SMILES: N#Cc1csc(N2CC[C@H](C(CF)n3cc(-c4ncnc5[nH]ccc45)cn3)C2)c1C#N]

Step 1. 4-bromo-2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile This compound was prepared according to the procedure of Example 76, step 8, using 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7) and 2,4-dibromothiophene-3-carbonitrile as the starting material. LCMS (M+H)+: 616.2, 618.2.

Step 2. 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3,4-dicarbonitrile This compound was prepared according to the procedure of Example 79, step 1, using 4-bromo-2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3-carbonitrile as the starting material. LCMS (M+H)+: 563.2.

Step 3. 2-((3S)-3-{2-fluoro-1-[4-(7H-pyrrolo[2,3-d]pyrimidin-4-yl)-1H-pyrazol-1-yl]ethyl}pyrrolidin-1-yl)thiophene-3,4-dicarbonitrile This compound was prepared according to the procedure of Example 77, using 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)thiophene-3,4-dicarbonitrile as the starting material. 1H NMR (300 MHz, DMSO-D6): δ 8.73 (s, 1H); 8.61 (s, 1H); 8.33 (s, 1H); 7.61 (s, 1H); 7.53 (d, 1H); 6.91 (d, 1H); 4.97-4.69 (m, 3H); 3.73 (m, 1H); 3.55 (m, 1H), 3.45 (m, 2H), 2.94 (m, 1H); 1.72 (m, 2H) LCMS (M+H)+: 433.1.

Example 81

2-(3-{2-cyano-1-[3-(7H-pyrrolo[2,3-d]pyrimidin-4-yl)-1H-pyrrol-1-yl]ethyl}pyrrolidin-1-yl)thiophene-3,4-dicarbonitrile (two enantiomers isolated)

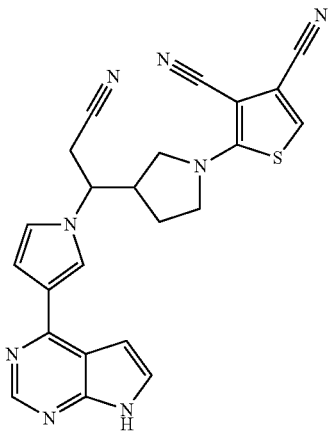 [SMILES: N#CCC(C1CCN(c2scc(C#N)c2C#N)C1)n1ccc(-c2ncnc3[nH]ccc23)c1]

Step 1. 4-bromo-2-(3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)thiophene-3-carbonitrile This compound was prepared according to the procedure of Example 76, step 8, using 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (from Example 33, step 3) and 2,4-dibromothiophene-3-carbonitrile as the starting materials. LCMS calculated for $C_{28}H_{33}BrN_7OSSi(M+H)^+$: m/z=622.1, 624.1.

Step 2. 2-(3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)thiophene-3,4-dicarbonitrile This compound was prepared according to the procedure of Example 79, step 1, using 4-bromo-2-(3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)thiophene-3-carbonitrile as the starting material. This material was separated by chiral HPLC (Chiral Technologies Chiralpak AD-H, 5μ, 20×250 mm, eluting with 80% EtOH/Hexanes, 8 mL/min) to afford enantiomer 1 (first to elute) and enantiomer 2 (second to elute). LCMS (M+H)+: 569.2.

Step 3. 2-(3-{2-cyano-1-[3-(7H-pyrrolo[2,3-d]pyrimidin-4-yl)-1H-pyrrol-1-yl]ethyl}pyrrolidin-1-yl)thiophene-3,4-dicarbonitrile (two enantiomers isolated)

Each enantiomer from last step was deprotected separately by stirring sequentially in a mixture of 1:1 TFA/DCM for 1 h, removal of solvent, then stirring in methanol (1.5 mL) containing EDA (0.2 mL) for 30 min. Preparative-HPLC/MS (C18 column (19×100 mm) eluting with a gradient of ACN/H$_2$O containing 0.15% NH$_4$OH) was used to purify the products. Enantiomer 1 LCMS (M+H)$^+$: 439.0; Enantiomer 2 LCMS (M+H)$^+$: 439.1.

Example 82

4-038)-3-{(1S)-2-cyano-1-[4-(7H-pyrrolo[2,3-d]pyrimidin-4-yl)-1H-pyrazol-1-yl]ethyl}pyrrolidin-1-yl)-1,3-thiazole-5-carbonitrile

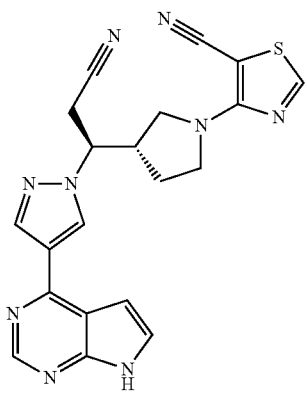 [SMILES: N#CC[C@@H]([C@H]1CCN(c2ncsc2C#N)C1)n1cc(-c2ncnc3[nH]ccc23)cn1]

Step 1. 2,4-dichloro-1,3-thiazole-5-carbaldehyde

To a suspension of 2,4-thiazolidinedione (10.0 g, 85.4 mmol) in phosphoryl chloride (48.0 mL, 515 mmol) at 0° C. was added DMF (7.3 mL, 94 mmol) drop-wise. The reaction mixture was allowed to warm to ambient temperature and stirred for 1 h. The mixture was then heated at 85° C. for 1 h before stirring at 115° C. for 3.5 h. After cooling to ambient temperature, the mixture was carefully poured onto ice with slow stirring. The aqueous layer was extracted with DCM three times. The combined organic extracts were washed with saturated NaHCO$_3$, water, dried over MgSO$_4$, filtered, and concentrated. The residue was purified by silica gel column (0% to 20% ethyl acetate/hexanes) to give the desired product as off white solid (8.1 g, 52%). $^1$H NMR (300 MHz, DMSO-d$_6$): δ 9.92 (s, 1H); LCMS (M+H−CO)$^+$: 153.9

Step 2. 2,4-dichloro-5-(1,3-dioxolan-2-yl)-1,3-thiazole

To a mixture of 2,4-dichloro-1,3-thiazole-5-carbaldehyde (4.0 g, 22 mmol) and 1,2-ethanediol (3.6 mL, 64 mmol) in anhydrous toluene (50 mL) was added p-toluenesulfonic acid monohydrate (0.31 g, 1.6 mmol). The flask was fitted with a Dean-Stark trap and the mixture heated to reflux for 3.5 h. After cooling to ambient temperature, the reaction was quenched with 10% Na$_2$CO$_3$ solution. The aqueous layer was extracted with ethyl acetate three times. The combined extracts were washed with brine, dried over MgSO$_4$, filtered, and concentrated. The residue was purified by silica gel column (0% to 30% ethyl acetate/hexanes) to give the desired product as yellow oil (4.17 g, 84%). $^1$H NMR (300 MHz, CDCl$_3$): δ 6.03 (s, 1H); 4.10 (m, 4H); LCMS (M+H)$^+$: 225.9.

Step 3. 4-chloro-5-(1,3-dioxolan-2-yl)-1,3-thiazole

To a solution of 2,4-dichloro-5-(1,3-dioxolan-2-yl)-1,3-thiazole (1.0 g, 4.4 mmol) in THF (20 mL) at −78° C. was added 2.5 M of n-butyllithium in hexane (2.28 mL, 5.69 mmol) drop-wise. The resulting dark solution was stirred at −78° C. for 75 min. The reaction was quenched with water and then poured into brine. The aqueous layer was extracted with ethyl acetate three times. The combined extracts were dried over MgSO$_4$, filtered, and concentrated. The residue was purified by silica gel column (0% to 30% ethyl acetate/hexane) to give the desired product as a yellow oil (770 mg, 91%). $^1$H NMR (300 MHz, CDCl$_3$): δ 8.74 (s, 1H), 6.18 (s, 1H); 4.10 (m, 4H); LCMS (M+H)$^+$: 191.9.

Step 4. 4-chloro-1,3-thiazole-5-carbaldehyde

To a solution of 4-chloro-5-(1,3-dioxolan-2-yl)-1,3-thiazole (0.75 g, 3.9 mmol) in THF (10 mL) was added 5.0 M of HCl solution in water (2 mL, 10 mmol). The resulting mixture was stirred at ambient temperature for 2 h. The reaction solution was poured into brine and extracted with ethyl acetate three times. The combined extracts were washed with saturated sodium bicarbonate, brine, dried over MgSO$_4$, filtered, and concentrated to give the desired product as an off-white solid (0.53 g, 92%). $^1$H NMR (300 MHz, CDCl$_3$): δ 10.16 (s, 1H), 9.03 (s, 1H).

Step 5. 4-chloro-1,3-thiazole-5-carbaldehyde oxime

To a stirred solution of sodium bicarbonate (0.17 g, 2.0 mmol) in water (6.4 mL) was added hydroxylamine hydrochloride (0.14 g, 2.0 mmol) in portions. To the mixture was added a solution of 4-chloro-1,3-thiazole-5-carbaldehyde (0.30 g, 2.0 mmol) in ethanol (2.0 mL). The mixture was stirred for 1 h at ambient temperature. The reaction solution was diluted with water. The resultant precipitate was collected and dried under vacuum to give the desired product as white solid (0.25 g, 76%). $^1$H NMR (300 MHz, CD$_3$OD): δ 9.02 (s, 1 H), 7.83 (s, 1H); LCMS (M+H)$^+$: 162.9.

Step 6. 4-chloro-1,3-thiazole-5-carbonitrile

A mixture of 4-chloro-1,3-thiazole-5-carbaldehyde oxime (0.24 g, 1.5 mmol) and acetic anhydride (1.2 mL, 13 mmol) was heated at 140° C. for 3 h. The mixture was concentrated in vacuo to give a brown solid (65 mg, 30%). The crude material was used in the next step without further purification.

Step 7. 4-(3-{2-cyano-1-[4-(7H-pyrrolo[2,3-d]pyrimidin-4-yl)-1H-pyrazol-1-yl]ethyl}pyrrolidin-1-yl)-1,3-thiazole-5-carbonitrile (single enantiomer)

This compound was prepared according to the procedure of Example 74, step 2, using (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (from Example 15, step 3) and 4-chloro-1,3-thiazole-5-carbonitrile as the starting materials. LCMS (M+H)$^+$: 416.1.

Example 83

5-(3-{2-fluoro-1-[3-(7H-pyrrolo[2,3-d]pyrimidin-4-yl)-1H-pyrrol-1-yl]ethyl}pyrrolidin-1-yl)-1,3-thiazole-4-carbonitrile (single enantiomer)

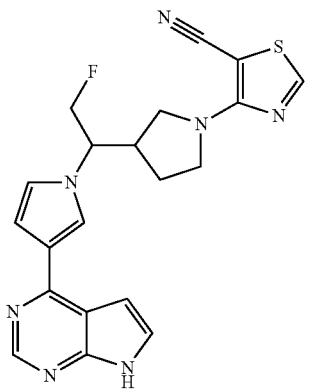 [SMILES: N#Cc1scnc1N1CCC(C(CF)n2ccc(-c3ncnc4[nH]ccc34)c2)C1]

Step 1. tert-butyl 3-[(E)-2-fluoro-2-(phenylsulfonyl)vinyl]pyrrolidine-1-carboxylate To a mixture of tert-butyl 3-[2-fluoro-1-hydroxy-2-(phenylsulfonyl)ethyl]pyrrolidine-1-carboxylate (synthesized according to the procedure of Example 70 step 3, using tert-butyl-3-formylpyrrolidine-1-carboxylate as the starting material, 0.53 g, 1.4 mmol) and triethylamine (0.80 mL, 5.7 mmol) in DCM (7.0 mL) at 0° C. was added methanesulfonyl chloride (132 mL, 1.70 mmol). The mixture was stirred at 0° C. for 1 h then warmed to ambient temperature. After 4 h, another portion of triethylamine (2.0 eq) was added and stirred overnight. The reaction solution was diluted with brine and the aqueous layer was extracted with DCM three times. The combined extracts were dried over MgSO$_4$, filtered, and concentrated. The residue was purified by silica gel column (0% to 40% ethyl acetate/hexanes) to give the desired product (350 mg, 69%). LCMS (M+Na)$^+$: 378.1.

Step 2 tert-butyl 3-{2-fluoro-2-(phenylsulfonyl)-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate To a mixture of 4-(1H-pyrrol-3-yl)-7-{[2-(trimethylsilyl)ethoxy]methyl}-7H-pyrrolo[2,3-d]pyrimidine (from Example 33, Step 1; 0.33 g, 1.0 mmol) and tert-butyl 3-[(E)-2-fluoro-2-(phenylsulfonyl)vinyl]pyrrolidine-1-carboxylate (0.35 g, 0.98 mmol) in acetonitrile (6.0 mL) was added 1,8-diazabicyclo[5.4.0]undec-7-ene (180 µL, 1.2 mmol) and the reaction solution was stirred at 65° C. for 36 h. The solvent was removed in vacuo and the residue was purified by silica gel column (0% to 50% ethyl acetate/hexanes) to give the desired product as 1:1 two diastereomers (134 mg, 20%). LCMS (M+H)$^+$: 670.3.

Step 3. tert-butyl 3-{2-fluoro-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate This compound was prepared according to the procedure of Example 70, step 4, using tert-butyl 3-{2-fluoro-2-(phenylsulfonyl)-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate as the starting material. Two diastereomes were isolated using silica gel column eluting with 5-60% ethyl acetate/hexanes. LCMS (M+H)$^+$: 530.1.

Step 4. 4-[1-(2-fluoro-1-pyrrolidin-3-ylethyl)-1H-pyrrol-3-yl]-7-{[2-(trimethylsilyl)ethoxy]methyl}-7H-pyrrolo[2,3-d]pyrimidine To a solution of tert-butyl 3-{2-fluoro-1-[3-(7-{[2-(trimethylsilyl)ethoxy]methyl}-7H-pyrrolo[2,3-d]pyrimidin-4-yl)-1H-pyrrol-1-yl]ethyl}pyrrolidine-1-carboxylate (104 mg, 0.196 mmol;) in DCM (0.5 mL) was added 4.0 M of hydrogen chloride in 1,4-dioxane (0.5 mL, 2.0 mmol). The reaction solution was stirred at RT for 90 min. The solvent was removed in vacuo and the residue was dissolved in ethyl acetate. The organic layer was washed with 1.0 N NaOH solution. The aqueous was extracted with ethyl acetate. The combined extracts were dried over MgSO$_4$, filtered, and concentrated to give the desired product as a brown sticky gum (86 mg, 100%). LCMS (M+H)$^+$: 430.1.

Step 5. 5-(3-{2-fluoro-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)-1,3-thiazole-4-carbonitrile To a mixture of 4-[1-(2-fluoro-1-pyrrolidin-3-ylethyl)-1H-pyrrol-3-yl]-7-{[2-(trimethylsilyl)ethoxy]methyl}-7H-pyrrolo[2,3-d]pyrimidine (diastereomer 2 from step 3) (54 mg, 0.12 mmol) and 5-bromo-1,3-thiazole-4-carbonitrile (29.5 mg, 0.156 mmol) was added 1-butyl-3-methyl-1H-imidazol-3-ium tetrafluoroborate (0.2 mL) and DIPEA (32.4 µL, 0.186 mmol). The resulting mixture was stirred at 120° C. for 3 h then cooled to ambient temperature. The reaction solution was diluted with ethyl acetate and washed with water. The organic layer was dried over MgSO$_4$, filtered, and concentrated. The residue was diluted with methanol and purified by preparative LCMS (C18 column (19×100 mm) eluting with a gradient of ACN/H$_2$O containing 0.15% NH$_4$OH) to give the desired product (20 mg, 28%). The enantiomers were separated by chiral HPLC (Chiral Technologies Chiralcel OD-H, 5µ, 20×250 mm, 20% EtOH/Hexanes, 12 mL/min). Desired enantiomer 1 (first to elute) was collected (12.7 mg, 18%). LCMS (M+H)+: 538.2. Another enantiomer 2 (second to elute) was collected (6.2 mg, 9%). LCMS (M+H)+: 538.2

Step 6. 5-(3-{2-fluoro-1-[3-(7H-pyrrolo[2,3-d]pyrimidin-4-yl)-1H-pyrrol-1-yl]ethyl}pyrrolidin-1-yl)-1,3-thiazole-4-carbonitrile (single enantiomer)

The desired enantiomer 1 (from step 5) was treated with 1:1 TFA/DCM for 1 h, concentrated again, and stirred in a solution of methanol (1 mL) containing 0.2 mL EDA for 30 min. The product was purified via preparative LCMS (C18 column (19×100 mm) eluting with a gradient of ACN/H₂O containing 0.15% NH₄OH) to give the desired product. LCMS (M+H)⁺: 408.1.

Example 84

4-((S)-3-((S)-1-(4-(7H-pyrrolo[2,3-d]pyrimidin-4-yl)-1H-pyrazol-1-yl)-2-cyanoethyl)pyrrolidin-1-yl)pyrimidine-5-carbonitrile trifluoroacetate

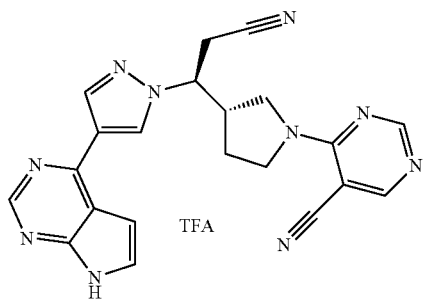 [SMILES: N#CC[C@@H]([C@H]1CCN(c2ncncc2C#N)C1)n1cc(-c2ncnc3[nH]ccc23)cn1]

Step 1: (3S)-3-[(3S)-1-(5-iodopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (60.0 mg, 0.1371 mmol; from Example 15, step 3) was mixed with 4-chloro-5-iodopyrimidine (WO 2008/079965; 48.35 mg, 0.2011 mmol) and DIPEA (36.0 μL, 0.2067 mmol) and was dissolved in NMP (0.40 mL). The reaction was heated at 130° C. for 2 h at which time LCMS analysis showed mainly product. The residue was purified on preparative LC to give the product. This was partitioned between EtOAc and saturated NaHCO₃ and the EtOAc extract was washed with brine, dried (MgSO₄), and stripped in vacuo and was carried on to the next reaction. MS (EI): 642 (M+H)

Step 2: 4-((S)-3-((S)-2-cyano-1-(4-(7-((2-(trimethylsilyl)ethoxy)methyl)-7H-pyrrolo[2,3-c]pyrimidin-4-yl)-1H-pyrazol-1-yl)ethyl)pyrrolidin-1-yl)pyrimidine-5-carbonitrile Into a 1-neck round-bottom flask 3-[1-(5-iodopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (32.0 mg, 0.0499 mmol) was dissolved in DMF (0.3 mL) and zinc cyanide (17.6 mg, 0.150 mmol) was added. The reaction was degassed, tetrakis(triphenylphosphine)palladium(0) (11.5 mg, 0.00998 mmol) was added and heated at 100° C. for 4 h at which time LCMS analysis showed that there was mainly product. The reaction was filtered and the product was purified by preparative LC. MS (EI): 541 (M+H)

Step 3: 4-((S)-3-((S)-1-(4-(7H-pyrrolo[2,3-d]pyrimidin-4-yl)-1H-pyrazol-1-yl)-2-cyanoethyl)pyrrolidin-1-yl)pyrimidine-5-carbonitrile trifluoroacetate The product from step 2 was deprotected (CH₂Cl₂/TFA; MeOH/NH₄OH) as in Example 1, and the product was purified by LC (ACN/water/TFA method as in Example 5). MS (EI): 411 (M+H).

Example 85

4-(1-{2-fluoro-1-[(3S)-1-(5-fluoro-2,3-dihydrothieno[2,3-b]pyridin-6-yl)pyrrolidin-3-yl]ethyl}-1H-pyrazol-4-yl)-7H-pyrrolo[2,3-d]pyrimidine bis(trifluoroacetate)

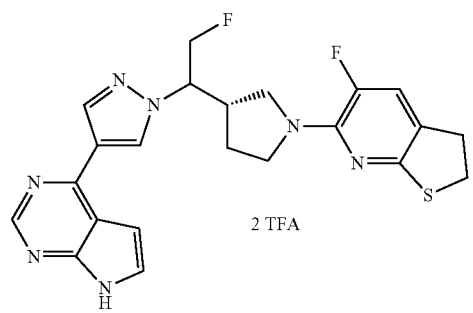 [SMILES: FCC([C@H]1CCN(c2nc3c(cc2F)CCS3)C1)n1cc(-c2ncnc3[nH]ccc23)cn1]

Step 1: 3-[(E)-2-ethoxyvinyl]-2,5,6-trifluoropyridine

Into a 1-neck round-bottom flask 3-chloro-2,5,6-trifluoropyridine (from Lancaster Synthesis Inc.; 1.0 g, 5.97 mmol) was dissolved in toluene (6.7 mL) with (2-ethoxyethenyl)tri-n-butyltin (from Synthonix Corporation; 2.01 g, 5.57 mmol) and tetrakis(triphenylphosphine) palladium(0) (348.0 mg, 0.3012 mmol) and was degassed. The reaction was heated to reflux for 4 h after which time TLC analysis showed most of the starting material had been consumed. The reaction mixture was chromatographed using 3% EtOAc/hexanes to give 3-[(E)-2-ethoxyvinyl]-2,5,6-trifluoropyridine contaminated with some butyltin chloride. ¹H NMR (400 MHz, CDCl₃): δ 8.41 (m, 1H), 6.40 (dd, 1H0, 5.35 (dd, 1H), 4.10 (q, 2H), 1.30 (t, 3H).

Step 2: 1-ethoxy-2-(2,5,6-trifluoropyridin-3-yl)ethanol

The 3-[(E)-2-ethoxyvinyl]-2,5,6-trifluoropyridine from step 1 in THF (26.6 mL) and 5.0 M of HCl in water (17 mL, 83 mmol) was added and stirred at 25° C. for 20 h at which time TLC analysis of a worked up sample (EtOAc/NaHCO₃) showed absence of starting material. The reaction was neutralized with NaHCO₃ and was partitioned between ether and water and the ether extract was washed with brine, dried (MgSO₄), and stripped in vacuo. NMR analysis showed no aldehyde peaks and was consistent with the ethyl hemiacetal 1-ethoxy-2-(2,5,6-trifluoropyridin-3-yl)ethanol. The product was purified by chromatography on silica gel using 30% ether/hexanes to give the product (0.75 g, 61% for the two steps). HPLC analysis showed one peak. ¹H NMR (400 MHz, CDCl₃): δ 7.72 (m, 1H), 5.42 (m, 1H), 5.02 (m, 1H), 4.38 (m, 1H), 3.70-3.85 (m, 2H), 2.90 (m, 2H), 1.35 (m, 2H), 1.22 (m, 3H).

Step 3: 2-(2,5,6-trifluoropyridin-3-yl)ethanol

Into a 10 mL sealed tube 1-ethoxy-2-(2,5,6-trifluoropyridin-3-yl)ethanol (250.0 mg, 1.130 mmol) was dissolved in THF (10.0 mL) and 1.0 M of HCl in water (5.0 mL, 5.0 mmol) was added The reaction was heated at 75° C. for 90 min. and was neutralized with NaHCO₃ and was extracted with ether. The reaction mixture was evaporated to dryness and NMR analysis of the crude indicated that it was the aldehyde hydrate 2-(2,5,6-trifluoropyridin-3-yl)ethane-1,1-diol.

Into a 10 mL sealed tube the crude 2-(2,5,6-trifluoropyridin-3-yl)ethane-1,1-diol (138.0 mg, 0.7146 mmol) was dissolved in isopropyl alcohol (6.0 mL) and sodium tetrahydroborate (16.22 mg, 0.4287 mmol) was added. The reaction was stirred at 0° C. for 2 h and was quenched with NH₄Cl and was extracted with ether. The product was purified by silica gel chromatography to give 2-(2,5,6-trifluoropyridin-3-yl)ethanol (80 mg). ¹H NMR (400 MHz, CD₃OD): δ 7.90 (m, 1H), 3.75 (m, 2H), 2.80 (m, 2H).

Step 4: S-[2-(2,5,6-trifluoropyridin-3-yl)ethyl] ethanethioate

Into a 1-neck round-bottom flask 2-(2,5,6-trifluoropyridin-3-yl)ethanol (0.520 g, 2.94 mmol) was dissolved in THF (13.0 mL) with triphenylphosphine (0.770 g, 2.94 mmol). The solution was cooled at 0° C., diisopropyl azodicarboxylate (0.578 mL, 2.94 mmol) was added, and 10 min later, thioacetic acid (0.210 mL, 2.94 mmol) was added. The mixture was stirred at 0° C. for 60 min. TLC, LC and LCMS showed 50% conversion to the product. The reaction was quenched with saturated NaHCO₃ and was partitioned between EtOAc and water and EtOAc extract was washed with brine, dried (MgSO₄), and stripped in vacuo. The reaction was chromatographed on silica gel using 2% EtOAc/hexanes to give the product contaminated with small amount of impurities (0.30 g). ¹H NMR (400 MHz, CDCl₃): δ 7.60 (m, 1H), 3.10 (m, 2H), 2.85 (m, 2H), 2.30 (s, 3H).

Step 5: 5,6-difluoro-2,3-dihydrothieno[2,3-b]pyridine

Into a 1-neck round-bottom flask S-[2-(2,5,6-trifluoropyridin-3-yl)ethyl]ethanethioate (190.0 mg, 0.80773 mmol) was dissolved in THF (30.0 mL) and water (30.0 mL) and was degassed. Into the reaction was added 1.0 M of sodium hydroxide in water (7.0 mL) and was stirred at 25° C. for 1 h at which time LCMS analysis showed mainly 2-(2,5,6-trifluoropyridin-3-yl)ethanethiol. The reaction was stirred for 2 days at which time LCMS analysis showed disulfide, and some product. The reaction mixture was partitioned between ether and water and ether extract was washed with brine, dried (MgSO₄), and stripped in vacuo. Then it was chromatographed on silica gel using 3% EtOAc/hexanes to give the product (13 mg). ¹H NMR (400 MHz, CDCl₃): δ 7.29 (m, 1H), 3.50 (m, 2H), 3.25 (m, 2H).

Step 6: 4-(1-{2-fluoro-1-[(3S)-1-(5-fluoro-2,3-dihydrothieno[2,3-b]pyridin-6-yl)pyrrolidin-3-yl]ethyl}-1H-pyrazol-4-yl)-7-{[2-(trimethylsilyl)ethoxy]methyl}-7H-pyrrolo[2,3-d]pyrimidine 4-(1-{2-Fluoro-1-[(3S)-pyrrolidin-3-yl]ethyl}-1H-pyrazol-4-yl)-7-{[2-(trimethylsilyl)ethoxy]methyl}-7H- pyrrolo [2,3-d]pyrimidine (from Example 70, Step 7; 31.58 mg, 0.073332 mmol) was mixed with 5,6-difluoro-2,3-dihydrothieno[2,3-b]pyridine (12.7 mg, 0.0733 mmol) and DIPEA (21.88 mL, 0.1256 mmol) and was dissolved in NMP (0.24 mL). The reaction was heated at 130° C. for 5 h at which time LCMS analysis showed some product present. The product was purified by LC (ACN/TFA/water method as in Example 5) to give the purified material. MS (EI): 584 (M+H).

Step 7: 4-(1-{2-fluoro-1-[(3S)-1-(5-fluoro-2,3-dihydrothieno[2,3-b]pyridin-6-yl)pyrrolidin-3-yl]ethyl}-1H-pyrazol-4-yl)-7H-pyrrolo[2,3-d]pyrimidine bis (trifluoroacetate)

4-(1-{2-Fluoro-1-[(3S)-1-(5-fluoro-2,3-dihydrothieno[2,3-b]pyridin-6-yl)pyrrolidin-3-yl]ethyl}-1H-pyrazol-4-yl)-7-{[2-(trimethylsilyl)ethoxy]methyl}-7H-pyrrolo[2,3-d]pyrimidine was deprotected (TFA/CH₂Cl₂; MeOH/NH₄OH) as in Example 1, and the deprotected compound was purified on preparative LC (ACN/TFA method as in Example 5) to give the product. MS (EI): 454 (M+H). ¹H NMR (CD₃OD): δ 8.92 (m, 1H), 8.86 (m, 1H), 8.55 (m, 1H), 7.85 (m, 1H), 7.30 (m, 1H), 7.10 (m, 1H), 5.05 (m, 1H), 4.80 (m, 2H), 3.85 (m, 1H), 3.62 (m, 1H), 3.50 (m, 2H), 3.35 (m, 2H), 3.10 (m, 2H), 2.95 (m, 1H), 1.80 (m, 2H).

Example 86

4-(1-{2-fluoro-1-[(3S)-1-(5-fluoro-1,1-dioxido-2,3-dihydrothieno[2,3-b]pyridin-6-yl)pyrrolidin-3-yl] ethyl}-1H-pyrazol-4-yl)-7H-pyrrolo[2,3-d]pyrimidine tetrakis(trifluoroacetate)

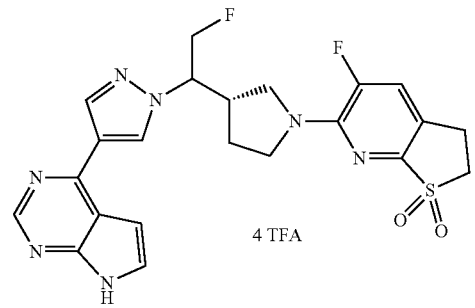 [SMILES: O=S1(=O)CCc2cc(F)c(N3CC[C@H](C(CF)n4cc(-c5ncnc6[nH]ccc56)cn4)C3)nc21]

Into a 1-neck round-bottom flask 4-(1-{2-fluoro-1-[(3S)-1-(5-fluoro-2,3-dihydrothieno[2,3-b]pyridin-6-yl)pyrrolidin-3-yl]ethyl}-1H-pyrazol-4-yl)-7H-pyrrolo[2,3-d]pyrimidine bis(trifluoroacetate) (from Example 85; 3.0 mg, 0.0044 mmol) was dissolved in methanol (1.0 mL) and water (0.30 mL) was added. Into the reaction was added Oxone® (5.4 mg, 0.0088 mmol) and was stirred at 25° C. overnight at which time LCMS analysis showed mainly sulfone and over-oxidized sulfone. The reaction was filtered and the product was purified by preparative LC (ACN/TFA method as in Example 5) to give 4-(1-{2-fluoro-1-[(3S)-1-(5-fluoro-1,1-dioxido-2, 3-dihydrothieno[2,3-b]pyridin-6-yl)pyrrolidin-3-yl]ethyl}-1H-pyrazol-4-yl)-7H-pyrrolo[2,3-d]pyrimidine tetrakis(trifluoroacetate). MS (EI) 486 (M+1). ¹H NMR (DMSO-d6): δ12.2 (brs, 1H), δ 8.82 (s, 1H), 8.70 (s, 1H), 8.40 (s, 1H), 7.60

(m, 2H), 7.00 (m, 1H), 5.00 (m, 1H), 4.90 (m, 2H), 4.80 (m, 2H), 3.90 (m, 1H), 3.70 (m, 1H), 3.50 (m, 2H), 3.10 (m, 2H), 2.9 (m, 1H), 1.65 (m, 2H).

Example 87

(3S)-3-[(3S)-1-(5-fluoro-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile bis(trifluoroacetate)

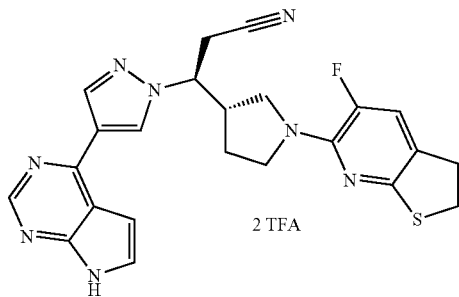 [SMILES: N#CC[C@@H]([C@H]1CCN(c2nc3c(cc2F)CCS3)C1)n1cc(-c2ncnc3[nH]ccc23)cn1]

Step 1: but-3-yn-1-yl methanesulfonate

In a 1-neck round-bottom flask 3-butyn-1-ol (0.50 mL, 6.6 mmol) was dissolved in DCM (7.0 mL) and DIPEA (1.6 mL, 9.2 mmol) was added and was cooled at 0° C. Into the reaction was added methanesulfonyl chloride (0.61 mL, 7.9 mmol) and was stirred at 0° C. for 1 h at which time TLC analysis showed absence of starting material. The reaction mixture was partitioned between EtOAc and water and EtOAc extract was washed with water, 1 N HCl, NaHCO$_3$, brine, dried (MgSO$_4$), and stripped in vacuo. The resulting but-3-yn-1-yl methanesulfonate was used in the next reaction without purification. $^1$H NMR (300 MHz, CDCl$_3$): δ 4.52 (m, 2H), 3.10 (s, 3H), 2.65 (m, 2H), 2.05 (M, 1H).

Step 2: S-but-3-yn-1-yl ethanethioate

Into a 1-neck round-bottom flask cesium carbonate (0.57 g, 1.8 mmol) was dissolved in methanol (5.0 mL, 123 mmol) and thioacetic acid (0.241 mL, 3.37 mmol) was added. The reaction was stirred for 30 min. and but-3-yn-1-yl methanesulfonate (0.50 g, 3.4 mmol) in methanol (4.0 mL) was added and was stirred at 25° C. overnight at which time TLC analysis showed starting material and product. The reaction was evaporated to dryness and DMF (5.0 mL) was added and was stirred at 25° C. overnight at which time TLC analysis showed no starting material. The reaction mixture was partitioned between EtOAc and water and EtOAc extract was washed with water, brine, dried (MgSO$_4$), and stripped in vacuo. Used in the next reaction without purification. $^1$H NMR (300 MHz, CDCl$_3$): δ 3.01 (m, 2H), 2.45 (s, 3H), 2.35 (m, 2H), 2.02 (M, 1H).

Step 2a: 2-chloro-5-fluoro-4-[(4-methoxybenzyl)oxy]pyrimidine

Into a 1-neck round-bottom flask 2,4-dichloro-5-fluoropyrimidine (from Frontier Scientific, Inc.; 0.80 g, 4.8 mmol) was mixed with sodium hydride (60% in mineral oil, 0.23 g, 5.7 mmol) and was dried. The reaction was cooled at 0° C. and THF (9.0 mL) was added followed by 4-methoxybenzenemethanol (0.60 mL, 4.8 mmol). The reaction was stirred at 25° C. overnight. Then it was partitioned between EtOAc and water and EtOAc extract was washed with brine, dried (MgSO$_4$), and stripped in vacuo. The residue was chromatographed on silica gel using 5% EtOAc/hexanes to give the product (1.2 g). $^1$H NMR (400 MHz, CDCl$_3$): δ 8.20 (s, 1H), 7.42 (d, 2H), 6.91 (d, 2H), 5.42 (s, 2H), 3.80 (s, 3H)

Step 3: 2-(but-3-yn-1-ylthio)-5-fluoropyrimidin-4-ol

Into a 1-neck round-bottom flask S-but-3-yn-1-yl ethanethioate (0.69 g, 5.4 mmol) was dissolved in DMF (4.0 mL) with 2-chloro-5-fluoro-4-[(4-methoxybenzyl)oxy]pyrimidine (1.4 g, 5.4 mmol) and lithium hydroxide (0.259 g, 10.8 mmol) and water (0.5 mL) was added and stirred at 60° C. overnight at which time HPLC analysis and LCMS analysis showed debenzylated product and starting material. The reaction was continued for 24 h without much change. Then it was partitioned between EtOAc and water and EtOAc extract was washed with brine, dried (MgSO$_4$), and stripped in vacuo. The organic extract did not contain any product. The water layer was evaporated to dryness and was washed with methanol and was filtered. The methanol wash was evaporated and was chromatographed using 1:1 EtOAc/hexanes and EtOAc as eluent to give the product 2-(but-3-yn-1-ylthio)-5-fluoropyrimidin-4-ol (0.2 g). $^1$H NMR (300 MHz, DMSO D$_6$): δ 7.90 (m, 1H), 3.30 (m, 2H), 2.60 (m, 2H), 2.35 (m, 1H).

Step 4: 5-fluoro-2,3-dihydrothieno[2,3-b]pyridin-6-ol

Into a 10 mL sealed tube 2-(but-3-yn-1-ylthio)-5-fluoropyrimidin-4-ol (185 mg, 0.931 mmol) was dissolved in NMP (1.0 mL) and was heated at 200° C. for 3 h at which time LCMS analysis showed mainly product. The reaction mixture was purified by preparative LC to give 5-fluoro-2,3-dihydrothieno[2,3-b]pyridin-6-ol (81 mg). LCMS: 172(M+1). $^1$H NMR (300 MHz, DMSO D$_6$): δ 7.36 (d, 1H), 3.55 (m, 2H), 3.16 (m, 2H).

Step 5: 5-fluoro-2,3-dihydrothieno[2,3-b]pyridin-6-yl trifluoromethanesulfonate

5-Fluoro-2,3-dihydrothieno[2,3-b]pyridin-6-ol (40.0 mg, 0.234 mmol) was dissolved in DCM (1.72 mL) and triethylamine (48.85 μL, 0.3505 mmol) was added, the solution was cooled to 0° C. and N-phenylbis(trifluoromethane-sulphonimide) (0.1043 g, 0.2921 mmol) was added. The reaction was stirred at 25° C. for 48 h, at which time LCMS analysis showed absence of starting material. The reaction was chromatographed on silica gel using 20% EtOAc/hexanes to give the product 5-fluoro-2,3-dihydrothieno[2,3-b]pyridin-6-yl trifluoromethanesulfonate contaminated with a small amount of reagent. $^1$H NMR (300 MHz, CDCl$_3$): δ 7.55 (m, 1H), 3.50 (m, 2H), 3.30 (m, 2H).

Step 6: (3S)-3-[(3S)-1-(5-fluoro-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile Into a 10 mL sealed tube (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (0.08246 g, 0.1884 mmol; from Example 15, step 3) was mixed with 5-fluoro-2,3-dihydrothieno[2,3-b]pyridin-6-yl trifluoromethanesulfonate (0.067 g, 0.22 mmol) in NMP (0.24 mL) with DIPEA (21.88 μL, 0.1256 mmol) and was heated at 130° C. for 2 h at which time LCMS analysis showed mostly product. The product was purified by LC (ACN/TFA/water method as in Example 5) to give (3S)-3-[(3S)-1-(5-fluoro-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile. MS (EI): 591(M+1)

Step 7(3S)-3-[(3S)-1-(5-fluoro-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile bis(trifluoroacetate)

(3S)-3-[(3S)-1-(5-fluoro-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile was deprotected (TFA/CH$_2$Cl$_2$; MeOH/NH$_4$OH) as in Example 1, and the deprotected compound was purified on preparative LC (ACN/TFA/water method as in Example 5) to give the product (3S)-3-[(3S)-1-(5-fluoro-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile bis(trifluoroacetate). Mass spec (EI):461 (M+1). $^1$H NMR (400 MHz CD$_3$OD): δ 9.00 (s, 1H), 8.90 (m, 1H), 8.55 (m, 1H), 7.85 (d, 1H), 7.26 (d, 1H), 7.08 (d, 1H), 4.85 (m, 1H), 3.85 (m, 1H), 3.40-3.60 (m, 2H), 3.20-3.40 (m, 4H), 3.10 (m, 2H), 2.95 (m, 1H), 1.80 (m, 2H).

Example 88

(3S)-3-[(3S)-1-(6-bromo-3-fluoropyridin-2-yl)pyrrolidin-3-yl]-3-[4-(7H-pyrrolo[2,3-d]pyrimidin-4-yl)-1H-pyrazol-1-yl]propanenitrile bis(trifluoroacetate)

and

Example 89

(3S)-3-[(3S)-1-(5,6-difluoropyridin-2-yl)pyrrolidin-3-yl]-3-[4-(7H-pyrrolo[2,3-d]pyrimidin-4-yl)-1H-pyrazol-1-yl]propanenitrile trifluoroacetate

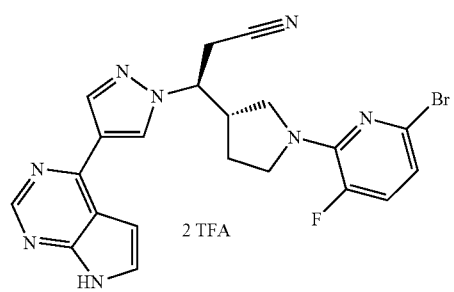

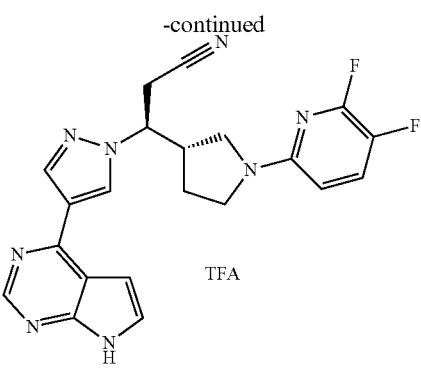

Step 1: 2,3-difluoro-6-hydrazinopyridine

Into a 1-neck round-bottom flask 2,3,6-trifluoropyridine (from Alfa Aesar; 0.40 mL, 4.5 mmol) was dissolved in THF (5.0 mL) and hydrazine hydrate (0.44 mL, 9.012 mmol) was added and was stirred at 25° C. overnight and was heated to reflux for 2 h. The reaction mixture was evaporated to dryness to provide 2,3-difluoro-6-hydrazinopyridine which was used in the next reaction without purification.

Step 2: 6-bromo-2,3-difluoropyridine

Into a 1-neck round-bottom flask 2,3-difluoro-6-hydrazinopyridine (0.65 g, 4.5 mmol) was suspended in chloroform (5.0 mL) and bromine (0.46 mL, 9.0 mmol) was added dropwise. The reaction was heated to reflux for 3 h with an acid trap and was quenched with NaHSO$_3$ and neutralized with NaHCO$_3$. Then it was partitioned between ether and water and ether extract was washed with brine, dried (MgSO$_4$), and stripped in vacuo. NMR analysis of the crude mixture indicated that it consisted of a 2:1 mixture of 6-bromo-2,3-difluoropyridine and 2,3-dibromo-5,6-difluoropyridine. The reaction mixture was chromatographed on silica gel using 5% ether/hexanes to give the product. $^1$H NMR (300 MHz, CDCl$_3$): δ 7.55 (m, 1H), 6.90 (m, 1H).

Step 3: (3S)-3-[(3S)-1-(6-bromo-3-fluoropyridin-2-yl)pyrrolidin-3-yl]-3-[4-(7H-pyrrolo[2,3-d]pyrimidin-4-yl)-1H-pyrazol-1-yl]propanenitrile trifluoroacetate and (3S)-3-[(3S)-1-(5,6-difluoropyridin-2-yl)pyrrolidin-3-yl]-3-[4-(7H-pyrrolo[2,3-d]pyrimidin-4-yl)-1H-pyrazol-1-yl]propanenitrile trifluoroacetate (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (100.0 mg, 0.22851 mmol; from Example 15, step 3) was mixed with 6-bromo-2,3-difluoropyridine (53.2 mg, 0.27421 mmol) and DIPEA (50.0 μL, 0.2870 mmol) and was dissolved in NMP (0.62 mL). The reaction was heated at 130° C. for 2 h at which time LCMS analysis showed mainly the two products (3S)-3-[(3S)-1-(6-bromo-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile. The reaction mixture was purified by preparative LC (ACN/TFA/water method as in Example 5) to give the two compounds: (3S)-3-[(3S)-1-(6-bromo-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile and (3S)-3-[(3S)-1-(5,6-difluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile which were deprotected (TFA/CH$_2$Cl$_2$; MeOH/NH$_4$OH) as in Example 1, and the deprotected compounds were purified on preparative LC (ACN/TFA method as in Example 5) to give (3S)-3-[(3S)-1-(5,6-difluoropyridin-2-yl)pyrrolidin-3-yl]-3-[4-(7H-pyrrolo[2,3-d]pyrimidin-4-yl)-1H-pyrazol-1-yl]propanenitrile as the TFA salt {m/z: 421 (M+1). $^1$H NMR (400 MHz CD$_3$OD): δ 8.95 (s, 1H), 8.85 (s, 1H), 8.55 (s, 1H), 7.80 (d, 1H), 7.35 (m, 1H), 7.20 (d, 1H), 6.04 (m, 1H), 4.85 (m, 1H), 3.93 (m, 1H), 3.70 (m, 1H), 3.51 (m, 2H), 3.40 (m, 1H), 2.95 (m, 1H), 1.80 (m, 2H)} and (3S)-3-[(3S)-1-(6-bromo-3-fluoropyridin-2-yl)pyrrolidin-3-yl]-3-[4-(7H-pyrrolo[2,3-d]pyrimidin-4-yl)-1H-pyrazol-1-yl]propanenitrile as the bisTFA salt {m/z: 482, 484 (M+1). $^1$H NMR (400 MHz CD$_3$OD): δ 9.00 (s, 1H), 8.90 (s, 1H), 8.55 (s, 1H), 7.85 (d, 1H), 7.35 (m, 1H), 7.25 (d, 1H), 6.39 (m, 1H), 4.85 (m, 1H), 3.80 (m, 1H), 3.20-3.50 (m, 5H), 3.04 (m, 1H), 1.85 (m, 2H)}.

Example 90

(3S)-3-{(3S)-1-[6-chloro-3-fluoro-5-(hydroxymethyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate

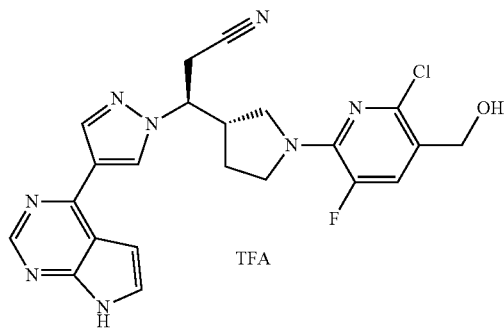 [SMILES: N#CC[C@@H]([C@H]1CCN(c2nc(Cl)c(CO)cc2F)C1)n1cc(-c2ncnc3[nH]ccc23)cn1]

TFA

Step 1: (2,6-dichloro-5-fluoropyridin-3-yl)methanol

A solution of 2,6-dichloro-5-fluoronicotinic acid (from Aldrich; 0.50 g, 2.4 mmol) in THF (10.0 mL) was cooled to 0° C. and 1.0 M of borane in THF (2.8 mL) was added slowly, the reaction was allowed to warm at 25° C. and was stirred overnight. LCMS analysis of the reaction mixture showed starting material present and 1.0 M of borane in THF (1.50 mL) was added and was stirred at 25° C. overnight at which time LCMS analysis showed mainly product. The reaction was quenched with water and 1 N HCl and was partitioned between EtOAc and water and EtOAc extract was washed with brine, dried (MgSO$_4$), and stripped in vacuo to give (2,6-dichloro-5-fluoropyridin-3-yl)methanol. Used in the next reaction without purification. m/z 197 (M+1)

Step 2: (3S)-3-{(3S)-1-[6-chloro-3-fluoro-5-(hydroxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (52.0 mg, 0.1188 mmol; from Example 15, step 3) was mixed with (2,6-dichloro-5-fluoropyridin-3-yl)methanol (62.0 mg, 0.316 mmol) and DIPEA (25.0 μL, 0.1435 mmol) and was dissolved in NMP (0.31 mL). The reaction was heated at 130° C. for 2 h at which time LCMS analysis showed some product. This was purified by LC (ACN/TFA/water method as in Example 5) give the product (3S)-3-{(3S)-1-[6-chloro-3-fluoro-5-(hydroxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile.

Step 3: (3S)-3-{(3S)-1-[6-chloro-3-fluoro-5-(hydroxymethyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate (3S)-3-{(3S)-1-[6-Chloro-3-fluoro-5-(hydroxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile was deprotected (TFA/CH$_2$Cl$_2$; MeOH/NH$_4$OH) as in Example 1, and the deprotected compound was purified on preparative LC (ACN/TFA method as in Example 5) to give (3S)-3-{(3S)-1-[6-chloro-3-fluoro-5-(hydroxymethyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate. MS (EI): 466(M+1). $^1$H NMR (300 MHz, CD$_3$OD): δ 8.95 (s, 1H), 8.85 (s, 1H), 8.55 (s, 1H), 7.80 (d, 1H), 7.40 (m, 1H), 7.20 (d, 1H), 4.85 (m, 1H), 4.46 (s, 2H), 2.90-4.00 (m, 7H), 1.80 (m, 2H)

Example 91

(S)-3-(4-(7H-pyrrolo[2,3-d]pyrimidin-4-yl)-1H-pyrazol-1-yl)-3-((S)-1-(5-amino-6-chloro-3-fluoropyridin-2-yl)pyrrolidin-3-yl)propanenitrile bis(trifluoroacetate)

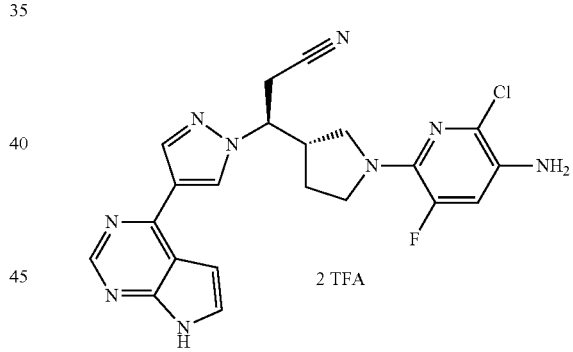

2 TFA

Step 1: 2-chloro-6-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoronicotinic acid trifluoroacetate (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (250.0 mg, 0.57128 mmol; from Example 15, step 3) was mixed with 2,6-dichloro-5-fluoronicotinic acid (167.95 mg, 0.79979 mmol) and DIPEA (125.0 μL, 0.7176 mmol) and was dissolved in NMP (1.5 mL). The reaction was heated at 130° C. for 3 h at which time LCMS analysis showed mostly product in a 5:1 regiomeric mixture. Purified by preparative LC as in Example 5 to give the product 2-chloro-6-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoronicotinic acid trifluoroacetate (248 mg).

Step 2: (3S)-3-[(3S)-1-(5-amino-6-chloro-3-fluoro-pyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile Into a 1-neck round-bottom flask 2-chloro-6-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoronicotinic acid (50.0 mg, 0.08181 mmol) was dissolved in THF (1.0 mL) and triethylamine (30.0 µL, 0.2152 mmol) was added, followed by diphenylphosphonic azide (19.39 µL, 0.090 mmol). The reaction was stirred at 25° C. for 3 h at which time LCMS analysis showed mainly the isocyanate intermediate: (3S)-3-[(3S)-1-(6-chloro-3-fluoro-5-isocyanatopyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile. Into the reaction mixture was added water (150.0 µL, 8.3263 mmol) and was heated to reflux for 2 h at which time LCMS analysis showed mainly amine (3S)-3-[(3S)-1-(5-amino-6-chloro-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile. The product was purified by preparative LC (ACN/TFA/water method as in Example 5) and was carried to the deprotection step. MS (EI): 582 (M+1)

Step 3: 3-[(3S)-1-(5-amino-6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile bis(trifluoroacetate)

(3S)-3-[(3S)-1-(5-Amino-6-chloro-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile was deprotected (TFA/CH₂Cl₂; MeOH/NH₄OH) as in Example 1, and the deprotected compound was purified on preparative LC (ACN/TFA method as in Example 5) to give the product 3-[(3S)-1-(5-amino-6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile bis(trifluoroacetate) MS (EI): 452 (M+1). ¹H NMR (300 MHz CD₃OD): δ 9.00 (s, 1H), 8.90 (s, 1H), 8.55 (s, 1H), 7.85 (m, 1H), 7.30 (m, 1H), 7.00 (m, 1H), 4.85 (m, 1H), 3.90 (m, 1H), 3.20-3.50 (m, 5H), 3.00 (m, 1H), 1.85 (m, 2H).
The isomeric amine (3S)-3-[(3S)-1-(3-amino-6-chloro-5-fluoropyridin-2-yl)pyrrolidin-3-yl]-3-[4-(7H-pyrrolo[2,3-d]pyrimidin-4-yl)-1H-pyrazol-1-yl]propanenitrile bis(trifluoroacetate) was also isolated MS (EI): 452 (M+1).

Example 92

N-(2-((S)-3-((S)-1-(4-(7H-pyrrolo[2,3-d]pyrimidin-4-yl)-1H-pyrazol-1-yl)-2-cyanoethyl)pyrrolidin-1-yl)-6-chloro-5-fluoropyridin-3-yl)formamide trifluoroacetate

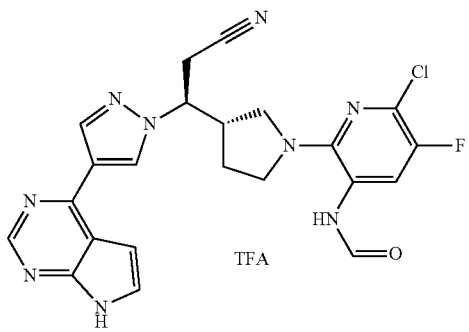 [SMILES: N#CC[C@@H]([C@H]1CCN(c2nc(Cl)c(F)cc2NC=O)C1)n1cc(-c2ncnc3[nH]ccc23)cn1]

Into a 1-neck round-bottom flask 2-chloro-6-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoronicotinic acid (from example 91, step 1; 200.0 mg, 0.32726 mmol) was dissolved in THF (4.5 mL) and triethylamine (120.0 µL, 0.8610 mmol) was added, followed by diphenylphosphonic azide (77.58 µL, 0.36 mmol). The reaction was stirred at 25° C. for 3 h at which time LCMS analysis showed mainly the isocyanate intermediate.

The reaction was hydrogenated under an atmosphere of hydrogen (1 atm) for 30 min. at which time LCMS analysis showed mainly formamide and some dechlorinated by-product. This was purified by LC (ACN/TFA/water method as in Example 5) and deprotected as in Example 1, and purified by preparative LC (ACN/TFA/water method as in Example 5) to give both amide regiomers.

N-[2-Chloro-6-((3S)-3-{2-cyano-1-[4-(7H-pyrrolo[2,3-d]pyrimidin-4-yl)-1H-pyrazol-1-yl]ethyl}pyrrolidin-1-yl)-5-fluoropyridin-3-yl]formamide trifluoroacetate MS (EI): 481 (M+1), ¹H NMR (300 MHz, CD₃OD): δ 8.95 (s, 1H), 8.85 (s, 1H), 8.55 (s, 1H), 7.80 (d, 1H), 7.58 (d, 1H), 7.20 (d, 1H), 4.85 (m, 1H), 4.46 (s, 2H), 2.90-4.00 (m, 7H), 1.80 (m, 2H); and N-[6-chloro-2-((3S)-3-{2-cyano-1-[4-(7H-pyrrolo[2,3-d]pyrimidin-4-yl)-1H-pyrazol-1-yl]ethyl}pyrrolidin-1-yl)-5-fluoropyridin-3-yl]formamide trifluoroacetate MS (EI): 481 (M+1)

Example 93

(3S)-3-{(3S)-1-[6-(ethylsulfonyl)-3-fluoropyridin-2-yl]pyrrolidin-3-yl}-3-[4-(7H-pyrrolo[2,3-d]pyrimidin-4-yl)-1H-pyrazol-1-yl]propanenitrile trifluoroacetate

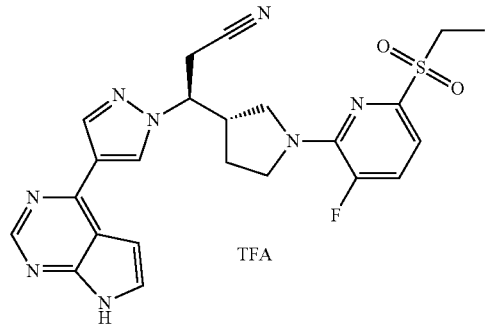 [SMILES: CCS(=O)(=O)c1ccc(F)c(N2CC[C@H]([C@H](CC#N)n3cc(-c4ncnc5[nH]ccc45)cn3)C2)n1]

Step 1: 6-(ethylsulfonyl)-2,3-difluoropyridine

Into a vial, 2,3,6-trifluoropyridine (0.1 mL, 1.13 mmol) was dissolved in THF (2.0 mL) and sodium hydride (60% in mineral oil, 0.050 g, 1.2 mmol) was added and was cooled at 0° C. Ethanethiol (0.077 g, 1.2 mmol) was added and was stirred at 25° C. for 16 h and evaporated to dryness to give 6-(ethylthio)-2,3-difluoropyridine.

This was dissolved in methanol (10.0 mL) and water (5.0 mL) and Oxone® (1.38 g, 2.25 mmol) was added and was stirred at 25° C. for 16 h. Then the reaction mixture was partitioned between EtOAc and water and EtOAc extract was washed with brine, dried (MgSO₄), and stripped in vacuo. LCMS analysis showed mainly product MS(EI): 207 (M+1).

Step 2: (3S)-3-{(3S)-1-[6-(ethylsulfonyl)-3-fluoropy-ridin-2-yl]pyrrolidin-3-yl}-3-[4-(7H-pyrrolo[2,3-d]pyrimidin-4-yl)-1H-pyrazol-1-yl]propanenitrile trifluoroacetate (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (50.0 mg, 0.1142 mmol; from Example 15, step 3) was mixed with 6-(ethylsulfonyl)-2,3-difluoropyridine (33.143 mg, 0.15996 mmol) and DIPEA (25.0 μL, 0.1435 mmol) and was dissolved in NMP (0.3 mL). The reaction was heated at 130° C. for 2 h at which time LCMS analysis showed mostly product. This was purified by preparative LC as in Example 5 to give (3S)-3-{(3S)-1-[6-(ethylsulfonyl)-3-fluoropyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile. The SEM group was cleaved as in Example 1 and purified by preparative LC (ACN/TFA/water method as in Example 5) to give (3S)-3-{(3S)-1-[6-(ethylsulfonyl)-3-fluoropyridin-2-yl]pyrrolidin-3-yl}-3-[4-(7H-pyrrolo[2,3-d]pyrimidin-4-yl)-1H-pyrazol-1-yl]propanenitrile trifluoroacetate contaminated with 10% of the regiomer. MS (EI): 495 (M+1), $^1$H NMR (300 MHz, CD$_3$OD): δ 8.95 (s, 1H), 8.85 (s, 1H), 8.55 (s, 1H), 7.82 (d, 1H), 7.58 (m, 1H), 7.20 (d, 1H), 6.75 (dd, 1H), 4.85 (m, 1H), 4.46 (s, 2H), 2.90-4.00 (m, 9H), 1.90 (m, 2H), 1.30 (t, 3H).

Example 94

(3S)-3-[(3S)-1-(6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile trifluoroacetate

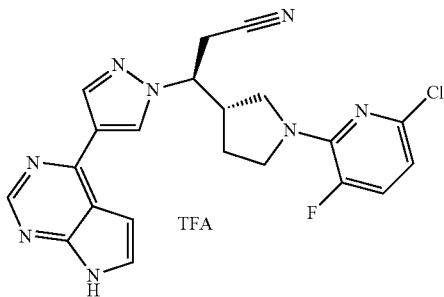 [SMILES: N#CC[C@@H]([C@H]1CCN(c2nc(Cl)ccc2F)C1)n1cc(-c2ncnc3[nH]ccc23)cn1]

Into a 1-neck round-bottom flask (3S)-3-[(3S)-1-(5-amino-6-chloro-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile bistrifluoroacetate (Example 91; 60.02 mg, 0.08621 mmol) was dissolved in THF (2.0 mL) and tert-butyl nitrite (15.0 μL, 0.1135 mmol) was added. The reaction was heated to reflux for 3 h at which time LCMS analysis showed (3S)-3-[(3S)-1-(6-chloro-3-fluoropyridin-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile product and no starting material. The product was purified by preparative LC (ACN/TFA/water method as in Example 5) and was deprotected as in Example 1, and purified as in Example 5 to give (3S)-3-[(3S)-1-(6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile trifluoroacetate. MS (EI): 437 (M+1).

Example 95

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-5-fluoro-4-(methoxymethyl)nicotinonitrile bis(trifluoroacetate)

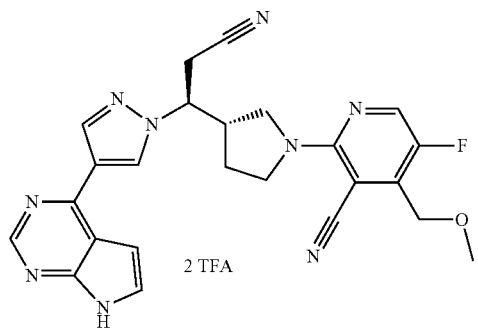 [SMILES: COCc1c(F)cnc(N2CC[C@H]([C@H](CC#N)n3cc(-c4ncnc5[nH]ccc45)cn3)C2)c1C#N]

Step 1:
2,3-dibromo-5-fluoro-4-(methoxymethyl)pyridine

Into a 1-neck round-bottom flask N,N-diisopropylamine (0.09898 mL, 0.7062 mmol) was dissolved in THF (2.14 mL) and cooled at −78° C. Into the reaction was added 1.6 M of n-butyl lithium in hexane (0.3825 mL, 0.6120 mmol) and was stirred at −78° C. for 30 min. and a solution of 2,3-dibromo-5-fluoropyridine (from Matrix Scientific; 120.0 mg, 0.4708 mmol) in THF (2.0 mL) was added and was stirred at −78° C. for 2 h and bromomethyl methyl ether (0.079 mL, 0.96 mmol) was added and was stirred at 78° C. for 1 h. The reaction was quenched with saturated NH$_4$Cl and partitioned between EtOAc and water and EtOAc extract was washed with brine, dried (MgSO$_4$), and stripped in vacuo. NMR analysis showed mostly product 2,3-dibromo-5-fluoro-4-(methoxymethyl)pyridine. Used in the next reaction without purification. $^1$H NMR (400 MHz, CDCl$_3$): δ 8.24 (s, 1H), 4.65 (d, 2H), 3.02 (s, 3H).

Step 2: (3S)-3-{(3S)-1-[3-bromo-5-fluoro-4-(methoxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (80.0 mg, 0.1828 mmol; from Example 15, step 3) was mixed with 2,3-dibromo-5-fluoro-4-(methoxymethyl)pyridine (100.0 mg, 0.3345 mmol) and DIPEA (60.0 μL, 0.3445 mmol) and was dissolved in NMP (0.40 mL). The reaction was heated at 130° C. for 3 h. The residue was purified by preparative LC (ACN/TFA/water method as in Example 5) to give the product (3S)-3-{(3S)-1-[3-bromo-5-fluoro-4-(methoxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile. This was evaporated and was partitioned between EtOAc and saturated NaHCO$_3$ and EtOAc extract was washed with brine, dried (MgSO$_4$), and stripped in vacuo (33 mg). LCMS (EI): 656 (M+1).

Step 3: 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoro-4-(methoxymethyl)nicotinonitrile Into a 1-neck round-bottom flask (3S)-3-{(3S)-1-[3-bromo-5-fluoro-4-(methoxymethyl)pyridin-2-yl]pyrrolidin-3-yl}-3-[4-(7-{[2-(trimethylsilyl)ethoxy]-methyl}-7H-pyrrolo[2,3-d]pyrimidin-4-yl)-1H-pyrazol-1-yl]propanenitrile (33.0 mg, 0.0503 mmol) was dissolved in NMP (0.4 mL) and zinc cyanide (17.7 mg, 0.151 mmol) and zinc powder (9.87 mg, 0.151 mmol) were added. The reaction was degassed and bis(tri-t-butylphosphine)palladium (12.9 mg, 0.0252 mmol) was added, degassed and heated at 130° C. for 100 min. at which time LCMS analysis showed that it was consisted mainly of product. The reaction was filtered and the product was purified by preparative LC (ACN/TFA/water method as in Example 5) to give 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoro-4-(methoxymethyl)nicotinonitrile. MS (EI): 602 (M+1).

Step 3: 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-5-fluoro-4-(methoxymethyl)nicotinonitrile bis(trifluoroacetate)

2-((3S)-3-{(1S)-2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-5-fluoro-4-(methoxymethyl)nicotinonitrile was deprotected as in Example 1. The deprotected product was purified by LC (ACN/TFA/water method as in Example 5) to give the titled product. MS (EI): 472 (M+1). $^1$H NMR (400 MHz CD$_3$OD): δ 8.95 (s, 1H), 8.86 (s, 1H), 8.55 (s, 1H), 8.22 (d, 1H), 7.83 (d, 1H), 7.23 (d, 1H), 4.85 (m, 1H), 4.52 (s, 2H), 4.00 (m, 1H), 3.70-3.80 (m, 3H), 3.40 (s, 3H), 3.00-3.40 (m, 5H)

Example 96

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methoxymethyl)nicotinonitrile tris (trifluoroacetate)

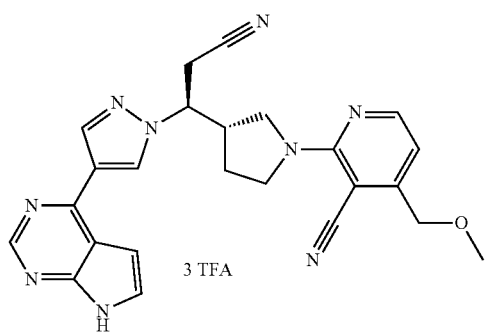 [SMILES: COCc1ccnc(N2CC[C@H]([C@H](CC#N)n3cc(-c4ncnc5[nH]ccc45)cn3)C2)c1C#N]

Step 1: 2,3-dibromo-4-(methoxymethyl)pyridine

Into a 1-neck round-bottom flask N,N-diisopropylamine (3.550 mL, 25.33 mmol) was dissolved in THF (60.0 mL) and was cooled at −78° C. and 1.6 M of n-butyl lithium in hexane (14.51 mL, 23.22 mmol) was added and was stirred for 30 min. Into the reaction was added 2,3-dibromopyridine (5.0 g, 21.1 mmol) in THF (33 mL) and was stirred at −78° C. for 1 h and bromomethyl methyl ether (1.895 mL, 23.22 mmol) was added and was stirred for 30 min. at −78° C. LCMS analysis showed a ~3:1 mixture of 2,3-dibromo-4-(methoxymethyl)pyridine and 2,4-dibromo-3-(methoxymethyl) pyridine. The reaction was quenched with saturated NH$_4$Cl and was partitioned between EtOAc and water and EtOAc extract was washed with brine, dried (MgSO$_4$), and stripped in vacuo. The residue was chromatographed on silica gel using 5% EtOAc/hexanes to give the product 2,3-dibromo-4-(methoxymethyl)pyridine. MS: 282 (M+1). $^1$H NMR (400 MHz, CDCl$_3$): δ 8.36 (d, 1H), 7.00 (d, 1H), 4.48 (s, 2H), 3.50 (s, 3H).

Step 2: (3S)-3-{(3S)-1-[3-bromo-4-(methoxymethyl) pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (600.0 mg, 1.371 mmol; from Example 15, step 3) was mixed with 2,3-dibromo-4-(methoxymethyl)pyridine (610.0 mg, 2.17 mmol) and DIPEA (235 µL, 1.35 mmol) and was dissolved in NMP (1.6 mL). The reaction was heated at 140° C. for 3 h at which time LCMS analysis showed mainly product. The residue was purified by chromatography to give the product (3S)-3-{(3S)-1-[3-bromo-4-(methoxymethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile. (391 mg). MS (EI): 637, 639 (M+1).

Step 3: 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(methoxymethyl)nicotinonitrile Into a 1-neck round-bottom flask (3S)-3-{(3S)-1-[3-bromo-4-(methoxymethyl)-pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (390.0 mg, 0.6116 mmol) was dissolved in NMP (4.0 mL) and zinc cyanide (215 mg, 1.83 mmol) and zinc powder (120 mg, 1.83 mmol) was added. The reaction was degassed and bis(tri-t-butylphosphine)palladium (50.0 mg, 0.09784 mmol) was added and was heated at 130° C. for 100 min. at which time LCMS analysis showed that it was mainly starting material and some product in a ~3:1 ratio. Into the reaction was added bis(tri-t-butylphosphine)palladium (80.0 mg, 0.156 mmol) and was heated at 130° C. for 100 min. at which time LCMS analysis showed mainly product. The mixture was filtered and was purified by chromatography to give the product (190 mg). MS (EI): 584 (M+1)

Step 4: 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methoxymethyl)nicotinonitrile tris(trifluoroacetate)

Into a 1-neck round-bottom flask 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(methoxymethyl)nicotinonitrile (0.380 g, 0.651 mmol)

was dissolved in DCM (2.0 mL) and TFA (1.0 mL, 13.0 mmol) was added. The reaction was stirred at 25° C. for 2 h at which time LCMS analysis showed a 3:1 product and starting material. Then an additional amount of TFA (1.0 mL, 13.0 mmol) was added and was stirred for 1 h at which time LCMS analysis showed only product. The reaction mixture was evaporated to dryness and was dissolved in methanol (4.0 mL) and 16 M of ammonia in water (1.0 mL, 16.4 mmol) was added and was stirred at 25° C. for 1 h at which time LCMS analysis showed mainly product. The reaction mixture was evaporated and was purified by preparative LCMS as in Example 5 to give the product. MS (EI): 454 (M+1). $^1$H NMR (400 MHz CD$_3$OD): δ 9.00 (s, 1H), 8.90 (s, 1H), 8.57 (s, 1H), 8.22 (d, 1H), 7.85 (d, 1H), 7.25 (d, 1H), 6.80 (d, 1H), 4.90 (m, 1H), 4.50 (s, 2H), 4.02 (m, 1H), 3.82 (m, 1H), 3.75 (m, 2H), 3.42 (s, 3H), 3.40 (m, 1H), 3.22 (m, 1H), 3.03 (m, 1H), 1.86 (m, 2H).

The examples in the table below were made by procedures analogous to those for producing Examples 84-96.

| Ex. | Structure | Name | M + H |
|---|---|---|---|
| 98 | 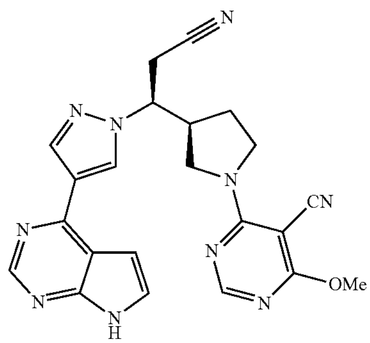 [SMILES: COc1ncnc(N2CC[C@H]([C@H](CC#N)n3cc(-c4ncnc5[nH]ccc45)cn3)C2)c1C#N] | 4-((S)-3-((S)-1-(4-(7H-pyrrolo[2,3-d]pyrimidin-4-yl)-1H-pyrazol-1-yl)-2-cyanoethyl)pyrrolidin-1-yl)-6-methoxypyrimidine-5-carbonitrile trifluoroacetate | 441 |
| 99 | 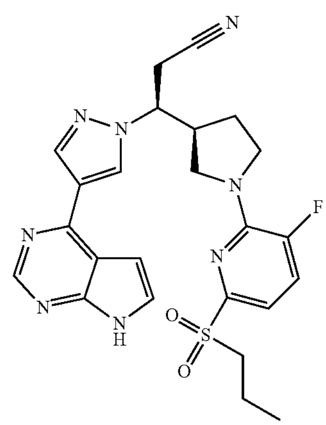 [SMILES: CCCS(=O)(=O)c1ccc(F)c(N2CC[C@H]([C@H](CC#N)n3cc(-c4ncnc5[nH]ccc45)cn3)C2)n1] | (S)-3-(4-(7H-pyrrolo[2,3-d]pyrimidin-4-yl)-1H-pyrazol-1-yl)-3-((S)-1-(6-(ethylsulfonyl)-3-fluoropyridin-2-yl)pyrrolidin-3-yl)propanenitrile trifluoroacetate | 509 |
| 100 | 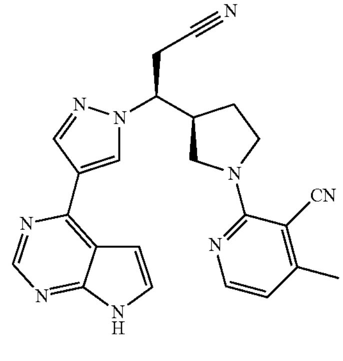 [SMILES: Cc1ccnc(N2CC[C@H]([C@H](CC#N)n3cc(-c4ncnc5[nH]ccc45)cn3)C2)c1C#N] | 2-((S)-3-((S)-1-(4-(7H-pyrrolo[2,3-d]pyrimidin-4-yl)-1H-pyrazol-1-yl)-2-cyanoethyl)pyrrolidin-1-yl)-4-methylnicotinonitrile trifluoroacetate | 424 |

| Ex. | Structure | Name | M + H |
|---|---|---|---|
| 101 | 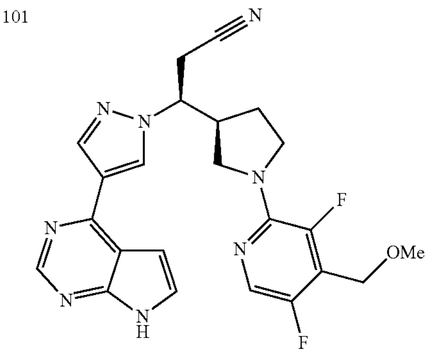 | (3S)-3-{(3S)-1-[3,5-difluoro-4-(methoxymethyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate | 465 |

Example 102

(3S)-3-[4-(7H-pyrrolo[2,3-d]pyrimidin-4-yl)-1H-pyrazol-1-yl]-3-[(3S)-1-[1,3]thiazolo[5,4-d]pyrimidin-5-ylpyrrolidin-3-yl]propanenitrile bis(trifluoroacetate)

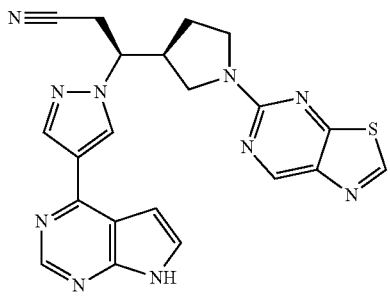 [SMILES: N#CC[C@@H]([C@H]1CCN(c2ncc3ncsc3n2)C1)n1cc(-c2ncnc3[nH]ccc23)cn1]

Step 1. 5-amino-2-chloropyrimidine-4-thiol

Sodium hydrogen sulfide (1.0 g, 18 mmol) was added to a solution of 2,4-dichloropyrimidin-5-amine (1 g, 6 mmol), in ethanol (40 mL), under $N_2$. Stirred at 60° C. for 2 h. LCMS showed almost complete reaction, and showed the expected product (M+H: 162), and also showed some disulfide (M+H: 321). The reaction mixture was evaporated, added water (25 mL) followed by acetic acid (5 mL, 90 mmol) to adjust to pH 3. The mixture was stirred for 2 days, filtered, rinsed with water, air dried, then dried under high vacuum. The isolated product (0.6 g, 60% yield) probably contains some sulfur. LCMS calculated for $C_4H_5ClN_3S(M+H)^+$: m/z=161.989.

Step 2. 5-chloro[1,3]thiazolo[5,4-d]pyrimidine

5-Amino-2-chloropyrimidine-4-thiol (0.3 g, 2 mmol) was stirred in ethyl orthoformate (3 mL, 20 mmol) for 2 h at 21° C. LCMS showed nearly complete (very weak M+H 172). The reaction mixture was evaporated to dryness. The residue was extracted with ACN and filtered to remove sulfur, etc. The product was isolated by preparative HPLC using a Waters Fraction-Lynx instrument and a 30 mm×100 mm Xbridge C18 column; 25% $CH_3OH$—$H_2O$ (0.1% TFA), 0.6 min; 6 min gradient to 45%; 60 mL/min; detector set at 220 nm; retention time 3.7 min. The collected fractions were evaporated to dryness to give a yellow solid in 5% yield. HPLC showed product $UV_{max}$ 220 nm. LCMS calculated for $C_5H_3ClN_3S(M+H)^+$: m/z=171.974.

Step 3. (3S)-3-[4-(7H-pyrrolo[2,3-d]pyrimidin-4-yl)-1H-pyrazol-1-yl]-3-[(3S)-1-[1,3]thiazolo[5,4-d]pyrimidin-5-ylpyrrolidin-3-yl]propanenitrile bis(trifluoroacetate)

(3S)-3-[(3S)-Pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (38 mg, 0.087 mmol; from Example 15, step 3), was dissolved in NMP (0.41 mL) and 4-methylmorpholine (24 mL, 0.22 mmol). 5-chloro[1,3]thiazolo[5,4-d]pyrimidine (15 mg, 0.087 mmol) was added. Stirred at 120° C. in a microwave reactor for 10 min. LCMS showed nearly complete reaction to the expected intermediate (M+H, 573). The product was isolated by preparative HPLC/MS using a Waters Fraction-Lynx instrument and a 30 mm×100 mm Sunfire C18 column; 30% ACN—H2O (0.1% TFA), 2.0 min; 10 min gradient to 60%; 60 mL/min; retention time 10.9 min. The product fractions were freeze dried to give 20 mg (TFA salt).

Deprotection: The above residue was dissolved in $CH_2Cl_2$ (0.4 mL) at 21° C., and TFA (0.34 mL, 4.4 mmol) was added and stirred for 1.2 h. The solution was concentrated to remove TFA. The residue was dissolved in acetonitrile (0.8 mL) and 15.0 M of ammonium hydroxide in water (0.20 mL, 2.9 mmol) was added. The solution was stirred at 21° C. for 3 h. LCMS showed the reaction to be complete. The reaction mixture was concentrated. The product was isolated by preparative HPLC/MS using a Waters Fraction-Lynx instrument and a 19 mm×100 mm Sunfire C18 column; 9% ACN—H2O (0.1% TFA), 2.5 min; 10 min gradient to 35%; 30 mL/min; retention time 11.8 min. The collected fractions were freeze-dried to give white solid (11 mg; presumed bis-TFA salt). HPLC showed $UV_{max}$ at 228, 268, 288, and 330 nm. $^1H$ NMR (300 MHz, DMSO-$D_6$): δ 12.5 (s, 1H); 8.98 (s, 1H); 8.95 (s, 2H); 8.77 (s, 1H); 8.48 (s, 1H); 7.72 (s, 1H); 7.08 (s, 1H); 4.84 (m, 1H); 3.86 (m, 1H); 3.61 (m, 1H); 3.35 (m, 4H); 2.88 (m, 1H); 1.64 (m, 2H); LCMS calculated for $C_{21}H_{19}N_{10}S(M+H)^+$: m/z=443.151; found 443.

Example 103

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(difluoromethyl)nicotinonitrile bis(trifluoroacetate)

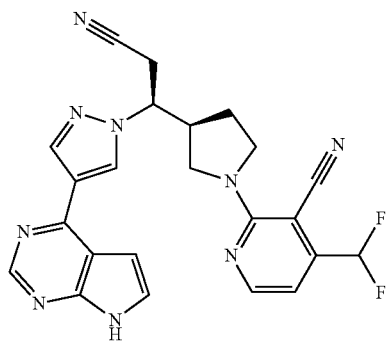 [SMILES: N#CC[C@@H]([C@H]1CCN(c2nccc(C(F)F)c2C#N)C1)n1cc(-c2ncnc3[nH]ccc23)cn1]

Step 1. 2,3-dichloro-4-(difluoromethyl)pyridine 2,3-Dichloroisonicotinaldehyde (146 mg, 0.830 mmol), was stirred in 2-methoxy-N-(2-methoxyethyl)-N-(trifluoro-λ(4)-sulfanyl)ethanamine (Aldrich; 0.30 mL, 1.6 mmol) at 21° C. Ethanol (10 mL, 0.2 mmol) was added to provide HF catalyst. After 1.5 h, LCMS showed clean conversion to product (did not ionize). The reaction was quenched by pouring into 5% $NaHCO_3$ solution followed by extraction with EtOAc. The EtOAc layer was shaken with 5% citric acid to remove bis(methoxyethyl)amine. The organic extracts were evaporated to dryness to give 130 mg oil, which slowly crystallized. The product was clean enough to use without purification. HPLC showed $UV_{max}$ 216 & 280 nm. The FMR showed a doublet for the $CHF_2$ at −118.9 ppm. $^1$H NMR (300 MHz, $CDCl_3$): δ 8.46 (d, J=4.9 Hz, 1H); 7.53 (d, J=4.9 Hz, 1H); 6.90 (t, J=53.8 Hz, 1H); LCMS calculated for $C_6H_4Cl_2F_2N(M+H)^+$: m/z=197.969.

Step 2. (3S)-3-{(3S)-1-[3-chloro-4-(difluoromethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile Into a vial was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (68 mg, 0.16 mmol; from Example 15, step 3), NMP (0.75 mL); 4-methylmorpholine (34 mL, 0.31 mmol), and 2,3-dichloro-4-(difluoromethyl)pyridine (46 mg, 0.23 mmol). Stirred at 150° C. for 15 min in a microwave reactor. LCMS & HPLC showed 80% reaction, with about 60% conversion to product (M+H 599). The product was isolated by preparative HPLC using a Waters Fraction-Lynx instrument and a 30 mm×100 mm Xbridge C18 column; 67% $CH_3OH$—$H_2O$ (0.1% TFA), 0.5 min; then 5 min gradient to 85%; 60 mL/min; detector set at 254 nm; retention time 5.6 min. The collected eluate was evaporated to dryness to give 40 mg (36% yield; probably TFA salt). HPLC gave $UV_{max}$ 208, 226, 260, & 314 nm. LCMS calculated for $C_{28}H_{34}ClF_2N_8OSi(M+H)^+$: m/z=599.228.

Step 3. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(difluoromethyl)nicotinonitrile bis(trifluoroacetate)

(3S)-3-{(3S)-1-[3-Chloro-4-(difluoromethyl)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (34 mg, 0.057 mmol; 40 mg TFA salt), was stirred in NMP (1.0 mL). Zinc cyanide (21 mg, 0.18 mmol) and tetrakis(triphenylphosphine)palladium(0) (14 mg, 0.012 mmol) were added and the solution was flushed with nitrogen (subsurface). The vial was sealed. The solution was heated at 180° C. for 15 min in a microwave reactor. LCMS showed about 50% reaction to give M+H 590. The reaction mixture was diluted with MeOH and filtered. The product was isolated by preparative LCMS using a Waters Fraction-Lynx instrument and a 30 mm×100 mm Sunfire C18 column; 40% ACN—$H_2O$ (0.1% TFA), 2.0 min; 10 min gradient to 65%; 60 mL/min; detector set at m/z 590 & 599; retention time, 10.5 & 11.8 min. The collected fractions were evaporated to dryness.

Deprotection: The above was dissolved in DCM (0.35 mL) and TFA (0.35 mL, 4.5 mmol) and was stirred for 1.1 h. The solution was concentrated to remove TFA. To the residue was added acetonitrile (0.8 mL) and 15.0 M of ammonium hydroxide in water (0.21 mL, 3.2 mmol). The reaction was stirred at 20° C. for 2 h. LCMS showed reaction to be complete. The reaction mixture was concentrated. The product was isolated by preparative HPLC/MS using a Waters Fraction-Lynx instrument and a 30 mm×100 mm Sunfire C18 column; 18% ACN—$H_2O$ (0.1% TFA), 2.5 min; 10 min gradient to 44%; 60 mL/min; detector set at m/z 460; retention time 11.8 min. The product fractions were collected and freeze-dried to give 6 mg white solid. HPLC: $UV_{max}$ 220, 266, 292, and 330 nm. The FMR showed the product to be the di-TFA salt, and showed two doublets for the $CHF_2$ (at −116.8 ppm), from two rotamers. $^1$H NMR (400 MHz, DMSO-$D_6$): δ 12.5 (s, 1H); 8.98 (s, 1H); 8.81 (s, 1H); 8.52 (s, 1H); 8.46 (d, J=5.0 Hz, 1H); 7.75 (s, 1H); 7.13 (t, J=53.8 Hz, 1H); 7.11 (s, 1H); 6.93 (d, J=5.0 Hz, 1H); 4.90 (m, 1H); 3.95 (m, 1H); 3.81 (m, 1H); 3.66 (m, 2H); 3.35 (m, 2H); 2.90 (m, 1H); 1.72 (m, 2H); LCMS calculated for $C_{23}H_{20}F_2N_9(M+H)^+$: m/z=460.181; found 460.

Examples 104-116

The examples in the table below were made by procedures analogous to those for producing Examples 47-50.

| Ex. | Structure | Name | M + H |
|---|---|---|---|
| 104 | 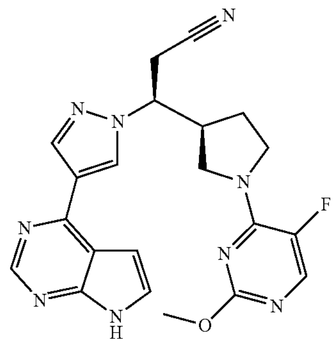 [SMILES: COc1ncc(F)c(N2CC[C@H]([C@H](CC#N)n3cc(-c4ncnc5[nH]ccc45)cn3)C2)n1] | (S)-3-(4-(7H-pyrrolo[2,3-d]pyrimidin-4-yl)-1H-pyrazol-1-yl)-3-((S)-1-(5-fluoro-2-methoxypyrimidin-4-yl)pyrrolidin-3-yl)propanenitrile trifluoroacetate salt | 434 |
| 105 | 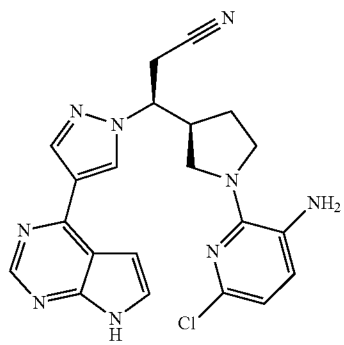 [SMILES: N#CC[C@@H]([C@H]1CCN(c2nc(Cl)ccc2N)C1)n1cc(-c2ncnc3[nH]ccc23)cn1] | (S)-3-(4-(7H-pyrrolo[2,3-d]pyrimidin-4-yl)-1H-pyrazol-1-yl)-3-((S)-1-(3-amino-6-chloropyridin-2-yl)pyrrolidin-3-yl)propanenitrile trifluoroacetate salt | 434 |
| 106 | 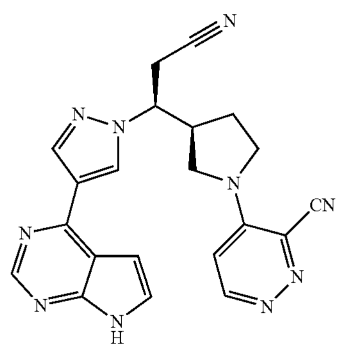 [SMILES: N#CC[C@@H]([C@H]1CCN(c2ccnnc2C#N)C1)n1cc(-c2ncnc3[nH]ccc23)cn1] | 4-((S)-3-((S)-1-(4-(7H-pyrrolo[2,3-d]pyrimidin-4-yl)-1H-pyrazol-1-yl)-2-cyanoethyl)pyrrolidin-1-yl)pyridazine-3-carbonitrile trifluoroacetate salt | 411 |
| 107 | 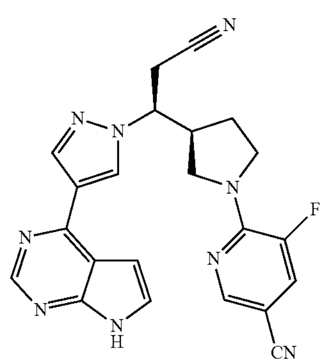 [SMILES: N#CC[C@@H]([C@H]1CCN(c2ncc(C#N)cc2F)C1)n1cc(-c2ncnc3[nH]ccc23)cn1] | 6-((S)-3-((S)-1-(4-(7H-pyrrolo[2,3-d]pyrimidin-4-yl)-1H-pyrazol-1-yl)-2-cyanoethyl)pyrrolidin-1-yl)-5-fluoronicotinonitrile trifluoroacetate salt | 428 |

| Ex. | Structure | Name | M + H |
|---|---|---|---|
| 108 | 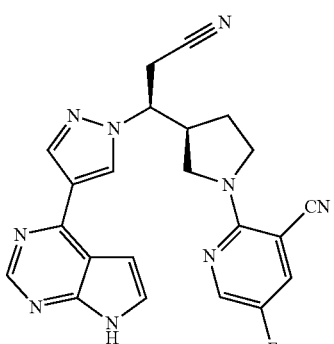 | 2-((S)-3-((S)-1-(4-(7H-pyrrolo[2,3-d]pyrimidin-4-yl)-1H-pyrazol-1-yl)-2-cyanoethyl)pyrrolidin-1-yl)-5-fluoronicotinonitrile trifluoroacetate salt | 428 |
| 109 | 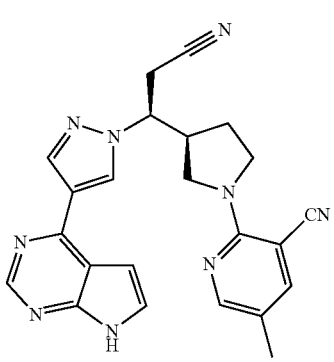 [SMILES: Cc1cnc(N2CC[C@H]([C@H](CC#N)n3cc(-c4ncnc5[nH]ccc45)cn3)C2)c(C#N)c1] | 2-((S)-3-((S)-1-(4-(7H-pyrrolo[2,3-d]pyrimidin-4-yl)-1H-pyrazol-1-yl)-2-cyanoethyl)pyrrolidin-1-yl)-5-methylnicotinonitrile trifluoroacetate salt | 424 |
| 110 | 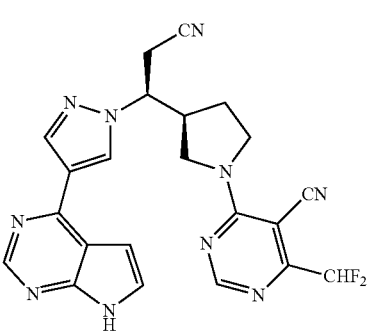 [SMILES: N#CC[C@@H]([C@H]1CCN(c2ncnc(C(F)F)c2C#N)C1)n1cc(-c2ncnc3[nH]ccc23)cn1] | 4-((S)-3-((S)-1-(4-(7H-pyrrolo[2,3-d]pyrimidin-4-yl)-1H-pyrazol-1-yl)-2-cyanoethyl)pyrrolidin-1-yl)-6-(difluoromethyl)pyrimidine-5-carbonitrile trifluoroacetate salt | 461 |
| 111 | 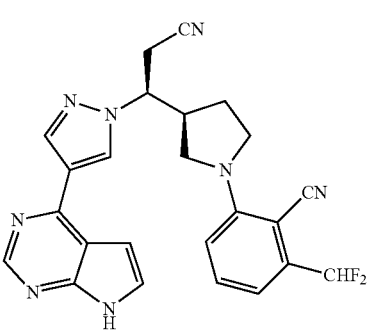 [SMILES: N#CC[C@@H]([C@H]1CCN(c2cccc(C(F)F)c2C#N)C1)n1cc(-c2ncnc3[nH]ccc23)cn1] | 2-((S)-3-((S)-1-(4-(7H-pyrrolo[2,3-d]pyrimidin-4-yl)-1H-pyrazol-1-yl)-2-cyanoethyl)pyrrolidin-1-yl)-6-(difluoromethyl)benzonitrile trifluoroacetate salt | 459 |

-continued

| Ex. | Structure | Name | M + H |
|---|---|---|---|
| 112 | 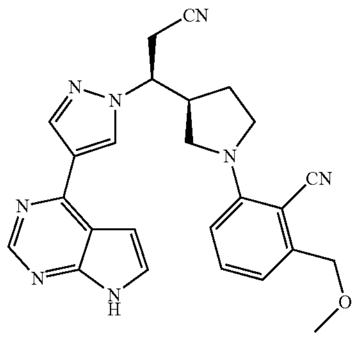 [SMILES: COCc1cccc(N2CC[C@H]([C@H](CC#N)n3cc(-c4ncnc5[nH]ccc45)cn3)C2)c1C#N] | 2-((S)-3-((S)-1-(4-(7H-pyrrolo[2,3-d]pyrimidin-4-yl)-1H-pyrazol-1-yl)-2-cyanoethyl)pyrrolidin-1-yl)-6-(methoxymethyl)benzonitrile | 453 |
| 113 | 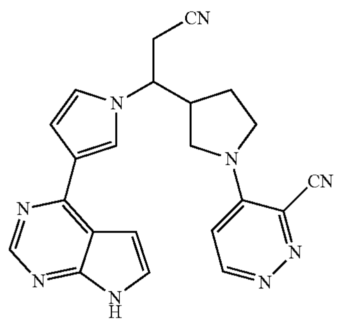 [SMILES: N#CCC(C1CCN(c2ccnnc2C#N)C1)n1ccc(-c2ncnc3[nH]ccc23)c1] | 4-(3-(1-(3-(7H-pyrrolo[2,3-d]pyrimidin-4-yl)-1H-pyrrol-1-yl)-2-cyanoethyl)pyrrolidin-1-yl)pyridazine-3-carbonitrile trifluoroacetate salt, racemate | 410 |
| 114 | 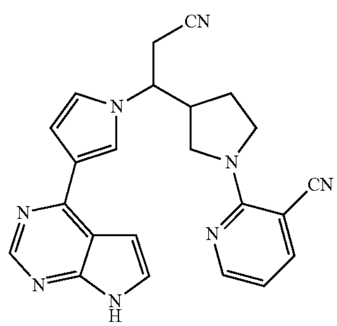 [SMILES: N#CCC(C1CCN(c2ncccc2C#N)C1)n1ccc(-c2ncnc3[nH]ccc23)c1] | 2-(3-(1-(3-(7H-pyrrolo[2,3-d]pyrimidin-4-yl)-1H-pyrrol-1-yl)-2-cyanoethyl)pyrrolidin-1-yl)nicotinonitrile trifluoroacetate salt, single enantiomer | 409 |
| 115 | 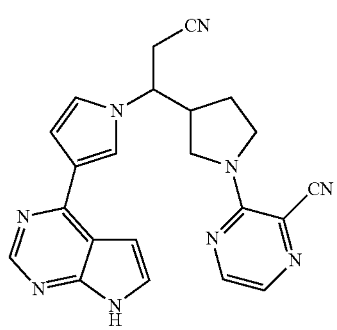 [SMILES: N#CCC(C1CCN(c2nccnc2C#N)C1)n1ccc(-c2ncnc3[nH]ccc23)c1] | 3-(3-(1-(3-(7H-pyrrolo[2,3-d]pyrimidin-4-yl)-1H-pyrrol-1-yl)-2-cyanoethyl)pyrrolidin-1-yl)pyrazine-2-carbonitrile trifluoroacetate salt, single enantiomer | 410 |

| Ex. | Structure | Name | M + H |
|---|---|---|---|
| 116 | 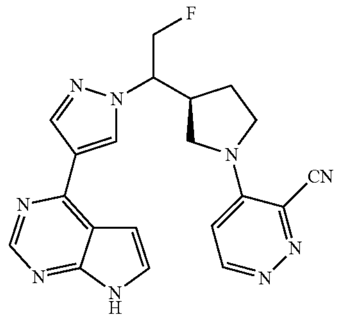 [SMILES: N#Cc1nnccc1N1CC[C@H](C(CF)n2cc(-c3ncnc4[nH]ccc34)cn2)C1] | 4-((3S)-3-(1-(4-(7H-pyrrolo[2,3-d]pyrimidin-4-yl)-1H-pyrazol-1-yl)-2-fluoroethyl)pyrrolidin-1-yl)pyridazine-3-carbonitrile trifluoroacetate salt, single enantiomer | 404 |

| Ex. | $^1$H NMR |
|---|---|
| 104 | n/a |
| 105 | $^1$H NMR (400 MHz, DMSO-D6): δ 12.8 (s, 1H); 9.01 (s, 1H); 8.84 (s, 1H); 8.53 (s, 1H); 7.80 (s, 1H); 7.16 (s, 1H); 6.94 (d, 1H); 6.63 (d, 1H); 4.79 (m, 1H); 3.49 (m, 1H); 3.29 (m, 5H); 2.77 (m, 1H); 1.52 (m, 2H) |
| 106 | $^1$H NMR (400 MHz, DMSO-D6): δ 12.6 (s, 1H); 9.2 (br s, 1H); 8.98 (s, 1H); 8.86 (br s, 1H); 8.52 (s, 1H); 7.75 (s, 1H); 7.24 (br s, 1H); 7.12 (s, 1H); 4.86 (m, 1H); 3.76 (br s, 2H); 3.53 (br s, 2H); 3.40 (dd, 1H); 3.26 (dd, 1H); 2.91 (m, 1H); 1.77 (m, 1H); 1.62 (m, 1H) |
| 107 | $^1$H NMR (500 MHz, DMSO-D6): δ 12.6 (s, 1H); 8.99 (s, 1H); 8.84 (s, 1H); 8.53 (s, 1H); 8.33 (t, 1H); 7.87 (dd, 1H); 7.78 (s, 1H); 7.13 (s, 1H); 4.88 (m, 1H); 3.95 (m, 1H); 3.76 (m, 1H); 3.56 (m, 2H); 3.41 (dd, 1H); 3.32 (dd, 1H); 2.88 (m, 1H); 1.68 (m, 2H) |
| 108 | $^1$H NMR (300 MHz, DMSO-D6): δ 12.5 (s, 1H); 8.97 (s, 1H); 8.88 (s, 1H); 8.51 (s, 1H); 8.37 (d, 1H); 8.07 (dd, 1H); 7.75 (s, 1H); 7.11 (s, 1H); 4.87 (m, 1H); 3.86 (m, 1H); 3.72 (m, 1H); 3.67 (m, 2H); 3.40 (dd, 1H); 3.26 (dd, 1H); 2.87 (m, 1H); 1.69 (m, 2H) |
| 109 | n/a |
| 110 | n/a |
| 111 | $^1$H NMR (400 MHz, DMSO-D6): δ 12.6 (s, 1H); 8.99 (s, 1H); 8.82 (s, 1H); 8.53 (s, 1H); 8.17 (s, 1H); 7.77 (s, 1H); 7.52 (t, 1H); 7.13 (s, 1H); 7.07 (t, J = 54 Hz, 1H); 6.98 (d, 2H); 4.88 (m, 1H); 3.73 (m, 1H); 3.60 (m, 2H); 3.53 (m, 1H); 3.40 (dd, 1H); 3.27 (dd, 1H); 2.92 (m, 1H); 1.68 (m, 2H) |
| 112 | $^1$H NMR (300 MHz, DMSO-D6): δ 12.1 (s, 1H); 8.81 (s, 1H); 8.62 (s, 1H); 8.37 (s, 1H); 7.54 (s, 1H); 7.34 dd, 1H); 6.93 (s, 1H); 6.75 (d, 1H); 6.71 (d, 1H); 4.78 (m, 1H); 4.39 (s, 2H); 3.61 (m, 1H); 3.51 (m, 2H); 3.39 (m, 1H); 3.15-3.35 (m, 2H); 3.26 (s, 3H); 2.85 (m, 1H); 1.61 (m, 2H) |
| 113 | n/a |
| 114 | $^1$H NMR (300 MHz, DMSO-D6): δ 13.2 (s, 1H); 8.90 (s, 1H); 8.41 (s, 1H); 8.31 (dd, 1H); 7.94 (m, 2H); 7.38 (m, 2H); 7.19 (s, 1H); 6.72 (dd, 1H); 4.68 (m, 1H); 3.90 (m, 1H); 3.78 (m, 1H); 3.64 (m, 1H); 3.51 (m, 2H); 3.29 (m, 1H); 2.87 (m, 1H); 1.67 (m, 2H) |
| 115 | $^1$H NMR (300 MHz, DMSO-D6): δ 12.9 (s, 1H); 8.78 (s, 1H); 8.33 (d, 1H); 8.25 (s, 1H); 7.93 (d, 1H); 7.80 (s, 1H); 7.28 (s, 1H); 7.21 (s, 1H); 7.08 (s, 1H); 4.61 (m, 1H); 3.86 (m, 1H); 3.75 (m, 1H); 3.35-3.69 (m, 3H); 3.23 (m, 1H); 2.83 (m, 1H); 1.64 (m, 2H) |
| 116 | n/a |

Example 117

3-((3S)-3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile trifluoroacetate

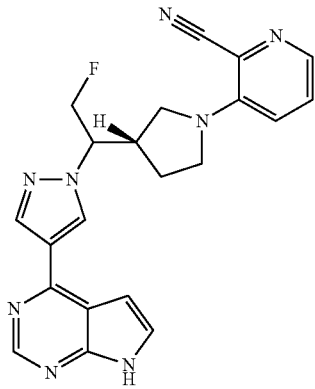 [SMILES: N#Cc1ncccc1N1CC[C@H](C(CF)n2cc(-c3ncnc4[nH]ccc34)cn2)C1]

A solution of 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 37 mg, 0.087 mmol), and DIPEA (30.0 µL, 0.17 mmol), in NMP (0.7 mL) with 3-fluoropyridine-2-carbonitrile (from Alfa Aesar; 16 mg, 0.13 mmol), was heated to 130° C. for 2 h. LCMS showed conversion to the expected intermediate. The reaction mixture was partitioned between water and EtOAc, the aqueous phase was extracted another 2× with EtOAc. The combined organic phases were washed with brine, dried over MgSO$_4$, filtered and concentrated in vacuo. The crude residue was dissolved in 5 mL of MeOH/ACN with a smaller amount of water and were purified by preparative LCMS as in Example 5 at pH 2 to recover the product. The purified product was concentrated in vacuo and taken on to deprotection.

To the residue was added DCM (0.5 mL) and TFA (0.5 mL), the reaction was stirred at ambient temperature for 1 h, evaporated to dryness, then added methanol (0.5 mL) and ammonium hydroxide (0.5 mL), after 45 min LCMS showed complete deprotection. The solvents were removed and the residue was dissolved in MeOH/ACN/water and purified by preparative LCMS as in Example 5 at pH 2, the product tubes were combined and lyophilized to dryness to give the product as a TFA salt. $^1$H NMR (300 MHz, DMSO-D$_6$): δ 12.8 (s, 1H); 8.9 (s, 1H); 8.8 (s, 1H); 8.5 (s, 1H); 7.9 (m, 1H); 7.8 (s, 1H); 7.4 (m, 1H); 7.25 (m, 1H); 7.2 (s, 1H); 4.8 (m, 3H); 3.7 (m, 1H); 3.5 (m, 3H); 2.9 (m, 1H); 1.7 (m, 2H). LCMS calculated for C$_{21}$H$_{20}$FN$_8$(M+H)$^+$: m/z=403.179, observed 403.2.

Example 118

2-((3S)-3-{2-fluoro-1-[4-(7H-pyrrolo[2,3-d]pyrimidin-4-yl)-1H-pyrazol-1-yl]ethyl}pyrrolidin-1-yl)nicotinonitrile trifluoroacetate

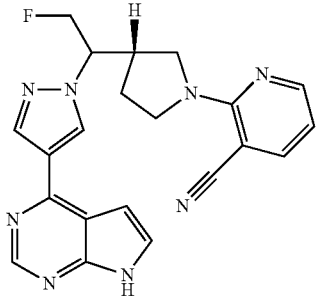 [SMILES: N#Cc1cccnc1N1CC[C@H](C(CF)n2cc(-c3ncnc4[nH]ccc34)cn2)C1]

A solution was prepared by dissolving 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 37 mg, 0.087 mmol) and DIPEA (30 mL, 0.17 mmol) in NMP (0.7 mL) with 2-fluoronicotinonitrile (from Alfa Aesar; 16 mg, 0.13 mmol) was heated to 130° C. for 2 h. The reaction mixture was partitioned between water and EtOAc, the aqueous phase was extracted another 2× with EtOAc. The combined organic phase was washed with brine, dried over MgSO$_4$, filtered and concentrated in vacuo and was purified by preparative LCMS as in Example 5 at pH 2 to recover the product. This was concentrated in vacuo and the SEM group was removed as in Example 1. The solvent was evaporated and the residue was dissolved in MeOH/ACN/water and purified by preparative LCMS as in Example 5 at pH 2, the product tubes were combined and lyophilized to dryness to give the product as a TFA salt. $^1$H NMR (300 MHz, DMSO-D$_6$): δ 12.8 (s, 1H); 8.95 (s, 1H); 8.85 (s, 1H); 8.5 (s, 1H); 8.3 (m, 1H); 7.9 (m, 1H); 7.8 (s, 1H); 7.2 (s, 1H); 6.7 (m, 1H); 4.9 (m, 3H); 3.9 (m, 1H); 3.8 (m, 1H); 3.6 (m, 2H); 2.9 (m, 1H); 1.7 (m, 2H). LCMS calculated for C$_{21}$H$_{20}$FN$_8$(M+H)$^+$: m/z=403.179, observed 403.1.

Example 119

4-(1-{1-[(3S)-1-(1,1-dioxido-2,3-dihydrothieno[2,3-b]pyridin-6-yl)pyrrolidin-3-yl]-2-fluoroethyl}-1H-pyrazol-4-yl)-7H-pyrrolo[2,3-d]pyrimidine trifluoroacetate

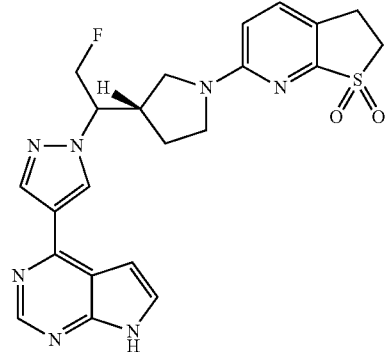 [SMILES: O=S1(=O)CCc2ccc(N3CC[C@H](C(CF)n4cc(-c5ncnc6[nH]ccc56)cn4)C3)nc21]

A solution was prepared by dissolving 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 25 mg, 0.058 mmol) and DIPEA (2.0E1 mL, 0.12 mmol) in NMP (0.2 mL). To this solution was added 6-chloro-2,3-dihydrothieno[2,3-b]pyridine 1,1-dioxide (from Example 28, Step 4; 18 mg, 0.087 mmol) and the reaction was heated to 100° C. for 2 h, at which time LCMS analysis showed conversion to the desired product. The reaction was cooled to ambient temperature and partitioned between water and EtOAc. The phases were separated and the aqueous phase was washed with additional EtOAc. The combined organic phase was washed with brine, dried over MgSO$_4$, filtered and concentrated in vacuo to provide the crude product, which was then dissolved in ACN/MeOH and purified by preparative LCMS, at pH 2 MeOH/water method as in Example 5, to recover the product. The product tubes were evaporated to dryness, and the residue was treated with DCM (0.4 mL) and TFA (0.4 mL) for 30 min. The solvents were removed and ammonium hydroxide (0.4 mL) and methanol (0.4 mL) were added and the reaction was stirred at ambient temperature for 45 min. The solvents were evaporated to dryness, the residue was dissolved in MeOH/ACN/water and purified by preparative LCMS as in Example 5 at pH 2. The product tubes were combined and lyophilized to dryness to give the product as a TFA salt. $^1$H NMR (300 MHz, DMSO-D$_6$): δ 12.5 (s, 1H); 8.95 (s, 1H); 8.75 (s, 1H); 8.4 (s, 1H); 7.5 (s, 1H); 7.4 (d, 1H); 7.1 (s, 1H); 6.7 (d, 1H); 4.95 (m, 1H); 4.8 (m, 2H); 3.75 (m, 1H); 3.5 (m, 1H); 3.45 (t, 2H); 3.25 (m, 2H); 3.05 (t, 2H); 2.85 (m, 1H); 1.65 (m, 2H). LCMS calculated for C$_{22}$H$_{23}$FN$_7$O$_2$S(M+H)$^+$: m/z=468.162, observed 468.15.

Example 120

2-((3S)-3-(1-(4-(7H-pyrrolo[2,3-d]pyrimidin-4-yl)-1H-pyrazol-1-yl)-2-fluoroethyl)pyrrolidin-1-yl)pyridine-3,4-dicarbonitrile trifluoroacetate

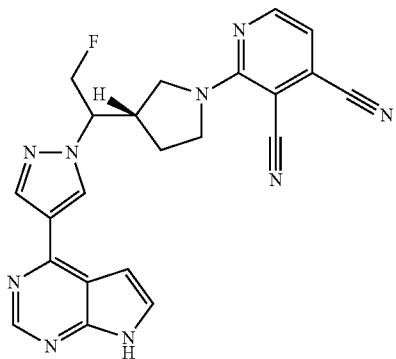 [SMILES: N#Cc1ccnc(N2CC[C@H](C(CF)n3cc(-c4ncnc5[nH]ccc45)cn3)C2)c1C#N]

Step 1. 3-chloro-2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)isonicotinonitrile A solution was prepared by dissolving 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 60 mg, 0.1 mmol) and DIPEA (48 mL, 0.28 mmol) in NMP (0.5 mL). To this solution was added 2,3-dichloroisonicotinonitrile (36 mg, 0.21 mmol) and the reaction was heated to 130° C. for 1.5 h. LCMS showed clean conversion to the desired product, (m/z=567/569). The reaction was cooled to ambient temperature and partitioned between water and EtOAc, the phases were separated and the aqueous phase was extracted with additional EtOAc. The combined organic phase was washed with brine, dried over MgSO$_4$, filtered and concentrated in vacuo to provide the crude product. LCMS calculated for C$_{27}$H$_{33}$ClFN$_8$OSi (M+H)$^+$: m/z=567.222, observed 567.15.

Step 2. 2-(3-{2-fluoro-1-[4-(7H-pyrrolo[2,3-d]pyrimidin-4-yl)-1H-pyrazol-1-yl]ethyl}pyrrolidin-1-yl)pyridine-3,4-dicarbonitrile trifluoroacetate Into a 1-neck round-bottom flask 3-chloro-2-(3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)isonicotinonitrile (35.7 mg, 0.0629 mmol) was dissolved in NMP (0.4 mL) and zinc cyanide (22.2 mg, 0.189 mmol) and zinc (12.3 mg, 0.189 mmol) were added. The reaction was degassed with vacuum/N$_2$ and bis(tri-t-butylphosphine)palladium (16.1 mg, 0.0315 mmol) was added. The reaction was degassed again and was then heated to 130° C. for 3 h. The reaction was cooled to ambient temperature and partitioned between water and EtOAc, the phases were separated and the aqueous phase was extracted with additional EtOAc. The combined organic phase was washed with water, then brine, dried over MgSO$_4$, filtered and concentrated in vacuo to provide the crude product, which was dissolved in MeOH/ACN and purified by preparative LCMS as in Example 5. The eluate was concentrated in vacuo and treated with DCM (0.5 mL) and TFA (0.2 mL), the reaction was stirred at ambient temperature for 1 h, evaporated to dryness, then added methanol (0.5 mL) and ammonium hydroxide (0.5 mL) and stirred for 1 h. The solvents were evaporated and the residue was dissolved in MeOH/ACN/water and purified by preparative LCMS at pH 2 as in Example 5. The product tubes were lyophilized to dryness to give the product as TFA salt. LCMS calculated for C$_{22}$H$_{18}$FN$_9$(M+H)$^+$: m/z=428.175, observed 428.10.

Example 121

3-((3S)-3-{2-fluoro-1-[4-(7H-pyrrolo[2,3-d]pyrimidin-4-yl)-1H-pyrazol-1-yl]ethyl}pyrrolidin-1-yl)phthalonitrile trifluoroacetate

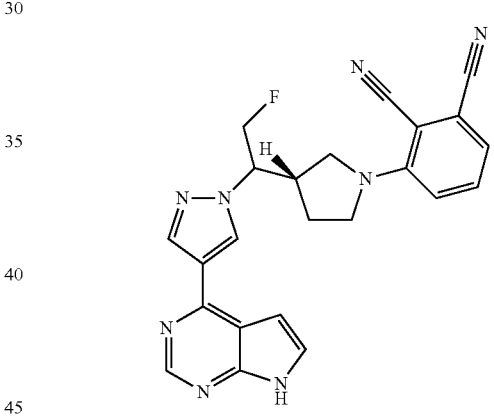

Step 1. 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-iodobenzonitrile A solution was prepared by dissolving 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 45 mg, 0.10 mmol) and DIPEA (36 μL, 0.21 mmol) in NMP (0.4 mL). To this solution was added 2-fluoro-6-iodobenzonitrile (39 mg, 0.16 mmol) and the solution was heated to 100° C. for 2 h. The reaction was cooled to ambient temperature, partitioned between water and EtOAc, the phases were separated and the aqueous phase was washed with additional EtOAc. The combined organic phase was washed with water, then brine, dried over MgSO$_4$, filtered and concentrated in vacuo to provide the crude product, which was purified by silica gel chromatography eluting with hexanes→5% MeOH/CH$_2$Cl$_2$. LCMS calculated for C$_{28}$H$_{34}$FIN$_7$OSi (M+H)$^+$: m/z=658.68, observed 658.15.

Step 2. 3-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)phthalonitrile To a solution of 2-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-iodobenzonitrile (22 mg, 0.033 mmol) in NMP (0.764 mL) was added zinc cyanide (58.1 mg, 0.495 mmol). The mixture was degassed with two vacuum/$N_2$ cycles, then tetrakis(triphenylphosphine) palladium(0) (38.1 mg, 0.0330 mmol) was added, the reaction was again degassed with two vacuum/$N_2$ cycles. The reaction was heated to 130° C for 2 h, then LCMS showed formation of desired product. The reaction was cooled to ambient temperature and filtered to remove solids, then was partitioned between water and EtOAc, the phases were separated and the aqueous phase was extracted with additional EtOAc. The combined organic phase was washed with water, then brine, dried over $MgSO_4$, filtered and concentrated in vacuo to provide the crude product. The crude product was purified by preparative LCMS as in Example 5, the product tubes were evaporated to dryness to give 3-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)phthalonitrile. LCMS calculated for $C_{29}H_{34}FN_8OSi$ $(M+H)^+$: m/z=557.261, observed 557.25.

Step 3. 3-((3S)-3-{2-fluoro-1-[4-(7H-pyrrolo[2,3-d]pyrimidin-4-yl)-1H-pyrazol-1-yl]ethyl}pyrrolidin-1-yl)phthalonitrile trifluoroacetate To the residue from step 3 was added DCM (0.5 mL) and TFA (0.5 mL), the reaction was stirred at ambient temperature for 1 h, evaporated to dryness, then added methanol (0.5 mL) and ammonium hydroxide (0.5 mL). After 30 min, LCMS shows complete deprotection. The solvents were removed and the residue was dissolved in MeOH/ACN/water and purified by preparative LCMS at pH 2 as in Example 5. The product tubes were combined and lyophilized to dryness to give the product 3-((3S)-3-{2-fluoro-1-[4-(7H-pyrrolo[2,3-d]pyrimidin-4-yl)-1H-pyrazol-1-yl]ethyl}pyrrolidin-1-yl)phthalonitrile as a TFA salt. LCMS calculated for $C_{23}H_{20}FN_8$ $(M+H)^+$: m/z=427.179, observed 427.05.

Example 122

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-iodonicotinnitrile trifluoroacetate

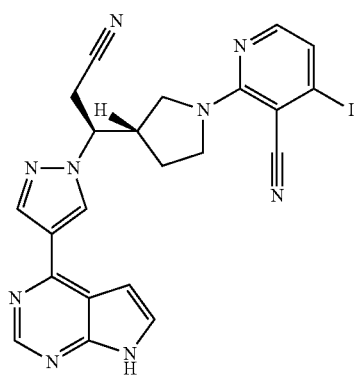 [SMILES: N#CC[C@@H]([C@H]1CCN(c2nccc(I)c2C#N)C1)n1cc(-c2ncnc3[nH]ccc23)cn1]

Step 1. 2-chloro-4-iodonicotinonitrile

To 2-chloro-4-iodonicotinaldehyde (1.0 g, 3.7 mmol) dissolved in THF (11 mL) was added ammonium hydroxide (11 mL, 280 mmol) followed by iodine (1040 mg, 4.11 mmol), the reaction was held at ambient temperature 3.5 h, color visibly lightens as reaction progresses until the end when it is nearly colorless. LCMS indicates reaction to be complete. Reaction was quenched by addition of saturated $NaHSO_3$, extracted into EtOAc. The organic phase was washed with brine, dried over $MgSO_4$, filtered and concentrated in vacuo to provide the crude product, 926 mg. Dissolved in $CHCl_3$/MeOH and applied to 120 g silica gel column, the product fractions were concentrated in vacuo to give 728 mg product. The purified material was taken directly to next step.

Step 2. 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-iodonicotinonitrile and 2-chloro-4-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile To a solution of 2-chloro-4-iodonicotinonitrile (50.8 mg, 0.192 mmol) in NMP (0.112 mL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (56.0 mg, 0.128 mmol; from Example 15, step 3) followed by DIPEA (31.9 µL, 0.183 mmol), the reaction was capped and heated to 100° C. in a heating block for 3 h. LCMS showed formation of product resulting from iodo displacement (major) with minor product from chloride displacement. The reaction was cooled to ambient temperature and diluted with ACN/MeOH and the products were separated by preparative LCMS as in Example 5 to recover the two products 2-chloro-4-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile (LCMS calculated for $C_{28}H_{33}IN_9OSi$ $(M+H)^+$: m/z=666.162, observed 666.20) and 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-iodonicotinonitrile (LCMS calculated for $C_{28}H_{33}ClN_9OSi$ $(M+H)^+$: m/z=574.227, observed 574.20).

Step 3. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-iodonicotinonitrile trifluoroacetate 2-((3S)-3-{(1S)-2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-iodonicotinonitrile was dissolved in DCM (400 µL) and TFA (400 µL). After 1 h, LCMS shows complete reaction, evaporated solvent, and added methanol (800 µL) and ammonium hydroxide (400 µL), LCMS shows complete deprotection. Evaporated solvent and took up residue in MeOH/ACN, purified by preparative LCMS as in Example 5 (ACN/water, at pH 2) to give the product as TFA salt. $^1$H NMR (300 MHz, DMSO-$d_6$): δ 12.6 (s, 1H); 9.0 (s, 1H); 8.8 (s, 1H); 8.5 (s, 1H); 7.9 (d, 1H); 7.75 (s, 1H); 7.25 (d, 1H); 7.1 (s, 1H); 4.9 (m, 1H); 3.9 (m, 1H); 3.7 (m, 1H); 3.6 (m, 2H); 3.3 (m, 2H); 2.9 (m, 1H); 1.7 (m, 2H); LCMS calculated for $C_{22}H_{19}IN_9$ $(M+H)^+$: m/z=536.081, observed 535.85.

Example 123

2-chloro-4-((3S)-3-{(1S)-2-cyano-1-[4-(7H-pyrrolo[2,3-d]pyrimidin-4-yl)-1H-pyrazol-1-yl]ethyl}pyrrolidin-1-yl)nicotinonitrile trifluoroacetate

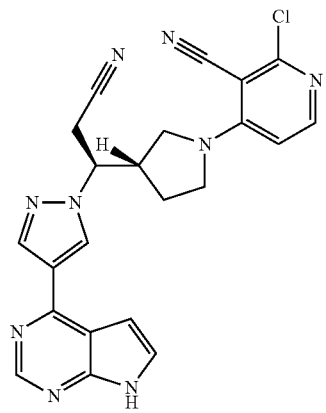 [SMILES: N#CC[C@@H]([C@H]1CCN(c2ccnc(Cl)c2C#N)C1)n1cc(-c2ncnc3[nH]ccc23)cn1]

2-Chloro-4-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile (from Example 122, step 2) was deprotected and purified as in Example 122, step 3, to provide the product as TFA salt. $^1$H NMR (300 MHz, DMSO-$d_6$): δ 12.5 (s, 1H); 8.95 (s, 1H); 8.8 (s, 1H); 8.5 (s, 1H); 8.0 (d, 1H); 7.75 (s, 1H); 7.1 (s, 1H); 6.65 (d, 1H); 4.9 (m, 1H); 3.8 (m, 1H); 3.7 (m, 1H); 3.6 (m, 2H); 3.3 (m, 2H); 2.9 (m, 1H); 1.7 (m, 1H); 1.6 (m, 1H); LCMS calculated for $C_{22}H_{19}ClN_9$ (M+H)$^+$: m/z=444.15, observed 443.90.

Example 124

4-((3S)-3-{(1S)-2-cyano-1-[4-(7H-pyrrolo[2,3-d]pyrimidin-4-yl)-1H-pyrazol-1-yl]ethyl}pyrrolidin-1-yl)pyridine-2,3-dicarbonitrile trifluoroacetate

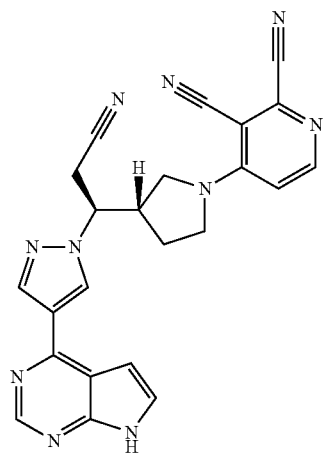 [SMILES: N#CC[C@@H]([C@H]1CCN(c2ccnc(C#N)c2C#N)C1)n1cc(-c2ncnc3[nH]ccc23)cn1]

To a solution of 2-chloro-4-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile (Example 123; 32 mg, 0.056 mmol) in NMP (1.00 mL) was added zinc cyanide (26.2 mg, 0.223 mmol). The mixture was degassed with two vacuum/$N_2$ cycles, then tetrakis(triphenylphosphine)palladium(0) (51.5 mg, 0.0446 mmol) was added, the reaction was again degassed with two vacuum/$N_2$ cycles. Reaction was heated to 120° C. for 16 h. LCMS showed nearly complete conversion to product. Rxn cooled to ambient temperature and partitioned between water and EtOAc, the phases were separated and the aqueous phase was extracted with EtOAc. The combined organic phase was washed with water, then brine, dried over $MgSO_4$, filtered and concentrated in vacuo to provide the crude product. The crude product was purified by preparative LCMS as in Example 5. The product tubes were evaporated to dryness. The product was dissolved in DCM (800 μL) and TFA (800 μL); after evaporated to dryness and added methanol (800 μL) and ammonium hydroxide (800 μL). After 45 min, LCMS showed complete deprotection. The solvents were evaporated and the product purified by preparative LCMS at pH 2 as in Example 5. The product tubes were combined and lyophilized to dryness to give (4-((3S)-3-{(1S)-2-cyano-1-[4-(7H-pyrrolo[2,3-d]pyrimidin-4-yl)-1H-pyrazol-1-yl]ethyl}pyrrolidin-1-yl)pyridine-2,3-dicarbonitrile as a TFA salt. $^1$H NMR (300 MHz, DMSO-$D_6$): δ 12.5 (s, 1H); 8.9 (s, 1H); 8.8 (s, 1H); 8.5 (s, 1H); 8.3 (d, 1H); 7.75 (s, 1H); 7.1 (s, $^1$H); 6.9 (d, 1H); 4.85 (m, 1H); 3.8 (m, 1H); 3.7 (m, 1H); 3.6 (m, 2H); 3.3 (m, 2H); 2.95 (m, 1H); 1.75 (m, 1H); 1.6 (m, 1H); LCMS calculated for $C_{23}H_{19}N_{10}$ (M+H)$^+$: m/z=435.179, observed 434.90.

Example 125

(3S)-3-[(3S)-1-(2,6-dichloropyridin-3-yl)pyrrolidin-3-yl]-3-[4-(7H-pyrrolo[2,3-d]pyrimidin-4-yl)-1H-pyrazol-1-yl]propanenitrile trifluoroacetate

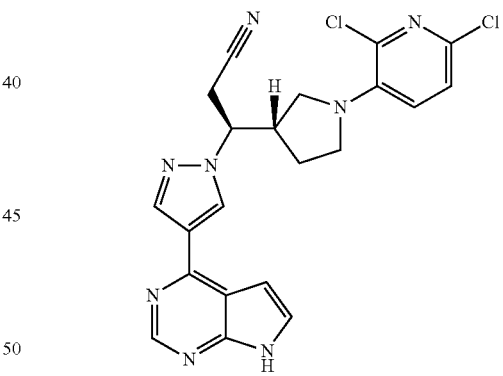

Step 1. (3S)-3-[(3S)-1-(2,6-dichloropyridin-3-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile To a solution of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (18.4 mg, 0.0422 mmol; from Example 15, step 3) and DIPEA (11.0 μL, 0.0633 mmol) in NMP (0.1 mL) was added 2,6-dichloro-3-fluoropyridine (1 equivalent) and the reaction was heated to 100° C. for 24 h. The reaction was diluted with MeOH/ACN/water and purified by preparative LCMS as in Example 5 to separate the two products (3S)-3-[(3S)-1-(6-chloro-5-fluoropyridin- 2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile and (3S)-3-[(3S)-1-(2,6-dichloropyridin-3-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile. The fractions were pooled and evaporated to dryness to provide the di-chloro product. LCMS calculated for $C_{27}H_{33}Cl_2N_8OSi$ (M+H)$^+$: m/z=583.192, observed 583.05.

Step 2. (3S)-3-[(3S)-1-(2,6-dichloropyridin-3-yl)pyrrolidin-3-yl]-3-[4-(7H-pyrrolo[2,3-d]pyrimidin-4-yl)-1H-pyrazol-1-yl]propanenitrile trifluoroacetate To (3S)-3-[(3S)-1-(2,6-dichloropyridin-3-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile was added DCM (300 μL) and TFA (200 μL), the reaction was stirred at ambient temperature for 1 h, evaporated to dryness, then added methanol (300 μL) and ammonium hydroxide (300 μL). After 45 min, LCMS showed complete deprotection. The solvents were evaporated and the residue was dissolved in MeOH/ACN/water and purified by preparative LCMS at pH 2 as in Example 5. The product tubes were combined and lyophilized to dryness to give the product as a TFA salt. LCMS calculated for $C_{22}H_{19}ClN_9$ (M+H)$^+$: m/z=453.111, observed 453.00.

Example 126

5-((3S)-3-{2-fluoro-1-[4-(7H-pyrrolo[2,3-d]pyrimidin-4-yl)-1H-pyrazol-1-yl]ethyl}pyrrolidin-1-yl)-1,3-thiazole-4-carbonitrile trifluoroacetate

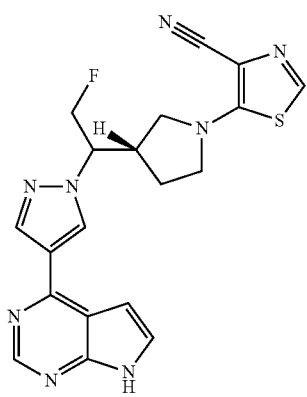 [SMILES: N#Cc1ncsc1N1CC[C@H](C(CF)n2cc(-c3ncnc4[nH]ccc34)cn2)C1]

Step 1. 5-bromo-1,3-thiazole-4-carbonitrile

To a mixture of 5-bromo-1,3-thiazole-4-carboxamide (prepared according to the procedure reported in WO2008/057336 from 5-bromo-1,3-thiazole-4-carboxylic acid obtained from SynChem; 714 mg, 3.45 mmol)) and triethylamine (7.21 mL, 51.7 mmol) in DCM (10 mL) was added trichloroacetic anhydride (6.30 mL, 34.5 mmol) drop-wise at 0° C. The mixture was stirred at 0° C. for 1 h. The reaction was quenched with saturated aqueous $NaHCO_3$ solution, extracted with DCM, dried over $MgSO_4$, filtered and concentrated in vacuo. Crude product was dissolved in $CHCl_3$ and applied to 120 g silica gel column, eluted to recover 593 mg product. $^1$H NMR (300 MHz, $CDCl_3$): δ 8.82 (s, 1H).

Step 2. 5-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-1,3-thiazole-4-carbonitrile A mixture of 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 84.8 mg, 0.000197 mol), 5-bromo-1,3-thiazole-4-carbonitrile (66 mg, 0.00035 mol) and DIPEA (62 μL, 0.00035 mol) in 1-butyl-3-methyl-1H-imidazol-3-ium tetrafluoroborate (350 μL, 0.0019 mol) was heated at 120° C. for 3 h. Cooled to ambient temperature, partitioned between water and EtOAc, the phases were separated and the aqueous phase was extracted with EtOAc. The combined organic phase was washed with water, then brine, dried over $MgSO_4$, filtered and concentrated in vacuo to provide the crude product. This was dissolved in $CHCl_3$/hexanes and applied to 4 g silica gel column; recovered 29.5 mg of 5-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-1,3-thiazole-4-carbonitrile. LCMS calculated for $C_{25}H_{32}FN_8OSSi$ (M+H)$^+$: m/z=539.217, observed 539.05.

Step 3. 5-((3S)-3-{2-fluoro-1-[4-(7H-pyrrolo[2,3-c]pyrimidin-4-yl)-1H-pyrazol-1-yl]ethyl}pyrrolidin-1-yl)-1,3-thiazole-4-carbonitrile trifluoroacetate To the chromatographed 5-((3S)-3-{2-fluoro-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-1,3-thiazole-4-carbonitrile was added DCM (0.50 mL) and TFA (0.50 mL), the reaction was stirred at ambient temperature for 2 h, evaporated to dryness; then added methanol (1 mL) and ammonium hydroxide (1 mL). Allowed to stir overnight. The solvents were evaporated and the residue was dissolved in MeOH/ACN/water and purified by preparative LCMS at pH 2 as in Example 129 (MeOH/water/TFA). The product tubes were combined and lyophilized to dryness to give 5-((3O)-3-{2-fluoro-1-[4-(7H-pyrrolo[2,3-d]pyrimidin-4-yl)-1H-pyrazol-1-yl]ethyl}pyrrolidin-1-yl)-1,3-thiazole-4-carbonitrile as the bis-TFA salt ($^{19}$F NMR). $^1$H NMR (300 MHz, DMSO-D$_6$): δ 12.7 (s, 1H); 8.95 (s, 1H); 8.85 (s, 1H); 8.55 (s, 1H); 8.15 (s, 1H); 7.8 (s, 1H); 7.2 (s, 1H); 4.9 (m, 3H); 3.75 (m, 1H); 3.6 (m, 1H); 3.5 (m, 2H); 3.0 (m, 1H); 1.75 (m, 2H); LCMS calculated for $C_{19}H_{18}FN_8S$ (M+H)$^+$: m/z=409.136, observed 409.00.

Example 127

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methylthio)nicotinonitrile trifluoroacetate

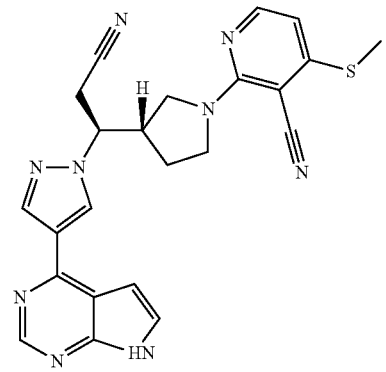 [SMILES: CSc1ccnc(N2CC[C@H]([C@H](CC#N)n3cc(-c4ncnc5[nH]ccc45)cn3)C2)c1C#N]

Step 1. 2-chloro-4-(methylthio)nicotinonitrile

2-Chloro-4-iodonicotinonitrile (from Example 122, Step 1; 209.5 mg, 0.7922 mmol) was dissolved in 1,4-dioxane (1.85 mL) and sodium methyl mercaptide (61.0 mg, 0.871 mmol) was added. The reaction was stirred at ambient temperature. After 40 h the reaction mixture was partitioned between water and EtOAc, the phases were separated and the aqueous phase was extracted with EtOAc. The combined organic phase was washed with water, then brine, dried over $MgSO_4$, filtered and concentrated in vacuo to provide 180 mg of the crude product. Dissolved in $CHCl_3$/hexanes and applied to 40 g silica gel column; product recovered: 52 mg. LCMS calculated for $C_7H_6ClN_2S$ $(M+H)^+$: m/z=184.994, observed 184.90.

Step 2. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methylthio)nicotinonitrile trifluoroacetate To a solution of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (62 mg, 0.14 mmol; from Example 15, step 3) in NMP (0.23 mL) was added 2-chloro-4-(methylthio)nicotinonitrile (52 mg, 0.28 mmol) followed by DIPEA (35.1 mL, 0.202 mmol), the reaction was capped and heated to 130° C. in an oil bath for 3 h. LCMS showed nearly complete reaction to desired product. Isolated by preparative LCMS acetone/water/at pH 2 method (Waters Fraction-Lynx instrument, 20×100 mm C18 column, acetone/water (0.1% TFA), 30 mL/min). The product tubes were evaporated to near dryness. Added $NaHCO_3$ then extracted with EtOAc. The organic phase was washed with water, then brine, dried over $MgSO_4$, filtered and concentrated in vacuo to provide the 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(methylthio)nicotinonitrile.

To the residue was added DCM (400 µL) and TFA (400 µL), the reaction was stirred at ambient temperature for 1 h, evaporated to dryness, then added methanol (600 µL) and ammonium hydroxide (600 µL), allowed to stir overnight. LCMS showed complete deprotection. The solvents were evaporated and the residue was dissolved in MeOH/ACN/water and purified by preparative LCMS as in Example 129 at pH 2, the product tubes were combined and lyophilized to dryness to give the product 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methylthio)nicotinonitrile as a TFA salt. LCMS calculated for $C_{23}H_{22}N_9S$ $(M+H)^+$: m/z=456.172, observed 456.00.

Example 128

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methylsulfonyl)nicotinonitrile

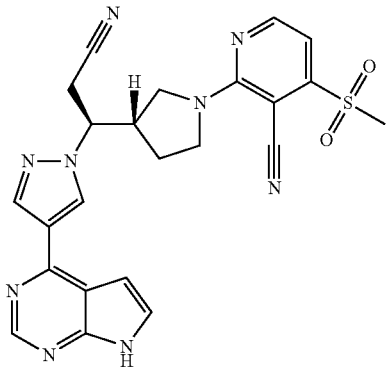 [SMILES: CS(=O)(=O)c1ccnc(N2CC[C@H]([C@H](CC#N)n3cc(-c4ncnc5[nH]ccc45)cn3)C2)c1C#N]

2-((3S)-3-{(1S)-2-Cyano-1-[4-(7H-pyrrolo[2,3-d]pyrimidin-4-yl)-1H-pyrazol-1-yl]ethyl}pyrrolidin-1-yl)-4-(methylthio)nicotinonitrile (from Example 127; 30.0 mg, 0.0658 mmol) was dissolved in methanol (0.2 mL) and water (0.2 mL). Oxone® (81.0 mg, 0.132 mmol) was added and the solution was stirred at ambient temperature for 4 h. LCMS showed nearly complete oxidation to sulfone (some sulfoxide remained), and no evidence of over-oxidation. Reaction was concentrated in vacuo and residue was dissolved in DMSO/MeOH; insolubles were removed by filtration, then the filtrate was purified by preparative LCMS as in Example 5, ACN/water at pH 2 to recover the 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(methylsulfonyl)nicotinonitrile. $^1H$ NMR (500 MHz, DMSO-$d_6$): δ 12.5 (s, 1H); 8.95 (s, 1H); 8.8 (s, 1H); 8.55 (d, 1H); 8.5 (s, 1H); 7.7 (s, 1H); 7.2 (d, 1H); 7.1 (s, 1H); 4.9 (m, 1H); 4.0 (m, 1H); 3.8 (m, 1H); 3.7 (m, 2H); 3.4 (m, 1H); 3.35 (s, 3H); 3.3 (m, 1H); 2.9 (m, 1H); 1.7 (m, 2H); LCMS calculated for $C_{23}H_{22}N_9O_2S$ $(M+H)^+$: m/z=488.162, observed 487.90.

Example 129

(3S)-3-{(3S)-1-[3,5-difluoro-6-(methylthio)pyridin-2-yl]pyrrolidin-3-yl}-3-[4-(7H-pyrrolo[2,3-d]pyrimidin-4-yl)-1H-pyrazol-1-yl]propanenitrile trifluoroacetate

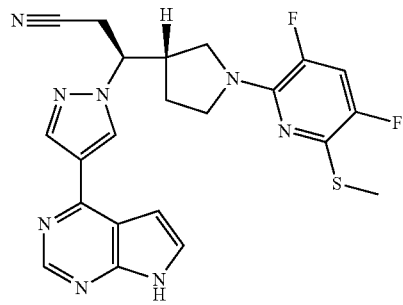 [SMILES: CSc1nc(N2CC[C@H]([C@H](CC#N)n3cc(-c4ncnc5[nH]ccc45)cn3)C2)c(F)cc1F]

Step 1. 2,3,5-trifluoro-6-(methylthio)pyridine 2,3,5,6-Tetrafluoropyridine (310 µL, 3.0 mmol) was dissolved in THF (2.0 mL) and cooled to 0° C. To this solution was gradually added sodium methyl mercaptide (227.8 mg, 3.25 mmol) in MeOH (1 mL). The reaction was held at 0° C. for 70 min at which time, HPLC analysis indicated complete reaction. The reaction mixture was partitioned between water and $Et_2O$, the phases were separated and the aqueous phase was washed with additional $Et_2O$. The combined organic phase was washed with water followed by brine, then dried over $MgSO_4$ and concentrated in vacuo to provide the crude product, 424 mg. This material was used directly in the next step. $^1H$ NMR (300 MHz, $CDCl_3$): δ 7.29 (m, 1H), 2.53 (s, 3H).

Step 2. (3S)-3-{(3S)-1-[3,5-difluoro-6-(methylthio)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile To a solution of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (86 mg, 0.20 mmol; from Example 15, step 3) in NMP (0.32 mL) was added 2,3,5-trifluoro-6-(methylthio)pyridine (70.1 mg, 0.391 mmol) followed by DIPEA (48.8 µL, 0.280 mmol), the reaction was capped and heated to 100° C. in an oil bath for 3.5 h at which time LCMS analysis indicated complete reaction. The reaction was cooled to ambient temperature and diluted with methanol and acetonitrile (total solvent added 2 mL) and purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), the product was isolated as a TFA salt, 43 mg. LCMS calculated for $C_{28}H_{35}F_2N_8OSSi$ $(M+H)^+$: m/z=597.239, observed 597.30.

Step 3. (3S)-3-{(3S)-1-[3,5-difluoro-6-(methylthio)pyridin-2-yl]pyrrolidin-3-yl}-3-[4-(7H-pyrrolo[2,3-d]pyrimidin-4-yl)-1H-pyrazol-1-yl]propanenitrile trifluoroacetate To (3S)-3-{(3S)-1-[3,5-Difluoro-6-(methylthio)pyridin-2-yl]pyrrolidin-3-yl}-3-[4-(7-{[2-(trimethylsilyl)ethoxy]methyl}-7H-pyrrolo[2,3-d]pyrimidin-4-yl)-1H-pyrazol-1-yl]propanenitrile (43 mg, 0.072 mmol) was added DCM (0.5 mL) and TFA (0.5 mL). The reaction was stirred at ambient temperature for 1 h, then the solvents were removed in vacuo and methanol (0.5 mL) and $NH_4OH$ (0.5 mL) were added. After 30 min, LCMS analysis indicated complete removal of SEM group. The solvents were removed and the residual material was purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), the product was isolated as a TFA salt, 18.9 mg. $^1$H NMR (300 MHz, DMSO-$D_6$): δ 12.58 (bs, 1H), 8.92 (s, 1H), 8.75 (s, 1H), 8.47 (s, 1H), 7.71 (s, 1H), 7.58 (m, 1H), 7.08 (m, 1H), 4.77 (m, 1H), 3.75 (m, 1H), 3.50 (m, 1H), 3.40 (m, 3H), 3.31 (m, 2H), 2.82 (m, 1H), 2.42 (s, 3H), 1.57 (m, 2H); LCMS calculated for $C_{22}H^{21}F_2N_8S$ $(M+H)^+$: m/z=467.158, observed 466.95.

Example 130

(3S)-3-{(3S)-1-[3,5-difluoro-6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile trifluoroacetate

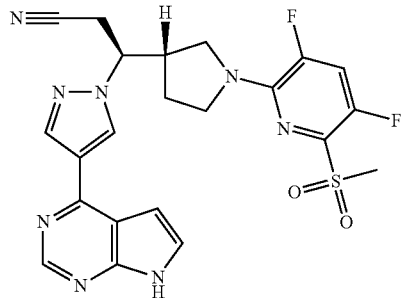 [SMILES: CS(=O)(=O)c1nc(N2CC[C@H]([C@H](CC#N)n3cc(-c4ncnc5[nH]ccc45)cn3)C2)c(F)cc1F]

(3S)-3-{(3S)-1-[3,5-Difluoro-6-(methylthio)pyridin-2-yl]pyrrolidin-3-yl}-3-[4-(7H-pyrrolo[2,3-d]pyrimidin-4-yl)-1H-pyrazol-1-yl]propanenitrile (from Example 129; 45 mg, 0.096 mmol) was dissolved in water (0.3 mL) and Oxone® (119 mg, 0.193 mmol) was added, the solution was stirred at ambient temperature for 3.5 h at which time LCMS analysis indicated presence of sulfoxide and sulfone overoxidized to N-oxide. The reaction mixture was partitioned between water and 3:1 $CHCl_3$/IPA, The organic phase was concentrated in vacuo and the residue was dissolved in MeOH and DMSO (~4 mL total). The mixture was filtered to remove insoluble solids and the filtrate was purified by reverse phase preparative HPLC to recover the product. The product was dissolved in EtOH (3.0 mL) and 10% Pd/C (15 mg) was added and the reaction was hydrogenated on a Parr shaker at 20 psi $H_2$ for 1 h at which time LCMS analysis indicated reduction of N-oxide. The reaction was filtered and concentrated in vacuo to provide the crude product, which was purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), to recover the sulfone product as a TFA salt, 2.0 mg. LCMS calculated for $C_{22}H_{21}F_2N_8O_2S$ $(M+H)^+$: m/z=499.147, observed 499.20.

Examples 131-133

The examples in the following table were made by procedures analogous to those used to prepare Example 130.

| Ex. | Structure | Name | MS (M + H |
|---|---|---|---|
| 131 | 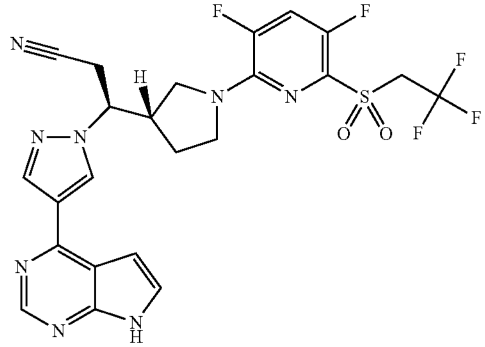 [SMILES: N#CC[C@@H]([C@H]1CCN(c2nc(S(=O)(=O)CC(F)(F)F)c(F)cc2F)C1)n1cc(-c2ncnc3[nH]ccc23)cn1] | (3S)-3-((3S)-1-{3,5-difluoro-6-[(2,2,2-trifluoroethyl)-sulfonyl]pyridin-2-yl}pyrrolidin-3-yl)-3-[4-(7H-pyrrolo[2,3-d]pyrimidin-4-yl)-1H-pyrazol-1-yl]propanenitrile trifluoroacetate | 567 |

| Ex. | Structure | Name | MS (M + H) |
|---|---|---|---|
| 132 | 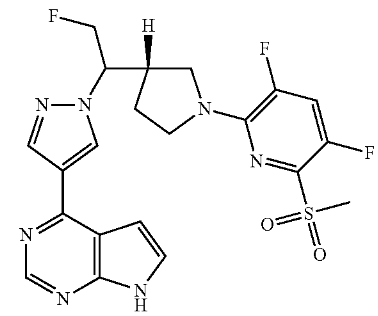 [SMILES: CS(=O)(=O)c1nc(N2CC[C@H](C(CF)n3cc(-c4ncnc5[nH]ccc45)cn3)C2)c(F)cc1F] | 4-[1-(1-{(3S)-1-[3,5-difluoro-6-(methylsulfonyl)py 2-yl]pyrrolidin-3-yl}- 2-fluoroethyl)-1H-pyrazol-4-yl]-7H-pyrrolo [2,3-d]pyrimidine trifluoroacetate | 492 |
| 13 | 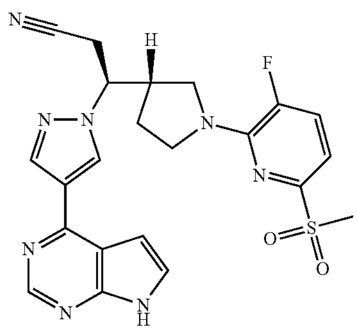 [SMILES: CS(=O)(=O)c1ccc(F)c(N2CC[C@H]([C@H](CC#N)n3cc(-c4ncnc5[nH]ccc45)cn3)C2)n1] | (3S)-3-{(3S)-1-[3-fluoro-6-(methylsulfonyl) pyridin-2-yl]pyrrolidin-3-yl}-3-[4-(7H-pyrrolo [2,3-d]pyrimidin-4-yl)-1H-pyrazol-1-yl] propanenitrile trifluoroacetate | 481 |

Example 134

(3S)-3-{(3S)-1-[2,5-difluoro-6-(methylsulfonyl)pyridin-3-yl]pyrrolidin-3-yl}-3-[4-(7H-pyrrolo[2,3-d]pyrimidin-4-yl)-1H-pyrazol-1-yl]propanenitrile trifluoroacetate

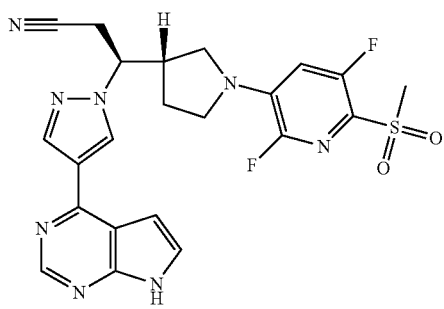 [SMILES: CS(=O)(=O)c1nc(F)c(N2CC[C@H]([C@H](CC#N)n3cc(-c4ncnc5[nH]ccc45)cn3)C2)cc1F]

Step 1. 2,3,5-trifluoro-6-(methylsulfonyl)pyridine 2,3,5-Trifluoro-6-(methylthio)pyridine (74 mg, 0.42 mmol) was dissolved in DCM (5 mL) and m-chloroperbenzoic acid (208 mg, 0.904 mmol) was added The solution was stirred at ambient temperature for 4 h at which time HPLC analysis indicated complete reaction. The reaction mixture was partitioned between water and $Et_2O$, the phases were separated and the aqueous phase was washed with additional $Et_2O$. The combined organic phase was washed with saturated $NaHSO_3$, saturated $NaHCO_3$, water, then brine, and was dried over $MgSO_4$ and concentrated in vacuo to provide the crude product as a white solid, 80 mg. The product was used in next step without further purification.

Step 2. (S)-3-((S)-1-(2,5-difluoro-6-(methylsulfonyl) pyridin-3-yl)pyrrolidin-3-yl)-3-(4-(7-((2-(trimethylsilyl)ethoxy)methyl)-7H-pyrrolo[2,3-d]pyrimidin-4-yl)-1H-pyrazol-1-yl)propanenitrile To a solution of (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (26 mg, 0.059 mmol; from Example 15, step 3) in NMP (0.096 mL) was added 2,3,5-trifluoro-6-(methylsulfonyl)pyridine (25.1 mg, 0.119 mmol) followed by DIPEA (14.8 µL, 0.0851 mmol). The reaction was capped and heated to 100° C. in an oil bath for 1.5 h at which time LCMS analysis indicated complete reaction. The reaction was cooled to ambient temperature and diluted with methanol and acetonitrile (total solvent added: 2 mL) and purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), to give the product. LCMS calculated for $C_{28}H_{35}F_2N_8O_3SSi$ $(M+H)^+$: m/z=629.229, observed 629.00.

Step 3. (3S)-3-{(3S)-1-[2,5-difluoro-6-(methylsulfonyl)pyridin-3-yl]pyrrolidin-3-yl}-3-[4-(7H-pyrrolo[2,3-d]pyrimidin-4-yl)-1H-pyrazol-1-yl]propanenitrile trifluoroacetate To (S)-3-((S)-1-(2,5-difluoro-6-(methylsulfonyl)pyridin-3-yl)pyrrolidin-3-yl)-3-(4-(7-((2-(trimethylsilyl)ethoxy)methyl)-7H-pyrrolo[2,3-d]pyrimidin-4-yl)-1H-pyrazol-1-yl)propanenitrile was added DCM (0.5 mL) and TFA (0.5 mL).

The reaction was stirred at ambient temperature for 1 h, then the solvents were removed in vacuo and methanol (0.5 mL) and NH₄OH (0.5 mL) were added. After 30 min, LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 14 mg. ¹H NMR (300 MHz, DMSO-D₆): δ 12.60 (bs, 1H), 8.98 (s, 1H), 8.80 (s, 1H), 8.52 (s, 1H), 7.74 (s, 1H), 7.11 (s, 1H), 7.05 (m, 1H), 4.82 (m, 1H), 3.75 (m, 1H), 3.56 (m, 1H), 3.20 (m, 4H), 3.19 (s, 3H), 2.90 (m, 1H), 1.65 (m, 2H); LCMS calculated for C₂₂H₂₁F₂N₈O₂S (M+H)⁺: m/z=499.148, observed 498.95.

Example 136

2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(1-fluoroethyl)nicotinonitrile trifluoroacetate

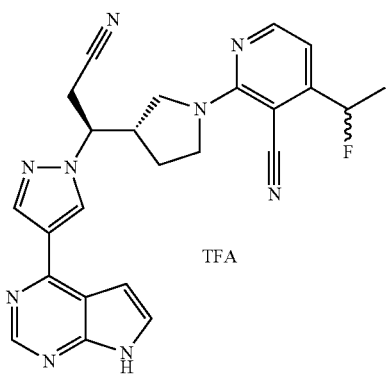 [SMILES: CC(F)c1ccnc(N2CC[C@H]([C@H](CC#N)n3cc(-c4ncnc5[nH]ccc45)cn3)C2)c1C#N]

Step 1. 2-chloro-4-(1-ethoxyvinyl)nicotinonitrile

A solution of 2-chloro-4-iodonicotinonitrile (from Example 122, Step 1; 240.0 mg, 0.9075 mmol) and tributyl (1-ethoxyvinyl)tin (398.58 mL, 1.1798 mmol) in toluene (3.2 mL) was degassed, and tetrakis(triphenylphosphine)palladium(0) (104.9 mg, 0.09075 mmol) was added. The reaction was degassed again and heated to 100° C. for 16 h. The reaction mixture was partitioned between water and EtOAc, the phases were separated and the aqueous phase was washed with additional EtOAc. The combined organic phase was washed with brine, dried over MgSO₄ and filtered and concentrated in vacuo to provide the crude product, 195.6 mg. Crude product was chromatographed on 40 g column, recovered 143 mg product. ¹H NMR (300 MHz CDCl₃): δ 8.51 (d, 1H), 7.44 (d, 1H), 4.85 (d, 1H), 4.60 (d, 1H), 3.97 (q, 2H), 1.42 (t, 3H).

Step 2. 4-acetyl-2-chloronicotinonitrile

2-Chloro-4-(1-ethoxyvinyl)nicotinonitrile (143 mg, 0.685 mmol) was dissolved in THF (9.1 mL) and 3.0 M of hydrogen chloride in water (5.7 mL, 17 mmol) was added, the reaction was stirred at 25° C. for 20 h, at which time LCMS analysis showed hydrolysis progressing, but not complete. The reaction mixture was partitioned between water and EtOAc, and the aqueous phase was extracted with additional EtOAc. The combined organic phase was washed with water, then brine, dried over MgSO₄ and filtered and concentrated in vacuo to provide the crude product. This was then dissolved in CHCl₃/hexanes and applied to 12 g ISCO column and chromatographed to give the purified product, 95.6 mg. ¹H NMR (300 MHz CDCl₃): δ 8.76 (d, 1H), 2.71 (s, 3H).

Step 3. 4-acetyl-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile To a solution of 4-acetyl-2-chloronicotinonitrile (95 mg, 0.53 mmol) in NMP (0.85 mL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (230 mg, 0.53 mmol; from Example 15, step 3) followed by DIPEA (131 μL, 0.754 mmol), the reaction was capped and heated to 100° C. in an oil bath for 2 h. The reaction was cooled to ambient temperature and partitioned between water and EtOAc, the phases were separated and the aqueous phase was washed with additional EtOAc. The combined organic phase was washed with water, then brine, dried over MgSO₄ and filtered and concentrated in vacuo to provide the crude product, 320 mg. The crude product was dissolved in CHCl₃/hexanes and applied to 40 g ISCO column, and was chromatographed to give the product (98.5 mg), 4-acetyl-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile. MS (EI): 582 (M+1).

Step 4. 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(1-fluoroethyl)nicotinonitrile To 4-acetyl-2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)nicotinonitrile (50.0 mg, 0.0859 mmol) in methanol (0.5 mL) cooled to 0° C. was added sodium tetrahydroborate (6.50 mg, 0.172 mmol), and was stirred for 10 min. The reaction was quenched with 1N HCl to acidic pH (lots of off-gassing), then neutralized with solid NaHCO₃ to pH 8, extracted 2× with EtOAc. EtOAc phase was washed with brine, dried over MgSO₄ and filtered. The EtOAc phase was evaporated to dryness to leave crude alcohol MS (EI): 584 (M+1). To a mixture of 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(1-hydroxyethyl)nicotinonitrile in DCM (0.89 mL) was added 2-methoxy-N-(2-methoxyethyl)-N-(trifluoro-λ(4)-sulfanyl)ethanamine (47.5 mL, 0.258 mmol) followed by one drop ethanol (9.4 mL, 0.16 mmol). The reaction was stirred at RT for 5.5 h and was partitioned between water and EtOAc, the phases were separated and the aqueous phase was washed with additional EtOAc. The combined organic phase was washed with water, then brine, dried over MgSO₄ and filtered and concentrated in vacuo to provide the crude product, 41.3 mg. Crude product was dissolved in MeOH/ACN and purified by preparative LCMS as in Example 129, to give 26.6 mg purified fluoride.

Step 5. 2-((3S)-3-{(1S)-2-cyano-1-[4-(7H-pyrrolo[2,3-d]pyrimidin-4-yl)-1H-pyrazol-1-yl]ethyl}pyrrolidin-1-yl)-4-(1-fluoroethyl)nicotinonitrile trifluoroacetate To the purified 2-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-4-(1-fluoroethyl)nicotinonitrile was added DCM (1.0 mL) and TFA (1.0 mL, 0.02 mol), after 1 h solvent was removed and added methanol (1.0 mL) and ammonium hydroxide (1.0, 0.03 mol), and was stirred for 20 min, and the residue after solvent removal was dissolved in ACN/MeOH and purified by preparative LMCS to recover the product as a TFA salt. MS (EI): 456 M+1). $^1$H NMR (300 MHz DMSO-D6): δ 12.5 (brs, 1H), 9.02 (s, 1H), 8.83 (s, 1H), 8.55 (s, 1H), 8.35 (dd, 1H), 7.82 (m, 1H), 7.18 (m, 1H), 6.80 (dd, 1H), 5.88 (m, 1H), 4.80 (m, 1H), 3.2.00-4.00 (m, 6H), 2.90 (m, 1H), 1.70 (m, 2H), 1.60 (m, 3H).

Example 138

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(difluoromethyl)pyrazine-2-carbonitrile trifluoroacetate

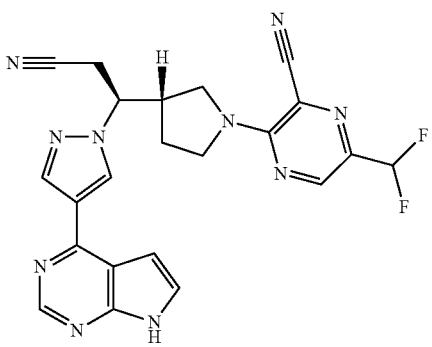 [SMILES: N#CC[C@@H]([C@H]1CCN(c2ncc(C(F)F)nc2C#N)C1)n1cc(-c2ncnc3[nH]ccc23)cn1]

Step 1. 3-amino-6-bromopyrazine-2-carbonitrile

A mixture of NaCN (140 mg, 2.85 mmol) and copper (I) cyanide (255 mg, 2.85 mmol) in anhydrous DMF (13 mL) was stirred at 120° C. for 20 min under an atmosphere of $N_2$. To the resulting clear solution was added drop-wise a solution of 3,5-dibromopyrazin-2-amine (from Aldrich; 800 mg, 3.16 mmol) in DMF (4.8 mL) and stirring was continued at 120° C. The reaction was held at 120° C. for 40 h at which time LCMS analysis indicated complete conversion. The reaction was cooled to ambient temperature and partitioned between water and EtOAc, the phases were separated and the aqueous phase was washed with additional EtOAc. The combined organic phase was washed with water followed by brine, then dried over $MgSO_4$ and concentrated in vacuo to provide the crude product, 597.1 mg, which was used without any further purification.

Step 2. 6-bromo-3-chloropyrazine-2-carbonitrile

To a solution of 3-amino-6-bromopyrazine-2-carbonitrile (587 mg, 2.95 mmol) in acetonitrile (29.4 mL) was added copper(II) chloride (470 mg, 3.5 mmol). The reaction was heated to 60° C. for 10 min, then t-butyl nitrite (510 mL, 4.3 mmol) was added drop-wise. The reaction was held at 60° C. for 16 h at which point LCMS indicated complete reaction. The reaction was cooled to ambient temperature and partitioned between 1N HCl and EtOAc and the phases were separated. The organic phase was washed 2× with water followed by brine, then dried over $MgSO_4$ and concentrated in vacuo to provide the crude product which crystallized upon standing. The product was purified (120 g prepacked $SiO_2$ cartridge, 85 mL/min, gradient from 0-20% EtOAc/hexanes over 12 min) to recover the desired product, 442 mg. $^1$H NMR (300 MHz, CDCl$_3$): δ 8.68 (s, 1H).

Step 3. 3-chloro-6-[(E)-2-ethoxyvinyl]pyrazine-2-carbonitrile

A solution of 6-bromo-3-chloropyrazine-2-carbonitrile (220 mg, 1.01 mmol) and (2-ethoxyethenyl)tri-n-butyltin (434 μL, 1.31 mmol) in toluene (1.8 mL) was degassed with $N_2$ and tetrakis(triphenylphosphine)palladium(0) (67.8 mg, 0.0587 mmol) was added. The reaction was degassed again and heated to 100° C. for 16 h at which time LCMS indicated complete conversion to desired product. The reaction was cooled to ambient temperature and partitioned between water and EtOAc, the phases were separated and the aqueous phase was washed with additional EtOAc. The combined organic phase was washed with water followed by brine, then dried over $MgSO_4$ and concentrated in vacuo to provide the crude product. This was purified (40 g prepacked $SiO_2$ cartridge, 40 mL/min, gradient from 0-50% EtOAc/hexanes over 20 min) to recover the product, 134 mg. $^1$H NMR (300 MHz, CDCl$_3$): δ 9.19 (s, 1H), 6.69 (d, 1H), 5.52 (d, 1H), 4.14 (m, 2H), 1.41 (t, 3H); LCMS calculated for $C_9H_9ClN_3O(M+H)^+$: m/z=210.043, observed 209.9.

Step 4. 3-chloro-6-formylpyrazine-2-carbonitrile

To 3-chloro-6-[(E)-2-ethoxyvinyl]pyrazine-2-carbonitrile (70.5 mg, 0.303 mmol) was added 1,4-dioxane (8.8 mL), water (2.2 mL), and sodium periodate (190 mg, 0.91 mmol), followed by a 4% solution of osmium tetraoxide in water (66.7 mL, 0.0105 mmol). The reaction was stirred at ambient temperature for 16 h at which time TLC analysis indicated complete reaction. The reaction mixture was partitioned between water and EtOAc, the phases were separated and the aqueous phase was washed with additional EtOAc. The combined organic phase was washed with water, then brine, dried over $MgSO_4$ and concentrated in vacuo to provide the crude product. This was purified (12 g prepacked $SiO_2$ cartridge, 30 mL/min, gradient from 0-50% EtOAc/hexanes over 16 min) to recover the product as a crystalline solid, 43.2 mg. $^1$H NMR (300 MHz, CDCl$_3$). δ 10.12 (s, 1H), 9.11 (s, 1H).

Step 5.
3-chloro-6-(difluoromethyl)pyrazine-2-carbonitrile

To 3-chloro-6-formylpyrazine-2-carbonitrile (31.0 mg, 0.185 mmol) in DCM (1.9 mL) was added 2-methoxy-N-(2-methoxyethyl)-N-(trifluoro-λ(4)-sulfanyl)ethanamine (100 μL, 0.55 mmol) followed by one drop of ethanol. The reaction was held at ambient temperature for 16 h at which time TLC analysis (3:1 hexanes:EtOAc) indicated complete reaction. The reaction mixture was partitioned between water and CHCl$_3$. The phases were separated and the aqueous phase was washed with additional CHCl$_3$. The combined organic phase was washed with brine, dried over $MgSO_4$ and concentrated in vacuo to provide the product, 43 mg. The product was used without further purification. $^1$H NMR (400 MHz, CDCl$_3$): δ 8.92 (s, 1H), 6.73 (t, 1H).

Step 6. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(difluoromethyl)pyrazine-2-carbonitrile To a solution of 3-chloro-6-(difluoromethyl)pyrazine-2-carbonitrile (30.0 mg, 0.158 mmol) in NMP (257 μL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (69 mg, 0.16 mmol; from Example 15, step 3) followed by DIPEA (39.5 µL, 0.227 mmol). The reaction was sealed and heated to 100° C. for 1 h at which time LCMS analysis indicated complete reaction. The reaction was cooled to ambient temperature and partitioned between water and EtOAc, the phases were separated and the aqueous phase was washed with additional EtOAc. The combined organic phase was washed with water, then brine, dried over MgSO$_4$ and concentrated in vacuo to provide the crude product. This was purified (4 g prepacked SiO$_2$ cartridge, 20 mL/min, gradient from 10-90% EtOAc/hexanes over 16 min) to recover the product, 49 mg. LCMS calculated for $C_{28}H_{33}F_2N_{10}OSi$ (M+H)$^+$: m/z=591.257, observed 591.05.

Step 7. 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(difluoromethyl)pyrazine-2-carbonitrile trifluoroacetate To 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(difluoromethyl)pyrazine-2-carbonitrile (49 mg, 0.083 mmol) was added DCM (0.5 mL) and TFA (0.5 mL). The reaction was stirred at ambient temperature for 1 h, then the solvents were removed in vacuo and methanol (0.5 mL) and NH$_4$OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), the product was isolated as a TFA salt, 34 mg. $^1$H NMR (400 MHz, CD$_3$OD): δ 9.00 (s, 1H), 8.89 (s, 1H), 8.57 (s, 1H), 8.51 (s, 1H), 7.86 (d, 1H), 7.28 (d, 1H), 6.63 (t, 1H), 4.90 (m, 2H), 4.15 (m, 1H), 3.97 (m, 1H), 3.75 (m, 2H), 3.22 (m, 1H), 3.12 (m, 1H), 3.09 (m, 1H), 1.91 (m, 2H). LCMS calculated for $C_{22}H_{19}F_2N_{10}$ (M+H)$^+$: m/z=461.18, observed 460.90.

Example 139

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(2,2-difluoroethyl)pyrazine-2-carbonitrile trifluoroacetate

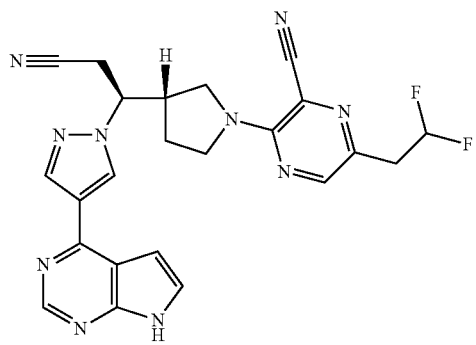 [SMILES: N#CC[C@@H]([C@H]1CCN(c2ncc(CC(F)F)nc2C#N)C1)n1cc(-c2ncnc3[nH]ccc23)cn1]

Step 1.
3-chloro-6-(2-oxoethyl)pyrazine-2-carbonitrile

3-Chloro-6-[(E)-2-ethoxyvinyl]pyrazine-2-carbonitrile (from Example 138, Step 3; 395 mg, 1.88 mmol) was dissolved in THF (25 mL) and 3.0 M HCl (16 mL, 47 mmol) was added. The reaction was heated to 60° C. for 3.5 h at which time LCMS indicated complete reaction. The reaction mixture was partitioned between saturated aqueous NaHCO$_3$ and EtOAc, the phases were separated and the aqueous phase was washed with additional EtOAc. The combined organic phase was washed with water followed by brine, then dried over MgSO$_4$ and concentrated in vacuo to provide the crude product, 417 mg. This material was used directly in the next reaction as it was found to decompose upon standing $^1$H NMR (300 MHz, CDCl$_3$): δ 9.91 (s, 1H), 8.53 (s, 1H), 4.08 (s, 2H).

Step 2. 3-chloro-6-(2,2-difluoroethyl)pyrazine-2-carbonitrile

Freshly prepared 3-chloro-6-(2-oxoethyl)pyrazine-2-carbonitrile (90.0 mg, 0.496 mmol; was dissolved in DCM (5.1 mL) and 2-methoxy-N-(2-methoxyethyl)-N-(trifluoro-λ(4)-sulfanyl)ethanamine (274 µL, 1.49 mmol) was added followed by one drop ethanol. The reaction was stirred at ambient temperature for 16 h at which time TLC and LCMS analysis indicated complete reaction. The reaction mixture was partitioned between water and CHCl$_3$. The phases were separated and the aqueous phase was washed with additional CHCl$_3$. The combined organic phase was washed with brine, dried over MgSO$_4$ and concentrated in vacuo to provide the crude product, 109 mg. This material was used directly in the next step. $^1$H NMR (300 MHz, CDCl$_3$): δ 8.49 (s, 1H), 6.12 (tt, 1H), 3.38 (m, 2H).

Step 3. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(2,2-difluoroethyl)pyrazine-2-carbonitrile trifluoroacetate To a solution of 3-chloro-6-(2,2-difluoroethyl)pyrazine-2-carbonitrile (100 mg, 0.49 mmol) in NMP (400 µL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (110 mg, 0.24 mmol; from Example 15, step 3) followed by DIPEA (61.3 µL, 0.352 mmol). The reaction was capped and heated to 100° C. in an oil bath for 1.5 h at which time LCMS analysis indicated complete reaction. The reaction was cooled to ambient temperature and diluted with methanol and acetonitrile (total solvent added: 2 mL) and purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min), the product was isolated as a TFA salt, 19 mg. LCMS calculated for $C_{29}H_{35}F_2N_{10}OSi$ (M+H)$^+$: m/z=605.273, observed 605.00.

Example 140

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(hydroxymethyl)pyrazine-2-carbonitrile trifluoroacetate

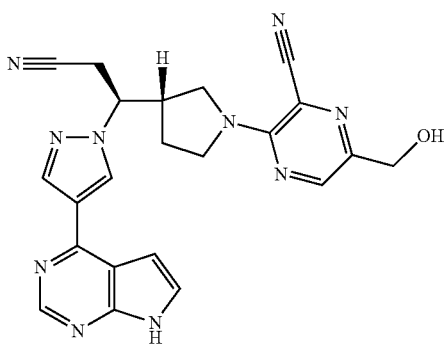 [SMILES: N#CC[C@@H]([C@H]1CCN(c2ncc(CO)nc2C#N)C1)n1cc(-c2ncnc3[nH]ccc23)cn1]

Step 1. chloro-6-(hydroxymethyl)pyrazine-2-carbonitrile

To 3-chloro-6-formylpyrazine-2-carbonitrile (from Example 138, Step 4; 20.0 mg, 0.12 mmol) was added ether (0.79 mL). The mixture was cooled to −78° C. and 1.0 M of borane in THF (140 μL, 0.14 mmol) was added. The reaction was held at −78° C. for 1.5 h, and was then quenched by addition of 0.1N HCl at −78° C. The solution was allowed to warm and EtOAc was added. The phases were separated and the aqueous phase was neutralized with NaHCO₃ and washed with additional EtOAc. The combined organic phase was washed with water followed by brine, then dried over MgSO₄ and concentrated in vacuo to provide the crude product, 20 mg. This material was taken directly on to next reaction. ¹H NMR (300 MHz, CD₃OD): δ 8.78 (s, 1H), 4.77 (s, 2H).

Step 2. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(hydroxymethyl)pyrazine-2-carbonitrile To a solution of 3-chloro-6-(hydroxymethyl)pyrazine-2-carbonitrile (20.0 mg, 0.106 mmol) in NMP (172 μL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (46 mg, 0.11 mmol; from Example 15, step 3) followed by DIPEA (26.5 mL, 0.152 mmol), the reaction was capped and heated to 100° C. in an oil bath for 1 h at which time LCMS analysis indicated complete reaction. The crude reaction solution was diluted with MeOH/ACN (total solvent added 2 mL) and purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min).

The purified product was lyophilized to dryness to recover the product as a TFA salt, 34 mg. LCMS calculated for $C_{28}H_{32}N_{10}O_2Si$ (M+H)⁺: m/z=571.271, observed 571.00.

Step 3. 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(hydroxymethyl)pyrazine-2-carbonitrile trifluoroacetate To 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(2,2-difluoroethyl)pyrazine-2-carbonitrile (12 mg, 0.02 mmol) was added DCM (0.5 mL) and TFA (0.5 mL). The reaction was stirred at ambient temperature for 1 h, then the solvents were removed in vacuo and methanol (0.5 mL) and NH₄OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 4.9 mg. LCMS calculated for $C_{22}H_{21}N_{10}O$ (M+H)⁺: m/z=441.190, observed 441.00.

Example 141

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(methoxymethyl)pyrazine-2-carbonitrile trifluoroacetate

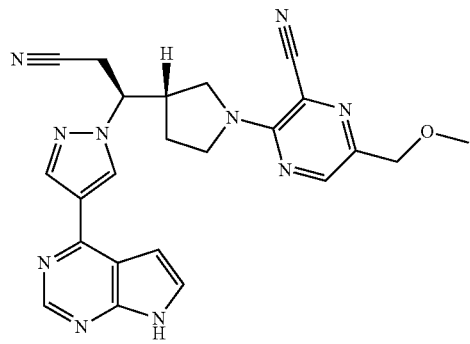 [SMILES: COCc1cnc(N2CC[C@H]([C@H](CC#N)n3cc(-c4ncnc5[nH]ccc45)cn3)C2)c(C#N)n1]

3-((3S)-3-{(1S)-2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-(hydroxymethyl)pyrazine-2-carbonitrile (Example 140; 24.3 mg, 0.0426 mmol) was combined with silver(II) oxide (52.7 mg, 0.426 mmol) and iodomethane (53.0 μL, 0.852 mmol) in THF (0.2 mL). The reaction was heated in sealed vessel for 3.5 h at which time LCMS analysis indicated complete reaction. The reaction was cooled to ambient temperature and filtered through a 0.45 μm Teflon filter. The filter was rinsed with methanol and the resulting organic filtrate was concentrated in vacuo to provide the crude product. To the crude product was added DCM (0.5 mL) and TFA (0.5 mL). The reaction was stirred at ambient temperature for 1 h, then the solvents were removed in vacuo and methanol (0.5 mL) and NH₄OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 5.5 mg. LCMS calculated for $C_{23}H_{23}N_{10}O$ (M+H)$^+$: m/z=455.206, observed 455.0.

Example 142

6-bromo-3-((3S)-3-{(1S)-2-cyano-1-[4-(7H-pyrrolo [2,3-d]pyrimidin-4-yl)-1H-pyrazol-1-yl] ethyl}pyrrolidin-1-yl)pyrazine-2-carbonitrile trifluoroacetate

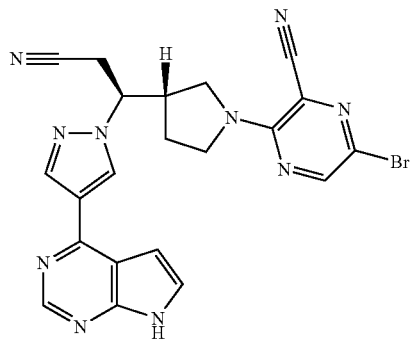 [SMILES: N#CC[C@@H]([C@H]1CCN(c2ncc(Br)nc2C#N)C1)n1cc(-c2ncnc3[nH]ccc23)cn1]

Step 1. 6-bromo-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile To a solution of 6-bromo-3-chloropyrazine-2-carbonitrile (Example 138 Step 2; 29 mg, 0.13 mmol) in NMP (216 mL) was added (3S)-3-[(3)S-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (58 mg, 0.13 mmol; from Example 15, step 3) followed by DIPEA (33.1 mL, 0.190 mmol). The reaction was capped and heated to 100° C. in an oil bath for 1 h at which time LCMS analysis indicated complete reaction. The reaction was cooled to ambient temperature and was partitioned between water and EtOAc, the phases were separated and the aqueous phase was washed with additional EtOAc. The combined organic phase was washed with water, followed by brine, then dried over $MgSO_4$ and concentrated in vacuo to provide the crude product. The product was purified (4 g prepacked $SiO_2$ cartridge, 20 mL/min, gradient from 0-75% EtOAc/hexanes over 18 min) to recover the desired product, 51 mg. LCMS calculated for $C_{27}H_{32}BrN_{10}OSi$ (M+H)$^+$: m/z=619.17, observed 618.90.

Step 2. 6-bromo-3-((3S)-3-{(1S)-2-cyano-1-[4-(7H-pyrrolo[2,3-d]pyrimidin-4-yl)-1H-pyrrolo-1-yl] ethyl}pyrrolidin-1-yl)pyrazine-2-carbonitrile trifluoroacetate To 6-bromo-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile (51 mg, 0.08 mmol) was added was added DCM (0.5 mL) and TFA (0.5 mL). The reaction was stirred at ambient temperature for 1 h, then the solvents were removed in vacuo and methanol (0.5 mL) and $NH_4OH$ (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 34 mg. LCMS calculated for $C_{21}H_{18}BrN_{10}$(M+H)$^+$: m/z=489.090, observed 489.10.

Example 143

3-((3S)-3-{(1S)-2-cyano-1-[4-(7H-pyrrolo[2,3-d] pyrimidin-4-yl)-1H-pyrazol-1-yl]ethyl}pyrrolidin-1-yl)-6-ethynylpyrazine-2-carbonitrile trifluoroacetate

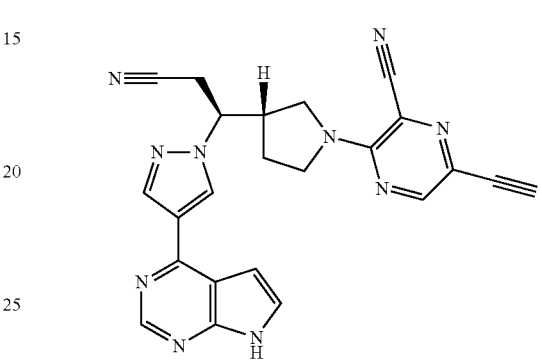

Step 1. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-[(trimethylsilyl)ethynyl]pyrazine-2-carbonitrile 6-Bromo-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile (Example 142; 40.0 mg, 0.0646 mmol) was dissolved in DMF (0.323 mL), and CuI (0.969 mg, 0.00509 mmol) was added. The reaction mixture was degassed with three vacuum/$N_2$ purge cycles, then $Et_3N$ (13.34 mL, 0.09568 mmol) and trimethylsilylacetylene (18.2 mL, 0.129 mmol) were added, followed by bis(triphenylphosphine)palladium (II) chloride (1.93 mg, 0.00276 mmol). The reaction was held at ambient temperature for 1.5 h at which time LCMS analysis indicated complete reaction. The reaction was treated with ether and a 9:1 solution of saturated aqueous $NH_4Cl/NH_4OH$ and the phases were separated. The aqueous phase was extracted with additional ether, the combined ether solution was washed with $H_2O$ followed by brine, then dried over $MgSO_4$ and concentrated in vacuo provide the crude product. The product was purified (4 g prepacked $SiO_2$ cartridge, 20 mL/min, gradient from 0-75% EtOAc/hexanes over 18 min) to recover the desired product, 41 mg. LCMS calculated for $C_{32}H_{41}N_{10}OSi_2$(M+H)$^+$: m/z=637.300, observed 637.10.

Step 2. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-ethynylpyrazine-2-carbonitrile 3-((3S)-3-{(1S)-2-Cyano-1-[4-(7-{[2-(trimethylsilyl) ethoxy]methyl}-7H-pyrrolo[2,3-d]pyrimidin-4-yl)-1H-pyrazol-1-yl]ethyl}pyrrolidin-1-yl)-6-[(trimethylsilyl)ethynyl]pyrazine-2-carbonitrile (41 mg, 0.064 mmol) was dissolved in THF (51.0 μL), this solution was cooled to 0° C., and water (3.4 μL) was added, followed by drop-wise addition of 1.0 M of TBAF in THF (75 μL, 0.075 mmol). The reaction was allowed to warm from 0° C. to 15° C. over 1 h at which time LCMS analysis indicated complete reaction. The reaction mixture was partitioned between water and EtOAc, the phases were separated and the aqueous phase was washed with additional EtOAc. The combined organic phase was washed with 3× water, followed by brine, then dried over MgSO$_4$ and concentrated in vacuo to provide the crude product, 44 mg. LCMS calculated for $C_{29}H_{33}N_{10}OSi(M+H)^+$: m/z=565.261, observed 565.00.

Step 3. 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-ethynylpyrazine-2-carbonitrile trifluoroacetate To 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-ethynylpyrazine-2-carbonitrile (10.8 mg, 0.0191 mmol) was added DCM (0.5 mL) and TFA (0.5 mL), the reaction was stirred at ambient temperature for 3 h. The reaction was evaporated to dryness, then methanol (0.5 mL) and NH$_4$OH (0.5 mL) were added. The reaction was stirred 30 min. at which time LCMS indicated complete deprotection. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 4.8 mg. $^1$H NMR (300 MHz, DMSO-D$_6$): δ 12.40 (bs, 1H), 8.90 (s, 1H), 8.73 (s, 1H), 8.43 (m, 2H), 7.70 (s, 1H), 7.03 (s, 1H), 4.82 (m, 1H), 3.89 (m, 1H), 3.78 (m, 1H), 3.60 (m, 2H), 3.29 (m, 3H), 2.85 (m, 1H), 1.68 (m, 2H); LCMS calculated for $C_{23}H_{19}N_{10}(M+H)^+$: m/z=435.179, observed 434.95.

Example 144

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-ethylpyrazine-2-carbonitrile trifluoroacetate

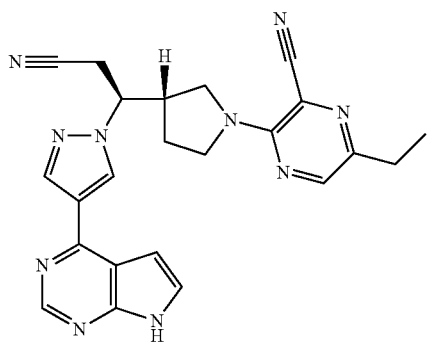 [SMILES: CCc1cnc(N2CC[C@H]([C@H](CC#N)n3cc(-c4ncnc5[nH]ccc45)cn3)C2)c(C#N)n1]

3-((3S)-3-{(1S)-2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-ethynylpyrazine-2-carbonitrile (Example 143; 33 mg, 0.058 mmol) was dissolved in EtOH (2.3 mL) and 10% Pd/C (8.7 mg, 0.0082 mmol) was added. The mixture was hydrogenated at 29 psi in a Parr shaker for 3 h at which time LCMS analysis indicated complete reduction. The reaction was filtered through a 0.45 μm Teflon filter and the filter was rinsed with MeOH. The filtrate was concentrated in vacuo to provide the product. To the residue was added DCM (0.5 mL) and TFA (0.5 mL). The reaction was stirred at ambient temperature for 1 h, then the solvents were removed in vacuo and methanol (0.5 mL) and NH$_4$OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 9.8 mg. $^1$H NMR (300 MHz, DMSO-D$_6$): δ 12.62 (bs, 1H), 8.99 (s, 1H), 8.82 (s, 1H), 8.53 (s, 1H), 8.29 (s, 1H), 7.76 (s, 1H), 7.12 (s, 1H), 4.90 (m, 1H), 3.90 (m, 1H), 3.74 (m, 1H), 3.59 (m, 2H), 3.36 (m, 3H), 2.90 (m, 1H), 2.61 (m, 2H), 1.70 (m, 2H), 1.11 (m, 3H); LCMS calculated for $C_{23}H_{23}N_{10}(M+H)^+$: m/z=439.211, observed 438.95.

Example 145

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile trifluoroacetate

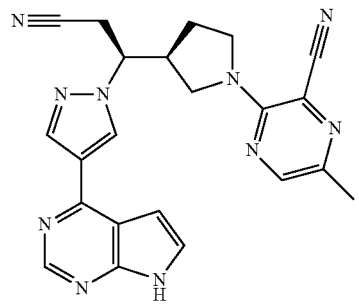 [SMILES: Cc1cnc(N2CC[C@H]([C@H](CC#N)n3cc(-c4ncnc5[nH]ccc45)cn3)C2)c(C#N)n1]

Step 1. 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-methylpyrazine-2-carbonitrile 6-Bromo-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile (Example 142; 55.8 mg, 0.09 mmol) and tetrakis(triphenylphosphine)palladium(0) (4.16 mg, 0.00360 mmol) were dissolved in THF (0.28 mL) and 2.0 M of trimethylaluminum in toluene (90.0 μL, 0.180 mmol) was added dropwise. The reaction was heated to 70° C. for 3.5 h at which time LCMS analysis indicated complete reaction. The reaction was cooled to ambient temperature and was diluted with toluene (0.28 mL) and MeOH (71 μL) was added drop-wise until reactivity subsided. The reaction was then reheated to 70° C. for 10 min, then 2 mL of saturated aqueous NH$_4$Cl was added, continued heating at 70° C. for 10 min. The reaction was cooled to ambient temperature and partitioned between water and EtOAc, the phases were separated and the aqueous phase was washed with additional EtOAc. The combined organic phase was washed with water, followed by brine, then dried over MgSO$_4$ and concentrated in vacuo to provide the crude product. The product was purified (4 g prepacked SiO$_2$ cartridge, 20 mL/min, gradient from 0-90% EtOAc/hexanes over 20 min) to recover the desired product, 44 mg. LCMS calculated for $C_{28}H_{35}N_{10}OSi$ (M+H)$^+$: m/z=555.276, observed 555.05.

Step 2. 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile trifluoroacetate To 3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-6-methylpyrazine-2-carbonitrile (44 mg, 0.08 mmol) was added DCM (0.5 mL) and TFA (0.5 mL). The reaction was stirred at ambient temperature for 1 h, then the solvents were removed in vacuo and methanol (0.5 mL) and NH$_4$OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 25.8 mg. LCMS calculated for $C_{22}H_{21}N_{10}$(M+H)$^+$: m/z=425.195, observed 425.20.

Example 146

3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile trifluoroacetate

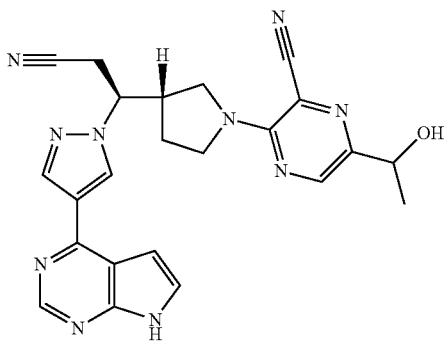 [SMILES: CC(O)c1cnc(N2CC[C@H]([C@H](CC#N)n3cc(-c4ncnc5[nH]ccc45)cn3)C2)c(C#N)n1]

Step 1.
3-chloro-6-(1-ethoxyvinyl)pyrazine-2-carbonitrile

A solution of 6-bromo-3-chloropyrazine-2-carbonitrile (Example 138 Step 2; 39.4 mg, 0.18 mmol) and tributyl(1-ethoxyvinyl)tin (79.2 μL, 0.23 mmol) in toluene (0.64 mL) was degassed with three vacuum/N$_2$ cycles, and tetrakis(triphenylphosphine)palladium(0) (20.84 mg, 0.01804 mmol) was added. The reaction was degassed again and heated to 100° C. for 3 h at which time LCMS analysis indicated complete reaction. The reaction was cooled to ambient temperature and was partitioned between water and EtOAc, the phases were separated and the aqueous phase was washed with additional EtOAc. The combined organic phase was washed with brine, dried over MgSO$_4$ and concentrated in vacuo to provide the crude product, 119.4 mg. The product was purified (4 g prepacked SiO$_2$ cartridge, 20 mL/min, gradient from 0-20% EtOAc/hexanes over 10 min) to recover the desired product, 19 mg. $^1$H NMR (300 MHz, CDCl$_3$): δ 8.87 (s, 1H), 5.54 (d, 1H), 4.59 (d, 1H), 4.01 (m, 2H), 1.48 (t, 3H); LCMS calculated for $C_9H_9ClN_3O$(M+H)$^+$: m/z=209.85; found 209.85.

Step 2. 6-acetyl-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile To a solution of 3-chloro-6-(1-ethoxyvinyl)pyrazine-2-carbonitrile (9.0 mg, 0.043 mmol) in NMP (0.0806 mL) was added (3S)-3-[(3S)-pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (22 mg, 0.050 mmol; from Example 15, step 3) followed by DIPEA (12.4 μL, 0.0710 mmol). The reaction was capped and heated to 100° C. in an oil bath for 2 h at which time LCMS analysis indicated complete reaction. The reaction was cooled to ambient temperature and partitioned between water and EtOAc, the phases were separated and the aqueous phase was washed with additional EtOAc. The combined organic phase was washed with water followed by brine, then dried over MgSO$_4$ and concentrated in vacuo to provide the crude product, 32.8 mg. This was purified (4 g prepacked SiO$_2$ cartridge, 20 mL/min, gradient from 0-90% EtOAc/hexanes over 14 min) to recover the desired product, 22 mg. LCMS calculated for $C_{29}H_{35}N_{10}O_2Si$(M+H)$^+$: m/z=583.271, observed 583.05.

Step 3. 3-((3S)-3-{(1S)-2-cyano-1-[4-(7H-pyrrolo[2,3-d]pyrimidin-4-yl)-1H-pyrazol-1-yl]ethyl}pyrrolidin-1-yl)-6-(1-hydroxyethyl)pyrazine-2-carbonitrile trifluoroacetate A solution of 6-acetyl-3-((3S)-3-{(1S)-2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyrazine-2-carbonitrile (22 mg, 0.038 mmol) in MeOH (219.6 μL) was cooled to 0° C. and sodium tetrahydroborate (2.86 mg, 0.0755 mmol) was added. The reaction was held at 0° C. for 10 min. at which time TLC analysis indicated complete reduction of ketone. The reaction was quenched with dropwise addition of 1N HCl to give pH 3, then the reaction was neutralized by gradual addition of solid NaHCO$_3$ to pH 8. The reaction was extracted 2× with EtOAc and the resulting organic solution was washed with brine, dried over MgSO$_4$ concentrated in vacuo to provide the crude product. LCMS calculated for $C_{29}H_{37}N_{10}O_2Si$ (M+H)$^+$: m/z=585.287, observed 585.05. To this product was added DCM (0.5 mL) and TFA (0.5 mL). The reaction was stirred at ambient temperature for 1 h, then the solvents were removed in vacuo and methanol (0.5 mL) and NH$_4$OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 μm particle size, 30×100 mm, mobile phase A: water (0.1% TFA), B: methanol (0.1% TFA), flow rate 60 mL/min), the product was isolated as a TFA salt, 5.2 mg. $^1$H NMR (400 MHz, CDCl$_3$): δ NMR (300 MHz, CD$_3$OD): δ 8.98 (s, 1H), 8.89 (s, 1H), 8.57 (s, 1H), 8.42 (s, 1H), 7.85 (d, 1H), 7.26 (d, 1H), 4.77 (m, 2H), 4.08 (m, 1H), 3.90 (m, 1H), 3.71 (m, 2H), 3.40 (m, 1H), 3.22 (m, 2H), 3.08 (m, 1H), 1.90 (m, 2H), 1.42 (m, 3H); LCMS calculated for $C_{23}H_{23}N_{10}O$(M+H)$^+$: m/z=455.206, observed 454.95.

Example 147

3-fluoro-5-((3S)-3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile trifluoroacetate

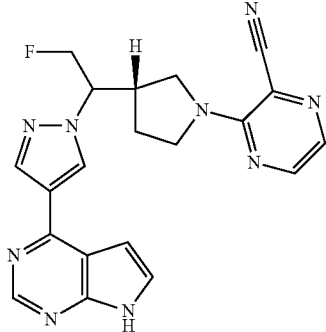 [SMILES: N#Cc1nccnc1N1CC[C@H](C(CF)n2cc(-c3ncnc4[nH]ccc34)cn2)C1]

To a solution of 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 37 mg, 0.087 mmol) and DIPEA (3.0E1 µL, 0.17 mmol) in NMP (0.7 mL) was added 3-chloropyrazine-2-carbonitrile and the reaction was heated to 130° C. for 2 h at which time LCMS analysis indicated complete reaction. The reaction mixture was partitioned between water and EtOAc, the aqueous phase was extracted another 2× with EtOAc. The combined organic phase was washed with brine, dried over MgSO$_4$ and concentrated in vacuo to provide the crude product. LCMS calculated for C$_{26}$H$_{33}$FN$_9$OSi (M+H)$^+$: m/z=534.256, observed 534.15. The crude product was treated with DCM (0.5 mL) and TFA (0.5 mL). The reaction was stirred at ambient temperature for 1 h, then the solvents were removed in vacuo and methanol (0.5 mL) and NH$_4$OH (0.5 mL) were added. After 30 min LCMS analysis indicated complete removal of SEM group. The solvents were removed and the residual material was purified by reverse phase preparative LCMS on a Waters Fraction-Lynx system using mass directed fractionation (column Waters SunFire C18, 5 µm particle size, 30×100 mm, mobile phase A: water (0.1% TFA), B: methanol (0.1% TFA), flow rate 60 mL/min, the product was isolated as a TFA salt, 13.4 mg. LCMS calculated for C$_{21}$H$_{20}$FN$_8$(M+H)$^+$: m/z=403.179, observed 404.10.

Example 148

3-{1-[2-(ethylsulfonyl)pyridin-4-yl]pyrrolidin-3-yl}-3-[3-(7H-pyrrolo[2,3-d]pyrimidin-4-yl)-1H-pyrrol-1-yl]propanenitrile (racemate)

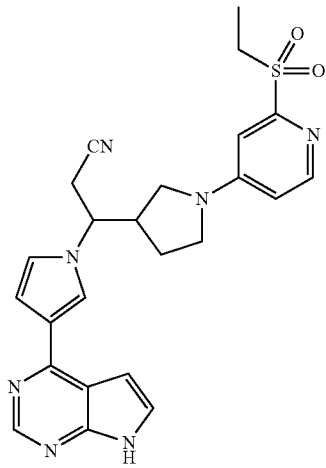 [SMILES: CCS(=O)(=O)c1cc(N2CCC(C(CC#N)n3ccc(-c4ncnc5[nH]ccc45)c3)C2)ccn1]

Step 1. 4-chloro-2-(ethylsulfonyl)pyridine

To a solution of 2,4-dichloropyridine (0.20 mL, 1.8 mmol) and ethanethiol (0.14 mL, 1.8 mmol) in 1,4-dioxane (1 mL), was added sodium hydride (60% in mineral oil, 0.074 g, 1.8 mmol), in one portion. The mixture was stirred at RT for 3 days. Water was added into the reaction and the product was extracted with diethyl ether. The extracts were dried over sodium sulfate, decanted and the solvent removed by rotary evaporation. Flash column chromatography, eluting with a gradient of 0-10% ethyl acetate in hexanes, was used for partial purification of product. The product was dissolved in DCM (10 mL) and treated with m-chloroperbenzoic acid (0.28 g, 1.1 mmol) and stirred for 2 h. The mixture was washed with NaHCO$_3$ solution and the DCM layer was dried over sodium sulfate, decanted and concentrated. Purification by flash column chromatography, eluting with a gradient of 0-50% ethyl acetate in hexanes afforded product (48 mg, 12%). $^1$H NMR (400 MHz, CDCl$_3$): δ 8.65 (d, 1H), 8.11 (d, 1H), 7.56 (dd, 1H), 3.44 (q, 2H), 1.32 (t, 3H); LCMS (M+H)$^+$: 206.0.

Step 2. 3-{1-[2-(ethylsulfonyl)pyridin-4-yl]pyrrolidin-3-yl}-3-[3-(7H-pyrrolo[2,3-d]pyrimidin-4-yl)-1H-pyrrol-1-yl]propanenitrile A solution of 4-chloro-2-(ethylsulfonyl)pyridine (15 mg, 0.073 mmol) and 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (32 mg, 0.073 mmol, from Example 33, Step 3) in NMP (0.20 mL) and 4-methylmorpholine (16 µL) was heated to 120° C. in the microwave for 15 min. The reaction mixture was partitioned between water and ethyl acetate. The layers were separated and the aqueous layer was extracted a total of three times with ethyl acetate. The extracts were dried over sodium sulfate, decanted and concentrated. The crude product was deprotected by stirring in 50% TFA/DCM for 1 h, evaporated and then stirred with excess EDA in methanol. The product was purified by preparative HPLC-MS, eluting with a gradient of ACN and H$_2$O containing 0.15% NH$_4$OH, frozen and lyophilized to afford the product as the free base (11 mg, 31%). $^1$H NMR (400 MHz, DMSO-d6): δ 11.96 (br s, 1H), 8.61 (s, 1H), 8.25 (d, 1H), 8.01 (t, 1H), 7.52 (d, 1H), 7.16 (t, 1H), 7.06 (br s, 1H), 6.95 (dd, 1H), 6.94 (d, 1H), 6.68 (dd, 1H), 4.54 (td, 1H), 3.63 (dd, 1H), 3.52-3.22 (m, 7H), 2.97-2.85 (m, 1H), 1.76-1.59 (m, 2H), 1.10 (t, 3H); LCMS (M+H)$^+$: 476.1.

Example 149

5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile (both racemic and single enantiomers isolated)

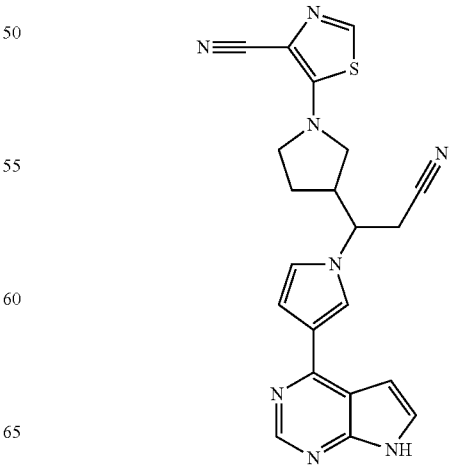

Step 1. 5-bromo-1,3-thiazole-4-carbonitrile

To a mix of 5-bromo-1,3-thiazole-4-carboxamide (prepared according to the procedure reported in WO2008/057336 from 5-bromo-1,3-thiazole-4-carboxylic acid obtained from SynChem; 2.75 g, 13.3 mmol) and triethylamine (9.26 mL, 66.4 mmol) in DCM (50 mL) was added trichloroacetic anhydride (7.28 mL, 39.8 mmol) drop-wise at 0° C. The mixture was stirred at 0° C. for 1 h. The reaction was quenched by the addition of saturated aqueous $NaHCO_3$ solution, extracted with DCM, dried over $MgSO_4$, concentrated and purified on silica gel (eluting with a gradient from 0-20% EtOAc/Hexanes) to afford product (2.19 g, 87%). LCMS $(M+H)^+$: 190.9/188.9.

Step 2. 5-(3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)-1,3-thiazole-4-carbonitrile 5-Bromo-1,3-thiazole-4-carbonitrile (24 mg, 0.13 mmol) and 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (51 mg, 0.12 mmol, from Example 33, Step 3) were mixed with 1-butyl-3-methyl-1H-imidazol-3-ium tetrafluoroborate (0.15 g, 0.66 mmol), and 4-methylmorpholine (14 µL, 0.13 mmol) was added. The mixture was heated at 120° C. for 2 h, then cooled to RT, partitioned between EtOAc and brine, and the brine layer was extracted with EtOAc three times. The combined organic extracts were dried over sodium sulfate and concentrated. Flash column chromatography, eluting with a gradient of 0-100% ethyl acetate in hexanes afforded product (27 mg, 42%). $^1$H NMR (300 MHz, CDCl$_3$): δ 8.82 (s, 1H), 7.91 (s, 1H), 7.72 (s, 1H), 7.36 (d, 1H), 7.04-6.99 (m, 1H), 6.94 (t, 1H), 6.84 (d, 1H), 5.66 (s, 2H), 4.28-4.16 (m, 1H), 3.96 (dd, 1H), 3.68-3.41 (m, 5H), 3.20-3.02 (m, 1H), 2.97 (m, 2H), 2.09-1.73 (m, 2H), 0.99-0.85 (m, 2H), −0.06 (s, 9H); LCMS $(M+H)^+$: 545.2.

A portion of this material was deprotected to afford the racemate in the following procedure, Step 3.

A portion (20 mg) of this SEM-protected product was separated into its enantiomers by chiral chromatography (Chiral Technologies ChiralCel OD-H: 30×250 mm, 5 µm, 45% EtOH/55% Hexanes at 15 mL/min; enantiomer 1: retention time 41.8 min; enantiomer 2: retention time 47.4 min). Each enantiomer was evaporated and deprotected separately according to the following procedures in Step 4 and Step 5.

Step 3. 5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile (racemic)

Racemic 5-(3-{2-cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)-1,3-thiazole-4-carbonitrile (7.0 mg, 0.013 mmol) was dissolved in a mixture of 1:1 DCM/TFA, stirred for 1 h, and concentrated. The residue was dissolved in MeOH (1 mL), and 0.2 mL EDA was added and the reaction was stirred for 15 min. Preparative HPLC-MS, eluting with a gradient of ACN and H$_2$O containing 0.15% NH$_4$OH, followed by lyophilization afforded the product as the free base (3.5 mg, 66%). $^1$H NMR (400 MHz, DMSO-d6): δ 11.97 (br s, 1H), 8.61 (s, 1H), 8.20 (s, 1H), 7.99 (t, 1H), 7.52 (d, 1H), 7.14 (t, 1H), 6.96-6.92 (m, 2H), 4.58 (td, 1H), 3.68 (dd, 1H), 3.66-3.59 (m, 1H), 3.54-3.37 (m, 3H), 3.22 (dd, 1H), 3.02-2.91 (m, 1H), 1.80-1.63, (m, 2H); LCMS $(M+H)^+$: m/z=415.0.

Step 4. 5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile (single enantiomer 1)

5-(3-{2-Cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)-1,3-thiazole-4-carbonitrile (6.0 mg, 0.011 mmol; Peak 1 from Step 2) was dissolved in a mixture of 1:1 DCM/TFA, the mixture was stirred for 1 h, then concentrated. The residue was redissolved in 1 mL MeOH, and 0.2 mL EDA was added. Preparative HPLC-MS, eluting with a gradient of ACN and H$_2$O containing 0.15% NH$_4$OH, followed by lyophilization afforded the product as the free base (2.5 mg, 54%). $^1$H NMR (400 MHz, DMSO-d6): δ 11.97 (br s, 1H), 8.61 (s, 1H), 8.19 (s, 1H), 7.99 (t, 1H), 7.52 (dd, 1H), 7.14 (dd, 1H), 6.96-6.93 (m, 2H), 4.58 (td, 1H), 3.68 (dd, 1H), 3.66-3.59 (m, 1H), 3.54-3.36 (m, 3H), 3.22 (dd, 1H), 3.03-2.90 (m, 1H), 1.80-1.64 (m, 2H); LCMS $(M+H)^+$: 415.0.

Step 5. 5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile (single enantiomer 2)

5-(3-{2-Cyano-1-[3-(7-{[2-(trimethylsilyl)ethoxy]methyl}-7H-pyrrolo[2,3-d]pyrimidin-4-yl)-1H-pyrrol-1-yl]ethyl}pyrrolidin-1-yl)-1,3-thiazole-4-carbonitrile (6.0 mg, 0.011 mmol; Peak 2 from Step 2) was dissolved in a mixture of 1:1 DCM/TFA, the mixture was stirred for 1 h, then concentrated. The residue was redissolved in 1 mL MeOH, 0.2 mL EDA was added. Preparative HPLC-MS, eluting with a gradient of ACN and H$_2$O containing 0.15% NH$_4$OH, followed by lyophilization afforded the product as the free base (2.5 mg, 54%). $^1$H NMR (400 MHz, DMSO-d6): δ 11.97 (br s, 1H), 8.61 (s, 1H), 8.19 (s, 1H), 7.99 (t, 1H), 7.52 (dd, 1H), 7.14 (t, 1H), 6.96-6.93 (m, 2H), 4.58 (td, 1H), 3.68 (dd, 1H), 3.66-3.60 (m, 1H), 3.54-3.38 (m, 3H), 3.22 (dd, 1H), 3.02-2.90 (m, 1H), 1.81-1.62 (m, 2H); LCMS $(M+H)^+$: 415.0.

Example 150

3-[1-(2-mercaptopyrimidin-4-yl)pyrrolidin-3-yl]-3-[4-(7H-pyrrolo[2,3-d]pyrimidin-4-yl)-1H-pyrazol-1-yl]propanenitrile (single enantiomer)

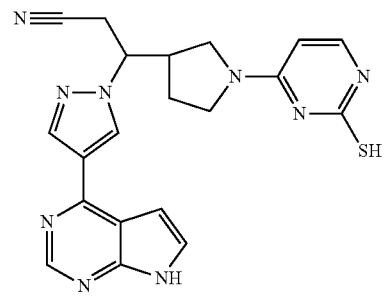 [SMILES: N#CCC(C1CCN(c2ccnc(S)n2)C1)n1cc(-c2ncnc3[nH]ccc23)cn1]

Step 1. 3-[7-(2-mercaptopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (150 mg, 0.34 mmol; from Example 15, Step 3) and 2,4-dichloropyrimidine (61 mg, 0.41 mmol) were dissolved in 1,4-dioxane (0.30 mL) and DIPEA (119 μL, 0.686 mmol) was added. The solution was heated to 100° C. for 30 min. The mixture was concentrated, ethanol (1.0 mL) was added, followed by sodium hydrogen sulfide dihydrate (82 mg, 0.9 mmol). The suspension was then stirred at RT for 24 h. Additional sodium hydrogen sulfide dihydrate (31 mg, 0.34 mmol) was added and stirred at RT for an additional 3 days. The mixture was diluted with acetonitrile and filtered. Preparative HPLC-MS, eluting with a gradient of ACN and H$_2$O containing 0.15% NH$_4$OH, followed by lyophilization afforded the product as the free base, 75 mg. LCMS (M+H)$^+$: 548.1.

Step 2. 3-[7-(2-mercaptopyrimidin-4-yl)pyrrolidin-3-yl]-3-[4-(7H-pyrrolo[2,3-d]pyrimidin-4-yl)-1H-pyrazol-1-yl]propanenitrile 3-[1-(2-Mercaptopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (19 mg, 0.024 mmol) was dissolved in a 1:1 mixture of TFA/DCM, stirred for 1 h at RT, then concentrated. The residue was dissolved in 1 mL methanol, and 0.2 mL EDA was added and the reaction stirred for 30 min. Preparative HPLC-MS, eluting with a gradient of ACN and H$_2$O containing 0.15% NH$_4$OH, followed by lyophilization afforded the product as the free base. $^1$H NMR (400 MHz, DMSO-d6): δ 8.87 (s, 1H), 8.69 (s, 1H), 8.43 (s, 1H), 7.61 (d, 1H), 7.50 (br d, 1H), 6.99 (d, 1H), 6.01 (br d, 1H), 4.82 (br m, 1H), 4.00-2.73 (m, 7H), 1.79-1.47 (m, 2H); LCMS (M+H)$^+$: 418.0.

Example 151

N-[4-(3-{2-cyano-1-[4-(7H-pyrrolo[2,3-d]pyrimidin-4-yl)-1H-pyrazol-1-yl]ethyl}pyrrolidin-1-yl)pyrimidin-2-yl]-N,N-dimethylsulfonamide (single enantiomer)

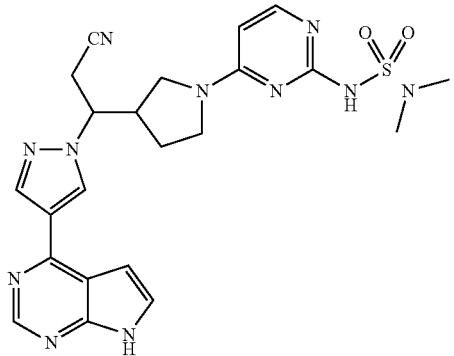

Step 1: 3-[7-(2-aminopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.100 g, 0.228 mmol, from Example 15, Step 3) and 4-chloropyrimidin-2-amine (0.031 g, 0.24 mmol, SynChem) in ethanol (0.1 mL) and DIPEA (0.1 mL, 0.6 mmol) was heated to 120° C. for 1.5 h. The reaction mixture was partitioned between water and ethyl acetate, and the aqueous phase was extracted three times. The extracts were dried over sodium sulfate, decanted and concentrated. The product was used without further purification in the following step (120 mg, 99%). LCMS (M+H)$^+$: 531.2.

Step 2. N-[4-(3-{2-cyano-1-[4-(7H-pyrrolo[2,3-d]pyrimidin-4-yl)-1H-pyrazol-1-yl]ethyl}pyrrolidin-1-yl)pyrimidin-2-yl]-N,N-dimethylsulfonamide 3-[1-(2-Aminopyrimidin-4-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (20 mg, 0.04 mmol) was dissolved in DCM (0.20 mL), and DIPEA (13 μL, 0.075 mmol) was added followed by dimethylsulfamoyl chloride (4.0 μL, 0.038 mmol). The reaction was stirred for 16 h. Additional dimethylsulfamoyl chloride (2.0 μL, 0.019 mmol) was added, stirred for a few h, then concentrated. The residue was stirred with 50% TFA/DCM for 1 h, concentrated, then re-dissolved in methanol and treated with excess EDA. Preparative HPLC-MS, eluting with a gradient of ACN and H$_2$O containing 0.15% NH$_4$OH, followed by lyophilization afforded the product as the free base. $^1$H NMR (500 MHz, CD$_3$OD) (rotamers): δ 8.82 (s, 1H), 8.77 (s, 1H), 8.49-8.45 (m, 1H), 7.68 (d, 1H), 7.67 and 7.54 (each as d, together=1H), 7.10 (d, 1H), 6.21 and 6.03 (each as d, together=1H), 4.86 (td, 1H), 4.04-2.95 (m, 7H), 2.81-2.77 (br singlets, together 6H), 2.00-1.77 (m, 2H); LCMS (M+H)$^+$: 508.1.

Example 152

4-(3-{2-cyano-1-[4-(7H-pyrrolo[2,3-d]pyrimidin-4-yl)-1H-pyrazol-1-yl]ethyl}pyrrolidin-1-yl)-N-methylpyridine-2-carboxamide (single enantiomer)

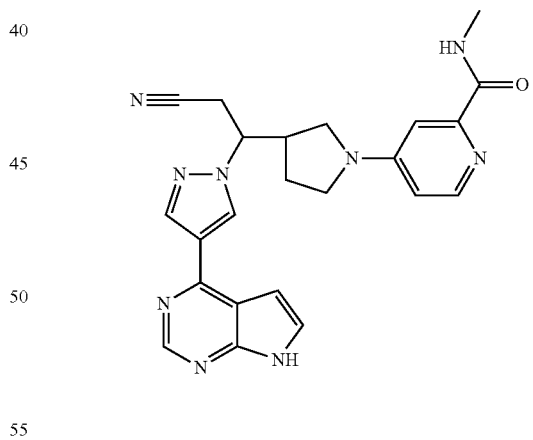

Step 1. 4-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyridine-2-carboxylic acid 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (250 mg, 0.57 mmol; from Example 15, Step 3) and 4-chloropyridine-2-carboxylic acid (135 mg, 0.857 mmol) were combined in ethanol (1.2 mL) and DIPEA (0.20 mL, 1.14 mmol) and heated to 120° C. in a sealed vial for 2 h, with additional 4-chloropyridine-2-carboxylic acid (0.135 g, 0.857 mmol) added after 1 h to drive the reaction to completion. Preparative HPLC-MS (eluting with a gradient of MeOH/H$_2$O containing 0.15% NH$_4$OH) was used to purify the product. The eluted fractions were evaporated to afford product as the ammonium carboxylate salt (150 mg, 47%). LCMS (M+H)$^+$: 559.2.

Step 2. 4-(3-{2-cyano-1-[4-(7H-pyrrolo[2,3-d]pyrimidin-4-yl)-1H-pyrazol-1-yl]ethyl}pyrrolidin-1-yl)-N-methylpyridine-2-carboxamide 4-(3-{2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)pyridine-2-carboxylic acid (20 mg, 0.036 mmol) was dissolved in DCM (1 mL). DIPEA (20 µL, 0.1 mmol) followed by N,N,N,N-tetramethyl-O-(7-azabenzotriazol-1-yl)uronium hexafluorophosphate (0.020 g, 0.054 mmol) were added, and stirred for 1 h. This was followed by addition of 2 M methylamine in THF (36 µL, 0.072 mmol). The reaction was continued for 16 h. Solvent was removed in vacuo. The crude product was deprotected by stirring in a mixture of 2:1 DCM/TFA for 3 h, evaporation, then stirring in a mixture of methanol (1.4 mL) and EDA (0.1 mL). Preparative HPLC-MS (eluting with a gradient of ACN/H$_2$O containing 0.15% NH$_4$OH) was used to purify the product. $^1$H NMR (300 MHz, DMSO-d6): δ 12.10 (br s, 1H), 8.88 (s, 1H), 8.69 (s, 1H), 8.66-8.59 (m, 1H), 8.44 (s, 1H), 8.14 (d, 1H), 7.61 (d, 1H), 7.17-7.14 (m, 1H), 6.99 (d, 1H), 6.58 (dd, 1H), 4.88-4.76 (m, 1H), 3.68-3.57 (m, 1H), 3.48-3.19 (m, 5H), 3.01-2.87 (m, 1H), 2.79 (d, 3H), 1.75-1.63 (m, 2H); LCMS (M+H)$^+$: 442.0.

Example 153

4-(3-{2-cyano-1-[4-(7H-pyrrolo[2,3-d]pyrimidin-4-yl)-1H-pyrazol-1-yl]ethyl}pyrrolidin-1-yl)-N,N-dimethylpyridine-2-carboxamide (single enantiomer)

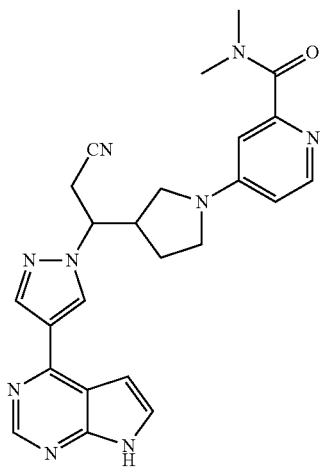 [SMILES: CN(C)C(=O)c1cc(N2CCC(C(CC#N)n3cc(-c4ncnc5[nH]ccc45)cn3)C2)ccn1]

Prepared as in Example 152, Step 2, substituting 2 M dimethylamine in THF (36 µL, 0.072 mmol) in place of methylamine. $^1$H NMR (300 MHz, DMSO-d6): δ 12.05 (br s, 1H), 8.80 (s, 1H), 8.62 (s, 1H), 8.36 (s, 1H), 8.10-7.98 (m, 1H), 7.54 (d, 1H), 6.92 (d, 1H), 6.54-6.46 (m, 1H), 6.42 (dd, 1H), 4.79-4.69 (m, 1H), 3.61-2.78 (m, 7H), 2.89 (s, 3H), 2.82 (s, 3H), 1.67-1.56 (m, 2H); LCMS (M+H)$^+$: 456.0.

Example 154

4-(3-{2-cyano-1-[4-(7H-pyrrolo[2,3-d]pyrimidin-4-yl)-1H-pyrazol-1-yl]ethyl}pyrrolidin-1-yl)-N-phenylpyridine-2-carboxamide (single enantiomer)

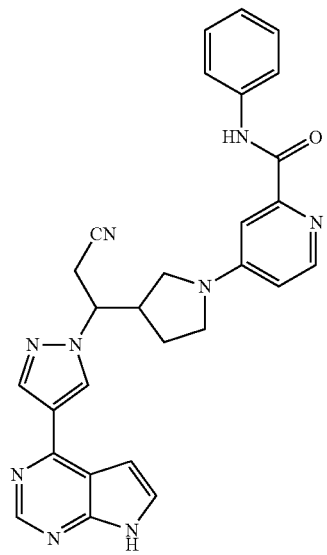 [SMILES: N#CCC(C1CCN(c2ccnc(C(=O)Nc3ccccc3)c2)C1)n1cc(-c2ncnc3[nH]ccc23)cn1]

Prepared as in Example 152, Step 2, substituting aniline (6.5 µL, 0.072 mmol) in place of methylamine. $^1$H NMR (300 MHz, CD$_3$OD): δ 8.68 (s, 1H), 8.66 (s, 1H), 8.42 (s, 1H), 8.19 (d, 1H), 7.80-7.72 (m, 2H), 7.50 (d, 1H), 7.42-7.30 (m, 3H), 7.18-7.10 (m, 1H), 6.94 (d, 1H), 6.62 (dd, 1H), 4.89-4.76 (m, 1H), 3.73 (dd, 1H), 3.55-3.17 (m, 5H), 3.16-3.01 (m, 1H), 1.92-1.80 (m, 2H); LCMS (M+H)$^+$: 504.1.

Example 155

3-[1-(2,3-dihydrofuro[2,3-b]pyridin-6-yl)pyrrolidin-3-yl]-3-[4-(7H-pyrrolo[2,3-d]pyrimidin-4-yl)-1H-pyrazol-1-yl]propanenitrile (single enantiomer)

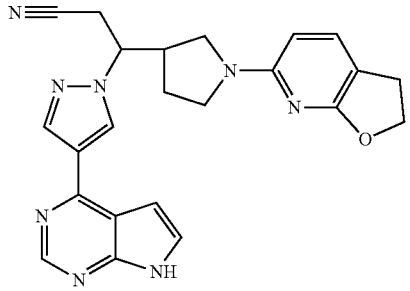 [SMILES: N#CCC(C1CCN(c2ccc3c(n2)OCC3)C1)n1cc(-c2ncnc3[nH]ccc23)cn1]

Step 1. 3-[7-(2,3-dihydrofuro[2,3-d]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (86.6 mg, 0.198 mmol, from Example 15, Step 3) was mixed with NMP (0.20 mL, 2.1 mmol), DIPEA (53.0 µL, 0.305 mmol), and 2,3-dihydrofuro[2,3-b]pyridin-6-yl trifluoromethanesulfonate (prepared as described in *Org. Lett.* 2006, 8(17), 3777-3779; 50.0 mg, 0.152 mmol) was added. The mixture was heated in the microwave at 130° C. for a total of 1 h. The reaction mixture was diluted with EtOAc, washed with water and brine, dried over sodium sulfate and concentrated. The product was purified by flash column chromatography, eluting with a gradient from 0-100% ethyl acetate in hexanes tp provide the purified product (16 mg, 17%). $^1$H NMR (300 MHz, CDCl$_3$): δ 8.85 (s, 1H), 8.36 (s, 2H), 7.40 (d, 1H), 7.28 (d, 1H), 6.80 (d, 1H), 5.81 (d, 1H), 5.68 (s, 2H), 4.57 (t, 2H), 4.43 (td, 1H), 3.88 (dd, 1H), 3.55 (dd, 2H), 3.55-3.38 (m, 1H), 3.38-3.26 (m, 2H), 3.22 (dd, 1H), 3.12 (t, 2H), 3.09-2.99 (m, 1H), 2.97 (dd, 1H), 1.98-1.85 (m, 1H), 1.82-1.64 (m, 1H), 0.92 (dd, 2H), −0.06 (s, 9H); LCMS (M+H)$^+$: 557.2.

Step 2. 3-[7-(2,3-dihydrofuro[2,3-d]pyridin-6-yl)pyrrolidin-3-yl]-3-[4-(7H-pyrrolo[2,3-d]pyrimidin-4-yl)-1H-pyrazol-1-yl]propanenitrile 3-[1-(2,3-Dihydrofuro[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (8 mg, 0.01 mmol) was dissolved in a 1:1 mixture of DCM:TFA, stirred at RT for 1 h, then concentrated. The residue was dissolved in 1.5 mL MeOH, and 0.2 mL EDA was added. The mixture was stirred for 30 min at RT, then preparative HPLC-MS (eluting with a gradient of ACN/H$_2$O containing 0.15% NH$_4$OH) was used to purify the product (3 mg, 49%). $^1$H NMR (400 MHz, DMSO-d6): δ 12.08 (br s, 1H), 8.86 (s, 1H), 8.68 (s, 1H), 8.42 (s, 1H), 7.60 (d, 1H), 7.35 (d, 1H), 6.98 (d, 1H), 5.85 (d, 1H), 4.79 (td, 1H), 4.46 (t, 2H), 3.64 (dd, 1H), 3.43-3.12 (m, 5H), 3.04 (t, 2H), 2.93-2.81 (m, 1H), 1.74-1.56 (m, 2H); LCMS (M+H)$^+$: 427.2.

Example 156

3-[4-(7H-pyrrolo[2,3-d]pyrimidin-4-yl)-1H-pyrazol-1-yl]-3-(1-thieno[2,3-b]pyridin-6-ylpyrrolidin-3-yl)propanenitrile (single enantiomer)

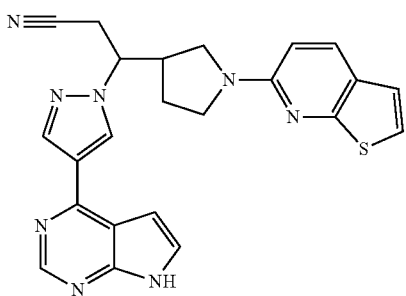 [SMILES: N#CCC(C1CCN(c2ccc3ccsc3n2)C1)n1cc(-c2ncnc3[nH]ccc23)cn1]

Step 1. 3-[7-(1-oxido-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.140 g, 0.320 mmol; from Example 15, Step 3) and 6-chloro-2,3-dihydrothieno[2,3-b]pyridine-1-oxide (50.0 mg, 0.266 mmol, from Example 28, Step 4) was dissolved in ethanol (0.20 mL) and DIPEA (83.6 µL, 0.480 mmol) was added. The mixture was heated in the microwave at 125° C. for 100 min LCMS showed more than 60% conversion to the desired product. The mixture was concentrated and purified by flash column chromatography (eluting with a gradient first from 0-100% ethyl acetate in hexanes, followed by 5% MeOH in ethyl acetate) to afford the product as a light yellow solid. (46 mg, 29%). LCMS (M+H)$^+$: 589.2.

Step 2. 3-[4-(7H-pyrrolo[2,3-d]pyrimidin-4-yl)-1H-pyrazol-1-yl]-3-(1-thieno[2,3-d]pyridin-6-ylpyrrolidin-3-yl)propanenitrile 3-[1-(1-Oxido-2,3-dihydrothieno[2,3-b]pyridin-6-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (15.0 mg, 0.0255 mmol) was heated to 140° C. in acetic anhydride (0.50 mL, 5.3 mmol) for 3 h. The mixture was concentrated, the residue was dissolved in a mixture of 1:1 TFA/DCM, stirred for 1 h at RT, and was concentrated again. The residue was then stirred with 0.2 mL of EDA in 1.0 mL MeOH. Preparative HPLC-MS (eluting with a gradient of ACN/H$_2$O containing 0.15% NH$_4$OH) was used to purify the product (3 mg, 26%). $^1$H NMR (300 MHz, CDCl$_3$): δ 9.16 (br s, 1H), 8.84 (s, 1H), 8.38 (s, 2H), 7.81 (d, 1H), 7.37 (dd, 1H), 7.06 (s, 1H), 6.79 (dd, 1H), 6.44 (d, 1H), 4.49 (td, 1H), 4.01 (dd, 1H), 3.66-3.54 (m, 1H), 3.51-3.38 (m, 2H), 3.27 (dd, 1H), 3.18-3.03 (m, 1H), 3.04 (dd, 1H), 2.05-1.91 (m, 1H), 1.88-1.72 (m, 1H); LCMS (M+H)$^+$: 441.1.

Example 157

3-[1-(7,7-difluoro-6,7-dihydro-5H-cyclopenta[b]pyridin-2-yl)pyrrolidin-3-yl]-3-[4-(7H-pyrrolo[2,3-d]pyrimidin-4-yl)-1H-pyrazol-1-yl]propanenitrile bis(trifluoroacetate) (single enantiomer)

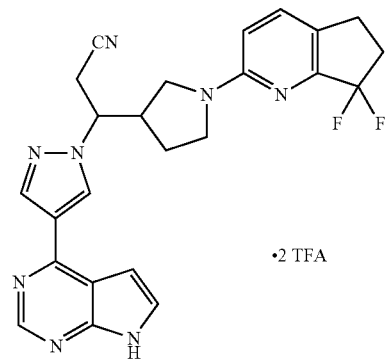 [SMILES: N#CCC(C1CCN(c2ccc3c(n2)C(F)(F)CC3)C1)n1cc(-c2ncnc3[nH]ccc23)cn1]

Step 1. 2-chloro-5,6-dihydro-7H-cyclopenta[b]pyridin-7-one

Dess-Martin periodinane (0.550 g, 1.30 mmol) was added to a solution of 2-chloro-6,7-dihydro-5H-cyclopenta[b]pyridin-7-ol (prepared as described in WO2006/103511; 0.200 g, 1.18 mmol) in DCM (5 mL). The solution was stirred for 2 h, then was washed with 1N NaOH, dried over sodium sulfate, decanted and concentrated. The product was used without further purification (180 mg, 91%). $^1$H NMR (400 MHz, in CDCl$_3$ and CD$_3$OD): δ 7.64 (d, 1H), 7.39 (d, 1H), 3.06-2.96 (m, 2H), 2.74-2.58 (m, 2H); LCMS (M+H)$^+$: 168.1.

Step 2. 2-chloro-7,7-difluoro-6,7-dihydro-5H-cyclopenta[b]pyridine

2-Methoxy-N-(2-methoxyethyl)-N-(trifluoro-λ(4)-sulfanyl)ethanamine (0.3 mL, 1.5 mmol) was added to a solution of 2-chloro-5,6-dihydro-7H-cyclopenta[b]pyridin-7-one (0.071 g, 0.42 mmol) in DCM (0.8 mL) and ethanol (4 µL) and the reaction was stirred over 4 days. Ethyl acetate and water were added, the layers separated, and the aqueous phase was extracted with two further portions of ethyl acetate. The combined extracts were dried over sodium sulfate, decanted and concentrated. Flash column chromatography (eluting with a gradient from 10-50% ethyl acetate in hexanes) afforded product as a colorless crystalline solid (26 mg, 32%). $^1$H NMR (300 MHz, CDCl$_3$): δ 7.64 (d, 1H), 7.39 (d, 1H), 3.05-2.96 (m, 2H), 2.74-2.58 (m, 2H); $^{19}$F NMR (300 MHz, CDCl$_3$): δ −92.88 (t); LCMS (M+H)$^+$: 190.1/192.0.

Step 3. 3-[1-(7,7-difluoro-6,7-dihydro-5H-cyclopenta[b]pyridin-2-yl)pyrrolidin-3-yl]-3-[4-(7H-pyrrolo[2,3-d]pyrimidin-4-yl)-1H-pyrazol-1-yl]propanenitrile bis(trifluoroacetate)

A solution of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.050 g, 0.11 mmol, from Example 15, Step 3) and 2-chloro-7,7-difluoro-6,7-dihydro-5H-cyclopenta[b]pyridine (0.026 g, 0.14 mmol) in 1-butyl-3-methyl-1H-imidazol-3-ium tetrafluoroborate (0.3 mL) containing 4-methylmorpholine (0.038 mL, 0.34 mmol) was heated to 120° C. for a total of 15 h. The reaction mixture was partitioned between water and ethyl acetate, and the aqueous phase was extracted a total of 3 times. The extracts were dried over sodium sulfate and concentrated. The residue was stirred with 1:1 TFA:DCM for 2 h and then concentrated. The mixture was reconstituted in methanol and excess of EDA was added. After stirring for 16 h, solid present in the reaction mixture was filtered off and the filtrate was purified by preparative HPLC-MS (eluting with a gradient of ACN and H$_2$O containing 0.1% TFA) to afford the product as the trifluoroacetate salt (2 mg, 2%). $^1$H NMR (400 MHz, DMSO-d6): δ 12.69 (br s, 1H), 9.03 (s, 1H), 8.86 (s, 1H), 8.56 (s, 1H), 7.81 (br s, 1H), 7.56 (d, 1H), 7.17 (br s, 1H), 6.60 (d, 1H), 4.88 (td, 1H), 3.77 (dd, 1H), 3.54-3.23 (m, 6H), 2.91 (dd, 1H), 2.85-2.77 (m, 2H), 2.59-2.49 (m, 1H), 1.78-1.60 (m, 2H); LCMS (M+H)$^+$: 461.2.

Example 158

3-[1-(7-fluoro-1,3-benzoxazol-2-yl)pyrrolidin-3-yl]-3-[3-(7H-pyrrolo[2,3-d]pyrimidin-4-yl)-1H-pyrrol-1-yl]propanenitrile (single enantiomers isolated)

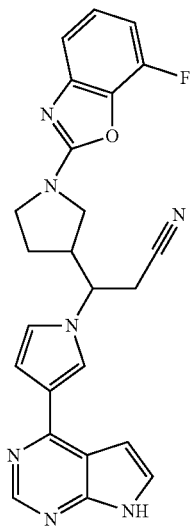 [SMILES: N#CCC(C1CCN(c2nc3cccc(F)c3o2)C1)n1ccc(-c2ncnc3[nH]ccc23)c1]

A mixture of 7-fluorobenzo[d]oxazole-2(3H)-thione (0.076 g, 0.45 mmol, prepared as in Example 21), 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (0.150 g, 0.240 mmol, from Example 33, Step 3) and DIPEA (250 μL, 1.4 mmol) in 1,4-Dioxane (1 mL) was heated to 80° C. for 3 h. The dioxane was removed in vacuo and was replaced with ethanol (1 mL). Silver nitrate (0.0817 g, 0.481 mmol) and ammonium hydroxide solution (0.2 mL) were added. After stilling overnight, the mixture was filtered and rinsed with methanol. After evaporation, the residue was purified by flash column chromatography, eluting with 0-10% MeOH/DCM. After evaporating the fractions containing product, the residue was dissolved in ethyl acetate and was washed with 1N NaOH, dried over sodium sulfate, and evaporated again. The product was deprotected by stirring in 25% TFA/DCM for 3 h, then evaporation and stirring with excess EDA in methanol overnight. Preparative HPLC-MS (eluting with a gradient of MeOH and H$_2$O containing NH$_4$OH) was used to afford the product as the free base. $^1$H NMR (300 MHz, CDCl$_3$): δ 9.37 (br s, 1H), 8.81 (s, 1H), 7.75 (t, 1H), 7.34 (d, 1H), 7.18-7.07 (m, 2H), 7.03 (dd, 1H), 6.97 (t, 1H), 6.84 (d, 1H), 6.82 (dd, 1H), 4.22 (td, 1H), 4.09 (dd, 1H), 3.85 (ddd, 1H), 3.65 (ddd, 1H), 3.49 (dd, 1H), 3.16-3.04 (m, 1H), 2.98 (app d, 2H), 2.13-1.99 (m, 1H), 1.91-1.74 (m, 1H); LCMS (M+H)$^+$: 442.2. Chiral HPLC (Phenomenex Lux Cellulose-1 column, 21.2×250 mm, 5 μm, eluting with 45% EtOH/55% Hexanes at a rate of 20 mL/min) was used to separate the racemic mixture into single enantiomers (enantiomer 1 retention time: 17.8 min; enantiomer 2 retention time: 20.1 min). Upon removal of solvent, the single enantiomer products were separately reconstituted in ACN/H$_2$O and lyophilized. Peak 1 (first to elute): $^1$H NMR (500 MHz, DMSO-d6, 90° C.): δ 11.71 (br s, 1H), 8.61 (s, 1H), 7.94 (t, 1H), 7.45 (dd, 1H), 7.17-7.09 (m, 3H), 6.94 (dd, 1H), 6.91-6.86 (m, 2H), 4.59 (td, 1H), 3.91 (dd, 1H), 3.69 (ddd, 1H), 3.57-3.49 (m, 2H), 3.40 (dd, 1H), 3.26 (dd, 1H), 3.03-2.94 (m, 1H), 1.84-1.69 (m, 2H); LCMS (M+H)$^+$: 442.2. Peak 2 (second to elute): $^1$H NMR (400 MHz, DMSO-d6): δ 11.96 (br s, 1H), 8.61 (s, 1H), 8.01 (t, 1H), 7.51 (dd, 1H), 7.18-7.10 (m, 3H), 6.96-6.89 (m, 3H), 4.58 (td, 1H), 3.86 (dd, 1H), 3.71-3.63 (m, 1H), 3.54-3.10 (m, 4H), 2.99-2.87 (m, 1H), 1.73-1.63 (m, 2H); LCMS (M+H)$^+$: 442.2.

Example 159

3-[1-(7-bromo-1,3-benzoxazol-2-yl)pyrrolidin-3-yl]-3-[4-(7H-pyrrolo[2,3-d]pyrimidin-4-yl)-1H-pyrazol-1-yl]propanenitrile trifluoracetate (single enantiomer)

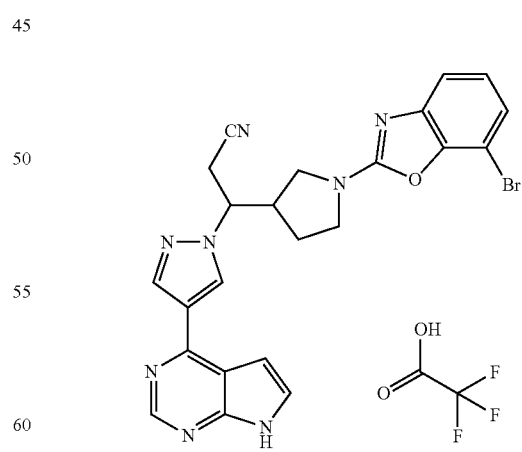

Step 1. 2-amino-6-bromophenol

2-Bromo-6-nitrophenol (Aldrich, 0.25 g, 1.1 mmol) was dissolved in THF (6.4 mL), water (6.4 mL) and stannous chloride dihydrate (1.3 g, 5.7 mmol) were added. The mixture was heated to 80° C. for 1 h. Upon cooling to RT, sat'd sodium bicarbonate was added, followed by ethyl acetate. Insoluble material was filtered off. The layers were separated and the aqueous phase was extracted with two further portions of ethyl acetate. The combined organic extracts were washed with brine, dried over sodium sulfate and concentrated to provide the desired product as an off-white crystalline solid, used without further purification (200 mg, 93%). LCMS (M+H)+: 188.0/190.0.

Step 2. 7-bromobenzo[d]oxazole-2(3H)-thione

Carbonothioic dichloride (0.122 mL, 1.60 mmol) was added drop-wise to a solution of 2-amino-6-bromophenol (0.20 g, 1.1 mmol) in THF (2.8 mL) at 0° C. The mixture was allowed to warm to RT and stir for 2 h. Solvent was removed in vacuo, and the crude solid was used in the next step without further purification. LCMS (M+H)+: m/z=229.9/231.9.

Step 3. 3-[7-(7-bromo-1,3-benzoxazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile A mixture of 7-bromobenzo[d]oxazole-2(3H)-thione (0.105 g, 0.457 mmol), DIPEA (0.159 mL, 0.914 mmol), and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.10 g, 0.23 mmol; from Example 15, Step 3) in 1,4-Dioxane (0.20 mL) was stirred at 80° C. for 3 h. The mixture was then concentrated. Flash column chromatography, eluting with a gradient from 0-100% ethyl acetate in hexanes afforded the product as a light yellow solid (47 mg, 32%). 1H NMR (300 MHz, CDCl3): 8.86 (s, 1H), 8.46 (s, 1H), 8.36 (s, 1H), 7.43 (d, 1H), 7.26 (dd, 1H), 7.14 (dd, 1H), 7.04 (t, 1H), 6.81 (d, 1H), 5.68 (s, 2H), 4.55 (td, 1H), 4.05 (dd, 1H), 3.88-3.78 (m, 1H), 3.69-3.45 (m, 4H), 3.27 (dd, 1H), 3.25-3.09 (m, 1H), 3.00 (dd, 1H), 2.07-1.77 (m, 2H), 0.92 (dd, 2H), −0.06 (s, 9H); LCMS (M+H)+: 633.1/635.1.

Step 4. 3-[7-(7-bromo-1,3-benzoxazol-2-yl)pyrrolidin-3-yl]-3-[4-(7H-pyrrolo[2,3-d]pyrimidin-4-yl)-1H-pyrazol-1-yl]propanenitrile trifluoracetate A solution of 3-[1-(7-bromo-1,3-benzoxazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (10 mg, 0.016 mmol) in 1:1 TFA/DCM was stirred for 1 h at RT, concentrated, then stirred in 1 mL MeOH, containing 0.2 mL EDA until deprotection was complete. Preparative HPLC-MS (eluting with a gradient of ACN/H2O containing 0.1% TFA), followed by lyophilization afforded the product as the trifluoroacetate salt (5.8 mg, 59%). 1H NMR (300 MHz, DMSO-d6): δ 12.45 (br s, 1H), 8.98 (s, 1H), 8.78 (s, 1H), 8.51 (s, 1H), 7.77-7.68 (m, 1H), 7.24 (dd, 1H), 7.17 (dd, 1H), 7.13-7.04 (m, 2H), 4.90 (td, 1H), 3.89 (dd, 1H), 3.70-2.86 (m, 6H), 1.81-1.63 (m, 2H); LCMS (M+H)+: m/z=503.0/505.1.

Example 160

2-(3-{2-cyano-1-[4-(7H-pyrrolo[2,3-d]pyrimidin-4-yl)-1H-pyrazol-1-yl]ethyl}pyrrolidin-1-yl)-1,3-benzoxazole-7-carbonitrile (single enantiomer)

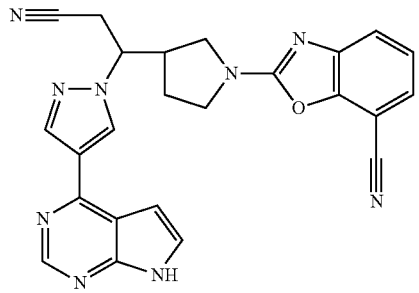 [SMILES: N#CCC(C1CCN(c2nc3cccc(C#N)c3o2)C1)n1cc(-c2ncnc3[nH]ccc23)cn1]

A mixture of 3-[1-(7-bromo-1,3-benzoxazol-2-yl)pyrrolidin-3-yl]-3-[4-(7-{[2-(trimethylsilyl)ethoxy]methyl}-7H-pyrrolo[2,3-d]pyrimidin-4-yl)-1H-pyrazol-1-yl]propanenitrile (22 mg, 0.035 mmol, from Example 159, Step 3), zinc cyanide (8.2 mg, 0.069 mmol), and tetrakis(triphenylphosphine)palladium(0) (8.0 mg, 0.0069 mmol) in DMF (0.3 mL) was heated in the microwave to 120° C. for 60 min. An additional portion of tetrakis(triphenylphosphine)palladium (0) (24 mg, 0.020 mmol) was added and was heated to 120° C. in an oil bath for 2 h. The mixture was then diluted with EtOAc, washed with water, brine, dried over sodium sulfate and concentrated. The crude product was stirred with 1:1 TFA/DCM for 1 h, concentrated, then stirred in 1 mL MeOH containing 0.2 mL EDA for 15 min. Preparative HPLC-MS (eluting with a gradient of ACN/H2O containing 0.15% NH4OH) afforded product as the free base (9 mg, 57%). 1H NMR (300 MHz, DMSO-d6): δ 8.89 (s, 1H), 8.67 (s, 1H), 8.43 (s, 1H), 7.60 (d, 1H), 7.57 (dd, 1H), 7.41 (dd, 1H), 7.28 (t, 1H), 6.98 (d, 1H), 4.87 (td, 1H), 3.91 (dd, 1H), 3.73-3.62 (m, 1H), 3.61-3.26 (m, 4H), 3.06-2.89 (m, 1H), 1.82-1.66 (m, 2H); LCMS (M+H)+: 450.1.

Example 161

3-[1-(7-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile (single enantiomer)

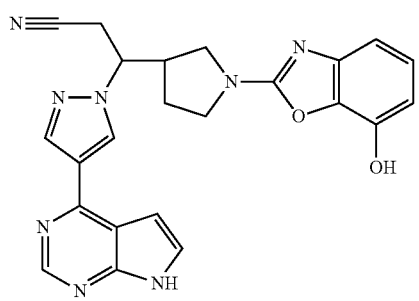 [SMILES: N#CCC(C1CCN(c2nc3cccc(O)c3o2)C1)n1cc(-c2ncnc3[nH]ccc23)cn1]

Step 1. 7-hydroxybenzo[d]oxazole-2(3H)-thione

A mixture of 3-aminobenzene-1,2-diol (prepared as described in WO2007/071434; 0.5 g, 4 mmol) and potassium O-ethyl dithiocarbonate (0.80 g, 5.0 mmol) in ethanol (5.2 mL) was heated to reflux for 1.5 h, then at RT over 3 days. Dilute HCl was added into the reaction, and the product was extracted with ethyl acetate. The combined extracts were dried over sodium sulfate, decanted and concentrated. Flash column chromatography, eluting with a gradient from 0-100% ethyl acetate, was used to purify the product (80 mg, 12%). $^1$H NMR (400 MHz, CD$_3$OD): δ 7.04 (t, 1H), 6.69 (dd, 1H), 6.64 (dd, 1H); LCMS (M+H)$^+$: 167.9.

Step 2. 3-[7-(7-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile 7-Hydroxybenzo[d]oxazole-2(3H)-thione (0.080 g, 0.48 mmol) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.17 g, 0.38 mmol, from Example 15, Step 3) in 1,4-dioxane (1 mL, 10 mmol) were heated to 80° C. for several h until the starting materials were consumed. The solvent was removed in vacuo and replaced with ethanol (1 mL). Silver nitrate (0.065 g, 0.38 mmol) and ammonium hydroxide solution (0.12 mL) were added and the reaction was continued for 16 h. The reaction mixture was partitioned between water and ethyl acetate, layers separated and the aqueous phase extracted a total of 3 times with ethyl acetate. The extracts were filtered to remove insoluble residue, dried over sodium sulfate, decanted and concentrated. Preparative HPLC-MS (eluting with a gradient of ACN/H$_2$O containing 0.15% NH$_4$OH) was used to purify the crude product before the deprotection step. The deprotection step was performed with 1:1 TFA:DCM for 2 h, followed by evaporation, then stirring with excess EDA in methanol for 1 h. Preparative HPLC-MS (eluting with a gradient of ACN/H$_2$O containing 0.15% NH$_4$OH) afforded product as the free base (12 mg, 7%). $^1$H NMR (400 MHz, DMSO-d6): δ 8.89 (s, 1H), 8.69 (s, 1H), 8.43 (s, 1H), 7.61 (d, 1H), 6.99 (d, 1H), 6.90 (t, 1H), 6.71 (dd, 1H), 6.50 (dd, 1H), 4.86 (td, 1H), 3.85 (dd, 1H), 3.67-3.60 (m, 1H), 3.51-3.19 (m, 4H), 3.02-2.91 (m, 1H), 1.79-1.63 (m, 2H); LCMS (M+H)$^+$: 441.0.

Example 162

3-[1-(7-methoxy-1,3-benzoxazol-2-yl)pyrrolidin-3-yl]-3-[4-(7H-pyrrolo[2,3-d]pyrimidin-4-yl)-1H-pyrazol-1-yl]propanenitrile (single enantiomer)

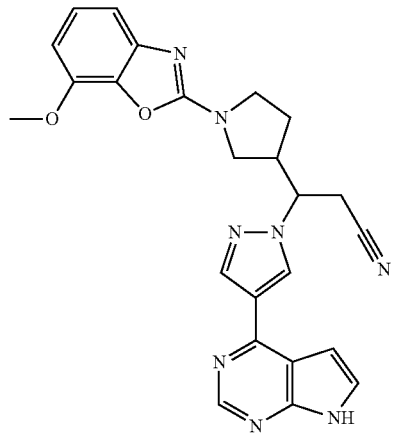 [SMILES: COc1cccc2nc(N3CCC(C(CC#N)n4cc(-c5ncnc6[nH]ccc56)cn4)C3)oc12]

Step 1. 7-methoxy-1,3-benzoxazole-2(3H)-thione

A mixture of 2-amino-6-methoxyphenol (prepared as described in EP333176; 1.2 g, 8.6 mmol) and potassium O-ethyl dithiocarbonate (1.7 g, 11 mmol) in ethanol (11 mL) was heated to reflux for 3 h, then cooled to RT, followed by cooling in an ice bath. Dilute HCl was added to the reaction, The white precipitate was isolated by filtration and washed with water. The resulting sticky solid was azeotroped with benzene (700 mg, 45%). $^1$H NMR (300 MHz, DMSO-d6): δ 13.86 (br s, 1H), 7.22 (t, 1H), 6.93 (dd, 1H), 6.82 (dd, 1H), 3.93 (s, 3H); LCMS (M+H)$^+$: 182.0.

Step 2. 3-[7-(7-methoxy-1,3-benzoxazol-2-yl)pyrrolidin-3-yl]-3-[4-(7H-pyrrolo[2,3-d]pyrimidin-4-yl)-1H-pyrazol-1-yl]propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.050 g, 0.11 mmol; from Example 15, Step 3) and 4-methoxy-1,3-benzoxazole-2(3H)-thione (0.031 g, 0.17 mmol) in 1,4-Dioxane (0.6 mL, 8 mmol) was heated to 80° C. for 3 h. Solvent was removed in vacuo and replaced with ethanol (0.6 mL). Silver nitrate (0.019 g, 0.11 mmol) and ammonium hydroxide solution (0.036 mL) were added and the reaction was stirred for 4 h. The mixture was filtered through a PTFE filter syringe, rinsing with methanol. The methanol was evaporated in vacuo. The residue was partitioned between ethyl acetate and water, layers separated and the aqueous phase was extracted a further two times. The combined extracts were dried over sodium sulfate, decanted and concentrated. The product was purified by preparative HPLC-MS, eluting with a gradient of ACN/H$_2$O containing 0.15% NH$_4$OH. This product was deprotected by stirring with 1:1 TFA/DCM for 1 h, followed by removal of solvents, then stirring with excess EDA in methanol until deprotection was complete. Purification via preparative HPLC-MS, eluting with a gradient of ACN/H$_2$O containing 0.15% NH$_4$OH, afforded product as the free base (10 mg, 19%). $^1$H NMR (300 MHz, DMSO-d6): δ 8.89 (s, 1H), 8.68 (s, 1H), 8.43 (s, 1H), 7.60 (d, 1H), 7.06 (t, 1H), 6.99 (d, 1H), 6.88 (dd, 1H), 6.69 (dd, 1H), 4.85 (td, 1H), 3.89 (s, 3H), 3.86 (dd, 1H), 3.67-3.59 (m, 1H), 3.52-3.29 (m, 4H), 3.02-2.90 (m, 1H), 1.79-1.63 (m, 2H); LCMS (M+H)$^+$: 455.1.

Example 163

3-(4-(7H-pyrrolo[2,3-d]pyrimidin-4-yl)-1H-pyrazol-1-yl)-3-(1-(7-ethoxybenzo[d]oxazol-2-yl)pyrrolidin-3-yl)propanenitrile (single enantiomer)

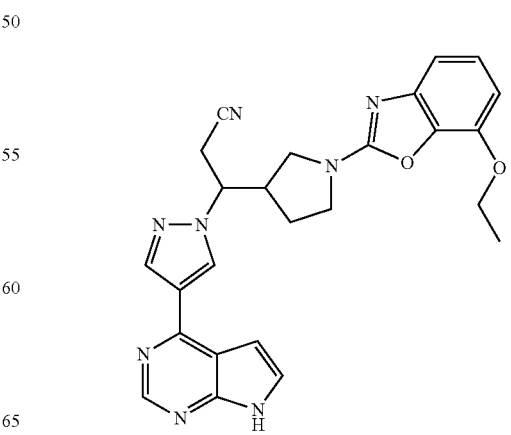

Step 1. 2-ethoxy-6-nitrophenol

Nitric acid (3.89 mL, 60 mmol) was added drop-wise to 2-ethoxy-phenol, (Aldrich, 5.00 mL, 39.4 mmol) in water (20 mL) and diethyl ether (49 mL). The resulting mixture became hot to the point of the reflux of the ether, and then was allowed to cool to RT and stir for 3 h. The reaction mixture was poured into water and was extracted three times with diethyl ether. The extracts were dried over sodium sulfate, decanted and concentrated. The residue was dissolved in a small volume of DCM and hexanes, and what the undissolved material was excluded in loading the silica gel column for flash chromatography. The product was eluted with a gradient from 20-50% chloroform in hexanes, to afford the product as an orange solid (1.36 g, 19%). $^1$H NMR (300 MHz, CDCl$_3$): δ 10.73 (br s, 1H), 7.68 (dd, 1H), 7.12 (dd, 1H), 6.88 (dd, 1H), 4.14 (q, 2H), 1.50 (t, 3H); LCMS (M+H)$^+$: 183.9.

Step 2. 2-amino-6-ethoxyphenol

To a suspension of 2-ethoxy-6-nitrophenol (1.36 g, 7.42 mmol) in water (30 mL) and methanol (30 mL) was added sodium dithionite (~85%, 9.58 g, 46.8 mmol). The reaction was heated to 60° C. for 30 min, until it turned colorless. Upon cooling to RT, brine was added, and the product was extracted with ethyl acetate. The extracts were dried over sodium sulfate, decanted and concentrated (1.01 g, 89%). $^1$H NMR (400 MHz, CD$_3$OD): δ 6.58 (t, 1H), 6.40 (dd, 1H), 6.38 (dd, 1H), 4.04 (q, 2H), 1.39 (t, 3H); LCMS (M+H)$^+$: 154.1.

Step 3. 7-ethoxy-1,3-benzoxazole-2(3H)-thione

Prepared from 2-amino-6-ethoxyphenol (1.01 g, 6.59 mmol) by the method of Example 162, Step 1 (1 g, 77%). $^1$H NMR (400 MHz, DMSO-d6): δ 13.86 (br s, 1H), 7.21 (t, 1H), 6.93 (dd, 1H), 6.81 (dd, 1H), 4.21 (q, 2H), 1.38 (t, 3H); LCMS (M+H)$^+$: 196.1.

Step 4. 3-(4-(7H-pyrrolo[2,3-c]pyrimidin-4-yl)-1H-pyrazol-1-yl)-3-(1-(7-ethoxybenzo[d]oxazol-2-yl)pyrrolidin-3-yl)propanenitrile To 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.070 g, 0.16 mmol, from Example 15, Step 3) in 1,4-Dioxane (1 mL) was added 7-ethoxy-1,3-benzoxazole-2(3H)-thione and the solution was heated to 80° C. for 3.5 h. Solvent was removed in vacuo and replaced with ethanol (1 mL). Silver nitrate (0.014 g, 0.080 mmol) and ammonium hydroxide solution (50 μL) were added and the reaction stirred for 16 h. Further silver nitrate (0.019 g, 0.11 mmol) and ammonium hydroxide solution (50 μL) were added and the reaction was continued for a further 7 h. 1N NaOH was added into the reaction, followed by ethyl acetate. The biphasic mixture was filtered and the layers separated. The aqueous phase was extracted with two further portions of ethyl acetate. The combined extracts were dried over sodium sulfate, filtered through a short pad of silica, then concentrated. The product was deprotected by stirring with 1:1 TFA/DCM for 1 h, followed by evaporated and stirring with EDA (0.1 mL) in a small quantity of MeOH. Purification via preparative HPLC-MS, eluting with a gradient of ACN/H$_2$O containing 0.15% NH$_4$OH, afforded product as the free base. $^1$H NMR (300 MHz, CD$_3$OD): δ 8.68 (s, 1H), 8.64 (d, 1H), 8.41 (s, 1H), 7.48 (dd, 1H), 7.03 (dt, 1H), 6.93 (dd, 1H), 6.83 (d, 1H), 6.64 (d, 1H), 4.91-4.79 (m, 1H), 4.18 (q, 2H), 3.96 (dd, 1H), 3.74-3.64 (m, 1H), 3.60-3.03 (m, 5H), 1.97-1.84 (m, 2H), 1.41 (t, 3H); LCMS (M+H)$^+$: 469.2.

Example 164

3-(4-(7H-pyrrolo[2,3-d]pyrimidin-4-yl)-1H-pyrazol-1-yl)-3-(1-(7-(difluoromethoxy)benzo[d]oxazol-2-yl)pyrrolidin-3-yl)propanenitrile (single enantiomer)

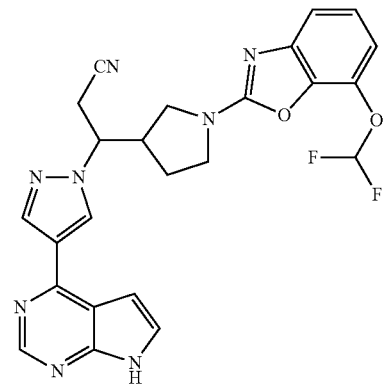 [SMILES: N#CCC(C1CCN(c2nc3cccc(OC(F)F)c3o2)C1)n1cc(-c2ncnc3[nH]ccc23)cn1]

Step 1. 2-(difluoromethoxy)-6-nitrophenol

To a solution of 2-(difluoromethoxy)phenol (prepared as described in U.S. Pat. No. 4,512,984; 0.90 g, 5.6 mmol) in acetic acid (1 mL) at 0° C. was added drop-wise white nitric acid (65%, 0.43 mL, 6.7 mmol). The reaction mixture was then poured into water and extracted with diethyl ether three times. The combined extracts were washed with brine, dried over sodium sulfate, decanted and concentrated. Flash column chromatography, eluting with a gradient from 20-50% CHCl$_3$ in hexanes afforded product as a yellow syrup (250 mg, 22%). $^1$H NMR (300 MHz, CDCl$_3$): δ 10.77 (s, 1H), 8.03 (dd, 1H), 7.56-7.51 (m, 1H), 6.99 (t, 1H), 6.67 (t, 1H).

Step 2. 2-amino-6-(difluoromethoxy)phenol

Prepared from 2-(difluoromethoxy)-6-nitrophenol (0.25 g, 1.2 mmol) by the method described for Example 163, Step 2 (170 mg, 79%). $^1$H NMR (400 MHz, CD$_3$OD): δ 6.67 (t, 1H), 6.63-6.60 (m, 2H), 6.50-6.47 (m, 1H); $^{19}$F NMR (400 MHz, CD$_3$OD): δ −83.03 (d); LCMS (M+H)$^+$: 176.1.

Step 3. 7-(difluoromethoxy)-1,3-benzoxazole-2(3H)-thione

Prepared from 2-amino-6-(difluoromethoxy)phenol (0.17 g, 0.97 mmol) by the method described for Example 162, Step 1 (120 mg, 57%). $^1$H NMR (400 MHz, DMSO-d6): δ 14.14 (br s, 1H), 7.38 (t, 1H), 7.32 (t, 1H), 7.16-7.11 (m, 2H); $^{19}$F NMR (400 MHz, DMSO-d6): δ −82.65 (d); LCMS (M+H)$^+$: 218.0.

Step 4. 3-(4-(7H-pyrrolo[2,3-d]pyrimidin-4-yl)-1H-pyrazol-1-yl)-3-(1-(7-(difluoromethoxy)benzo[d]oxazol-2-yl)pyrrolidin-3-yl)propanenitrile Prepared from 7-(difluoromethoxy)-1,3-benzoxazole-2 (3H)-thione (from step 3) by the method of Example 163, Step 4. $^1$H NMR (300 MHz, DMSO-d6): δ 8.88 (s, 1H), 8.69

(s, 1H), 8.43 (s, 1H), 7.59 (d, 1H), 7.30 (t, 1H), 7.15-7.11 (m, 2H) 6.99 (d, 1H), 6.85 (t, 1H), 4.86 (td, 1H), 3.89 (dd, 1H), 3.71-3.60 (m, 1H), 3.57-3.26 (m, 4H), 3.04-2.91 (m, 1H), 1.80-1.66 (m, 2H); LCMS (M+H)$^+$: 491.2.

Example 165

3-[1-(4-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile (single enantiomer)

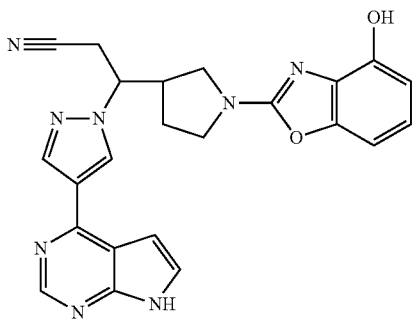 [SMILES: N#CCC(C1CCN(c2nc3c(O)cccc3o2)C1)n1cc(-c2ncnc3[nH]ccc23)cn1]

Step 1. 2-aminobenzene-1,3-diol 1.0 M of Boron tribromide in DCM (12 mL, 12 mmol) was added slowly drop-wise to a solution of 2,6-dimethoxyaniline (Alfa Aesar, 0.5 g, 3 mmol) in DCM (5 mL) at −45° C. under nitrogen. The mixture was stirred, with warming to RT, for 3 days. The mixture was cooled in an ice bath and water was added drop-wise. Saturated sodium bicarbonate solution was added to adjust pH to 5-6 and the aqueous phase was extracted with DCM. The aqueous layer, which contained product, was evaporated to afford a solid mixture. The solid was slurried in ethanol and the solids were filtered off. The ethanol solution was used in the next step. $^1$H NMR (400 MHz, CD$_3$OD): δ 6.68 (t, 1H), 6.37 (d, 2H).

Step 2. 4-hydroxybenzo[d]oxazole-2(3H)-thione

A solution of 2-aminobenzene-1,3-diol (0.37 g, 3.0 mmol) and Potassium O-ethyl dithiocarbonate (0.59 g, 3.7 mmol) in ethanol (3.8 mL) was heated to reflux for 3 h, then cooled to RT. Dilute HCl was added into the reaction, and the product was extracted with ethyl acetate. The combined extracts were dried over sodium sulfate, decanted and concentrated. Flash column chromatography (eluting with a gradient from 0-100% ethyl acetate-hexanes) afforded product (300 mg, 60%). $^1$H NMR (400 MHz, CD$_3$OD): δ 7.04 (t, 1H), 6.83 (dd, 1H), 6.70 (dd, 1H), 4.92 (br s, 2H); LCMS (M+H)$^+$: 168.0.

Step 3. 3-[7-(4-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.080 g, 0.18 mmol, from Example 15, Step 3) and 4-hydroxybenzo[d]oxazole-2(3H)-thione (0.046 g, 0.27 mmol) in 1,4-Dioxane (1 mL, 10 mmol) and DIPEA (excess) was heated to 100° C. for a 3 h. Solvent was removed in vacuo and was replaced with ethanol (1 mL). Silver nitrate (0.031 g, 0.18 mmol) and ammonium hydroxide (0.057 mL, 1.5 mmol) were added and the reaction was stirred for 16 h. 1N NaOH was added into the reaction, and the mixture was filtered through a PVDF filter syringe (Whatman), rinsing with methanol. The solvent was evaporated. The residue was partitioned between ethyl acetate and water, layers separated, and the aqueous phase extracted a total of three times. The combined extracts were dried over sodium sulfate, decanted and concentrated. The product was purified via preparative HPLC-MS, eluting with a gradient of ACN/H$_2$O containing 0.15% NH$_4$OH and the eluent was evaporated. The product was stirred with 1:1 TFA/DCM for 1 h, evaporated, then stirred with excess EDA in methanol until deprotection was complete. The product was isolated via preparative HPLC-MS, eluting with a gradient of ACN/H$_2$O containing 0.15% NH$_4$OH, to afford the product as the free base (5 mg, 6%). $^1$H NMR (400 MHz, DMSO-d6): δ 8.89 (s, 1H), 8.69 (s, 1H), 8.44 (s, 1H), 7.61 (d, 1H), 6.99 (d, 1H), 6.86 (dd, 1H), 6.82-6.77 (m, 1H), 6.58 (dd, 1H), 4.86 (td, 1H), 3.85 (dd, 1H), 3.67-3.60 (m, 1H), 3.50-3.25 (m, 4H), 3.02-2.90 (m, 1H), 1.79-1.62 (m, 2H); LCMS (M+H)$^+$: m/z=441.1.

Example 166

3-{1-[7-(hydroxymethyl)-1,3-benzoxazol-2-yl]pyrrolidin-3-yl}-3-[4-(7H-pyrrolo[2,3-d]pyrimidin-4-yl)-1H-pyrazol-1-yl]propanenitrile (single enantiomer)

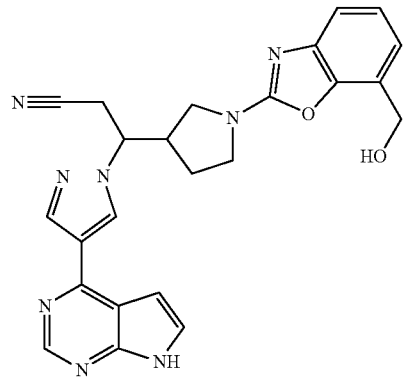 [SMILES: N#CCC(N/C=C(\C=N)c1ncnc2[nH]ccc12)C1CCN(c2nc3cccc(CO)c3o2)C1]

Step 1. methyl 2-thioxo-2,3-dihydro-1,3-benzoxazole-7-carboxylate

Prepared from methyl 3-amino-2-hydroxybenzoate (Apollo, 1.0 g, 6.0 mmol) according to the method of Example 162, Step 1 (830 mg, 66%). $^1$H NMR (400 MHz, DMSO-d6): δ 7.73 (dd, 1H), 7.49 (dd, 1H), 7.40 (t, 1H), 3.92 (s, 3H); LCMS (M+H)$^+$: 210.0.

Step 2. 7-(hydroxymethyl)-1,3-benzoxazole-2(3H)-thione 1.0 M of Diisobutylaluminum hydride in hexane (4.1 mL, 4.1 mmol) was added to a solution of methyl 2-thioxo-2,3-dihydro-1,3-benzoxazole-7-carboxylate (0.430 g, 2.06 mmol) in THF (8 mL) at 0° C. After 2 h, a further portion of 1.0 M of diisobutylaluminum hydride in hexane (4.1 mL, 4.1 mmol) was added, and the reaction was allowed to reach RT. A saturated solution of Rochelle's salt and ethyl acetate were added and stirred until layers separated. The aqueous phase was extracted once further with ethyl acetate, and the combined organic extracts were dried over sodium sulfate, decanted and concentrated (320 mg, 86%). LCMS (M+H)+: 182.0.

Step 3. 3-{1-[7-(hydroxymethyl)-1,3-benzoxazol-2-yl]pyrrolidin-3-yl}-3-[4-(7H-pyrrolo[2,3-d]pyrimidin-4-yl)-1H-pyrazol-1-yl]propanenitrile A mixture of 7-(hydroxymethyl)-1,3-benzoxazole-2(3H)-thione (0.32 g, 1.8 mmol) and 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.64 g, 1.5 mmol, from Example 15, Step 3) in 1,4-Dioxane (4 mL) was heated to 80° C. for 24 h. The desired SEM-protected product was isolated by preparative HPLC-MS (gradient of ACN/H$_2$O containing 0.1% TFA). The eluent containing desired product was basified using 1N NaOH and the product was extracted with ethyl acetate. The product was deprotected by stirring in 1:1 TFA/DCM for 1 h, evaporation of solvents, and stirring with EDA (0.1 mL) in MeOH until deprotection was complete. Preparative HPLC-MS (gradient of ACN/H$_2$O containing 0.15% NH$_4$OH) was used to afford the purified product as the free base (10 mg, 2%). $^1$H NMR (300 MHz, CD$_3$OD): δ 8.68 (s, 1H), 8.64 (s, 1H), 8.42 (s, 1H), 7.49 (d, 1H), 7.19-7.08 (m, 2H), 7.06-7.01 (m, 1H), 6.93 (d, 1H), 4.93-4.79 (m, 1H), 4.77 (s, 2H), 3.97 (dd, 1H), 3.77-3.67 (m, 1H), 3.62-3.49 (m, 2H), 3.40 (dd, 1H), 3.22 (dd, 1H), 3.15-3.04 (m, 1H), 1.96-1.84 (m, 2H); LCMS (M+H)+: 455.2.

Example 169

6-(3-{2-cyano-1-[4-(7H-pyrrolo[2,3-d]pyrimidin-4-yl)-1H-pyrazol-1-yl]ethyl}pyrrolidin-1-yl)furo[3,2-c]pyridine-7-carbonitrile (single enantiomer)

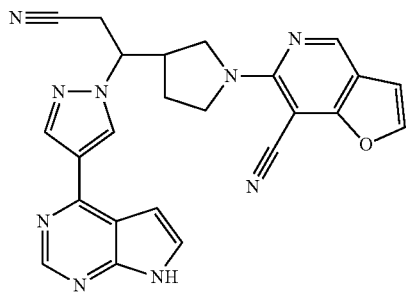

Step 1. 5-iodo-4-methoxy-2-oxo-1,2-dihydropyridine-3-carbonitrile

N-Iodosuccinimide (22 g, 0.10 mol) was added to a solution of 4-methoxy-2-oxo-1,2-dihydropyridine-3-carbonitrile (10.0 g, 0.0666 mol, Ryan Scientific) in 1,2-dichloroethane (200 mL). The mixture was heated to reflux overnight. To complete the reaction, additional N-iodosuccinimide (11.2 g, 0.0500 mol) was added and reflux continued for 5 h. Solvent was removed in vacuo. The residue was triturated with methanol to afford product as a white powder (16.4 g, 89%). $^1$H NMR (400 MHz, DMSO-d$_6$): δ 12.29 (br s, 1H), 8.01 (s, 1H), 4.28 (s, 3H); LCMS (M+H)+: 277.0.

Step 2. 4-hydroxy-5-iodo-2-oxo-1,2-dihydropyridine-3-carbonitrile

Iodotrimethylsilane (2.1 mL, 14 mmol) was added to a solution of 5-iodo-4-methoxy-2-oxo-1,2-dihydropyridine-3-carbonitrile (2.0 g, 7.2 mmol) in acetonitrile (80 mL). The mixture was stirred at RT for 1.5 h. Solvent was removed in vacuo. The product was triturated with DCM overnight, then filtered and washed with ether to provide product (1.69 g, 89%). $^1$H NMR (400 MHz, DMSO-d6): δ 11.56 (br s, 1H), 7.81 (s, 1H); LCMS (M+H)+: 262.9.

Step 3. 4-hydroxy-2-oxo-5-[(trimethylsilyl)ethynyl]-1,2-dihydropyridine-3-carbonitrile A solution of 4-hydroxy-5-iodo-2-oxo-1,2-dihydropyridine-3-carbonitrile (1.18 g, 4.50 mmol) in acetonitrile (15 mL), was degassed. Triethylamine (0.942 mL, 6.76 mmol) was added, followed by (trimethylsilyl)acetylene (0.955 mL, 6.76 mmol), bis(triphenylphosphine)palladium(II) chloride (0.190 g, 0.271 mmol) and copper(I) iodide (69 mg, 0.36 mmol). The mixture was degassed again, then was stirred at RT for 1 h. The mixture was adsorbed onto silica gel. Flash column chromatography, eluting with 0-15% methanol in DCM afforded product as the triethylamine salt (890 mg). $^1$H NMR (400 MHz, DMSO-d6): δ 10.01 (d, 1H), 9.04 (br s, 1H), 2.95 (dd, 6H), 1.03 (t, 9H), 0.14 (s, 9H); LCMS (M+H)+: 233.1.

Step 4. 6-oxo-5,6-dihydrofuro[3,2-c]pyridine-7-carbonitrile

Methanesulfonic acid (0.64 mL, 9.9 mmol) was added to a solution of 4-hydroxy-2-oxo-5-[(trimethylsilyl)ethynyl]-1,2-dihydropyridine-3-carbonitrile.TEA (1.32 g, from Step 3) in THF (25 mL). The reaction was stirred at RT for 16 h, then was heated to 40° C. for 8 h followed by 35° C. for 16 h. The solvent was removed in vacuo. Purification by flash column chromatography, eluting with a gradient from 0-10% methanol in DCM afforded desired product (150 mg, 23%). $^1$H NMR (400 MHz, DMSO-d6): δ 12.77 (br s, 1H), 8.29 (s, 1H), 7.89 (d, 1H), 6.90 (d, 1H); LCMS (M+H)+: 161.1.

Step 5. 7-cyanofuro[3,2-c]pyridin-6-yl trifluoromethanesulfonate

6-Oxo-5,6-dihydrofuro[3,2-c]pyridine-7-carbonitrile (10.0 mg, 0.062 mmol) and N-Phenylbis(trifluoromethanesulphonimide) (27.9 mg, 0.078 mmol) were dissolved in acetonitrile (0.35 mL), and triethylamine (17 μL, 0.12 mmol) was added. The mixture was heated to 50° C. for 40 min. The solvent was removed in vacuo, and the product was used directly in the next step. LCMS (M+H)+: 293.0.

Step 6. 6-(3-{2-cyano-1-[4-(7H-pyrrolo[2,3-d]pyrimidin-4-yl)-1H-pyrazol-1-yl]ethyl}pyrrolidin-1-yl)furo[3,2-c]pyridine-7-carbonitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (40.0 mg, 0.092 mmol, from Example 15, Step 3), was dissolved in NMP (0.20 mL) and 4-methylmorpholine (14 μL, 0.12 mmol) and crude 7-cyanofuro[3,2-c]pyridin-6-yl trifluoromethanesulfonate (18 mg, 0.062 mmol, formed in Step 5) was added. The reaction mixture was heated to 90° C. for 1 h. Solvent was removed in vacuo. The residue was taken up in water and ethyl acetate. The layers were separated and the aqueous phase was extracted with ethyl acetate three times. The combined organic extracts were dried over sodium sulfate, decanted and concentrated. Flash column chromatography, eluting with a gradient from 0-100% ethyl acetate in hexanes afforded desired product. The product was treated

Example 170

6-(3-{2-cyano-1-[3-(7H-pyrrolo[2,3-d]pyrimidin-4-yl)-1H-pyrrol-1-yl]ethyl}pyrrolidin-1-yl)furo[3,2-c]pyridine-7-carbonitrile (racemate)

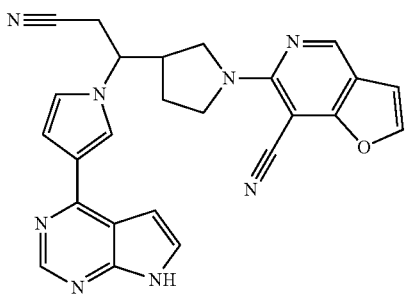 [SMILES: N#CCC(C1CCN(c2ncc3ccoc3c2C#N)C1)n1ccc(-c2ncnc3[nH]ccc23)c1]

To a solution of tert-butyl 3-(2-cyano-1-{3-[7-(diethoxymethyl)-7H-pyrrolo[2,3-d]pyrimidin-4-yl]-1H-pyrrol-1-yl}ethyl)pyrrolidine-1-carboxylate (0.62 g, 0.98 mmol, racemic diastereomer 1 from Example 32, Step 1) in 1,4-dioxane (20 mL) was added 4 M of HCl in 1,4-dioxane (6.9 mL, 28 mmol) and the reaction was stirred overnight. The solvent was removed in vacuo. Purification via preparative HPLC-MS afforded product as a light yellow solid (0.17 g, 56%). LCMS (M+H)$^+$: 307.1. A portion of this product (28 mg, 0.092 mmol), was dissolved in NMP (0.20 mL) and 4-methylmorpholine (14 µL, 0.12 mmol). Crude 7-cyanofuro[3,2-c]pyridin-6-yl trifluoromethanesulfonate (18 mg, 0.062 mmol, from Example 169, Step 5), was added. The reaction was heated to 60° C. for 1 h. Purification via preparative HPLC-MS (eluting with a gradient of ACN/H$_2$O containing 0.15% NH$_4$OH) afforded product as the free base (5.5 mg, 20%). $^1$H NMR (400 MHz, DMSO-d6): δ 11.96 (br s, 1H), 8.67 (s, 1H), 8.61 (s, 1H), 8.00 (t, 1H), 7.93 (d, 1H), 7.51 (d, 1H), 7.15 (dd, 1H), 7.01 (d, 1H), 6.96-6.93 (m, 2H), 4.59 (td, 1H), 3.96 (dd, 1H), 3.89-3.81 (m, 1H), 3.74-3.65 (m, 1H), 3.56 (dd, 1H), 3.47 (dd, 1H), 3.23 (dd, 1H), 2.93-2.81 (m, 1H), 1.79-1.60 (m, 2H); LCMS (M+H)$^+$: 449.2.

Example 171

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile 1,1-dioxide (racemic)

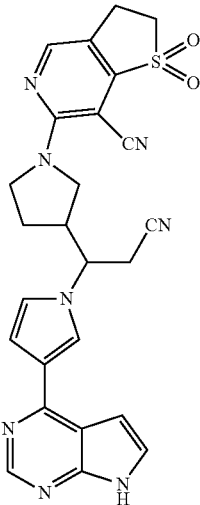 [SMILES: N#CCC(C1CCN(c2ncc3c(c2C#N)S(=O)(=O)CC3)C1)n1ccc(-c2ncnc3[nH]ccc23)c1]

Step 1: 2-(benzyloxy)-5-iodo-4-methoxynicotinonitrile

A mixture of 5-iodo-4-methoxy-2-oxo-1,2-dihydropyridine-3-carbonitrile (3.7 g, 13 mmol, from Example 169, Step 1), silver(I) oxide (3.4 g, 15 mmol) and benzyl chloride (2.00 mL, 17.4 mmol) in toluene (74 mL) was heated to 107° C. for 4.5 h. Additional benzyl chloride (1.54 mL, 13.4 mmol) was added and the reaction was heated to 120° C. for 16 h. The mixture was cooled to RT, and filtered. The solvent was removed from the filtrate in vacuo, and the product was triturated with diethyl ether, azeotroped with toluene, then dried under high vacuum to afford product as a white solid (4.30 g, 87%). $^1$H NMR (300 MHz, CDCl$_3$): δ 8.43 (s, 1H), 7.49-7.43 (m, 2H), 7.42-7.30 (m, 3H), 5.47 (s, 2H), 4.35 (s, 3H); LCMS (M+H)$^+$: 367.0.

Step 2: 2-(benzyloxy)-5-(2-hydroxyethyl)-4-methoxynicotinonitrile 2.5 M of n-Butyllithium in hexane (4.85 mL, 12.1 mmol) was added drop-wise to a solution of 2-(benzyloxy)-5-iodo-4-methoxynicotinonitrile (3.7 g, 10 mmol) in THF (150 mL) at −78° C. The reaction was held at −78° C. for 1.5 h, at which time 1,3,2-dioxathiolane 2,2-dioxide (1.25 g, 10.1 mmol, Aldrich) in THF (5.0 mL) was introduced drop-wise. The mixture was allowed to warm to RT and stir for 16 h. Conc. HCl was added (1.85 mL) and the mixture was stirred for 30 min. Saturated NaHCO$_3$ solution was added to adjust the pH to 7. Some water was added and the product was extracted with three portions of EtOAc. The extracts were combined, dried over sodium sulfate and concentrated. Flash column chromatography, eluting with a gradient from 0-70% ethyl acetate in hexanes afforded product as a white solid (1.62 g, 56%). $^1$H NMR (300 MHz, CDCl$_3$): δ 8.00 (s, 1H), 7.51-7.45 (m, 2H), 7.41-7.30 (m, 3H), 5.47 (s, 2H), 4.33 (s, 3H), 3.77 (dd, 2H), 2.77 (t, 2H); LCMS (M+H)$^+$: 285.1.

Step 3. 2-[6-(benzyloxy)-5-cyano-4-methoxypyridin-3-yl]ethyl 4-methylbenzenesulfonate To a solution of 2-(benzyloxy)-5-(2-hydroxyethyl)-4-methoxynicotinonitrile (1.21 g, 4.26 mmol) in DCM (50 mL) was added triethylamine (0.652 mL, 4.68 mmol) followed by p-toluenesulfonyl chloride (0.811 g, 4.26 mmol) and 4-dimethylaminopyridine (52 mg, 0.426 mmol). The reaction was stirred for 8 h. To drive the reaction to completion, additional p-toluenesulfonyl chloride (0.243 g, 1.28 mmol) was added and the reaction continued for 16 h. Solvent volume was reduced in vacuo and the product was purified by flash column chromatography, eluting with a gradient from 0-50% ethyl acetate in hexanes to afford product as a white solid (1.36 g, 73%). $^1$H NMR (300 MHz, CDCl$_3$): δ 7.86 (s, 1H), 7.56 (d, 2H), 7.56-7.48 (m, 2H), 7.44-7.30 (m, 3H), 7.14 (d, 2H), 5.47 (s, 2H), 4.18 (s, 3H), 4.15 (t, 2H), 2.79 (t, 2H), 2.42 (s, 3H); LCMS (M+H)$^+$: 438.9.

Step 4. S-{2-[6-(benzyloxy)-5-cyano-4-methoxypyridin-3-yl]ethyl}ethanethioate A solution of 2-[6-(benzyloxy)-5-cyano-4-methoxypyridin-3-yl]ethyl 4-methylbenzenesulfonate (1.36 g, 3.10 mmol) in acetonitrile (30 mL) and DMF (30 mL) was treated with potassium thioacetate (0.50 g, 4.4 mmol) and stirred for 16 h. Water was added and the product was extracted with three portions of ethyl acetate. The combined extracts were dried over sodium sulfate, decanted and concentrated. Flash column chromatography, eluting with a gradient from 0-50% ethyl acetate in hexanes, was used to purify the product (698 mg, 66%). $^1$H NMR (300 MHz, CDCl$_3$): δ 7.93 (s, 1H), 7.51-7.27 (m, 5H), 5.46 (s, 2H), 4.36 (s, 3H), 3.03 (t, 2H), 2.75 (t, 2H), 2.30 (s, 3H); LCMS (M+H)$^+$: 343.1.

Step 5. 6-(benzyloxy)-2,3-dihydrothieno[3,2-c]pyridine-7-carbonitrile

To a solution of S-{2-[6-(benzyloxy)-5-cyano-4-methoxypyridin-3-yl]ethyl}ethanethioate (0.698 g, 2.04 mmol) in methanol (90 mL) was added ammonium hydroxide solution (30 mL, 400 mmol), and the reaction was stirred for 8 h. Solvent was removed in vacuo to afford a white solid. Theoretical yield assumed and used without further purification. $^1$H NMR (400 MHz, CD$_3$OD): δ 7.98 (s, 1H), 7.48-7.25 (m, 5H), 5.43 (s, 2H), 3.56 (t, 2H), 3.36-3.27 (m, 2H); LCMS (M+H)$^+$: 268.9.

Step 6. 6-hydroxy-2,3-dihydrothieno[3,2-c]pyridine-7-carbonitrile

A solution of acetyl chloride (0.43 mL, 6.1 mmol) in methanol (90 mL) was stirred for 1.5 h, then this solution was added to 6-(benzyloxy)-2,3-dihydrothieno[3,2-c]pyridine-7-carbonitrile (0.547 g, 2.04 mmol). The reaction was stirred for 3 days, and the solvent was removed in vacuo. Theoretical yield was assumed and the product was used without further purification. $^1$H NMR (400 MHz, CD$_3$OD): δ 7.37 (s, 1H), 7.19 (s, 1H), 3.49 (t, 2H), 3.18 (t, 2H); LCMS (M+H)$^+$: 179.1.

Step 7. 6-chloro-2,3-dihydrothieno[3,2-c]pyridine-7-carbonitrile

6-Hydroxy-2,3-dihydrothieno[3,2-c]pyridine-7-carbonitrile (70 mg, 0.39 mmol) was heated in phosphoryl chloride (2 mL, 20 mmol) to 110° C. for 1 h. Excess reagent was removed in vacuo. The residue was dissolved in DCM and washed with 0.1 N NaOH. The aqueous phase was extracted with ethyl acetate three times and these extracts were combined with the DCM layer. The combined organics were dried over sodium sulfate, decanted and concentrated to afford the product as a beige crystalline solid (34 mg, 44%). $^1$H NMR (300 MHz, CDCl$_3$): δ 8.14 (s, 1H), 3.59 (dd, 2H), 3.41 (dd, 2H); LCMS (M+H)$^+$: 197.0/199.0.

Step 8. 6-chloro-2,3-dihydrothieno[3,2-c]pyridine-7-carbonitrile 1,1-dioxide To a solution of 6-chloro-2,3-dihydrothieno[3,2-c]pyridine-7-carbonitrile (34 mg, 0.17 mmol) in DCM (2 mL) at 0° C. was added m-Chloroperbenzoic acid (88 mg, 0.38 mmol). The reaction was stirred with warming to RT overnight. The reaction was diluted with 0.2 N NaOH and ethyl acetate. Solid NaCl was added to aid in layer separation. The aqueous phase was extracted with ethyl acetate thrice and the extracts were dried over sodium sulfate, decanted and concentrated. The product was used without further purification in Step 9. $^1$H NMR (300 MHz, CD$_3$OD): δ 8.78 (s, 1H), 3.71 (dd, 2H), 3.47 (dd, 2H); LCMS (M+H)$^+$: 228.9/230.8.

Step 9. 6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile 1,1-dioxide (racemic)

3-Pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (66 mg, 0.11 mmol, from Example 33, Step 3) and 6-chloro-2,3-dihydrothieno[3,2-c]pyridine-7-carbonitrile 1,1-dioxide (from Step 8) were dissolved in DMF (0.5 mL). 4-Methylmorpholine (0.037 mL, 0.34 mmol) was added and the reaction was heated to 80° C. for 1 h. Upon cooling to RT, the reaction mixture was partitioned between water and ethyl acetate. The aqueous phase was extracted with ethyl acetate three times. The combined extracts were washed with brine, dried over sodium sulfate, decanted and concentrated. The crude product was stirred with 1:1 TFA/DCM for 1 h, evaporated, then stirred with 0.4 mL EDA in methanol (4 mL) until deprotection was complete. Purification via preparative HPLC-MS (eluting with a gradient of ACN/H$_2$O containing 0.15% NH$_4$OH) afforded product as the free base (15 mg, 28%). $^1$H NMR (300 MHz, DMSO-d6): δ 11.96 (br s, 1H), 8.61 (s, 1H), 8.57 (s, 1H), 7.99 (br t, 1H), 7.51 (d, 1H), 7.15 (t, 1H), 6.97-6.91 (m, 2H), 4.59 (td, 1H), 3.95 (dd, 1H), 3.90-3.79 (m, 1H), 3.77-3.14 (m, 8H), 2.93-2.78 (m, 1H), 1.80-1.57 (m, 2H); LCMS (M+H)$^+$: 499.2.

Example 172

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide (single enantiomer)

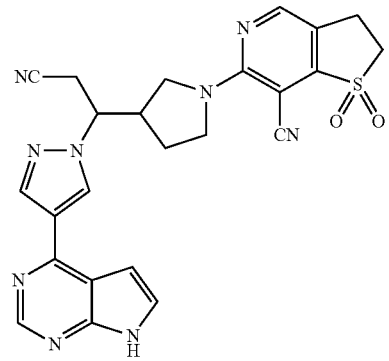 [SMILES: N#CCC(C1CCN(c2ncc3c(c2C#N)S(=O)(=O)CC3)C1)n1cc(-c2ncnc3[nH]ccc23)cn1]

m-Chloroperbenzoic acid (4.74 mg, 0.0212 mmol) in DCM (0.14 mL) was added to a solution of 6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile (3.3 mg, 0.0070 mmol, from Example 173) in DCM (0.60 mL) at 0° C. The reaction was stirred with warming to RT for 1.5 h, then the solvent was removed in vacuo. Purification via preparative HPLC-MS (eluting with a gradient of ACN/H₂O containing 0.15% NH₄OH) afforded product as the free base (800 mg, 22%). ¹H NMR (500 MHz, DMSO-d6): δ 12.09 (br s, 1H), 8.85 (s, 1H), 8.68 (s, 1H), 8.54 (s, 1H), 8.41 (s, 1H), 7.59 (d, 1H), 6.96 (d, 1H), 4.87 (td, 1H), 3.98 (dd, 1H), 3.85-3.79 (m, 1H), 3.72-3.63 (m, 4H), 3.41 (dd, 1H), 3.33-3.23 (m, 1H), 3.23-3.13 (m, 2H), 2.95-2.86 (m, 1H), 1.80-1.67 (m, 2H); LCMS (M+H)⁺: 500.0.

Example 173

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile (single enantiomer)

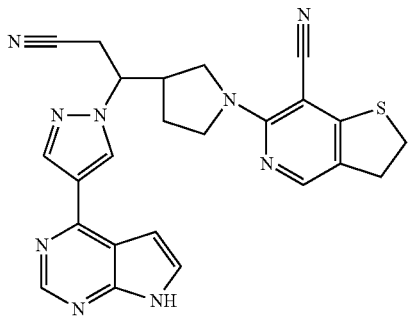 [SMILES: N#CCC(C1CCN(c2ncc3c(c2C#N)SCC3)C1)n1cc(-c2ncnc3[nH]ccc23)cn1]

Step 1. 2,4-dichloro-5-iodonicotinamide

To 2,4-dichloro-5-iodonicotinic acid (prepared as described in European Journal of Organic Chemistry, (7), 1371-1376; 2001; 2.95 g, 7.33 mmol) in benzene (20 mL) was added oxalyl chloride (1.24 mL, 14.6 mmol), followed by a catalytic amount of DMF (10 µL). The mixture was stirred at RT for 2 h. The solvent was removed in vacuo. The residue was dissolved in THF (34 mL) and ammonia gas was bubbled through the mixture for 5 min. The suspension was stirred, well sealed, for a further 20 min. Solvent was then removed in vacuo. The solid was dissolved in DCM (200 mL) and water (75 mL). The layers were separated and the aqueous phase was extracted with a further portion of DCM. The combined extracts were dried over sodium sulfate, decanted and concentrated. Flash column chromatography, eluting with a gradient from 0-100% ethyl acetate in hexanes was used to purify the product (1.64 g, 70%). ¹H NMR (300 MHz, CDCl₃ and CD₃OD): δ 8.67 (s, 1H); LCMS (M+H)⁺: 316.9/318.9.

Step 2. 2,4-dichloro-5-iodonicotinonitrile

To a mixture of 2,4-dichloro-5-iodonicotinamide (2.43 g, 7.67 mmol) and DCM (122 mL) at 0° C., was added triethylamine (10.7 mL, 76.7 mmol), followed by trichloroacetic anhydride (14.0 mL, 76.7 mmol). Following addition, the solution was stirred at 0° C. for 20 min. The mixture was quenched by the addition of water at this temperature, and was stirred for 30 min before being diluted with ethyl acetate. The biphasic mixture was separated. The organic layer was washed successively with saturated NaHCO₃, water, and brine, then dried over sodium sulfate, decanted and concentrated. Flash column chromatography, eluting with a gradient from 0-15% ethyl acetate in hexanes afforded product as a yellow solid (1.94 g, 84%). ¹H NMR (300 MHz, CDCl₃): δ 8.88 (s, 1H).

Step 3. 2,4-dichloro-5-[(Z)-2-ethoxyvinyl]nicotinonitrile

A mixture of 2,4-dichloro-5-iodonicotinonitrile (1.94 g, 6.49 mmol) and (2-ethoxyethenyl)tri-n-butyltin (2.58 g, 7.14 mmol) in toluene (16 mL) was degassed. Tetrakis(triphenylphosphine)palladium(0) (750 mg, 0.649 mmol) was added, and the reaction was heated to 110° C. for 5 h. The solvent was removed in vacuo. Flash column chromatography, eluting with a gradient from 0-20% ethyl acetate in hexanes was used to purify product (590 mg, 37%). ¹H NMR (300 MHz, CDCl₃): δ 9.26 (s, 1H), 6.55 (d, 1H), 5.47 (d, 1H), 4.09 (q, 2H), 1.37 (t, 3H).

Step 4. 2,4-dichloro-5-(2-oxoethyl)nicotinonitrile

A solution of 2,4-dichloro-5-[(Z)-2-ethoxyvinyl]nicotinonitrile (0.670 g, 2.76 mmol) in THF (10.0 mL) and 4.0 M of HCl in water (2.75 mL, 11.0 mmol) was heated to reflux for 1.5 h. The reaction was cooled to RT and poured into saturated sodium bicarbonate solution and the product was extracted with DCM. The organic extracts were washed with brine, dried over sodium sulfate, decanted and concentrated. Flash column chromatography, eluting with a gradient from 50-100% ethyl acetate in hexanes afforded product as an oil (500 mg, 84%). ¹H NMR (300 MHz, CDCl₃): δ 9.83 (br t, 1H), 8.39 (s, 1H), 4.00 (s, 2H).

Step 5. 2,4-dichloro-5-(2-hydroxyethyl)nicotinonitrile 1.0 M of diisobutylaluminum hydride in DCM (2.4 mL, 2.4 mmol) was added portion-wise over the course of 30 min to a solution of 2,4-dichloro-5-(2-oxoethyl)nicotinonitrile (500 mg, 2.4 mmol) in DCM (30 mL) at –78° C. When the reaction was considered complete by TLC and LCMS, it was quenched at –78° C. by the addition of water, then was allowed to warm to RT. A saturated solution of Rochelle's salt was added and the mixture was stirred until layers separated. The product was extracted with DCM three times. The extracts were dried over sodium sulfate, decanted and concentrated. Flash column chromatography, eluting with a gradient of 50-100% ethyl acetate in hexanes, was used to purify the product (120 mg, 23%). ¹H NMR (300 MHz, CDCl₃): δ 8.49 (s, 1H), 3.93 (dd, 2H), 3.04 (t, 2H); LCMS (M+H)⁺: 216.9/218.9.

Step 6. 6-chloro-2,3-dihydrothieno[3,2-c]pyridine-7-carbonitrile 2,4-Dichloro-5-(2-hydroxyethyl)nicotinonitrile (0.060 g, 0.28 mmol) and triphenylphosphine (0.109 g, 0.415 mmol) were dissolved in THF (2.12 mL). The solution was cooled at 0° C., and diethyl azodicarboxylate (65.3 µL, 0.415 mmol) was added. After stirring for 10 min, thioacetic acid (29.6 µL, 0.415 mmol) was added. The reaction mixture was stirred for 2 h at 0° C., then for 2 h at RT. Flash column chromatography, eluting with a gradient from 0-10% ethyl acetate in hexanes was used, to afford the product as an oil. A solution of this product in methanol (1.5 mL) was treated with acetyl chloride (59 µL, 0.829 mmol), stirred at RT for 7 h, then kept in the freezer for 3 days. Solvent was removed in vacuo. The residue was then stirred for 10 min in methanol (6.0 mL) and ammonium hydroxide solution (0.50 mL, 3.7 mmol). Solvent was removed in vacuo and the residue was partitioned between water and ethyl acetate. The aqueous layer was extracted with a further three portions of ethyl acetate. The extracts were dried over sodium sulfate and concentrated to afford product as a white solid, used directly in Step 7 (11 mg, 10%). LCMS (M+H)$^+$: 196.9/199.0.

Step 7. 6-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (24 mg, 0.056 mmol, from Example 15, Step 3) and 6-chloro-2,3-dihydrothieno[3,2-c]pyridine-7-carbonitrile (11 mg, 0.028 mmol) in NMP (100 µL) and DIPEA (9.7 µL, 0.056 mmol) was heated in the microwave at 135° C. for 15 min. Additional 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (18 mg, 0.042 mmol) was added and the reaction microwaved at the same temperature for a further 10 min. The reaction mixture was then diluted with water, extracted with ethyl acetate four times, the extracts dried over sodium sulfate and concentrated. Flash column chromatography, first eluting with a gradient from 0-100% ethyl acetate in hexanes, then 0-5% methanol in ethyl acetate, was used to purify the product (10 mg, 60%). $^1$H NMR (300 MHz, CDCl$_3$): δ 8.85 (s, 1H), 8.36 (s, 1H), 8.356 (s, 1H), 7.89 (s, 1H), 7.41 (d, 1H), 6.80 (d, 1H), 5.68 (s, 2H), 4.45 (td, 1H), 4.02 (dd, 1H), 3.92-3.82 (m, 1H), 3.81-3.68 (m, 1H), 3.65-1.63 (m, 12H), 0.92 (dd, 2H), −0.06 (s, 9H); LCMS (M+H)$^+$: 598.2.

Step 8. 6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 6-(3-{2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile (10.0 mg, 0.0167 mmol) was dissolved in DCM (1.5 mL) and TFA (0.8 mL) was added. The mixture was stirred at RT for 1 h, then solvents were removed in vacuo. The residue was dissolved in methanol (1 mL) and EDA (0.2 mL) was added and stirred for 30 min. Purification via preparative HPLC-MS (eluting with a gradient of ACN/H$_2$O containing 0.15% NH$_4$OH) afforded product as the free base (5.4 mg, 69%). $^1$H NMR (300 MHz, CDCl$_3$): δ 9.42 (br s, 1H), 8.85 (s, 1H), 8.38 (s, 1H), 8.37 (s, 1H), 7.90 (s, 1H), 7.39 (d, 1H), 6.80 (d, 1H), 4.46 (td, 1H), 4.02 (dd, 1H), 3.93-3.84 (m, 1H), 3.81-3.70 (m, 1H), 3.61 (dd, 1H), 3.50-3.41 (m, 2H), 3.31-3.19 (m, 3H), 3.14-2.98 (m, 1H), 2.99 (dd, 1H), 1.98-1.85 (m, 1H), 1.82-1.64 (m, 1H); LCMS (M+H)$^+$: 468.0.

Example 174

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile (single enantiomers isolated)

Step 1. 7-cyano-2,3-dihydrothieno[3,2-c]pyridin-6-yl trifluoromethanesulfonate

A solution of 6-hydroxy-2,3-dihydrothieno[3,2-c]pyridine-7-carbonitrile (24 mg, 0.13 mmol, from Example 171, Step 6) and N-phenylbis(trifluoromethanesulphonimide) (60 mg, 0.168 mmol) in acetonitrile (3 mL) and triethylamine (0.038 mL, 0.27 mmol) was heated to 50° C. for 3 h, then allowed to stir at RT overnight. Solvent was removed in vacuo and the product was used without further purification in the substitution step. LCMS (M+H)$^+$: 311.0.

Step 2. 6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile (single enantiomers isolated)

3-Pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (59 mg, 0.14 mmol, from Example 33, Step 3) was added to a solution of 7-cyano-2,3-dihydrothieno[3,2-c]pyridin-6-yl trifluoromethanesulfonate (40 mg, 0.13 mmol) in 4-methylmorpholine (45 µL, 0.41 mmol) and DMF (2 mL). The solution was heated to 60° C. for 45 min. Preparative HPLC-MS (eluting with a gradient of ACN/H$_2$O containing 0.15% NH$_4$OH) was used to pre-purify the SEM-protected adduct. Eluent was removed in vacuo. The SEM protecting group was removed by stirring in 25% TFA in DCM, followed by evaporation and stirring with excess EDA in methanol. The deprotected product was purified via preparative HPLC-MS (eluting with a gradient of ACN/H$_2$O containing 0.15% NH$_4$OH). Chiral HPLC was used to separate the racemic product into single enantiomers (Phenomenex Lux Cellulose-1 21.2×250 mm, 5 µm, eluting with 30% EtOH/70% Hexanes at 16 mL/min). Peak 1, (first to elute, retention time 17.6 min), and Peak 2 (second to elute, retention time 37.1 min) were separately evaporated. Peak 1: (2.1 mg, 3%), Peak 2: (2.3 mg, 3%). Peak 1: $^1$H NMR (500 MHz, CD$_3$OD): δ 8.59 (s, 1H), 7.88 (br m, 1H), 7.86 (t, 1H), 7.44 (d, 1H), 7.11 (t, 1H), 7.01 (dd, 1H), 6.94 (d, 1H), 4.50 (td, 1H), 3.99 (dd, 1H), 3.81 (ddd, 1H), 3.69 (m, 1H), 3.60 (dd, 1H), 3.49-3.44 (m, 2H), 3.28-3.23 (m, 3H), 3.11 (dd, 1H), 2.97-2.87 (m, 1H), 1.87 (pd, 1H), 1.76 (dq, 1H); LCMS (M+H)$^+$: 467.1. Peak 2: $^1$H NMR (500 MHz, CD$_3$OD): δ 8.58 (s, 1H), 7.88 (br m, 1H), 7.85 (t, 1H), 7.42 (d, 1H), 7.10 (dd, 1H), 7.01 (dd, 1H), 6.93 (d, 1H), 4.49 (td, 1H), 3.99 (dd, 1H), 3.80 (ddd, 1H), 3.69 (m, 1H), 3.59 (dd, 1H), 3.49-3.43 (m, 2H), 3.29-3.21 (m, 3H), 3.10 (dd, 1H), 2.97-2.88 (m, 1H), 1.87 (pd, 1H), 1.76 (dq, 1H); LCMS (M+H)$^+$: 467.1.

Example 175

6-(3-{2-cyano-1-[4-(7H-pyrrolo[2,3-d]pyrimidin-4-yl)-1H-pyrazol-1-yl]ethyl}pyrrolidin-1-yl)thieno[3,2-c]pyridine-7-carbonitrile (single enantiomer)

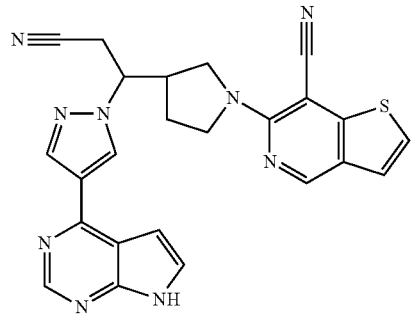 [SMILES: N#CCC(C1CCN(c2ncc3ccsc3c2C#N)C1)n1cc(-c2ncnc3[nH]ccc23)cn1]

Step 1. 6-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile A mixture of 3-pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (56 mg, 0.13 mmol, from Example 15, Step 3), 7-cyano-2,3-dihydrothieno[3,2-c]pyridin-6-yl trifluoromethanesulfonate (40 mg, 0.13 mmol, from Example 174, Step 1) and 4-methylmorpholine (42 μL, 0.39 mmol) in DMF (2 mL) was heated to 60° C. for 3 h. Preparative HPLC-MS (eluting with a gradient of ACN/H₂O containing 0.15% NH₄OH) was used to afford purified product (33 mg, 43%). LCMS (M+H)⁺: 598.2.

Step 2. 6-(3-{2-cyano-1-[4-(7H-pyrrolo[2,3-d]pyrimidin-4-yl)-1H-pyrazol-1-yl]ethyl}pyrrolidin-1-yl)thieno[3,2-c]pyridine-7-carbonitrile m-Chloroperbenzoic acid (0.017 g, 0.074 mmol) was added to a solution of 6-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile (33 mg, 0.055 mmol) in DCM (2 mL) at 0° C. The reaction was stirred at this temperature for 2 h. The reaction was diluted with DCM and washed with 0.1 N NaOH. The organic layer was dried over sodium sulfate, decanted and concentrated. The crude product was dissolved in acetic anhydride (0.5 mL, 5 mmol) and then heated to 140° C. for 24 h, to 150° C. for 2 h, then at 160° C. for 2 h, then in the microwave to 200° C. for 70 min. The solvent was then removed in vacuo. The crude reaction mixture was partitioned between 0.1 N NaOH and ethyl acetate. The aqueous portion was extracted with two further portions of ethyl acetate. The combined extracts were dried over sodium sulfate, decanted and concentrated. Deprotection of the SEM group was effected by stirring with 1:1 TFA in DCM followed by evaporation and stilling with excess EDA in methanol. Preparative HPLC-MS (gradient of ACN/H₂O containing 0.15% NH₄OH) was used to afford purified product (6 mg, 23%). ¹H NMR (300 MHz, DMSO-d6): δ 12.03 (br s, 1H), 8.81 (s, 1H), 8.79 (s, 1H), 8.61 (s, 1H), 8.37 (s, 1H), 7.53 (d, 1H), 7.46 (d, 1H), 7.37 (d, 1H), 6.92 (d, 1H), 4.86-4.76 (m, 1H), 3.94 (dd, 1H), 3.85-3.72 (m, 1H), 3.69-3.52 (m, 2H), 3.42-3.16 (m, 2H), 2.93-2.79 (m, 1H), 1.74-1.60 (m, 2H); LCMS (M+H)⁺: 466.2.

Example 176

6-(3-{2-cyano-1-[3-(7H-pyrrolo[2,3-d]pyrimidin-4-yl)-1H-pyrrol-1-yl]ethyl}pyrrolidin-1-yl)thieno[3,2-c]pyridine-7-carbonitrile (racemic)

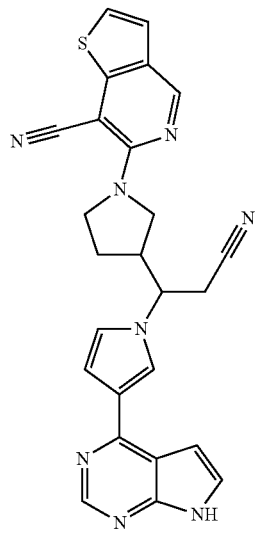 [SMILES: N#CCC(C1CCN(c2ncc3ccsc3c2C#N)C1)n1ccc(-c2ncnc3[nH]ccc23)c1]

Step 1. 6-chlorothieno[3,2-e]pyridine-7-carbonitrile

To a solution of 6-chloro-2,3-dihydrothieno[3,2-c]pyridine-7-carbonitrile (72 mg, 0.37 mmol, prepared as in Example 171, Step 7) in DCM (10 mL) at 0° C. was added m-Chloroperbenzoic acid (0.11 g, 0.49 mmol) and the reaction was stirred for 2 h. The reaction was further diluted with DCM, and washed with 0.1 N NaOH. The aqueous phase was back extracted with three portions of ethyl acetate and these were combined with the DCM solution. The combined extracts were dried over sodium sulfate, decanted and concentrated. The crude product was dissolved in acetic anhydride (3 mL) and heated to 140° C. for 16 h. The mixture was concentrated and the residue was dissolved in acetone (2.0 mL), and 1.0 M of sodium carbonate in water (2.0 mL) was added. The mixture was heated to 40° C. for 3.5 h. The acetone was removed in vacuo, and the product was extracted from the aqueous phase with 3 portions of DCM. The extracts were dried over sodium sulfate and concentrated. Flash column chromatography, eluting with 0-30% ethyl acetate in hexanes, afforded product as a white solid which was used in the next step without further purification. ¹H NMR (300 MHz, CDCl₃): δ 9.03 (s, 1H), 7.68 (d, 1H), 7.53 (d, 1H); LCMS (M+H)⁺: 195.0.

Step 2. 6-(3-{2-cyano-1-[3-(7H-pyrrolo[2,3-d]pyrimidin-4-yl)-1H-pyrrol-1-yl]ethyl}pyrrolidin-1-yl)thieno[3,2-e]pyridine-7-carbonitrile A mixture of 3-pyrrolidin-3-yl-3-[3-(7-{[2-(trimethylsilyl)ethoxy]methyl}-7H-pyrrolo[2,3-d]pyrimidin-4-yl)-1H-pyrrol-1-yl]propanenitrile (26 mg, 0.059 mmol; from Example 33, Step 3), 6-chlorothieno[3,2-c]pyridine-7-carbonitrile (23 mg, 0.059 mmol) and 4-methylmorpholine (0.019 mL, 0.18 mmol) in DMF (0.3 mL) was heated to 80° C. for 2 h. Upon cooling to RT, the reaction mixture was partitioned between water and ethyl acetate. The aqueous layer was extracted with two further portions of ethyl acetate. The combined organic extracts were washed with brine, dried over sodium sulfate, decanted and concentrated. The product was stirred with 1:1 TFA/DCM for 1 h, evaporated, then stirred with EDA (0.2 mL) in methanol (1.5 mL). When deprotection was complete, the product was purified by preparative HPLC-MS (gradient of ACN/H₂O containing 0.15% NH₄OH) (11 mg, 40%). ¹H NMR (400 MHz, DMSO-d6): δ 11.96 (br s, 1H), 8.88 (s, 1H), 8.61 (s, 1H), 8.01 (t, 1H), 7.54 (d, 1H), 7.51 (dd, 1H), 7.46 (d, 1H), 7.16 (t, 1H), 6.97-6.93 (m, 2H), 4.60 (td, 1H), 3.99 (dd, 1H), 3.91-3.83 (m, 1H), 3.77-3.68 (m, 1H), 3.60 (dd, 1H), 3.48 (dd, 1H), 3.25 (dd, 1H), 3.95-2.82 (m, 1H), 1.80-1.60 (m, 2H); LCMS (M+H)⁺: 464.9.

Example 177

6-(3-{2-cyano-1-[4-(7H-pyrrolo[2,3-d]pyrimidin-4-yl)-1H-pyrazol-1-yl]ethyl}pyrrolidin-1-yl)-1H-pyrrolo[3,2-c]pyridine-7-carbonitrile (single enantiomer)

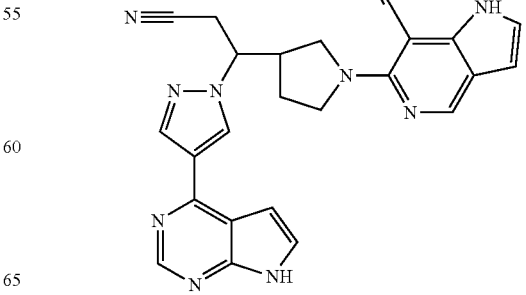

Step 1. 5-(2-aminoethyl)-2-(benzyloxy)-4-methoxynicotinonitrile

Sodium azide (330 mg, 5.1 mmol) was added to a solution of 2-[6-(benzyloxy)-5-cyano-4-methoxypyridin-3-yl]ethyl 4-methylbenzenesulfonate (1.5 g, 3.4 mmol, prepared as in Example 171, Step 3) in DMF (15 mL). The mixture was heated to 60° C. for a total of 85 min. Upon cooling to RT, the reaction mixture was partitioned between EtOAc and water. The organic layer was washed with water twice, saturated NaHCO$_3$ twice, water again once, brine, dried over sodium sulfate and concentrated to afford a light yellow oil. The oil was dissolved in a mixture of THF (27 mL) and water (3.0 mL), and triphenylphosphine (0.99 g, 3.8 mmol) was added. The reaction was stirred for 16 h, and the solvent was then removed in vacuo. Flash column chromatography, eluting with a gradient of 0-10% methanol in DCM containing 1% triethylamine, afforded product as a light yellow oil (780 mg, 80%). $^1$H NMR (300 MHz, CDCl$_3$): δ 7.96 (s, 1H), 7.50-7.45 (m, 2H), 7.41-7.27 (m, 3H), 5.46 (s, 2H), 4.32 (s, 3H), 2.86 (t, 2H), 2.63 (t, 2H); LCMS (M+H)$^+$: 284.0.

Step 2. 6-(benzyloxy)-2,3-dihydro-1H-pyrrolo[3,2-c]pyridine-7-carbonitrile

A solution of 5-(2-aminoethyl)-2-(benzyloxy)-4-methoxynicotinonitrile (0.78 g, 2.8 mmol) in methanol (80 mL) was treated with ammonium hydroxide solution (40 mL, 600 mmol) and was stirred at RT for 6 days. Removal of solvent in vacuo afforded the product as a white solid (700 mg, 100%). LCMS (M+H)$^+$: 252.1.

Step 3. 6-hydroxy-2,3-dihydro-1H-pyrrolo[3,2-c]pyridine-7-carbonitrile

A solution of acetyl chloride (0.50 mL, 7.0 mmol) in methanol (100 mL) was prepared and was stirred for 3 h. The solution was mixed with 6-(benzyloxy)-2,3-dihydro-1H-pyrrolo[3,2-c]pyridine-7-carbonitrile (0.59 g, 2.3 mmol), and was stirred at RT for 3 days. Solvent was removed in vacuo to afford product as a white powder, theoretical yield assumed. LCMS (M+H)$^+$: 162.1.

Step 4. 6-chloro-2,3-dihydro-1H-pyrrolo[3,2-c]pyridine-7-carbonitrile

A solution of 6-hydroxy-2,3-dihydro-1H-pyrrolo[3,2-c]pyridine-7-carbonitrile (0.38 g, 2.4 mmol) in phosphoryl chloride (12 mL, 130 mmol) was heated to 110° C. for 2 h. The mixture was cooled to RT and poured onto crushed ice. Solid NaOH was added slowly to the cooled solution to achieve a pH between 6 and 7. The solution was extracted with DCM three times. The combined extracts were dried over sodium sulfate, decanted and concentrated. The crude product was adsorbed onto silica gel. Flash column chromatography, eluting with a gradient of 0-10% MeOH in DCM, afforded product as a light yellow solid (230 mg, 49%). $^1$H NMR (300 MHz, DMSO-d6): δ 8.31 (br s, 1H), 7.76 (s, 1H), 3.73 (t, 2H), 3.02 (dt, 2H); (M+H)$^+$: 180.0/182.1.

Step 5. 6-(3-{2-cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydro-1H-pyrrolo[3,2-d]pyridine-7-carbonitrile 3-Pyrrolidin-3-yl-3-[4-(7-{[2-(trimethylsilyl)ethoxy]methyl}-7H-pyrrolo[2,3-d]pyrimidin-4-yl)-1H-pyrazol-1-yl]propanenitrile (0.14 g, 0.32 mmol, from Example 15, Step 3), 6-chloro-2,3-dihydro-1H-pyrrolo[3,2-c]pyridine-7-carbonitrile (0.045 g, 0.25 mmol) and 4-methylmorpholine (0.083 mL, 0.75 mmol) were combined in NMP (0.10 mL) and the reaction was heated at 90° C. for 15 h. Upon cooling to RT, the reaction mixture was partitioned between water and ethyl acetate. The aqueous phase was extracted with three additional portions of ethyl acetate. The combined organic extracts were washed with brine, dried over sodium sulfate, decanted and concentrated. Flash column chromatography, eluting with a gradient mixture of hexanes:EtOAc:MeOH (100:0:0) to (0:98:2), afforded the desired product (20 mg, 14%). LCMS (M+H)$^+$: 581.1.

Step 6. 6-(3-{2-cyano-1-[4-(7H-pyrrolo[2,3-d]pyrimidin-4-yl)-1H-pyrazol-1-yl]ethyl}pyrrolidin-1-yl)-1H-pyrrolo[3,2-c]pyridine-7-carbonitrile 6-(3-{2-Cyano-1-[4-(7-{[2-(trimethylsilyl)ethoxy]methyl}-7H-pyrrolo[2,3-d]pyrimidin-4-yl)-1H-pyrazol-1-yl]ethyl}pyrrolidin-1-yl)-2,3-dihydro-1H-pyrrolo[3,2-c]pyridine-7-carbonitrile (12 mg, 0.021 mmol) was treated with manganese(IV) oxide (12 mg, 0.14 mmol) in THF (0.37 mL). The mixture was stirred at RT for 1 h, and then was heated at 68° C. for 16 h. Additional manganese(IV) oxide (18 mg, 0.21 mmol) was added and heating continued at this temperature for 24 h. Upon cooling, the reaction was filtered, rinsing with methanol. The filtrate was concentrated, and the residue was stirred with 1:1 TFA/DCM for 1 h. Solvents were again removed in vacuo, and the residue was stirred in MeOH (1 mL) containing EDA (0.2 mL). Preparative HPLC-MS (eluting with a gradient of ACN/H$_2$O containing 0.15% NH$_4$OH) was used to afford the product as the free base (2.2 mg, 24%). $^1$H NMR (400 MHz, CD$_3$OD): δ 8.68 (d, 1H), 8.65 (s, 1H), 8.45 (s, 1H), 8.42 (s, 1H), 7.49 (d, 1H), 7.08 (d, 1H), 6.93 (d, 1H), 6.48 (d, 1H), 4.87-4.79 (m, 1H), 4.05 (dd, 1H), 3.87-3.69 (m, 3H), 3.39 (dd, 1H), 3.18 (dd, 1H), 3.08-2.96 (m, 1H), 1.89-1.82 (m, 2H); LCMS (M+H)$^+$: 449.1.

Example 178

6-((3S)-3-{2-fluoro-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide (single enantiomer)

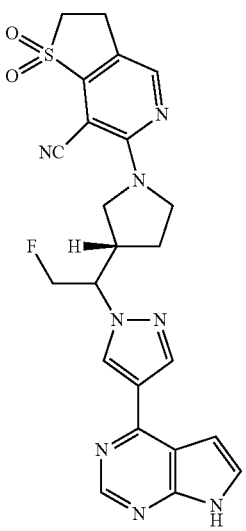 [SMILES: N#Cc1c(N2CC[C@H](C(CF)n3cc(-c4ncnc5[nH]ccc45)cn3)C2)ncc2c1S(=O)(=O)CC2]

A solution of 6-chloro-2,3-dihydrothieno[3,2-c]pyridine-7-carbonitrile 1,1-dioxide (from Example 171, Step 8; 0.015 g, 0.065 mmol) and 4-(1-{2-fluoro-1-[(3S)-pyrrolidin-3-yl]ethyl}-1H-pyrazol-4-yl)-7-{[2-(trimethylsilyl)ethoxy]methyl}-7H-pyrrolo[2,3-d]pyrimidine (from Example 70, Step 7; 0.020 g, 0.046 mmol) in DMF (1 mL) containing 4-methylmorpholine (15 mL, 0.14 mmol) was heated to 80° C. for 2 h. The crude reaction mixture was partitioned between ethyl acetate and water. The aqueous layer was extracted with three portions of ethyl acetate. The combined extracts were dried over sodium sulfate, decanted and concentrated. The product was deprotected by stirring in a solution of TFA and DCM (1:1) for one hour, followed by evaporation and stirring with excess ethylenediamine in methanol for 20 min. Preparative HPLC-MS, eluting with a gradient of ACN and $H_2O$ containing 0.15% $NH_4OH$, followed by lyophilization afforded the product as the free base. $^1H$ NMR (300 MHz, $CDCl_3$): δ 10.01 (br s, 1H), 8.85 (s, 1H), 8.38 (s, 1H), 8.36 (s, 1H), 8.34 (s, 1H), 7.42 (d, 1H), 6.81 (d, 1H), 5.04-4.69 (m, 2H), 4.57-4.40 (m, 1H), 4.15 (dd, 1H), 4.04-3.94 (m, 1H), 3.86-3.65 (m, 2H), 3.56 (t, 2H), 3.24 (t, 2H), 3.16-2.98 (m, 1H), 2.03-1.72 (m, 2H); LCMS $(M+H)^+$: 493.2.

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for Jak1, 30 μM for Jak2 and 3 μM for Jak3 for Km conditions. For the 1 mM $IC_{50}$ measurements, ATP concentration in the reactions was 1 mM. Reactions were carried out at RT for 1 h and then stopped with 20 μL 45 mM EDTA, 300 nM SA-APC, 6 nM Eu—Py20 in assay buffer (Perkin Elmer, Boston, Mass.). Binding to the Europium labeled antibody took place for 40 min and HTRF signal was measured on a Fusion plate reader (Perkin Elmer, Boston, Mass.).

Compounds herein were tested for inhibitory activity of JAK1 and JAK2 targets according to the assay of Example A (experiments run at Km or 1 mM as indicated). Data is shown in Tables A-E below. The symbol "+" indicates an $IC_{50}$≤50 nM; the symbol "++" indicates an $IC_{50}$>50 and ≤100 nM; and the symbol "+++" indicates an $IC_{50}$>100 and ≤500 nM.

TABLE A

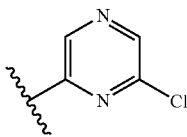 [SMILES: *c1cncc(Cl)n1]

| Example No. | R= | Salt Form | Assay Conditions | JAK1 $IC_{50}$ (nM) | JAK2/JAK1 $IC_{50}$ ratio |
|---|---|---|---|---|---|
| 1 (rac) | 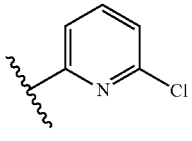 [SMILES: *c1cccc(Cl)n1] | — | Km | + | 3 |
| 2, Step 2a | 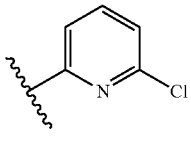 [SMILES: *c1cccc(Cl)n1] | — | Km | + | 7.3 |
| 2, Step 2b |  | — | Km | + | 3.7 |

TABLE A-continued
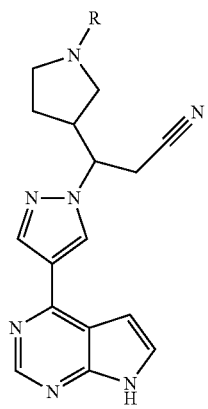
| Example No. | R= | Salt Form | Assay Conditions | JAK1 IC$_{50}$ (nM) | JAK2/JAK1 IC$_{50}$ ratio |
|---|---|---|---|---|---|
| 3, Step 2a | pyrimidine-Cl | — | Km | + | 2.3 |
| 3, Step 2b | pyrimidine-Cl | — | Km | + | 8.5 |
| 4a | pyrimidine-Cl | — | Km | + | 8.8 |
| 4b | pyrimidine-Cl | — | Km | + | 3.7 |
| 5 | thiazole-Br | TFA | Km | + | 2.2 |
| 6 | pyrimidine-N(Me)$_2$ | — | Km | + | >5 |
| 7 | pyrimidine-NHiPr | — | Km | + | 4.7 |

TABLE A-continued

| Example No. | R= | Salt Form | Assay Conditions | JAK1 IC$_{50}$ (nM) | JAK2/JAK1 IC$_{50}$ ratio |
| --- | --- | --- | --- | --- | --- |
| 9, Step 3a | benzoxazol-2-yl | — | Km | + | 1.9 |
| 9, Step 3b | benzoxazol-2-yl | — | Km | + | 6.3 |
| 10 | 5-chlorobenzoxazol-2-yl | — | Km | + | 1.9 |
| 11 | oxazolo[4,5-c]pyridin-2-yl | — | Km | + | 2.9 |
| 12 | oxazolo[4,5-b]pyridin-2-yl (pyrazino) | — | Km | + | 2.4 |
| 13a | oxazolo[5,4-b]pyridin-2-yl | — | Km | + | 12 |

TABLE A-continued

| Example No. | R= | Salt Form | Assay Conditions | JAK1 IC$_{50}$ (nM) | JAK2/JAK1 IC$_{50}$ ratio |
|---|---|---|---|---|---|
| 13b | | — | Km | + | 2.1 |
| 14 | | — | Km | + | 4 |
| 15 | | — | Km | + | 6.8 |
| 16 | | — | 1 mM | + | 11.4 |
| 17 | | — | 1 mM | +++ | 8 |
| 18 | | — | 1 mM | ++ | 10.3 |

TABLE A-continued
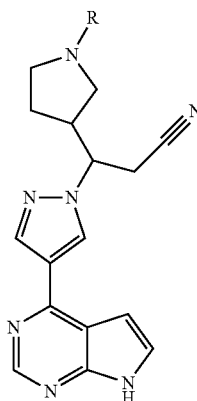
| Example No. | R= | Salt Form | Assay Conditions | JAK1 IC$_{50}$ (nM) | JAK2/JAK1 IC$_{50}$ ratio |
|---|---|---|---|---|---|
| 19 | 5-fluoro-benzoxazol-2-yl | — | 1 mM | + | 5.3 |
| 20 | 4-fluoro-benzoxazol-2-yl | — | 1 mM | + | 10.4 |
| 21 | 7-fluoro-benzoxazol-2-yl | — | 1 mM | + | 31.8 |
| 22 | 5,7-difluoro-benzoxazol-2-yl | — | 1 mM | + | >7 |
| 23 | 2-(methylthio)pyrimidin-4-yl | — | 1 mM | + | 2.3 |
| 24 | 2-(methylsulfinyl)pyrimidin-4-yl | — | 1 mM | + | 2.5 |

TABLE A-continued
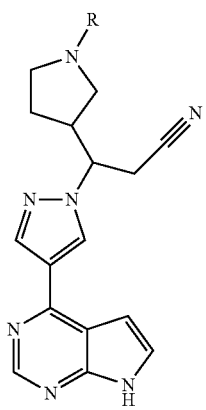
| Example No. | R= | Salt Form | Assay Conditions | JAK1 IC$_{50}$ (nM) | JAK2/JAK1 IC$_{50}$ ratio |
|---|---|---|---|---|---|
| 25 | 2-(methylsulfonyl)pyrimidin-4-yl | — | 1 mM | + | 34 |
| 26 | 6-(methylsulfonyl)pyridin-2-yl | — | 1 mM | ++ | 5.2 |
| 27 | 2-(methylsulfonyl)pyridin-4-yl | — | 1 mM | + | 14 |
| 28 | 7-oxo-2,3-dihydrothieno[2,3-b]pyridin-6-yl | — | 1 mM | + | 4 |
| 29 | 2,3-dihydrothieno[2,3-b]pyridin-6-yl | — | 1 mM | + | 12 |
| 30 | 7,7-dioxo-2,3-dihydrothieno[2,3-b]pyridin-6-yl | — | 1 mM | + | 14.5 |
| 36 | 5-chloro-1-methyl-2-oxo-1,2-dihydropyrazin-3-yl | TFA | 1 mM | ++ | 6 |

TABLE A-continued

| Example No. | R= | Salt Form | Assay Conditions | JAK1 IC$_{50}$ (nM) | JAK2/JAK1 IC$_{50}$ ratio |
|---|---|---|---|---|---|
| 37 | 1-methyl-2-oxo-pyrazin-3-yl | TFA | 1 mM | + | >8.7 |
| 38 | 3-chloro-4-cyano-pyridin-2-yl | TFA | 1 mM | ++ | 3.3 |
| 39 | 3-cyano-4-cyano-pyridin-2-yl | TFA | 1 mM | + | 15.5 |
| 40 | 2-cyano-3-(methylthio)phenyl | — | 1 mM | + | 7.1 |
| 41 | 2-cyano-3-(methylsulfonyl)phenyl | — | 1 mM | + | 11 |
| 42 | 8-chloroquinolin-2-yl | — | Km | + | 6.0 |

TABLE A-continued
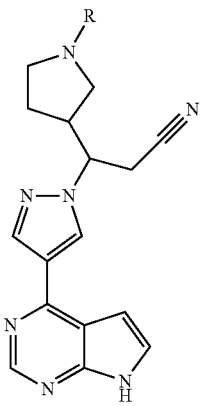
| Example No. | R= | Salt Form | Assay Conditions | JAK1 IC$_{50}$ (nM) | JAK2/JAK1 IC$_{50}$ ratio |
|---|---|---|---|---|---|
| 43 | 3-hydroxyquinoxalin-2-yl | 2TFA | Km | + | 2.5 |
| 44 | 8-chloroquinazolin-2-yl | 2TFA | Km | + | 3 |
| 45 | 6-chloropyridin-2-yl N-oxide | — | Km | + | 7.4 |
| 46 | 8-fluoroquinazolin-2-yl | — | 1 mM | + | 3.7 |
| 47 | 5-bromothiazol-2-yl | TFA | 1 mM | + | 6.9 |
| 48 | 2-cyano-3-chlorophenyl | TFA | 1 mM | + | >30 |
| 49 | 2,3-dicyanophenyl | TFA | 1 mM | + | 10.2 |

TABLE A-continued
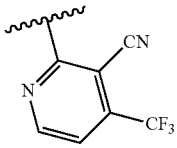 [SMILES: *c1nccc(C(F)(F)F)c1C#N]
| Example No. | R= | Salt Form | Assay Conditions | JAK1 IC$_{50}$ (nM) | JAK2/JAK1 IC$_{50}$ ratio |
|---|---|---|---|---|---|
| 50 | 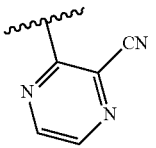 [SMILES: *c1nccnc1C#N] | TFA | 1 mM | + | 15.4 |
| 51 | 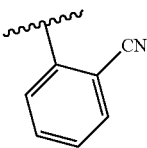 [SMILES: *c1ccccc1C#N] | TFA | 1 mM | + | 6.8 |
| 52 | 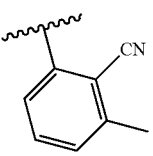 [SMILES: *c1cccc(C)c1C#N] | TFA | 1 mM | + | 2 |
| 53 | 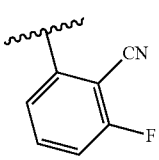 [SMILES: *c1cccc(F)c1C#N] | TFA | 1 mM | + | >7.7 |
| 54 | 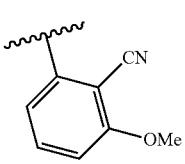 [SMILES: *c1cccc(OC)c1C#N] | TFA | 1 mM | + | 4.6 |
| 55 | 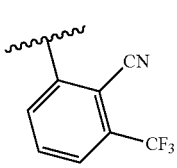 [SMILES: *c1cccc(C(F)(F)F)c1C#N] | TFA | 1 mM | + | >8 |
| 56 |  | TFA | 1 mM | + | >10 |

TABLE A-continued
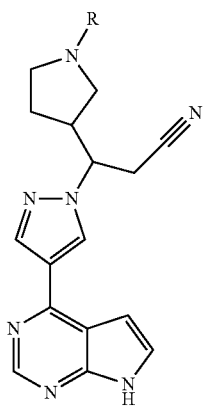
| Example No. | R= | Salt Form | Assay Conditions | JAK1 IC$_{50}$ (nM) | JAK2/JAK1 IC$_{50}$ ratio |
|---|---|---|---|---|---|
| 57 | 2-CN, 6-Br phenyl | TFA | 1 mM | + | 37 |
| 58 | 2-CN, 3-F phenyl | TFA | 1 mM | + | 8 |
| 59 | 2,6-diCN phenyl | TFA | 1 mM | + | 6.5 |
| 60 | 2-CN, 3,4-diF phenyl | TFA | 1 mM | + | 6.6 |
| 61 | 2-CN, 3,5,6-triF phenyl | TFA | 1 mM | + | 6.4 |
| 62 | 3-CN pyridin-2-yl | TFA | 1 mM | + | 7.1 |

TABLE A-continued
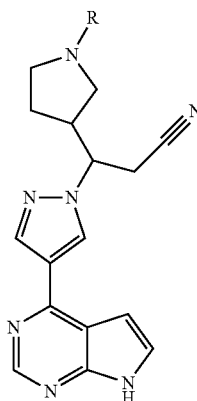
| Example No. | R= | Salt Form | Assay Conditions | JAK1 IC$_{50}$ (nM) | JAK2/JAK1 IC$_{50}$ ratio |
|---|---|---|---|---|---|
| 63 | 2-Cl, 3-F, 5-CN pyridinyl | TFA | 1 mM | + | 7.3 |
| 64 | 4-CN, 5-Cl pyridin-3-yl | TFA | 1 mM | + | 11 |
| 65 | 4-CN, 2,5,6-triF pyridin-3-yl | TFA | 1 mM | + | 9.4 |
| 66 | 3-CN, 4-CF$_3$ pyridin-2-yl | TFA | 1 mM | + | >20 |
| 67 | 3,5,6-triF pyridin-2-yl | TFA | 1 mM | + | 5.6 |
| 68 | 2-CN pyridin-3-yl | TFA | 1 mM | + | 8.2 |

TABLE A-continued
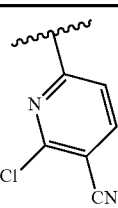
| Example No. | R= | Salt Form | Assay Conditions | JAK1 IC$_{50}$ (nM) | JAK2/JAK1 IC$_{50}$ ratio |
|---|---|---|---|---|---|
| 69 | 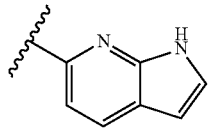 [SMILES: *c1ccc2cc[nH]c2n1] | TFA | 1 mM | + | 6.5 |
| 73 | 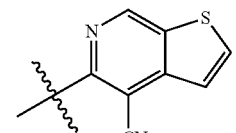 | TFA | 1 mM | + | 1.7 |
| 74 | 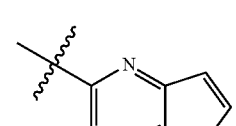 | — | 1 mM | + | 6.2 |
| 75 | 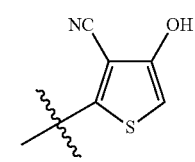 [SMILES: *c1scc(O)c1C#N] | — | 1 mM | + | 4.6 |
| 76 | 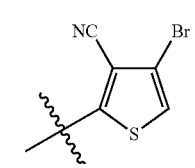 [SMILES: *c1scc(Br)c1C#N] | — | 1 mM | + | 51.1 |
| 77 | 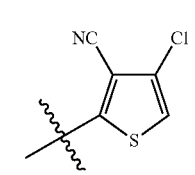 [SMILES: *c1scc(Cl)c1C#N] | — | 1 mM | + | 39.1 |
| 78 |  | — | 1 mM | + | 32.1 |

TABLE A-continued

| Example No. | R= | Salt Form | Assay Conditions | JAK1 IC$_{50}$ (nM) | JAK2/JAK1 IC$_{50}$ ratio |
| --- | --- | --- | --- | --- | --- |
| 79 | 3,4-dicyanothiophen-2-yl | — | 1 mM | + | 20.0 |
| 82 | 5-cyanothiazol-4-yl | — | 1 mM | + | 6.7 |
| 84 | 5-cyanopyrimidin-4-yl | TFA | 1 mM | + | 11.5 |
| 87 | 5-fluoro-2,3-dihydrothieno[2,3-b]pyridin-6-yl | 2TFA | 1 mM | + | 8.1 |
| 88 | 6-bromo-3-fluoropyridin-2-yl | 2TFA | 1 mM | + | 40.0 |
| 89 | 2,3-difluoropyridin-6-yl | TFA | 1 mM | + | 3.1 |
| 90 | 2-chloro-5-fluoro-3-(hydroxymethyl)pyridin-6-yl | TFA | 1 mM | + | 4.3 |

TABLE A-continued
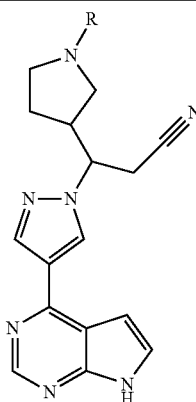
| Example No. | R= | Salt Form | Assay Conditions | JAK1 IC$_{50}$ (nM) | JAK2/JAK1 IC$_{50}$ ratio |
|---|---|---|---|---|---|
| 91A | F, NH$_2$, Cl-pyridine | 2TFA | 1 mM | + | 6.9 |
| 91B | H$_2$N, F, Cl-pyridine | 2TFA | 1 mM | + | 7.0 |
| 92 | formamido, F, Cl-pyridine | TFA | 1 mM | + | >12.5 |
| 93 | F, ethylsulfonyl-pyridine | TFA | 1 mM | + | 5.3 |
| 94 | F, Cl-pyridine | TFA | 1 mM | + | 17.9 |
| 95 | F, methoxymethyl, CN-pyridine | 2TFA | 1 mM | + | 16.4 |
| 96 | methoxymethyl, CN-pyridine | 3TFA | 1 mM | + | 16.3 |

TABLE A-continued

| Example No. | R= | Salt Form | Assay Conditions | JAK1 IC$_{50}$ (nM) | JAK2/JAK1 IC$_{50}$ ratio |
|---|---|---|---|---|---|
| 98 | | TFA | 1 mM | + | >9.1 |
| 99 | | TFA | 1 mM | + | 7.6 |
| 100 | | 2TFA | 1 mM | + | >7.4 |
| 101 | | 1.5TFA | 1 mM | + | 4.0 |
| 104 | | TFA | 1 mM | + | 5.9 |
| 105 | | TFA | 1 mM | + | 3.0 |

TABLE A-continued
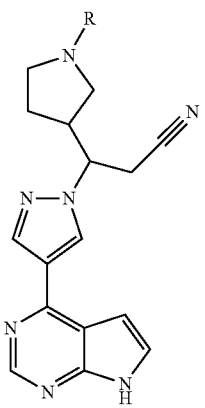
| Example No. | R= | Salt Form | Assay Conditions | JAK1 IC$_{50}$ (nM) | JAK2/JAK1 IC$_{50}$ ratio |
|---|---|---|---|---|---|
| 106 | 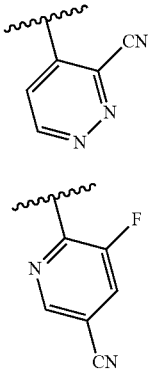 | TFA | 1 mM | + | 12.6 |
| 107 | 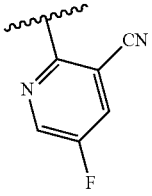 [SMILES: *c1ncc(F)cc1C#N] | TFA | 1 mM | + | 4.8 |
| 108 | 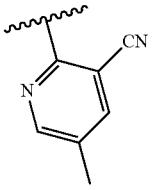 [SMILES: *c1ncc(C)cc1C#N] | TFA | 1 mM | + | 5.7 |
| 109 | 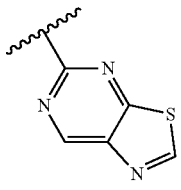 [SMILES: *c1ncc2ncsc2n1] | TFA | 1 mM | + | 5.0 |
| 102 | 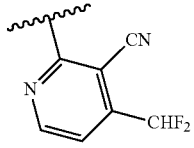 [SMILES: *c1nccc(C(F)F)c1C#N] | TFA | 1 mM | + | 12.8 |
| 103 |  | TFA | 1 mM | + | 22.8 |

TABLE A-continued
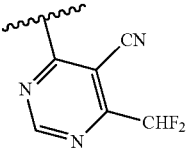 [SMILES: *c1ncnc(C(F)F)c1C#N]
| Example No. | R= | Salt Form | Assay Conditions | JAK1 IC$_{50}$ (nM) | JAK2/JAK1 IC$_{50}$ ratio |
|---|---|---|---|---|---|
| 110 | 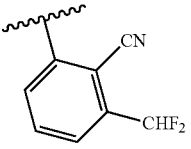 [SMILES: *c1cccc(C(F)F)c1C#N] | TFA | 1 mM | + | 17.6 |
| 111 | 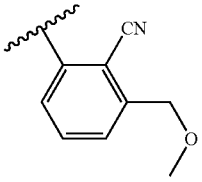 [SMILES: *c1cccc(COC)c1C#N] | TFA | 1 mM | + | 37.6 |
| 112 | 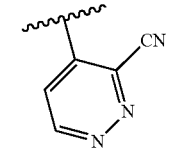 [SMILES: *c1ccnnc1C#N] | — | 1 mM | + | 35.7 |
| 116 | 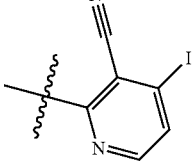 | TFA | 1 mM | + | 6.0 |
| 122 | 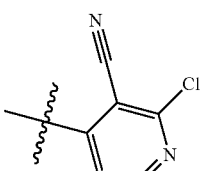 | TFA | 1 mM | + | 188.0 |
| 123 | | TFA | 1 mM | + | >16.7 |

TABLE A-continued
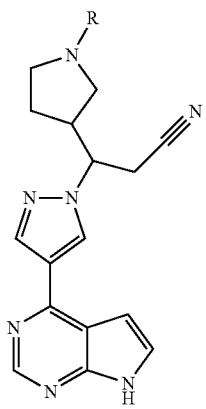
| Example No. | R= | Salt Form | Assay Conditions | JAK1 IC$_{50}$ (nM) | JAK2/JAK1 IC$_{50}$ ratio |
|---|---|---|---|---|---|
| 124 | 4-position of 2,3-dicyanopyridine | TFA | 1 mM | + | >10.5 |
| 125 | 3-position of 2,6-dichloropyridine | TFA | 1 mM | + | 132.5 |
| 127 | 2-position of 3-cyano-4-(methylthio)pyridine | TFA | 1 mM | + | 11.0 |
| 128 | 2-position of 3-cyano-4-(methylsulfonyl)pyridine | TFA | 1 mM | + | 4.7 |
| 129 | 2-position of 3,5-difluoro-6-(methylthio)pyridine | TFA | 1 mM | + | 5.9 |

TABLE A-continued
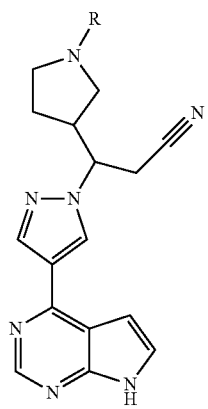
| Example No. | R= | Salt Form | Assay Conditions | JAK1 IC$_{50}$ (nM) | JAK2/JAK1 IC$_{50}$ ratio |
|---|---|---|---|---|---|
| 130 | 6-(methylsulfonyl)-3,5-difluoropyridin-2-yl | TFA | 1 mM | + | 14.8 |
| 131 | 6-((2,2,2-trifluoroethyl)sulfonyl)-3,5-difluoropyridin-2-yl | TFA | 1 mM | + | 8.1 |
| 133 | 6-(methylthio)-3-fluoropyridin-2-yl | TFA | 1 mM | ++ | 3 |
| 134 | 2-(methylsulfonyl)-3,6-difluoropyridin-5-yl | TFA | 1 mM | + | 17 |
| 136 | 3-cyano-4-(1-fluoroethyl)pyridin-2-yl | TFA | 1 mM | + | >5 |

TABLE A-continued
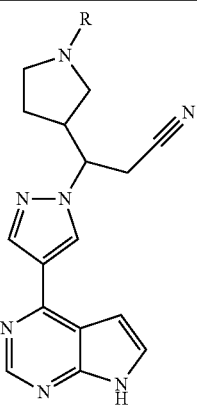
| Example No. | R= | Salt Form | Assay Conditions | JAK1 IC$_{50}$ (nM) | JAK2/JAK1 IC$_{50}$ ratio |
|---|---|---|---|---|---|
| 138 | | TFA | 1 mM | + | 17.5 |
| 139 | | TFA | 1 mM | + | 10.7 |
| 140 | | TFA | 1 mM | + | 17.4 |
| 141 | | TFA | 1 mM | + | 16.2 |
| 142 | | TFA | 1 mM | + | 14.2 |
| 143 | | TFA | 1 mM | + | >4.5 |

TABLE A-continued

[Structure: pyrrolotriazine-pyrazole-pyrrolidine with R group and nitrile substituent]

| Example No. | R= | Salt Form | Assay Conditions | JAK1 IC$_{50}$ (nM) | JAK2/JAK1 IC$_{50}$ ratio |
|---|---|---|---|---|---|
| 144 | [3-cyano-5-ethylpyrazin-2-yl] | TFA | 1 mM | + | >6.9 |
| 145 | [3-cyano-5-methylpyrazin-2-yl] | TFA | 1 mM | + | >11.1 |
| 146 | [3-cyano-5-(1-hydroxyethyl)pyrazin-2-yl] | TFA | 1 mM | + | >4.8 |
| 147 | [3-cyanopyrazin-2-yl] | TFA | 1 mM | + | 3.3 |
| 150 | [2-mercaptopyrimidin-4-yl] | — | 1 mM | + | 3.2 |
| 151 | [2-(N,N-dimethylsulfamoylamino)pyrimidin-4-yl, NHSO$_2$NMe$_2$] | — | 1 mM | + | 12.5 |

TABLE A-continued
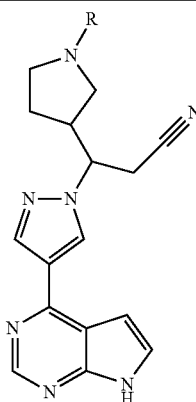
| Example No. | R= | Salt Form | Assay Conditions | JAK1 IC$_{50}$ (nM) | JAK2/JAK1 IC$_{50}$ ratio |
|---|---|---|---|---|---|
| 152 | pyridine-CONHMe | — | 1 mM | + | 6.7 |
| 153 | pyridine-CONMe$_2$ | — | 1 mM | + | >11.1 |
| 154 | pyridine-CONHPh | — | 1 mM | + | >11.8 |
| 155 | furo[2,3-b]pyridine | — | 1 mM | ++ | 5.3 |
| 156 | thieno[2,3-b]pyridine | — | 1 mM | + | 8.0 |
| 157 | 7,7-difluoro-6,7-dihydro-5H-cyclopenta[b]pyridine | 2 TFA | 1 mM | + | >5.3 |
| 159 | 7-bromobenzoxazole | TFA | 1 mM | + | 12.9 |
| 160 | 7-cyanobenzoxazole | — | 1 mM | + | >11.4 |

TABLE A-continued
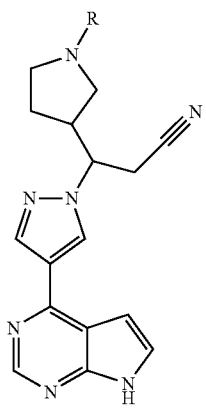
| Example No. | R= | Salt Form | Assay Conditions | JAK1 IC$_{50}$ (nM) | JAK2/JAK1 IC$_{50}$ ratio |
|---|---|---|---|---|---|
| 161 | benzoxazole-7-OH | — | 1 mM | + | 24.7 |
| 162 | benzoxazole-7-OMe | — | 1 mM | + | 7.7 |
| 163 | benzoxazole-7-OEt | — | 1 mM | + | 3.3 |
| 164 | benzoxazole-7-OCHF$_2$ | — | 1 mM | + | 10.9 |
| 165 | benzoxazole-4-OH | — | 1 mM | + | 7.1 |
| 166 | benzoxazole-7-CH$_2$OH | — | 1 mM | + | >8.7 |

TABLE A-continued
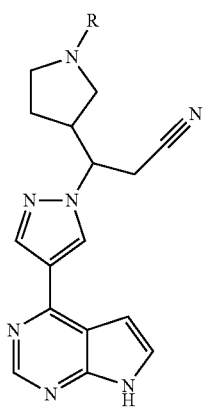
| Example No. | R= | Salt Form | Assay Conditions | JAK1 IC$_{50}$ (nM) | JAK2/JAK1 IC$_{50}$ ratio |
|---|---|---|---|---|---|
| 169 | furo[3,2-c]pyridine-CN | — | 1 mM | + | >13.3 |
| 172 | 2,3-dihydrothieno[3,2-c]pyridine-S,S-dioxide-CN | — | 1 mM | + | 20.0 |
| 173 | 2,3-dihydrothieno[3,2-c]pyridine-CN | — | 1 mM | + | >27.3 |
| 175 | thieno[3,2-c]pyridine-CN | — | 1 mM | + | 15.4 |
| 177 | 1H-pyrrolo[3,2-c]pyridine-CN | — | 1 mM | + | >5.4 |

TABLE B
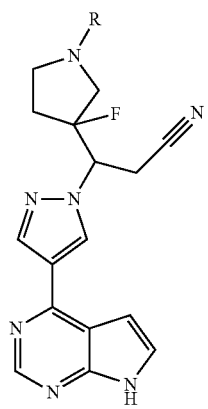
| Ex. No. | R= | Salt Form | Assay Conditions | JAK1 IC$_{50}$ (nM) | JAK2/ JAK1 IC$_{50}$ ratio |
|---|---|---|---|---|---|
| 31, Step 4a, enantiomer 1 | | — | 1 mM | ++ | 5.6 |
| 31, Step 4a, enantiomer 2 | | — | 1 mM | ++ | 5.1 |
| 31, Step 4b, enantiomer 1 | | — | 1 mM | +++ | >2.5 |
| 31, Step 4b, enantiomer 2 | | — | 1 mM | +++ | 0.8 |

TABLE C
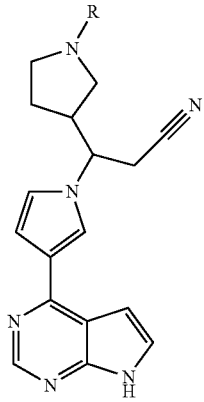
| Ex. No. | R= | Salt Form | Assay Conditions | JAK1 IC$_{50}$ (nM) | JAK2/JAK1 IC$_{50}$ ratio |
|---|---|---|---|---|---|
| 32, Step 2a, enantiomer 1 | 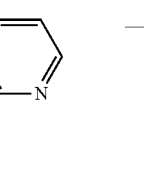 | — | Km | + | 3.7 |
| 32, Step 2a, enantiomer 2 | 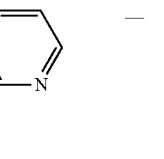 | — | Km | + | 5.7 |
| 32, Step 2b (racemate) | 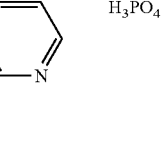 | — | Km | ++ | 0.2 |
| 33 | 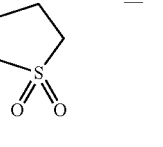 | H$_3$PO$_4$ | 1 mM | + | 34 |
| 34, enantiomer 1 | 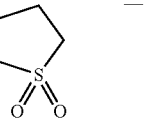 | — | 1 mM | + | 5.6 |
| 34, enantiomer 2 | | — | 1 mM | + | 13.8 |
| 35 | 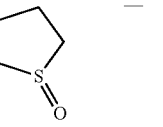 | — | 1 mM | + | 4.2 |

TABLE C-continued
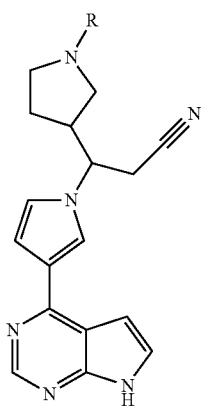
| Ex. No. | R= | Salt Form | Assay Conditions | JAK1 IC$_{50}$ (nM) | JAK2/JAK1 IC$_{50}$ ratio |
|---|---|---|---|---|---|
| 81 enantiomer 1 | NC, CN (thiophene) | — | 1 mM | + | 40.0 |
| 81 enantiomer 2 | NC, CN (thiophene) | — | 1 mM | + | 8.1 |
| 114, enantiomer 1 | NC-pyridine | TFA | 1 mM | + | 4.9 |
| 115, enantiomer 1 | NC-pyrazine | TFA | 1 mM | + | 9.3 |
| 113, (racemate) | NC-pyridazine | TFA | 1 mM | + | 8.7 |
| 148-rac | pyridine-SO$_2$Et | — | 1 mM | + | 4.0 |
| 149-rac | NC-thiazole | — | 1 mM | + | 14.5 |

TABLE C-continued
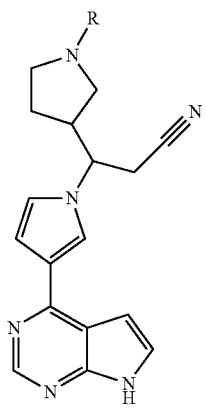
| Ex. No. | R= | Salt Form | Assay Conditions | JAK1 IC$_{50}$ (nM) | JAK2/JAK1 IC$_{50}$ ratio |
|---|---|---|---|---|---|
| 149-1 | 4-cyanothiazol-5-yl | — | 1 mM | + | 9.9 |
| 149-2 | 4-cyanothiazol-5-yl | — | 1 mM | + | 4.5 |
| 158-1 | 7-fluorobenzo[d]oxazol-2-yl | — | 1 mM | + | 22.5 |
| 158-2 | 7-fluorobenzo[d]oxazol-2-yl | — | 1 mM | + | 19.0 |
| 170-rac | 7-cyanofuro[3,2-c]pyridin-6-yl | — | 1 mM | + | 4.5 |
| 171-rac | 7-cyano-1,1-dioxido-2,3-dihydrothieno[3,2-c]pyridin-6-yl | — | 1 mM | + | 21.9 |
| 174-1 | 7-cyano-2,3-dihydrothieno[3,2-c]pyridin-6-yl | — | 1 mM | + | 28.5 |

TABLE C-continued
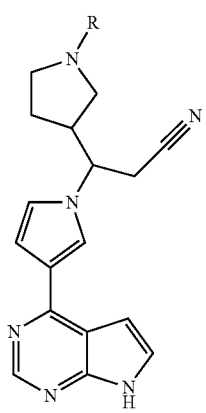
| Ex. No. | R= | Salt Form | Assay Conditions | JAK1 IC$_{50}$ (nM) | JAK2/JAK1 IC$_{50}$ ratio |
|---|---|---|---|---|---|
| 174-2 | 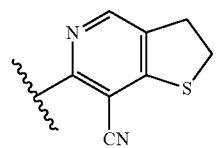 [SMILES: *c1ncc2c(c1C#N)SCC2] | — | 1 mM | + | 11.1 |
| 176-rac | 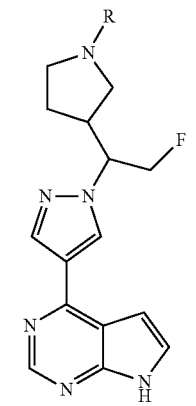 | — | 1 mM | + | 53.3 |
TABLE D
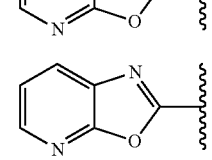
| Ex. No. | R= | Salt Form | Assay Conditions | JAK1 IC$_{50}$ (nM) | JAK2/JAK1 IC$_{50}$ ratio |
|---|---|---|---|---|---|
| 70 (3S-enantiomer) | | H$_3$PO$_4$ | 1 mM | + | 15 |
| 71 (3R-enantiomer) | | H$_3$PO$_4$ | 1 mM | + | 5.9 |

TABLE D-continued
| Ex. No. | R= | Salt Form | Assay Conditions | JAK1 IC$_{50}$ (nM) | JAK2/JAK1 IC$_{50}$ ratio |
|---|---|---|---|---|---|
| 80 | 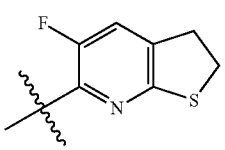 [SMILES: *c1nc2c(cc1F)CCS2] | — | 1 mM | + | 12.1 |
| 85 | 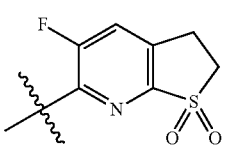 [SMILES: *c1nc2c(cc1F)CCS2(=O)=O] | 2TFA | 1 mM | + | 5.3 |
| 86 | 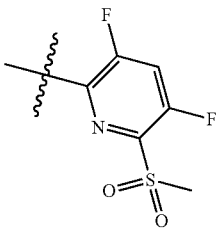 [SMILES: *c1nc(S(C)(=O)=O)c(F)cc1F] | 4TFA | 1 mM | + | 13.0 |
| 132 | 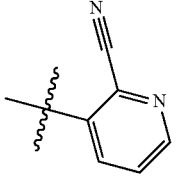 [SMILES: *c1cccnc1C#N] | TFA | 1 mM | + | 8.9 |
| 117 | 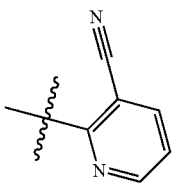 [SMILES: *c1ncccc1C#N] | TFA | 1 mM | + | 3.7 |
| 118 | | TFA | 1 mM | + | 2.8 |

TABLE D-continued
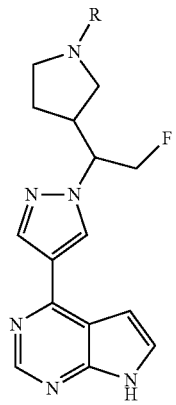
| Ex. No. | R= | Salt Form | Assay Conditions | JAK1 IC$_{50}$ (nM) | JAK2/JAK1 IC$_{50}$ ratio |
|---|---|---|---|---|---|
| 119 | | TFA | 1 mM | + | 7.6 |
| 120 | | TFA | 1 mM | + | 3.5 |
| 121 | | TFA | 1 mM | + | 4.4 |
| 126 | | TFA | 1 mM | + | 5.9 |
| 178 | | — | 1 mM | + | 31.8 |

TABLE E

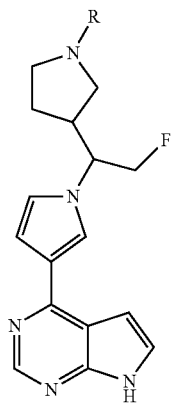

| Ex. No. | R= | Salt Form | Assay Conditions | JAK1 IC50 (nM) | JAK2/ JAK1 IC50 ratio |
|---|---|---|---|---|---|
| 83 | 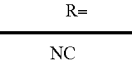 | — | 1 mM | + | 11.3 |

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 h at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 h or less) and cytokine stimulation of approximately 1 h or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/mL penicillin, 100 µg/mL streptomycin) at a density of $2 \times 10^6$ cells/mL at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound (s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today*. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2): 116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two h after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

A number of embodiments of the invention have been described. Nevertheless, it will be understood that various modifications may be made without departing from the spirit and scope of the invention. Each of the references mentioned herein, including patent, patent application, and non-patent literature, is incorporated herein by reference in its entirety.

What is claimed is:

1. A method of treating a disease selected from myelofibrosis, primary myelofibrosis (PMF), polycythemia vera (PV), essential thrombocythemia (ET), post polycythemia vera myelofibrosis (Post-PV MF), post essential thrombocythemia myelofibrosis (Post-ET MF), multiple myeloma, pancreatic cancer, breast cancer, lung cancer, colorectal cancer, rheumatoid arthritis, a skin disorder, lymphoma, leukemia, acute myelogenous leukemia, acute lymphoblastic leukemia, chronic myelogenous leukemia (CML), chronic myelomonocytic leukemia (CMML), graft versus host disease, cachexia, and Castleman's disease in a patient in need thereof, comprising administering to said patient a therapeutically effective amount of a compound of Formula I:

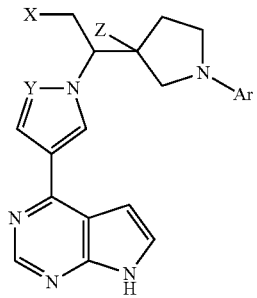

I or a pharmaceutically acceptable salt or N-oxide thereof; wherein:
X is cyano or halogen;
Y is CH or N;
Z is hydrogen, $C_{1-4}$ alkyl, $C_{1-4}$ fluorinated alkyl, or fluoro;
Ar is $C_{6-14}$ aryl, $C_{1-14}$ heteroaryl, $C_{7-14}$ fused cycloalkylaryl, $C_{6-14}$ fused heterocycloalkylaryl, $C_{2-14}$ fused cycloalkylheteroaryl, or $C_{2-14}$ fused heterocycloalkylheteroaryl, each of which is optionally substituted by 1, 2, 3, 4, 5, or 6 independently selected $R^1$ groups;
each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, $C_{1-13}$ heteroaryl-$C_{1-4}$-alkyl, $-OR^a$, $-SR^a$, $-S(=O)R^b$, $-S(=O)_2R^b$, $-S(=O)NR^eR^f$, $-C(=O)R^b$, $-C(=O)OR^b$, $-C(=O)NR^eR^f$, $-OC(=O)R^b$, $-OC(=O)NR^eR^f$, $-NR^cC(=O)R^d$, $-NR^cC(=O)OR^d$, $NR^cS(=O)_2R^d$, and $-NR^bS(=O)_2NR^eR^f$; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; and wherein said $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-13}$ heteroaryl, and $C_{1-13}$ heteroaryl-$C_{1-4}$-alkyl are each optionally substituted by 1, 2, 3, or 4 independently selected $R^{2a}$ groups;

each $R^{1a}$ is independently selected from halogen, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;
each $R^{2a}$ is independently selected from halogen, cyano, nitro, hydroxyl, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, di-$C_{1-4}$-alkylamino, $C_{1-4}$ alkylcarbonyl, carboxy, $C_{1-4}$ alkoxycarbonyl, $C_{1-4}$-alkylcarbonylamino, di-$C_{1-4}$-alkylcarbonylamino, $C_{1-4}$-alkoxycarbonylamino, $C_{1-4}$-alkoxycarbonyl-($C_{1-4}$ alkyl)amino, carbamyl, $C_{1-4}$ alkylcarbamyl, and di-$C_{1-4}$-alkylcarbamyl;
each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;
or any $R^c$ and $R^d$, together with the moiety to which they are attached, can form a 3-, 4-, 5-, 6-, or 7-membered heterocycloalkyl ring, wherein said heterocycloalkyl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;
or any $R^e$ and $R^f$, together with the nitrogen atom to which they are attached, can form a 3-, 4-, 5-, 6- or 7-membered heterocycloalkyl ring or heteroaryl ring, wherein said heterocycloalkyl or heteroaryl ring is optionally substituted with 1, 2, 3, or 4 groups independently selected from hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino;
each $R^x$ is independently selected from hydroxyl, $C_{1-4}$ alkoxy, $C_{1-4}$ haloalkoxy, amino, $C_{1-4}$ alkylamino, and di-$C_{1-4}$-alkylamino; and
each $R^y$ is independently selected from hydroxyl, halogen, cyano, nitro, $C_{1-4}$ alkyl, $C_{1-14}$ haloalkyl, $C_{1-14}$ alkoxy, $C_{1-4}$ haloalkoxy, amino, $C_{1-4}$ alkylamino, and di-$C_{1-4}$-alkylamino;
provided that the valency of each atom in the optionally substituted moieties is not exceeded.

2. A method according to claim 1, wherein said autoimmune disease is rheumatoid arthritis.

3. A method according to claim 1, wherein said skin disorder is atopic dermatitis, psoriasis, skin sensitization, skin irritation, skin rash, contact dermatitis or allergic contact sensitization.

4. A method according to claim 1, wherein said disease is breast cancer, lung cancer, colorectal cancer, Castleman's disease or pancreatic cancer.

5. A method according to claim 1, wherein said disease is lymphoma, leukemia, or multiple myeloma.

6. A method according to claim 1, wherein said disease is polycythemia vera (PV), essential thrombocythemia (ET), primary myelofibrosis (PMF), chronic myelogenous leukemia (CML), chronic myelomonocytic leukemia (CMML), acute myelogenous leukemia, acute lymphoblastic leukemia, post polycythemia vera myelofibrosis (Post-PV MF) or post essentioal thrombocythemia myelofibrosis (Post-ET MF).

7. A method according to claim 1, wherein said disease is myelofibrosis.

8. A method according to claim 1, wherein said disease is primary myelofibrosis (PMF).

9. A method according to claim 1, wherein Y is N.

10. A method according to claim 1, wherein X is cyano.

11. A method according to claim 1, wherein Z is hydrogen.

12. A method according to claim 1, wherein Ar is selected from phenyl, $C_{1-6}$ monocyclic heteroaryl, $C_{1-9}$ bicyclic heteroaryl, and bicyclic $C_{2-14}$ fused heterocycloalkylheteroaryl; each of which is optionally substituted with 1, 2, 3, 4, 5, or 6 independently selected $R^1$ groups.

13. A method according to claim 1, wherein Ar is selected from phenyl, thiazol-2-yl, pyridin-2-yl, pyridin-3-yl, pyridin-4-yl, pyrimidin-2-yl, pyrimidin-4-yl, pyrazin-2-yl, benzo[d]oxazol-2-yl, oxazolo[4,5-c]pyridin-2-yl, oxazo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected $R^1$ groups.

14. A method according to claim 1, wherein each $R^1$ is independently selected from halogen, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, and —$NR^cC(=O)R^d$.

15. A method according to claim 1, wherein each $R^1$ is independently selected from fluoro, bromo, chloro, cyano, hydroxyl, methyl, trifluoromethyl, methoxy, isopropylamino, dimethylamino, methylthio, methylsulfinyl, and methylsulfonyl.

16. A method according to claim 1, wherein each $R^a$, $R^b$, $R^c$, $R^d$, $R^e$, and $R^f$ is independently selected from H, $C_{1-6}$ alkyl, and $C_{1-6}$ haloalkyl.

17. A method according to claim 1, wherein:

X is cyano or fluoro;

Y is CH or N;

Z is hydrogen or fluoro;

Ar is selected from phenyl, $C_{1-6}$ monocyclic heteroaryl, $C_{1-6}$ bicyclic heteroaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, $C_{1-6}$ heteroaryl-$C_{1-4}$-alkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, —$NR^cC(=O)R^d$, and —$NR^cC(=O)OR^d$; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^{1a}$ groups; wherein said $C_{3-7}$ cycloalkyl, $C_{3-7}$ cycloalkyl-$C_{1-4}$-alkyl, $C_{2-6}$ heterocycloalkyl, $C_{2-6}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{2a}$ groups;

each $R^{1a}$ is independently selected from fluoro, chloro, bromo, cyano, nitro, hydroxyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino;

each $R^{2a}$ is independently selected from fluoro, chloro, bromo, cyano, nitro, hydroxyl, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ alkylsulfinyl, $C_{1-4}$ alkylsulfonyl, amino, $C_{1-4}$ alkylamino, and di-$C_{1-4}$-alkylamino;

each $R^a$, $R^b$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl; wherein said $C_{1-6}$ alkyl, $C_{1-6}$ haloalkyl, $C_{2-6}$ alkenyl, and $C_{2-6}$ alkynyl are each optionally substituted by 1, 2, 3, or 4 independently selected $R^x$ groups; and wherein said $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl are each optionally substituted by 1, 2, 3, or 4 independently selected $R^y$ groups;

each $R^x$ is independently selected from hydroxyl, $C_{1-4}$ alkoxy, amino, $C_{1-4}$ alkylamino, and di-$C_{1-4}$-alkylamino; and each $R^y$ is independently selected from hydroxyl, halogen, cyano, nitro, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$-alkylamino.

18. A method according to claim 1, wherein:

X is cyano or fluoro;

Y is CH or N;

Z is hydrogen or fluoro;

Ar is selected from phenyl, $C_{1-6}$ monocyclic heteroaryl, $C_{1-9}$ bicyclic heteroaryl, bicyclic $C_{2-14}$ fused cycloalkylheteroaryl, and bicyclic $C_{2-14}$ fused heterocycloalkylheteroaryl; each of which is optionally substituted with 1, 2, 3, 4, 5, or 6 independently selected $R^1$ groups;

each $R^1$ is independently selected from halogen, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)NR^eR^f$, —$NR^eR^f$, —$C(=O)R^b$, —$C(=O)OR^b$, —$C(=O)NR^eR^f$, and —$NR^cC(=O)R^d$; and each $R^a$, $R^b$, $R^c$, $R^d$, $R^e$, and $R^f$ is independently selected from H, $C_{1-6}$ alkyl, $C_{1-6}$ haloalkyl, $C_{3-7}$ cycloalkyl, $C_{3-7}$ cycloalkyl-$C_{1-4}$-alkyl, $C_{2-7}$ heterocycloalkyl, $C_{2-7}$ heterocycloalkyl-$C_{1-4}$-alkyl, phenyl, phenyl-$C_{1-4}$-alkyl, $C_{1-7}$ heteroaryl, and $C_{1-7}$ heteroaryl-$C_{1-4}$-alkyl.

19. A method according to claim 1, wherein:

X is cyano or fluoro;

Y is CH or N;

Z is hydrogen or fluoro;

Ar is selected from phenyl, thiazol-2-yl, pyridin-2-yl, pyridin-3-yl, pyridin-4-yl, pyrimidin-2-yl, pyrimidin-4-yl, pyrazin-2-yl, benzo[d]oxazol-2-yl, oxazolo[4,5-c]pyridin-2-yl, oxazolo[5,4-b]pyridin-2-yl, oxazolo[5,4-d]pyrimidin-2-yl, 7H-pyrrolo[2,3-d]pyrimidin-2-yl, 2,3-dihydrothieno[2,3-b]pyridin-6-yl, S-oxo-2,3-dihydrothieno[2,3-b]pyridin-6-yl, S,S-dioxo-2,3-dihydrothieno[2,3-b]pyridin-6-yl, quinazolin-2-yl, quinolin-2-yl, pyrrolo[2,3-b]pyridin-6-yl, oxazolo[4,5-b]pyridin-2-yl, 3-oxo-3,4-dihydropyrazin-2-yl, quinoxalin-2-yl, thiazol-4-yl, thiazol-5-yl, pyrimidin-5-yl, oxazolo[5,4-d]pyrimidin-2-yl, thieno[3,2-b]pyridin-5-yl, thieno[2,3-c]pyridin-5-yl, thiophen-2-yl, thiophen-3-yl, thiazolo[5,4-d]pyrimidin-5-yl, thieno[2,3-b]pyridin-6-yl, 2,3-dihydrofuro[2,3-b]pyridin-6-yl, 6,7-dihydro-5H-cyclopenta[b]pyridin-2-yl, furo[3,2-c]pyridin-6-yl, 2,3-dihydrothieno[3,2-c]pyridin-6-yl, S-oxo-2,3-dihydrothieno[3,2-c]pyridin-6-yl, S,S-dioxo-2,3-dihydrothieno[3,2-c]pyridin-6-yl, thieno[3,2-c]pyridin-6-yl, and 1H-pyrrolo[3,2-c]pyridin-6-yl; each of which is optionally substituted with 1, 2, 3, 4, 5, or 6 independently selected $R^1$ groups; and each $R^1$ is independently selected from fluoro, bromo, chloro, cyano, hydroxyl, methyl, trifluoromethyl, methoxy, isopropylamino, dimethylamino, methylthio, methylsulfinyl, and methylsulfonyl.

20. A method according to claim 1, having formula Ia:

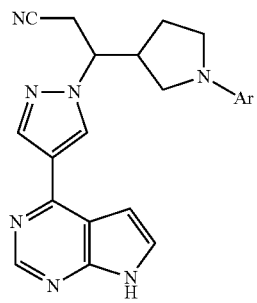

Ia or a pharmaceutically acceptable salt or N-oxide thereof.

21. A method according to claim 1, having formula Ib:

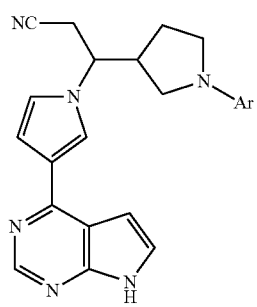

Ib or a pharmaceutically acceptable salt or N-oxide thereof.

22. A method according to claim 1, having formula Ic:

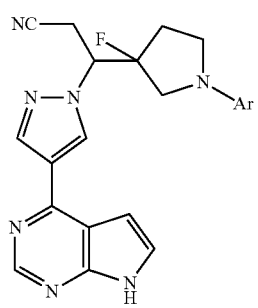

Ic or a pharmaceutically acceptable salt or N-oxide thereof.

23. A method according to claim 1, having formula Id:

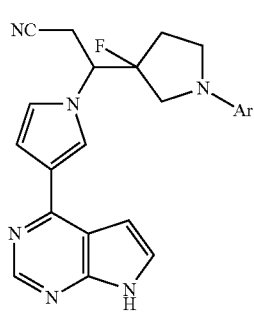

Id or a pharmaceutically acceptable salt or N-oxide thereof.

24. A method according to claim 1, having formula Ie:

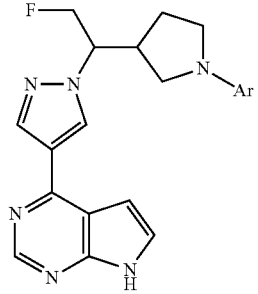

Ie or a pharmaceutically acceptable salt or N-oxide thereof.

25. A method according to claim 1, having formula If:

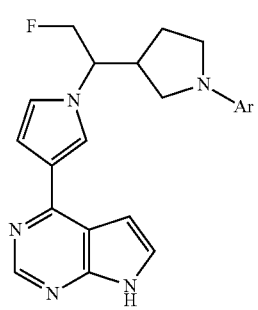

If or a pharmaceutically acceptable salt or N-oxide thereof.

26. A method according to claim 1, wherein said compound is selected from:

3-[1-(6-chloropyrazin-2-yl)pyrrolidin-3-yl]-3-[4-(7H-pyrrolo[2,3-d]pyrimidin-4-yl)-1H-pyrazol-1-yl]propanenitrile;

3-[1-(6-chloropyridin-2-yl)pyrrolidin-3-yl]-3-[4-(7H-pyrrolo[2,3-d]pyrimidin-4-yl)-1H-pyrazol-1-yl]propanenitrile;

3-[1-(2-chloropyrimidin-4-yl)pyrrolidin-3-yl]-3-[4-(7H-pyrrolo[2,3-d]pyrimidin-4-yl)-1H-pyrazol-1-yl]propanenitrile;

3-[1-(4-chloropyrimidin-2-yl)pyrrolidin-3-yl]-3-[4-(7H-pyrrolo[2,3-d]pyrimidin-4-yl)-1H-pyrazol-1-yl]propanenitrile;

3-[1-(4-bromo-1,3-thiazol-2-yl)pyrrolidin-3-yl]-3-[4-(7H-pyrrolo[2,3-d]pyrimidin-4-yl)-1H-pyrazol-1-yl]propanenitrile;

3-{1-[4-(dimethylamino)pyrimidin-2-yl]pyrrolidin-3-yl}-3-[4-(7H-pyrrolo[2,3-d]pyrimidin-4-yl)-1H-pyrazol-1-yl]propanenitrile;

3-{1-[4-(isopropylamino)pyrimidin-2-yl]pyrrolidin-3-yl}-3-[4-(7H-pyrrolo[2,3-d]pyrimidin-4-yl)-1H-pyrazol-1-yl]propanenitrile;

3-[1-(1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(5-chloro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-(1-[1,3]oxazolo[4,5-c]pyridin-2-ylpyrrolidin-3-yl)-3-[4-(7H-pyrrolo[2,3-d]pyrimidin-4-yl)-1H-pyrazol-1-yl]propanenitrile;

3-(1-[1,3]oxazolo[4,5-b]pyridin-2-ylpyrrolidin-3-yl)-3-[4-(7H-pyrrolo[2,3-d]pyrimidin-4-yl)-1H-pyrazol-1-yl]propanenitrile;

3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;

3-[1-(6-methyl[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile;

3-[1-(6-fluoro[1,3]oxazolo[5,4-b]pyridin-2-yl)pyrrolidin-3-yl]-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-[1-(7H-pyrrolo[2,3-d]pyrimidin-2-yl)pyrrolidin-3-yl]propanenitrile;

3-[1-(7-methyl-7H-pyrrolo[2,3-d]pyrimidin-2-yl)pyrrolidin-3-yl]-3-[4-(7H-pyrrolo[2,3-d]pyrimidin-4-yl)-1H-pyrazol-1-yl]propanenitrile;

3-(1-[1,3]oxazolo[5,4-d]pyrimidin-2-ylpyrrolidin-3-yl)-3-[4-(7H-pyrrolo[2,3-d]pyrimidin-4-yl)-1H-pyrazol-1-yl]propanenitrile;

3-[1-(5-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(4-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(7-fluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(5,7-difluoro-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-{1-[2-(methylthio)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[2-(methylsulfinyl)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[2-(methylsulfonyl)pyrimidin-4-yl]pyrrolidin-3-yl}-3-[4-(7H-pyrrolo[2,3-d]pyrimidin-4-yl)-1H-pyrazol-1-yl]propanenitrile;

3-{1-[6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;

3-{1-[2-(methylsulfonyl)pyrimidin-4-yl]pyrrolidin-3-yl}-3-[4-(7H-pyrrolo[2,3-d]pyrimidin-4-yl)-1H-pyrazol-1-yl]propanenitrile;

3-[1-(1-oxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(1,1-dioxido-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-(3-fluoro-1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;

3-(1-[1,3]oxazolo[5,4-b]pyridin-2-ylpyrrolidin-3-yl)-3-[3-(7H-pyrrolo[2,3-d]pyrimidin-4-yl)-1H-pyrrol-1-yl]propanenitrile;

3-[1-(1,1-dioxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile;

3-[1-(1-oxido-2,3-dihydrothieno[2,3-b]pyridin-6-yl)pyrrolidin-3-yl]-3-[3-(7H-pyrrolo[2,3-d]pyrimidin-4-yl)-1H-pyrrol-1-yl]propanenitrile;

3-[1-(6-chloro-4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile;

3-[1-(4-methyl-3-oxo-3,4-dihydropyrazin-2-yl)pyrrolidin-3-yl]-3-[4-(7H-pyrrolo[2,3-d]pyrimidin-4-yl)-1H-pyrazol-1-yl]propanenitrile;

3-chloro-2-(3-{2-cyano-1-[4-(7H-pyrrolo[2,3-d]pyrimidin-4-yl)-1H-pyrazol-1-yl]ethyl}pyrrolidin-1-yl)isonicotinonitrile;

2-(3-{2-cyano-1-[4-(7H-pyrrolo[2,3-d]pyrimidin-4-yl)-1H-pyrazol-1-yl]ethyl}pyrrolidin-1-yl)pyridine-3,4-dicarbonitrile;

2-(3-{2-cyano-1-[4-(7H-pyrrolo[2,3-d]pyrimidin-4-yl)-1H-pyrazol-1-yl]ethyl}pyrrolidin-1-yl)-6-(methylthio)benzonitrile;

2-(3-{2-cyano-1-[4-(7H-pyrrolo[2,3-d]pyrimidin-4-yl)-1H-pyrazol-1-yl]ethyl}pyrrolidin-1-yl)-6-(methylsulfonyl)benzonitrile;

3-[1-(8-chloroquinolin-2-yl)pyrrolidin-3-yl]-3-[4-(7H-pyrrolo[2,3-d]pyrimidin-4-yl)-1H-pyrazol-1-yl]propanenitrile;

3-[1-(3-hydroxyquinoxalin-2-yl)pyrrolidin-3-yl]-3-[4-(7H-pyrrolo[2,3-d]pyrimidin-4-yl)-1H-pyrazol-1-yl]propanenitrile;

3-[1-(8-chloroquinazolin-2-yl)pyrrolidin-3-yl]-3-[4-(7H-pyrrolo[2,3-d]pyrimidin-4-yl)-1H-pyrazol-1-yl]propanenitrile;

3-[1-(6-chloro-1-oxidopyridin-2-yl)pyrrolidin-3-yl]-3-[4-(7H-pyrrolo[2,3-d]pyrimidin-4-yl)-1H-pyrazol-1-yl]propanenitrile;

3-[1-(8-fluoroquinazolin-2-yl)pyrrolidin-3-yl]-3-[4-(7H-pyrrolo[2,3-d]pyrimidin-4-yl)-1H-pyrazol-1-yl]propanenitrile;

3-[1-(5-bromo-1,3-thiazol-2-yl)pyrrolidin-3-yl]-3-[4-(7H-pyrrolo[2,3-d]pyrimidin-4-yl)-1H-pyrazol-1-yl]propanenitrile;

2-chloro-6-(3-{2-cyano-1-[4-(7H-pyrrolo[2,3-d]pyrimidin-4-yl)-1H-pyrazol-1-yl]ethyl}pyrrolidin-1-yl)benzonitrile;

3-(3-{2-cyano-1-[4-(7H-pyrrolo[2,3-d]pyrimidin-4-yl)-1H-pyrazol-1-yl]ethyl}pyrrolidin-1-yl)phthalonitrile;

2-(3-{2-cyano-1-[4-(7H-pyrrolo[2,3-d]pyrimidin-4-yl)-1H-pyrazol-1-yl]ethyl}pyrrolidin-1-yl)-4-(trifluoromethyl)nicotinonitrile;

3-(3-{2-cyano-1-[4-(7H-pyrrolo[2,3-d]pyrimidin-4-yl)-1H-pyrazol-1-yl]ethyl}pyrrolidin-1-yl)pyrazine-2-carbonitrile;

2-(3-{2-cyano-1-[4-(7H-pyrrolo[2,3-d]pyrimidin-4-yl)-1H-pyrazol-1-yl]ethyl}pyrrolidin-1-yl)benzonitrile;

2-(3-{2-cyano-1-[4-(7H-pyrrolo[2,3-d]pyrimidin-4-yl)-1H-pyrazol-1-yl]ethyl}pyrrolidin-1-yl)-6-methylbenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-fluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-methoxybenzonitrile;

2-(3-{2-cyano-1-[4-(7H-pyrrolo[2,3-d]pyrimidin-4-yl)-1H-pyrazol-1-yl]ethyl}pyrrolidin-1-yl)-6-(trifluoromethyl)benzonitrile;

2-bromo-6-(3-{2-cyano-1-[4-(7H-pyrrolo[2,3-d]pyrimidin-4-yl)-1H-pyrazol-1-yl]ethyl}pyrrolidin-1-yl)benzonitrile;

2-(3-{2-cyano-1-[4-(7H-pyrrolo[2,3-d]pyrimidin-4-yl)-1H-pyrazol-1-yl]ethyl}pyrrolidin-1-yl)-3-fluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)isophthalonitrile;

6-(3-{2-cyano-1-[4-(7H-pyrrolo[2,3-d]pyrimidin-4-yl)-1H-pyrazol-1-yl]ethyl}pyrrolidin-1-yl)-2,3-difluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)-3,5,6-trifluorobenzonitrile;

2-(3-{2-cyano-1-[4-(7H-pyrrolo[2,3-d]pyrimidin-4-yl)-1H-pyrazol-1-yl]ethyl}pyrrolidin-1-yl)nicotinonitrile;

3-chloro-5-(3-{2-cyano-1-[4-(7H-pyrrolo[2,3-d]pyrimidin-4-yl)-1H-pyrazol-1-yl]ethyl}pyrrolidin-1-yl)isonicotinonitrile;

3-(3-{2-cyano-1-[4-(7H-pyrrolo[2,3-d]pyrimidin-4-yl)-1H-pyrazol-1-yl]ethyl}pyrrolidin-1-yl)-2,5,6-trifluoroisonicotinonitrile;

3-{1-[3-fluoro-4-(trifluoromethyl)pyridin-2-yl]pyrrolidin-3-yl}-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-[1-(3,5,6-trifluoropyridin-2-yl)pyrrolidin-3-yl]propanenitrile;

3-(3-{2-cyano-1-[4-(7H-pyrrolo[2,3-d]pyrimidin-4-yl)-1H-pyrazol-1-yl]ethyl}pyrrolidin-1-yl)pyridine-2-carbonitrile;

2-chloro-6-(3-{2-cyano-1-[4-(7H-pyrrolo[2,3-d]pyrimidin-4-yl)-1H-pyrazol-1-yl]ethyl}pyrrolidin-1-yl)nicotinonitrile;

2-(3-{2-fluoro-1-[4-(7H-pyrrolo[2,3-d]pyrimidin-4-yl)-1H-pyrazol-1-yl]ethyl}pyrrolidin-1-yl)[1,3]oxazolo[5,4-b]pyridine;

2-(3-(1-(4-(7H-pyrrolo[2,3-d]pyrimidin-4-yl)-1H-pyrazol-1-yl)-2-fluoroethyl)pyrrolidin-1-yl)oxazolo[5,4-b]pyridine; and 3-[1-(1H-pyrrolo[2,3-b]pyridin-6-yl)pyrrolidin-3-yl]-3-[4-(7H-pyrrolo[2,3-d]pyrimidin-4-yl)-1H-pyrazol-1-yl]propanenitrile, or a pharmaceutically acceptable salt or N-oxide thereof.

27. A method according to claim 1, wherein said compound is selected from:

5-(3-{2-cyano-1-[4-(7H-pyrrolo[2,3-d]pyrimidin-4-yl)-1H-pyrazol-1-yl]ethyl}pyrrolidin-1-yl)thieno[2,3-c]pyridine-4-carbonitrile;

5-(3-{2-cyano-1-[4-(7H-pyrrolo[2,3-d]pyrimidin-4-yl)-1H-pyrazol-1-yl]ethyl}pyrrolidin-1-yl)thieno[3,2-b]pyridine-6-carbonitrile;

2-(3-{2-cyano-1-[4-(7H-pyrrolo[2,3-d]pyrimidin-4-yl)-1H-pyrazol-1-yl]ethyl}pyrrolidin-1-yl)-4-hydroxythiophene-3-carbonitrile;

4-bromo-2-(3-{2-cyano-1-[4-(7H-pyrrolo[2,3-d]pyrimidin-4-yl)-1H-pyrazol-1-yl]ethyl}pyrrolidin-1-yl)thiophene-3-carbonitrile;

4-chloro-2-(3-{2-cyano-1-[4-(7H-pyrrolo[2,3-d]pyrimidin-4-yl)-1H-pyrazol-1-yl]ethyl}pyrrolidin-1-yl)thiophene-3-carbonitrile;

2-(3-{2-cyano-1-[4-(7H-pyrrolo[2,3-d]pyrimidin-4-yl)-1H-pyrazol-1-yl]ethyl}pyrrolidin-1-yl)thiophene-3,4-dicarbonitrile;

2-(3-{(1R)-2-fluoro-1-[4-(7H-pyrrolo[2,3-d]pyrimidin-4-yl)-1H-pyrazol-1-yl]ethyl}pyrrolidin-1-yl)thiophene-3,4-dicarbonitrile;

2-(3-{2-cyano-1-[3-(7H-pyrrolo[2,3-d]pyrimidin-4-yl)-1H-pyrrol-1-yl]ethyl}pyrrolidin-1-yl)thiophene-3,4-dicarbonitrile;

4-(3-{2-cyano-1-[4-(7H-pyrrolo[2,3-d]pyrimidin-4-yl)-1H-pyrazol-1-yl]ethyl}pyrrolidin-1-yl)-1,3-thiazole-5-carbonitrile;

5-(3-{2-fluoro-1-[3-(7H-pyrrolo[2,3-d]pyrimidin-4-yl)-1H-pyrrol-1-yl]ethyl}pyrrolidin-1-yl)-1,3-thiazole-4-carbonitrile;

4-(3-(1-(4-(7H-pyrrolo[2,3-d]pyrimidin-4-yl)-1H-pyrazol-1-yl)-2-cyanoethyl)pyrrolidin-1-yl)pyrimidine-5-carbonitrile;

4-(1-{2-fluoro-1-[1-(5-fluoro-2,3-dihydrothieno[2,3-b]pyridin-6-yl)pyrrolidin-3-yl]ethyl}-1H-pyrazol-4-yl)-7H-pyrrolo[2,3-d]pyrimidine;

4-(1-{2-fluoro-1-[1-(5-fluoro-1,1-dioxido-2,3-dihydrothieno[2,3-b]pyridin-6-yl)pyrrolidin-3-yl]ethyl}-1H-pyrazol-4-yl)-7H-pyrrolo[2,3-d]pyrimidine;

3-[1-(5-fluoro-2,3-dihydrothieno[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[1-(6-bromo-3-fluoropyridin-2-yl)pyrrolidin-3-yl]-3-[4-(7H-pyrrolo[2,3-d]pyrimidin-4-yl)-1H-pyrazol-1-yl]propanenitrile;

3-[1-(5,6-difluoropyridin-2-yl)pyrrolidin-3-yl]-3-[4-(7H-pyrrolo[2,3-d]pyrimidin-4-yl)-1H-pyrazol-1-yl]propanenitrile;

3-{1-[6-chloro-3-fluoro-5-(hydroxymethyl)pyridin-2-yl]pyrrolidin-3-yl}-3-[4-(7H-pyrrolo[2,3-d]pyrimidin-4-yl)-1H-pyrazol-1-yl]propanenitrile;

3-(4-(7H-pyrrolo[2,3-d]pyrimidin-4-yl)-1H-pyrazol-1-yl)-3-(1-(5-amino-6-chloro-3-fluoropyridin-2-yl)pyrrolidin-3-yl)propanenitrile;

N-(2-(3-(1-(4-(7H-pyrrolo[2,3-d]pyrimidin-4-yl)-1H-pyrazol-1-yl)-2-cyanoethyl)pyrrolidin-1-yl)-6-chloro-5-fluoropyridin-3-yl)formamide;
3-{1-[6-(ethylsulfonyl)-3-fluoropyridin-2-yl]pyrrolidin-3-yl}-3-[4-(7H-pyrrolo[2,3-d]pyrimidin-4-yl)-1H-pyrazol-1-yl]propanenitrile;
3-[1-(6-chloro-3-fluoropyridin-2-yl)pyrrolidin-3-yl]-3-[4-(7H-pyrrolo[2,3-d]pyrimidin-4-yl)-1H-pyrazol-1-yl]propanenitrile;
2-(3-{2-cyano-1-[4-(7H-pyrrolo[2,3-d]pyrimidin-4-yl)-1H-pyrazol-1-yl]ethyl}pyrrolidin-1-yl)-5-fluoro-4-(methoxymethyl)nicotinonitrile;
2-(3-{2-cyano-1-[4-(7H-pyrrolo[2,3-d]pyrimidin-4-yl)-1H-pyrazol-1-yl]ethyl}pyrrolidin-1-yl)-4-(methoxymethyl)nicotinonitrile;
4-(3-(1-(4-(7H-pyrrolo[2,3-d]pyrimidin-4-yl)-1H-pyrazol-1-yl)-2-cyanoethyl)pyrrolidin-1-yl)-6-methoxypyrimidine-5-carbonitrile;
3-(4-(7H-pyrrolo[2,3-d]pyrimidin-4-yl)-1H-pyrazol-1-yl)-3-(1-(6-(ethylsulfonyl)-3-fluoropyridin-2-yl)pyrrolidin-3-yl)propanenitrile;
2-(3-(1-(4-(7H-pyrrolo[2,3-d]pyrimidin-4-yl)-1H-pyrazol-1-yl)-2-cyanoethyl)pyrrolidin-1-yl)-4-methylnicotinonitrile;
3-{1-[3,5-difluoro-4-(methoxymethyl)pyridin-2-yl]pyrrolidin-3-yl}-3-[4-(7H-pyrrolo[2,3-d]pyrimidin-4-yl)-1H-pyrazol-1-yl]propanenitrile;
3-[4-(7H-pyrrolo[2,3-d]pyrimidin-4-yl)-1H-pyrazol-1-yl]-3-[1-[1,3]thiazolo[5,4-d]pyrimidin-5-ylpyrrolidin-3-yl]propanenitrile;
2-(3-{2-cyano-1-[4-(7H-pyrrolo[2,3-d]pyrimidin-4-yl)-1H-pyrazol-1-yl]ethyl}pyrrolidin-1-yl)-4-(difluoromethyl)nicotinonitrile;
3-(4-(7H-pyrrolo[2,3-d]pyrimidin-4-yl)-1H-pyrazol-1-yl)-3-(1-(5-fluoro-2-methoxypyrimidin-4-yl)pyrrolidin-3-yl)propanenitrile;
3-(4-(7H-pyrrolo[2,3-d]pyrimidin-4-yl)-1H-pyrazol-1-yl)-3-(1-(3-amino-6-chloropyridin-2-yl)pyrrolidin-3-yl)propanenitrile;
4-(3-(1-(4-(7H-pyrrolo[2,3-d]pyrimidin-4-yl)-1H-pyrazol-1-yl)-2-cyanoethyl)pyrrolidin-1-yl)pyridazine-3-carbonitrile;
6-(3-(1-(4-(7H-pyrrolo[2,3-d]pyrimidin-4-yl)-1H-pyrazol-1-yl)-2-cyanoethyl)pyrrolidin-1-yl)-5-fluoronicotinonitrile;
2-(3-(1-(4-(7H-pyrrolo[2,3-d]pyrimidin-4-yl)-1H-pyrazol-1-yl)-2-cyanoethyl)pyrrolidin-1-yl)-5-fluoronicotinonitrile;
2-(3-(1-(4-(7H-pyrrolo[2,3-d]pyrimidin-4-yl)-1H-pyrazol-1-yl)-2-cyanoethyl)pyrrolidin-1-yl)-5-methylnicotinonitrile;
4-(3-(1-(4-(7H-pyrrolo[2,3-d]pyrimidin-4-yl)-1H-pyrazol-1-yl)-2-cyanoethyl)pyrrolidin-1-yl)-6-(difluoromethyl)pyrimidine-5-carbonitrile;
2-(3-(1-(4-(7H-pyrrolo[2,3-d]pyrimidin-4-yl)-1H-pyrazol-1-yl)-2-cyanoethyl)pyrrolidin-1-yl)-6-(difluoromethyl)benzonitrile;
2-(3-(1-(4-(7H-pyrrolo[2,3-d]pyrimidin-4-yl)-1H-pyrazol-1-yl)-2-cyanoethyl)pyrrolidin-1-yl)-6-(methoxymethyl)benzonitrile;
4-(3-(1-(3-(7H-pyrrolo[2,3-d]pyrimidin-4-yl)-1H-pyrrol-1-yl)-2-cyanoethyl)pyrrolidin-1-yl)pyridazine-3-carbonitrile;
2-(3-(1-(3-(7H-pyrrolo[2,3-d]pyrimidin-4-yl)-1H-pyrrol-1-yl)-2-cyanoethyl)pyrrolidin-1-yl)nicotinonitrile;
3-(3-(1-(3-(7H-pyrrolo[2,3-d]pyrimidin-4-yl)-1H-pyrrol-1-yl)-2-cyanoethyl)pyrrolidin-1-yl)pyrazine-2-carbonitrile;
4-(3-(1-(4-(7H-pyrrolo[2,3-d]pyrimidin-4-yl)-1H-pyrazol-1-yl)-2-fluoroethyl)pyrrolidin-1-yl)pyridazine-3-carbonitrile;
3-(3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile;
2-(3-{2-fluoro-1-[4-(7H-pyrrolo[2,3-d]pyrimidin-4-yl)-1H-pyrazol-1-yl]ethyl}pyrrolidin-1-yl)nicotinonitrile;
4-(1-{1-[1-(1,1-dioxido-2,3-dihydrothieno[2,3-b]pyridin-6-yl)pyrrolidin-3-yl]-2-fluoroethyl}-1H-pyrazol-4-yl)-7H-pyrrolo[2,3-d]pyrimidine;
2-(3-(1-(4-(7H-pyrrolo[2,3-d]pyrimidin-4-yl)-1H-pyrazol-1-yl)-2-fluoroethyl)pyrrolidin-1-yl)pyridine-3,4-dicarbonitrile;
3-(3-{2-fluoro-1-[4-(7H-pyrrolo[2,3-d]pyrimidin-4-yl)-1H-pyrazol-1-yl]ethyl}pyrrolidin-1-yl)phthalonitrile;
2-(3-{2-cyano-1-[4-(7H-pyrrolo[2,3-d]pyrimidin-4-yl)-1H-pyrazol-1-yl]ethyl}pyrrolidin-1-yl)-4-iodonicotinonitrile;
2-chloro-4-(3-{2-cyano-1-[4-(7H-pyrrolo[2,3-d]pyrimidin-4-yl)-1H-pyrazol-1-yl]ethyl}pyrrolidin-1-yl)nicotinonitrile;
4-(3-{2-cyano-1-[4-(7H-pyrrolo[2,3-d]pyrimidin-4-yl)-1H-pyrazol-1-yl]ethyl}pyrrolidin-1-yl)pyridine-2,3-dicarbonitrile;
3-[1-(2,6-dichloropyridin-3-yl)pyrrolidin-3-yl]-3-[4-(7H-pyrrolo[2,3-d]pyrimidin-4-yl)-1H-pyrazol-1-yl]propanenitrile;
5-(3-{2-fluoro-1-[4-(7H-pyrrolo[2,3-d]pyrimidin-4-yl)-1H-pyrazol-1-yl]ethyl}pyrrolidin-1-yl)-1,3-thiazole-4-carbonitrile;
2-(3-{2-cyano-1-[4-(7H-pyrrolo[2,3-d]pyrimidin-4-yl)-1H-pyrazol-1-yl]ethyl}pyrrolidin-1-yl)-4-(methylthio)nicotinonitrile;
2-(3-{2-cyano-1-[4-(7H-pyrrolo[2,3-d]pyrimidin-4-yl)-1H-pyrazol-1-yl]ethyl}pyrrolidin-1-yl)-4-(methylsulfonyl)nicotinonitrile;
3-{1-[3,5-difluoro-6-(methylthio)pyridin-2-yl]pyrrolidin-3-yl}-3-[4-(7H-pyrrolo[2,3-d]pyrimidin-4-yl)-1H-pyrazol-1-yl]propanenitrile;
3-{1-[3,5-difluoro-6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;
3-(1-{3,5-difluoro-6-[(2,2,2-trifluoroethyl)-sulfonyl]pyridin-2-yl}pyrrolidin-3-yl)-3-[4-(7H-pyrrolo[2,3-d]pyrimidin-4-yl)-1H-pyrazol-1-yl]propanenitrile;
4-[1-(1-{1-[3,5-difluoro-6-(methylsulfonyl)pyridin-2-yl]pyrrolidin-3-yl}-2-fluoroethyl)-1H-pyrazol-4-yl]-7H-pyrrolo-[2,3-d]pyrimidine;
3-{1-[3-fluoro-6-(methylsulfonyl)pyridin-2-yl]pyrrolidin-3-yl}-3-[4-(7H-pyrrolo[2,3-d]pyrimidin-4-yl)-1H-pyrazol-1-yl]propanenitrile;
3-{1-[2,5-difluoro-6-(methylsulfonyl)pyridin-3-yl]pyrrolidin-3-yl}-3-[4-(7H-pyrrolo[2,3-d]pyrimidin-4-yl)-1H-pyrazol-1-yl]propanenitrile;
2-(3-{2-cyano-1-[4-(7H-pyrrolo[2,3-d]pyrimidin-4-yl)-1H-pyrazol-1-yl]ethyl}pyrrolidin-1-yl)-4-(1-fluoroethyl)nicotinonitrile;
3-(3-{2-cyano-1-[4-(7H-pyrrolo[2,3-d]pyrimidin-4-yl)-1H-pyrazol-1-yl]ethyl}pyrrolidin-1-yl)-6-(difluoromethyl)pyrazine-2-carbonitrile;
3-(3-{2-cyano-1-[4-(7H-pyrrolo[2,3-d]pyrimidin-4-yl)-1H-pyrazol-1-yl]ethyl}pyrrolidin-1-yl)-6-(2,2-difluoroethyl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-(hydroxymethyl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-(methoxymethyl)pyrazine-2-carbonitrile;

6-bromo-3-(3-{2-cyano-1-[4-(7H-pyrrolo[2,3-d]pyrimidin-4-yl)-1H-pyrazol-1-yl]ethyl}pyrrolidin-1-yl)pyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-ethynylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-ethylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile;

3-(3-{2-cyano-1-[4-(7H-pyrrolo[2,3-d]pyrimidin-4-yl)-1H-pyrazol-1-yl]ethyl}pyrrolidin-1-yl)-6-methylpyrazine-2-carbonitrile;

3-fluoro-5-(3-{2-fluoro-1-[4-(7H-pyrrolo[2,3-d]pyrimidin-4-yl)-1H-pyrazol-1-yl]ethyl}pyrrolidin-1-yl)pyridine-2-carbonitrile;

3-{1-[2-(ethylsulfonyl)pyridin-4-yl]pyrrolidin-3-yl}-3-[3-(7H-pyrrolo[2,3-d]pyrimidin-4-yl)-1H-pyrrol-1-yl]propanenitrile;

5-(3-{2-cyano-1-[3-(7H-pyrrolo[2,3-d]pyrimidin-4-yl)-1H-pyrrol-1-yl]ethyl}pyrrolidin-1-yl)-1,3-thiazole-4-carbonitrile;

3-[1-(2-mercaptopyrimidin-4-yl)pyrrolidin-3-yl]-3-[4-(7H-pyrrolo[2,3-d]pyrimidin-4-yl)-1H-pyrazol-1-yl]propanenitrile;

N-[4-(3-{2-cyano-1-[4-(7H-pyrrolo[2,3-d]pyrimidin-4-yl)-1H-pyrazol-1-yl]ethyl}pyrrolidin-1-yl)pyrimidin-2-yl]-N,N-dimethylsulfonamide;

4-(3-{2-cyano-1-[4-(7H-pyrrolo[2,3-d]pyrimidin-4-yl)-1H-pyrazol-1-yl]ethyl}pyrrolidin-1-yl)-N-methylpyridine-2-carboxamide;

4-(3-{2-cyano-1-[4-(7H-pyrrolo[2,3-d]pyrimidin-4-yl)-1H-pyrazol-1-yl]ethyl}pyrrolidin-1-yl)-N,N-dimethylpyridine-2-carboxamide;

4-(3-{2-cyano-1-[4-(7H-pyrrolo[2,3-d]pyrimidin-4-yl)-1H-pyrazol-1-yl]ethyl}pyrrolidin-1-yl)-N-phenylpyridine-2-carboxamide;

3-[1-(2,3-dihydrofuro[2,3-b]pyridin-6-yl)pyrrolidin-3-yl]-3-[4-(7H-pyrrolo[2,3-d]pyrimidin-4-yl)-1H-pyrazol-1-yl]propanenitrile;

3-[4-(7H-pyrrolo[2,3-d]pyrimidin-4-yl)-1H-pyrazol-1-yl]-3-(1-thieno[2,3-b]pyridin-6-ylpyrrolidin-3-yl)propanenitrile;

3-[1-(7,7-difluoro-6,7-dihydro-5H-cyclopenta[b]pyridin-2-yl)pyrrolidin-3-yl]-3-[4-(7H-pyrrolo[2,3-d]pyrimidin-4-yl)-1H-pyrazol-1-yl]propanenitrile;

3-[1-(7-fluoro-1,3-benzoxazol-2-yl)pyrrolidin-3-yl]-3-[3-(7H-pyrrolo[2,3-d]pyrimidin-4-yl)-1H-pyrrol-1-yl]propanenitrile;

3-[1-(7-bromo-1,3-benzoxazol-2-yl)pyrrolidin-3-yl]-3-[4-(7H-pyrrolo[2,3-d]pyrimidin-4-yl)-1H-pyrazol-1-yl]propanenitrile;

2-(3-{2-cyano-1-[4-(7H-pyrrolo[2,3-d]pyrimidin-4-yl)-1H-pyrazol-1-yl]ethyl}pyrrolidin-1-yl)-1,3-benzoxazole-7-carbonitrile;

3-[1-(7-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-[1-(7-methoxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-(4-(7H-pyrrolo[2,3-d]pyrimidin-4-yl)-1H-pyrazol-1-yl)-3-(1-(7-ethoxybenzo[d]oxazol-2-yl)pyrrolidin-3-yl)propanenitrile;

3-(4-(7H-pyrrolo[2,3-d]pyrimidin-4-yl)-1H-pyrazol-1-yl)-3-(1-(7-(difluoromethoxy)benzo[d]oxazol-2-yl)pyrrolidin-3-yl)propanenitrile;

3-[1-(4-hydroxy-1,3-benzoxazol-2-yl)pyrrolidin-3-yl]-3-[4-(7H-pyrrolo[2,3-d]pyrimidin-4-yl)-1H-pyrazol-1-yl]propanenitrile;

3-{1-[7-(hydroxymethyl)-1,3-benzoxazol-2-yl]pyrrolidin-3-yl}-3-[4-(7H-pyrrolo[2,3-d]pyrimidin-4-yl)-1H-pyrazol-1-yl]propanenitrile;

6-(3-{2-cyano-1-[4-(7H-pyrrolo[2,3-d]pyrimidin-4-yl)-1H-pyrazol-1-yl]ethyl}pyrrolidin-1-yl)furo[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)furo[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile 1,1-dioxide;

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide;

6-(3-{2-cyano-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)-2,3-dihydrothieno[3,2-c]pyridine-7-carbonitrile;

6-(3-{2-cyano-1-[4-(7H-pyrrolo[2,3-d]pyrimidin-4-yl)-1H-pyrazol-1-yl]ethyl}pyrrolidin-1-yl)thieno[3,2-c]pyridine-7-carbonitrile;

6-(3-{2-cyano-1-[3-(7H-pyrrolo[2,3-d]pyrimidin-4-yl)-1H-pyrrol-1-yl]ethyl}pyrrolidin-1-yl)thieno[3,2-c]pyridine-7-carbonitrile;

6-(3-{2-cyano-1-[4-(7H-pyrrolo[2,3-d]pyrimidin-4-yl)-1H-pyrazol-1-yl]ethyl}pyrrolidin-1-yl)-1H-pyrrolo[3,2-c]pyridine-7-carbonitrile; and 6-((3S)-3-{2-fluoro-1-[4-(7H-pyrrolo[2,3-d]pyrimidin-4-yl)-1H-pyrazol-1-yl]ethyl}pyrrolidin-1-yl)-2,3-dihydrothieno[3,2-c]pyridine-7-carbonitrile 1,1-dioxide, or a pharmaceutically acceptable salt or N-oxide thereof.

28. A method according to claim 1, wherein the compound is 6-(3-(1-(4-(7H-pyrrolo[2,3-d]pyrimidin-4-yl)-1H-pyrazol-1-yl)-2-cyanoethyl)pyrrolidin-1-yl)-2-chloro-5-fluoronicotinonitrile, or a pharmaceutically acceptable salt thereof.

29. A method, according to claim 1, wherein the compound is 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, or a pharmaceutically acceptable salt thereof.

30. A method, according to claim 1, wherein the compound is (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, or a pharmaceutically acceptable salt thereof.

31. A method, according to claim 1, wherein the compound is (S)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, or a pharmaceutically acceptable salt thereof.

32. A method according to claim 1, wherein the skin disorder is psoriasis.

33. A method according to claim 1, wherein the disease is cachexia.

34. A method according to claim 1, wherein the disease is graft versus host disease.

\* \* \* \* \*